US009216174B2

(12) United States Patent
Shen et al.

(10) Patent No.: US 9,216,174 B2
(45) Date of Patent: *Dec. 22, 2015

(54) MODULATORS OF CELLULAR ADHESION

(71) Applicant: SARcode Bioscience Inc., Brisbane, CA (US)

(72) Inventors: Wang Shen, San Mateo, CA (US); Kenneth Barr, Boston, MA (US); Johan D. Oslob, Sunnyvale, CA (US); Min Zhong, Foster City, CA (US)

(73) Assignee: SARCODE BIOSCIENCE INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,968

(22) Filed: Aug. 19, 2013

(65) Prior Publication Data

US 2014/0066476 A1  Mar. 6, 2014

Related U.S. Application Data

(60) Continuation of application No. 13/223,557, filed on Sep. 1, 2011, now abandoned, which is a continuation of application No. 13/020,992, filed on Feb. 4, 2011, now Pat. No. 8,071,617, which is a continuation of application No. 12/537,147, filed on Aug. 6, 2009, now Pat. No. 7,928,122, which is a continuation of application No. 11/934,049, filed on Nov. 1, 2007, now Pat. No. 7,790,743, which is a division of application No. 10/982,463, filed on Nov. 5, 2004, now Pat. No. 7,314,938.

(60) Provisional application No. 60/560,517, filed on Apr. 8, 2004, provisional application No. 60/517,535, filed on Nov. 5, 2003.

(51) Int. Cl.
| C07D 215/06 | (2006.01) |
| C07D 217/04 | (2006.01) |
| A61K 31/472 | (2006.01) |
| C04B 35/632 | (2006.01) |
| C07D 217/06 | (2006.01) |
| C07D 231/56 | (2006.01) |
| C07D 401/12 | (2006.01) |
| C07D 401/14 | (2006.01) |
| C07D 403/12 | (2006.01) |
| C07D 403/14 | (2006.01) |
| C07D 405/06 | (2006.01) |
| C07D 405/12 | (2006.01) |
| C07D 409/12 | (2006.01) |
| C07D 409/14 | (2006.01) |
| C07D 217/16 | (2006.01) |
| C07D 401/06 | (2006.01) |
| C07D 405/14 | (2006.01) |
| A61K 31/4725 | (2006.01) |
| A61K 45/06 | (2006.01) |
| C07D 217/26 | (2006.01) |

(52) U.S. Cl.
CPC ........... *A61K 31/472* (2013.01); *A61K 31/4725* (2013.01); *A61K 45/06* (2013.01); *C04B 35/632* (2013.01); *C07D 217/06* (2013.01); *C07D 217/16* (2013.01); *C07D 217/26* (2013.01); *C07D 231/56* (2013.01); *C07D 401/06* (2013.01); *C07D 401/12* (2013.01); *C07D 401/14* (2013.01); *C07D 403/12* (2013.01); *C07D 403/14* (2013.01); *C07D 405/06* (2013.01); *C07D 405/12* (2013.01); *C07D 405/14* (2013.01); *C07D 409/12* (2013.01); *C07D 409/14* (2013.01)

(58) Field of Classification Search
CPC ............................ C07D 215/06; C07D 217/04
USPC .......................................................... 546/146
See application file for complete search history.

(56) References Cited

U.S. PATENT DOCUMENTS 3,773,919 A  11/1973  Boswell et al.
3,989,816 A  11/1976  Rajadhyaksha
(Continued)

FOREIGN PATENT DOCUMENTS

CN  1511151 A  7/2004
CN  1914195 A  2/2007
(Continued)

OTHER PUBLICATIONS

Ayalasomayajula, et al. "Celecoxib, a selective cyclooxgenase-2 inhibitor, inhibits retinal vascular endothelial growth factor expression and vascular leakage in a streptozotocin- induced diabetic rat model" European Journal of Pharmacology. 2003; 458:283-289.
(Continued)

Primary Examiner — Shawquia Jackson
(74) Attorney, Agent, or Firm — Troutman Sanders LLP

(57) ABSTRACT

The present invention provides compounds having formula (I):

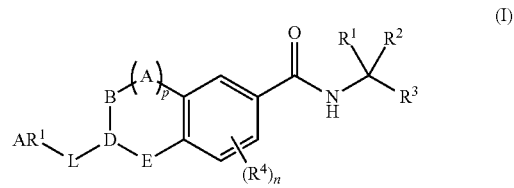

and pharmaceutically acceptable derivatives thereof, wherein $R_1$-$R_4$, n, p, A, B, D, E, L and $AR^1$ are as described generally and in classes and subclasses herein, and additionally provides pharmaceutical compositions thereof, and methods for the use thereof for the treatment of disorders mediated by the CD11/CD18 family of cellular adhesion molecules (e.g., LFA-1).

12 Claims, No Drawings

(56) References Cited

U.S. PATENT DOCUMENTS

| | | |
|---|---|---|
| 4,316,893 A | 2/1982 | Rajadhyaksha |
| 4,405,616 A | 9/1983 | Rajadhyaksha |
| 4,557,934 A | 12/1985 | Cooper |
| 4,568,343 A | 2/1986 | Leeper et al. |
| 4,668,506 A | 5/1987 | Bawa |
| 4,713,244 A | 12/1987 | Bawa |
| 4,767,628 A | 8/1988 | Hutchinson |
| 4,908,202 A | 3/1990 | Schulz |
| 4,931,279 A | 6/1990 | Bawa et al. |
| 4,992,445 A | 2/1991 | Lawter et al. |
| 5,001,139 A | 3/1991 | Lawter et al. |
| 5,023,252 A | 6/1991 | Hseih |
| 5,134,122 A | 7/1992 | Orsolini |
| 5,135,916 A | 8/1992 | Sims et al. |
| 5,149,780 A | 9/1992 | Plow et al. |
| 5,192,741 A | 3/1993 | Orsolini et al. |
| 5,236,704 A | 8/1993 | Fujioka et al. |
| 5,288,854 A | 2/1994 | Diamond et al. |
| 5,298,492 A | 3/1994 | Neustadt et al. |
| 5,340,800 A | 8/1994 | Liu et al. |
| 5,397,791 A | 3/1995 | Hartman et al. |
| 5,424,289 A | 6/1995 | Yang et al. |
| 5,424,399 A | 6/1995 | Arnaout |
| 5,445,832 A | 8/1995 | Orsolini et al. |
| 5,470,953 A | 11/1995 | Gallatin et al. |
| 5,585,359 A | 12/1996 | Breslin et al. |
| 5,597,567 A | 1/1997 | Whitcup et al. |
| 5,612,052 A | 3/1997 | Shalaby |
| 5,622,700 A | 4/1997 | Jardieu et al. |
| 5,624,837 A | 4/1997 | Fodor et al. |
| 5,672,659 A | 9/1997 | Shalaby et al. |
| 5,747,035 A | 5/1998 | Presta et al. |
| 5,840,332 A | 11/1998 | Lerner et al. |
| 5,843,884 A | 12/1998 | Sims |
| 5,843,885 A | 12/1998 | Benedict |
| 5,849,327 A | 12/1998 | Berliner et al. |
| 5,863,910 A | 1/1999 | Bolonick et al. |
| 5,877,224 A | 3/1999 | Brocchini et al. |
| 5,893,985 A | 4/1999 | Luo et al. |
| 5,922,356 A | 7/1999 | Koseki et al. |
| 5,936,089 A | 8/1999 | Carpino et al. |
| 5,968,895 A | 10/1999 | Gefter et al. |
| 5,973,188 A | 10/1999 | Alig et al. |
| 5,980,945 A | 11/1999 | Ruiz |
| 6,011,011 A | 1/2000 | Hageman |
| 6,162,432 A | 12/2000 | Wallner et al. |
| 6,180,608 B1 | 1/2001 | Gefter et al. |
| 6,203,793 B1 | 3/2001 | Lipsky et al. |
| 6,204,280 B1 | 3/2001 | Gante et al. |
| 6,294,522 B1 | 9/2001 | Zablocki et al. |
| 6,319,897 B1 | 11/2001 | Lambris et al. |
| 6,331,640 B1 | 12/2001 | Fotouhi et al. |
| 6,340,679 B1 | 1/2002 | Peyman et al. |
| 6,358,976 B1 | 3/2002 | Wityak et al. |
| 6,488,916 B1 | 12/2002 | Fowler |
| 6,515,124 B2 | 2/2003 | Fotouhi et al. |
| 6,521,619 B2 | 2/2003 | Link et al. |
| 6,524,581 B1 | 2/2003 | Adamis |
| 6,605,597 B1 | 8/2003 | Zablocki et al. |
| 6,620,422 B1 | 9/2003 | Maquin et al. |
| 6,630,447 B2 | 10/2003 | Larson |
| 6,630,492 B1 | 10/2003 | Bauer et al. |
| 6,642,225 B2 | 11/2003 | Albert et al. |
| 6,653,478 B2 | 11/2003 | Urbanski et al. |
| 6,667,060 B1 | 12/2003 | Vandecruys et al. |
| 6,667,318 B2 | 12/2003 | Burdick et al. |
| 6,670,321 B1 | 12/2003 | Adamis |
| 6,710,064 B2 | 3/2004 | Launay et al. |
| 6,764,681 B2 | 7/2004 | Wallner et al. |
| 6,773,916 B1 | 8/2004 | Thiel et al. |
| 6,787,542 B2 | 9/2004 | Wang et al. |
| 6,803,384 B2 | 10/2004 | Fotouhi et al. |
| 6,818,638 B2 | 11/2004 | Baenteli et al. |
| 6,867,203 B2 | 3/2005 | Gunawardana |
| 6,872,382 B1 | 3/2005 | Gamache et al. |
| 6,872,735 B2 | 3/2005 | Burdick et al. |
| 6,977,267 B2 | 12/2005 | Dhar et al. |
| 7,078,420 B2 | 7/2006 | Dhar et al. |
| 7,097,851 B1 | 8/2006 | Takada |
| 7,129,247 B2 | 10/2006 | Wang et al. |
| 7,166,568 B1 | 1/2007 | Sims |
| 7,186,727 B2 | 3/2007 | Dhar et al. |
| 7,199,125 B2 | 4/2007 | Dhar et al. |
| 7,211,586 B2 | 5/2007 | Fenton et |
| 7,217,728 B2 | 5/2007 | Fotouhi et al. |
| 7,314,938 B2 | 1/2008 | Shen et al. |
| 7,323,171 B2 | 1/2008 | Wallner et al. |
| 7,375,237 B2 | 5/2008 | Dhar et al. |
| 7,381,737 B2 | 6/2008 | DelMonte et al. |
| 7,396,530 B2 | 7/2008 | Goffe |
| 7,785,578 B2 | 8/2010 | Miller et al. |
| 7,790,743 B2 | 9/2010 | Shen et al. |
| 7,858,095 B2 | 12/2010 | Vaishnaw |
| 7,928,122 B2 | 4/2011 | Shen et al. |
| 7,989,626 B2 | 8/2011 | Shen et al. |
| 8,080,562 B2 | 12/2011 | Burnier et al. |
| 8,084,047 B2 | 12/2011 | Shen et al. |
| 8,168,655 B2 | 5/2012 | Gadek et al. |
| 2001/0006656 A1 | 7/2001 | Harlan et al. |
| 2001/0031260 A1 | 10/2001 | Lee et al. |
| 2002/0019446 A1 | 2/2002 | Brocchini et al. |
| 2002/0045582 A1 | 4/2002 | Margolin et al. |
| 2002/0115692 A1 | 8/2002 | Archibald et al. |
| 2002/0119994 A1 | 8/2002 | Burdick et al. |
| 2002/0132807 A1 | 9/2002 | Wang et al. |
| 2002/0143035 A1 | 10/2002 | Launay et al. |
| 2002/0176841 A1 | 11/2002 | Barker et al. |
| 2002/0177591 A1 | 11/2002 | O'Donnell et al. |
| 2003/0044406 A1 | 3/2003 | Dingivan |
| 2003/0064105 A1 | 4/2003 | Kim et al. |
| 2003/0068320 A1 | 4/2003 | Dingivan |
| 2003/0068384 A1 | 4/2003 | Brocchini et al. |
| 2003/0069560 A1 | 4/2003 | Adamis et al. |
| 2003/0138488 A1 | 7/2003 | Kohn et al. |
| 2003/0166630 A1 | 9/2003 | Auvin et al. |
| 2003/0171296 A1 | 9/2003 | Gefter et al. |
| 2003/0216307 A1 | 11/2003 | Kohn et al. |
| 2004/0006236 A1 | 1/2004 | Fotouhi et al. |
| 2004/0009998 A1 | 1/2004 | Dhar et al. |
| 2004/0028648 A1 | 2/2004 | Adamis |
| 2004/0038973 A1 | 2/2004 | Nahra et al. |
| 2004/0058968 A1 | 3/2004 | Burdick et al. |
| 2004/0120960 A1 | 6/2004 | Jardieu et al. |
| 2004/0122047 A1 | 6/2004 | Fenton et al. |
| 2004/0248920 A1 | 12/2004 | Dhar et al. |
| 2004/0259897 A1 | 12/2004 | Dhar et al. |
| 2005/0004153 A1 | 1/2005 | Dhar et al. |
| 2005/0080119 A1 | 4/2005 | Fotouhi et al. |
| 2005/0107399 A1 | 5/2005 | Boman et al. |
| 2005/0119279 A1 | 6/2005 | Dhar et al. |
| 2005/0142066 A1 | 6/2005 | Mentzer |
| 2005/0148588 A1 | 7/2005 | Burdick et al. |
| 2005/0203135 A1 | 9/2005 | Burdick et al. |
| 2005/0267098 A1 | 12/2005 | Shen et al. |
| 2006/0052434 A1 | 3/2006 | Dhar et al. |
| 2006/0074099 A1 | 4/2006 | Delmonte et al. |
| 2006/0142319 A1 | 6/2006 | Chen et al. |
| 2006/0148836 A1 | 7/2006 | Dhar et al. |
| 2006/0229588 A1 | 10/2006 | Demopulos et al. |
| 2006/0281739 A1 | 12/2006 | Gadek et al. |
| 2006/0281820 A1 | 12/2006 | Soda |
| 2006/0286108 A1 | 12/2006 | Bell |
| 2007/0025990 A1 | 2/2007 | Dingivan |
| 2007/0027101 A1 | 2/2007 | Guyer et al. |
| 2007/0048216 A1 | 3/2007 | Norenberg |
| 2007/0066585 A1 | 3/2007 | Wang et al. |
| 2007/0090205 A1 | 4/2007 | Kunze et al. |
| 2007/0105824 A1 | 5/2007 | Erickson-Miller et al. |
| 2007/0142317 A1 | 6/2007 | Warren et al. |
| 2007/0149593 A1 | 6/2007 | Ghosh et al. |
| 2007/0155671 A1 | 7/2007 | Fotouhi et al. |
| 2007/0256685 A1 | 11/2007 | Mueller-Walz |
| 2008/0019977 A1 | 1/2008 | Adamis |
| 2008/0108677 A1 | 5/2008 | Bjorklund et al. |

(56) References Cited

U.S. PATENT DOCUMENTS

| | | | |
|---|---|---|---|
| 2008/0176896 A1 | 7/2008 | Shen et al. |
| 2008/0182839 A1 | 7/2008 | Shen et al. |
| 2008/0234271 A1 | 9/2008 | Guckian |
| 2008/0242710 A1 | 10/2008 | Baumann |
| 2008/0249157 A1 | 10/2008 | Cossio Mora et al. |
| 2009/0155176 A1 | 6/2009 | Burnier et al. |
| 2009/0258069 A1 | 10/2009 | Burnier et al. |
| 2009/0258070 A1 | 10/2009 | Burnier et al. |
| 2009/0298869 A1 | 12/2009 | Burnier et al. |
| 2010/0092541 A1 | 4/2010 | Burnier et al. |
| 2010/0092542 A1 | 4/2010 | Burnier et al. |
| 2010/0093693 A1 | 4/2010 | Shen et al. |
| 2011/0015394 A1 | 1/2011 | Rao et al. |
| 2011/0092707 A1 | 4/2011 | Burnier et al. |
| 2011/0124669 A1 | 5/2011 | Shen et al. |
| 2011/0165228 A1 | 7/2011 | Burnier et al. |
| 2011/0165229 A1 | 7/2011 | Burnier et al. |
| 2012/0107404 A1 | 5/2012 | Burnier et al. |
| 2012/0115858 A1 | 5/2012 | Tesconi et al. |
| 2012/0232019 A1 | 9/2012 | Gadek et al. |
| 2013/0144063 A1 | 6/2013 | Burnier et al. |
| 2013/0150585 A1 | 6/2013 | Burnier et al. |

FOREIGN PATENT DOCUMENTS

| | | |
|---|---|---|
| EP | 0314863 A2 | 5/1989 |
| EP | 0362526 A2 | 4/1990 |
| EP | 0362526 B1 | 4/1990 |
| EP | 0362531 A1 | 4/1990 |
| EP | 0362531 B1 | 4/1990 |
| EP | 0326151 B1 | 6/1993 |
| EP | 0656789 B1 | 12/1997 |
| EP | 0467389 B1 | 10/1999 |
| EP | 1396490 A1 | 3/2004 |
| EP | 1392306 B1 | 1/2008 |
| JP | 4193895 | 7/1992 |
| JP | 2007-99641 | 11/2007 |
| WO | WO 90/03400 A1 | 4/1990 |
| WO | WO 90/10652 A1 | 9/1990 |
| WO | WO 90/13316 A1 | 11/1990 |
| WO | WO 91/19511 A1 | 12/1991 |
| WO | WO 92/03473 A1 | 3/1992 |
| WO | WO 93/16702 A1 | 9/1993 |
| WO | WO 93/24150 A1 | 12/1993 |
| WO | WO 94/03481 A1 | 2/1994 |
| WO | WO 94/06452 A1 | 3/1994 |
| WO | WO 94/11400 A1 | 5/1994 |
| WO | WO 94/15587 A2 | 7/1994 |
| WO | WO 95/04531 A1 | 2/1995 |
| WO | WO 95/28170 A1 | 10/1995 |
| WO | WO 96/09836 A1 | 4/1996 |
| WO | WO 97/04744 A1 | 2/1997 |
| WO | WO 97/26015 A1 | 7/1997 |
| WO | WO 97/40085 A2 | 10/1997 |
| WO | WO 98/13029 A1 | 4/1998 |
| WO | WO 98/25642 A2 | 6/1998 |
| WO | WO 98/46599 A1 | 10/1998 |
| WO | WO 99/49856 A2 | 10/1999 |
| WO | WO 00/21920 A1 | 4/2000 |
| WO | WO 00/38714 A1 | 7/2000 |
| WO | WO 00/44731 A1 | 8/2000 |
| WO | WO 00/72883 A2 | 12/2000 |
| WO | WO 01/01964 A2 | 1/2001 |
| WO | WO 01/12233 A2 | 2/2001 |
| WO | WO 01/27102 A1 | 4/2001 |
| WO | WO 01/49249 A2 | 7/2001 |
| WO | WO 01/49311 A1 | 7/2001 |
| WO | WO 01/58853 A1 | 8/2001 |
| WO | WO 01/87840 A1 | 11/2001 |
| WO | WO 02/30398 A2 | 4/2002 |
| WO | WO 02/38129 A2 | 5/2002 |
| WO | WO 02/50080 A1 | 6/2002 |
| WO | WO 02/058672 A2 | 8/2002 |
| WO | WO 02/059114 A1 | 8/2002 |
| WO | WO 02/074247 A2 | 9/2002 |
| WO | WO 02/098426 A1 | 12/2002 |
| WO | WO 03/053401 A2 | 7/2003 |
| WO | WO 03/075887 A1 | 9/2003 |
| WO | WO 2004/026406 A1 | 4/2004 |
| WO | WO 2005/014532 A1 | 2/2005 |
| WO | WO 2005/014533 A2 | 2/2005 |
| WO | WO 2005/042710 A1 | 5/2005 |
| WO | WO 2005/044817 A1 | 5/2005 |
| WO | WO 2005/080373 A1 | 9/2005 |
| WO | WO 2005/123706 A1 | 12/2005 |
| WO | WO 2006/047788 A2 | 5/2006 |
| WO | WO 2006/125119 A1 | 11/2006 |
| WO | WO 2009/139817 A2 | 11/2009 |

OTHER PUBLICATIONS

Bacon et al. "Tear and conjunctival changes during the allergin-induced early- and late-phase responses", J Allergy Clin Immunol. 2000;106(5):948-954.

Barouch, et al. "Integrin-mediated neutrophil adhesion and retinal leukostasis in diabetes" Invest Ophthalmol Vis Sci. 2000; 41(5):1153-1158.

Berge, et al. "Pharmaceutical salts" J Pharmaceutical Sciences. 1977; 66(1):1-19.

Boschelli, et al. "3-Alkoxybenzo[b]thiophene-2-carboxamides as inhibitors of neutrophil-endothelial cell adhesion" J Med Chem. 1994; 37(6): 717-8.

Boschelli, et al. "Inhibition of E-Selectin-, ICAM-1-, and VCAM-1-mediated cell adhesion by benzo[b]thiophene-, benzofuran-, indole-, and naphthalene-2-carboxamides: Identification of PD 144795 as an Antiinflammatory agent". J Med Chem. 1995; 38: 4597-614.

Brill et al. "Induction of mast cell interactions with blood vessel wall components by direct contact with intact T cells or T cell membranes in vitro" Clin Exp Allergy. 2004; 34(11):1725-1731.

Burdick, et al. "N-Benzoyl amino acids as ICAM/LFA-1 inhibitors. Part 2: Structure-activity relationship of the benzoyl moiety" Bioorganic & Medicinal Chemistry Letters. 2004; 14(9): 2055-9.

Burdick, et al. "N-Benzoyl amino acids as LFA-1/ICAM inhibitors 1: amino acid structure-activity relationship" Bioorganic & Medicinal Chemistry Letters. 2003; 13(6): 1015-8.

Callen. "Complications and adverse reactions in the use of newer biologic agents" Semin Cutan Med Surg. Mar. 2007; 26(1):6-14.

Chang, et al. "Effects of pharmacologic agents on the reversed passive Arthus reaction in the rat" Eur J Pharmacol. 1981; 69(2): 155-64.

Chavanpatil, et al. "Novel sustained release, swellable and bioadhesive gastroretentive drug delivery system for ofloxacin" Int J Pharm. 2006; 316(1-2): 86-92.

Chibber, et al. "Leukocytes in diabetic retinopathy" Curr Diabetes Rev. Feb. 2007; 3(1):3-14.

Choi et al. "Late-phase reaction in ocular allergy". Current Opinion in Allergy & Clinical Immunology. 2008; 8(5): 438-444.

Ciprandi, et al. "Allergic subjects express intercellular adhesion molecule—1 (ICAM-1 or CD54) on epithelial cells of conjunctiva after allergen challenge" J Allergy Clin Immunol. 1993; 91(3):783-792.

Coleman, et al. "Chemoselective Cleavage of Benzyl Ethers, Esters, and Carbamates in the Presence of Other Easily Reducible Groups" Synthesis. 1999; 1399-1400.

Cosimi, et al. "In vivo effects of monoclonal antibody to ICAM-1 (CD54) in nonhuman primates with renal allografts" J Immunol. 1990; 144(12): 4604-12.

Crocker, et al. "The role of fluorine substitution in the structure-activity relationships (SAR) of classical cannabinoids" Bioorg med chem lett. 2007; 17(6):1504-1507.

Cunhas-Vaz. "Characterization and relevance of different diabetic retinopathy phenotypes" Dev. Ophthal. 2007; 39: 13-30.

Davies et al. "Physiological Parameters in Laboratory Animals and Humans" Pharmaceutical Research. 1993; 10(7):1093-1095.

Diamond, et al. "The dynamic regulation of integrin adhesiveness" Current Biology. 1994; 4(6): 506-32.

Drugs.com "Genentech Announces Voluntary Withdrawal of Raptiva from the U.S. Market" Apr. 2009.

(56) References Cited

OTHER PUBLICATIONS

Earle et al. "A Simplified Clinical Procedure for Measurement of Glomerular Filtration Rate and Renal Plasma Flow". Proc. Soc. Exp. Biol. Med.1946; 62:262-269.
EMA. Press Release. "European Medicines Agency recommends suspension of the marketing authorisation of Raptiva (efalizumab)" Feb. 19, 2009.
European Office Action dated Mar. 28, 2012, which issued during prosecution of EP Application No. 11181066.9.
European Office Action dated Nov. 9, 2010, which issued during prosecution of EP Application No. 6770607.7.
European Office Action dated Nov. 24, 2011, which issued during prosecution of EP Application No. 06770607.7.
European Search Report dated Oct. 6, 2011 which issued during prosecution of EP Application No. 08842113.6.
European Search report dated Nov. 24, 1989, which issued during prosecution of EP Application No. 89115160.7 (EP0362526A3).
European Search Report dated Nov. 30, 2011 which issued during prosecution of EP Application No. 9732599.7.
European Search Report dated Nov. 30, 2011 which issued during prosecution of EP Application No. 9733386.8.
European Search Report dated Nov. 30, 2011 which issued during prosecution of EP Application No. 9733509.5.
European Search Report dated Dec. 20, 1989, which issued during prosecution of EP Application No. 88106902.5 (EP0314863A3).
European Search Report dated May 20, 2009 which issued during prosecution of European Application No. 06770607.7.
FDA. "FDA Advises Public of Serious Adverse Event with Psoriasis Drug Raptiva" Feb. 19, 2009.
FDA. "FDA Public Health Advisory Updated Safety Information about Raptiva (efalizumab)". Feb. 19, 2009.
FDA. "FDA Statement on the Voluntary Withdrawal of Raptiva From the U.S. Market" Apr. 8, 2009.
Fiore. "FDA Issues Boxed Warning for Efalizumab". MedPage Today. Published: Oct. 16, 2008.
Fischer, et al. "Prevention of graft failure by an anti-HLFA-1 monoclonal antibody in HLA-mismatched bone-marrow transplantation" The Lancet. 1986; 2: 1058-60.
Fischer, et al. "Role of the LFA-1 molecule in cellular interactions required for antibody production in humans[1]" J Immunol. May 1, 1986; 136(9):3198-203.
Fox. "Systemic diseases associated with dry eye" Int Ophthalmol Clin, 1994 Winter, 34(1):71-87.
Frenette. "Locking a leukocyte integrin with statins" N. Engl. J. Med. 2001; 345(19):1419-1421.
Frishberg, et al. "Cyclosporine A regulates T cell-epithelial cell adhesion by altering LFA-1 and ICAM-1 expression" Kidney Int. Jul. 1996; 50(1):45-53.
Gadek, et al. "Generation of an LFA-1 antagonist by the transfer of the ICAM-1 immunoregulatory epitope to a small molecule" Science. 2002; 295: 1086-9.
Gao, et al. "ICAM-1 expression predisposes ocular tissues to immune-based inflammation in dry eye patients and Sjögrens syndrome-like MRL/lpr mice" Exp Eye Res. Apr. 2004; 78(4):823-35.
Genentech. "Genentech Issues Dear Healthcare Provider Letter Regarding a Reported Case of PML in a Raptiva Patient" Oct. 2, 2008.
Genentech. "Genentech Issues Dear Healthcare Provider Letter Regarding a 2nd Case of PML in a Raptiva Patient" Nov. 17, 2008.
Genentech. "Voluntary U.S. Market withdrawal of Raptiva® (Efalizumab)" Apr. 8, 2009. (To patient).
Genentech. Voluntary U.S. Market withdrawal of Raptiva ® (Efalizumab). Apr. 8, 2009. (To professional).
Gennaro et al., Remington: The Science and Practice of Pharmacy, 1995, 19th Edition, Mack Publishing Company, pp. xiv-xvi, 1496-1503, 1562-1567, 1588-1589,1598-1599,1672-1677.
Goodman, et al. "Amino acid active esters. III. Base-catalyzed racemization of peptide active ester" Journal of Organic Chemistry, 1962; 27:3409-3416.

Gorski "The role of cell adhesion molecules in immunopathology" Immunology Today. 1994; 15: 251-5.
Green et al. "Dynamic shifts in LFA-1 affinity regulate neutrophil rolling, arrest, and transmigration on inflamed endothelium" Blood, 2006; 107:2101-11.
Guan, et al. "Retinal hemodynamics in early diabetic macular edema" Diabetes 2006; 55(3):813-8.
Hecht, et al. "Effects of methyl and fluorine substitution on the metabolic activation and tumorigenicity of polycyclic aromatic hydrocarbons" ACS Symposium series. 1985; 283(5):85-105. Abstract only.
Higuchi et al. Pro-drugs as Novel Delivery Systems. A. C. S. Symposium Series, and in Edward B. Roche, ed., Bioreversible Carriers in Drug Design, American Pharmaceutical Association and Pergamon Press. vol. 14. 1987.
Hildreth, et al. Monoclonal antibodies against porcine LFA-1: Species cross-reactivity and functional effects of β-subunit-specific antibodies Molecular Immunology. 1989; 26(9): 883-95.
Hoffman, et al. "Pharmacokinetic and pharmacodynamic aspects of gastroretentive dosage forms" Int J Pharm. 2004; 277(1-2): 141-53.
Huang, et al. "A binding interface of the I domain of lymphocyte function-associated antigen-1 (LFA-1) required for specific interaction with intercellular adhesion molecule 1 (ICAM-1)" J Biological Chemistry. 1995; 270(32): 19008-16.
Hughes, et al. "Vascular leucocyte adhesion molecules unaltered in the human retina in diabetes" Br J Ophthalmol. Apr. 2004;88(4):566-72.
International search report and written opinion dated Dec. 22, 2010 for PCT Application No. US2010/53571.
International search report dated Mar. 17, 2009 for PCT Application No. US2008/011878.
International search report dated Jul. 24, 2009 for PCT Application No. US2009/02385.
International search report dated Jul. 28, 2009 for PCT Application No. US2009/02388.
International search report dated Jul. 31, 2009 for PCT Application No. US2009/02389.
International search report dated Sep. 19, 2006 for PCT Application No. PCT/US2006/19327.
International Search Report dated Mar. 30, 2005 for PCT Application No. PCT/US2004/036942.
Joussen, et al. "Leukocyte-Mediated Endothelial Cell Injury and Death in the Diabetic Retina" J. Pathol. 2001; 158(1): 147-162.
Kaiser, et al. "Hydrolysis-induced racemization of amino acids" Limnol. Oceanogr. Methods. 2005; 3:318-325.
Kallen, et al. "Structural basis for LFA-1 inhibition upon lovastatin binding to the CD11a I-domain" J. Mol. Biol. 1999; 292:1-9.
Kavanaugh, et al. "Treatment of refractory rheumatoid arthritis with a monoclonal antibody to intercellular adhesion molecule 1" Arthritis Rheum. 1994; 37(7): 992-1004.
Keating, et al. "Competition between intercellular adhesion molecule-1 and a small-molecule antagonist for a common binding site on the α1 subunit of lymphocyte function-associated antigen-1" Protein Sci. 2006; 15(2):290-303.
Keating, et al. "Putting the pieces together: Contribution of fluorescence polarization assays to small molecule lead optimization" Proc. SPIE. 2000; vol. 3913, p. 128-137. (Online Publication Date: Jul. 2, 2003).
Kelly, et al. "Cutting edge: a small molecule antagonist of LFA-1-mediated cell adhesion" J. Immunol. 1999, 163:5173-5177.
Kishimoto, et al. "Integrins, ICAMs, and selectins: Role and regulation of adhesion molecules in neutrophil recruitment to inflammatory sites" Adv Pharmacol. 1994; 25: 117-69.
Klausner, et al. "Novel gastroretentive dosage forms: evaluation of gastroretentivity and its effect on levodopa absorption in humans" Pharm Res. 2003; 20(9): 1466-73.
Kunert, et al. "Analysis of Topical Cyclosporine Treatment of Patients with Dry Eye Syndrome" Arch Ophthalmol. Nov. 2000, 118:1489-1496.
Kunert, et al. "Goblet cell numbers and epithelial proliferation in the conjunctiva of patients with dry eye syndrome treated with cyclosporine" Arch Ophthalmol. Mar. 2002; 120(3):330-7.

(56) References Cited

OTHER PUBLICATIONS

Kuypers, et al. "Leukocyte membrane adhesion proteins LFA-1, CR3 and p150,95: a review of functional and regulatory aspects" Res. Immunol. 1989; 140:461-486.

Landegren. "Measurement of cell Nos. By means of the endogenous enzyme hexosaminidase. Applications to detection of lymphokines and cell surface antigens" J. Immunol. Methods 1984; 67, 379-388.

Lang, "Ocular drug delivery conventional ocular formulations", Advanced Drug Delivery Reviews, 16(1995) 39-43.

Le Mauff, et al. "Effect of anti-LFA1 (CD11a) monoclonal antibodies in acute rejection of human kidney transplantation" Transplantation. 1991; 52(2): 291-5.

Legarreta Eye Center, Dry Eye, Jan. 2002, printed from http://www.legarretaeyecenter.com/dry-eye.html with Google date entry, 2 pages.

Ley, et al. "Getting to the site of inflammation: the leukocyte adhesion cascade updated" Nat Rev Immunol. Sep. 2007; 7(9):678-689.

Li et al. "Lymphocyte Function-Associated Antigen-1-Dependent Inhibition of Corneal Wound Healing". Am J Pathology. 2006; 169(5):1590-1600.

Liebeskind, D. S. Paraneoplastic encephalopyelitis. eMedicine. Updated Jun. 11, 2009. Available at http://emedicine.medscape.com/article/1157060. Accessed Dec. 29, 2009.

Liu, et al. "Discovery of novel $p$-arylthio cinnamides as antagonists of leukocyte function-associated antigen-1/intracellular adhesion molecule-1 interaction. 1. Identification of an additional binding pocket based on an anilino diaryl sulfide lead" J. Med. Chem. 2000; 43, 4025-4040.

Liu, et al. "Novel $p$-arylthio cinnamides as antagonists of leukocyte function-associated antigen-1/intracellular adhesion molecule-1 interaction. 2. Mechanism of inhibition and structure-based improvement of pharmaceutical properties" J Med Chem. Apr. 12, 2001; 44(8):1202-1210.

Liu, G. "Inhibitors of LFA-1/ICAM-1 interaction: from monoclonal antibodies to small molecules" Drugs of the Future 2001; 26(8):767-78.

Liu, G. "Small molecule antagonists of the LFA-1/ICAM-1 interaction as potential therapeutic agents" Expert Opin Ther Patents. 2001; 119(9):1383-93.

Lo, et al. "Two leukocyte receptors (CD11a/CD18 and CD11b/CD18) mediate transient adhesion to endothelium by binding to different ligands" J Immunol. Nov. 15, 1989; 143(10):3325-9.

Lu, et al. "The binding sites for competitive antagonistic, allosteric antagonistic and agonistic antibodies to the I domain of the integrin LFA-1[1]" J Immunol. 2004; 173:3972-8.

Lupus erythematosus (online), retrieved on Dec. 28, 2006. Retrieved from the internet URL; http://en.wikipedia.org/wiki/Lupus_erythematosus.

Mekori et al. "Mast cell-T cell interactions" J Allergy Clin Immunol. 1999; 104(3):517- 23.

Mentzer, et al. "LFA-1 membrane molecule in the regulation of homotypic adhesions of human B lymphocytes" J Immunol Jul. 1985; 135(1):9-11.

Miyamoto et al. "In vivo quantification of leukocyte behavior in the retina during endotoxin-induced uveitis" Invest. Opthalmol. Vis. Sci. 1996; 37(13):2708-2715.

Miyamoto, et al. "In vivo demonstration of increased leukocyte entrapment in retinal microcirculation of diabetic rats" Invest. Opthalmol. Vis. Sci. 1998; 39(11):2190-2194.

Murphy, et al. "The Pharmacologic Assessment of a Novel Lymphocyte Function-Associated Antigen-1 Antagonist (SAR 1118) for the Treatment of Keratoconjunctivitis Sicca in Dogs" Invest Ophthalmol Vis Sci. May 16, 2011;52(6):3174-80.

Musza, et al. "Potent new cell adhesion inhibitory compounds from the root of *Trichilia rubra*" Tetrahedron. 1994; 50(39): 11369-78.

Nishiwaki et al. "Visualization and quantitative analysis of leukocyte dynamics in retinal microcirculation of rats" Invest. Opthalmol. Vis. Sci. 1996; 37(7):1341-1347.

Park, et al. "Effects of fluorine substitution on drug metabolism: pharmacological and toxicological implications" Drug Metab Rev. 1994; 26(3):605-43.

Park, et al. "Metabolism of fluorine-containing drugs" Annu Rev Pharmacol Toxicol. 2001; 41:443-70.

Paschides et al., "Evaluation of tear break-up time, Schirmer's-I test and rose bengal staining as confirmatory tests for keratoconjunctivitis sicca", Clin Exp Rheumatol. Mar.-Apr. 1989 7(2), printed from http://www.ncbi.nlm.nih.gov/pubmed/2736828, Abstract only.

Patani, et al. "Bioisosterism: A rational approach in drug design" Chem. Rev. 1996; 96:3147-3176.

Plobeck, et al. "New diarylmethylpiperazines as potent and selective nonpeptidic δopioid receptor agonists with increased in vitro metabolic stability" J Med Chem. 2000; 43: 3878-94.

Rao, et al. "Delivery of SAR 1118 to the retina via ophthalmic drops and its effectiveness in a rat streptozotocin (STZ) model of diabetic retinopathy (DR)" Invest Ophthalmol Vis Sci. Oct. 2010; 51(10):5198-204. Epub May 5, 2010.

Remington: The Science and Practice of Pharmacy, 21st edition, 2005, Philip Gerbino (Editor), p. 1158.

Rothlein, et al. "1. Leukocyte adhesion in inflammation: From discovery to the clinic" Adhesion Molecules. Wegner, C.D., Ed.; 1994: 1-8.

Salas, et al. "Rolling adhesion through an extended conformation of integrin $\alpha L \beta_2$ and relation to $\alpha$ I and $\beta$ I-like domain interaction" Immunity 2004; 20(4): 393-406.

Sanders, et al. "Characterization of the physical interaction between antigen-specific B and T cells[1]" J. Immunol. 1986; 137(8):2395-2404.

Sanfilippo, et al. "Novel thiazole based heterocycles as inhibitors of LFA-1/ICAM-1 mediated cell adhesion" J Med Chem. 1995; 38: 1057-9.

Sapirstein et al. Volumes of Distribution and Clearances of Intravenously Injected Creatinine in the Dog. *American Journal of Physiology*. 1955; 181:330-336.

Schappi et al. "Colitis in chronic granulomatous disease" Archives of Disease in Childhood 2001; 84:147-151.

Shimaoka, et al. "Reversibly locking a protein fold in an active conformation with a disulfide bond: Integrin αL I domains with high affinity and antagonist activity in vivo" PNAS. 2001; 98(11): 6009-14.

Shimaoka, et al. "Small molecule integrin antagonists that bind to the $\beta_2$ subunit I-like domain and activate signals in one direction and block them in the other" Immunity 2003; 19(3): 391-402.

Shimaoka, et al. "Structures of the αL I domain and its complex with ICAM-1 reveal a shape-shifting pathway for integrin regulation" Cell. 2003; 112(1): 99-111.

Shimaoka, et al. "Therapeutic antagonists and the conformational regulation of the $\beta_2$ integrins" Curr Topics Med Chem. 2004; 4: 1485-95.

Shulman, et al. "Lymphocyte crawling and transendothelial migration require chemokine triggering of high-affinity LFA-1 integrin" Immunity. Mar. 20, 2009; 30(3):384-396.

Skelly et al. "FDA and AAPS Report of the Workshop on Principles and Practices of In-Vitro Percutaneous Penetration Studies: Relevance to Bioavailability and Bioequivalence" Pharmaceutical Research. 1987; 4(3):265-276.

Solomans. Fundamentals of Organic Chemistry. 5th ed. 1982; 630.

Springer, T. "Adhesion receptors of the immune system" Nature. 1990; 346: 425-34.

Stein et al. "Reinventing Metered Dose Inhalers: From Poorly Efficient CFC MDIs to Highly Efficient HFA MDIs" Drug Delivery Technology 2003; 3(1):46-51.

Stern, et al. "Conjunctival T-cell subpopulations in Sjögren's and non-Sjögren's patients with dry eye" Invest Ophthalmol Vis Sci. Aug. 2002;43(8):2609-14.

Streubel, et al. "Gastroretentive drug delivery systems" Expert Opin Drug Deliv. 2006; 3(2): 217-33.

The Eye Digest, Eye Exam for Dry Eyes, Mar. 2003, printed from http://www.agingeye.net/dryeyes/dryeeyeseyeexam.php and google date.entry, 4 pages.

Thomson Scientific. Database WPI. Week 200746. London, GB. 2007.

(56) References Cited

OTHER PUBLICATIONS

U.S. Notice of Allowance dated Mar. 5, 2010, which issued during prosecution of U.S. Appl. No. 11/978,388.
U.S. Notice of allowance dated Mar. 9, 2010, which issued during prosecution of U.S. Appl. No. 11/934,049.
U.S. Office Action dated Jan. 16, 2013, which issued during prosecution of U.S. Appl. No. 13/011,760.
U.S. Office Action dated Jan. 16, 2013, which issued during prosecution of U.S. Appl. No. 13/011,775.
U.S. Office Action dated Jan. 22, 2010, which issued during prosecution of U.S. Appl. No. 11/436,906.
U.S. Office Action dated Mar. 13, 2012, which issued during prosecution of U.S. Appl. No. 13/011,760.
U.S. Office Action dated May 7, 2013, which issued during prosecution of U.S. Appl. No. 12/386,363.
U.S. Office Action dated May 8, 2012, which issued during prosecution of U.S. Appl. No. 12/386,363.
U.S. Office Action dated Jun. 7, 2011, which issued during prosecution of U.S. Appl. No. 11/436,906.
U.S. Office Action dated Jun. 8, 2011, which issued during prosecution of U.S. Appl. No. 12/508,367.
U.S. Office Action dated Jun. 25, 2012, which issued during prosecution of U.S. Appl. No. 12/909,241.
U.S. Office Action dated Jul. 22, 2010, which issued during prosecution of U.S. Appl. No. 11/436,906.
U.S. Office Action dated Sep. 8, 2011, which issued during prosecution of U.S. Appl. No. 12/386,361.
U.S. Office Action dated Sep. 15, 2011, which issued during prosecution of U.S. Appl. No. 13/011,760.
U.S. Office Action dated Sep. 27, 2011, which issued during prosecution of U.S. Appl. No. 12/386,363.
U.S. Office Action dated Sep. 28, 2010, which issued during prosecution of U.S. Appl. No. 12/508,311.
U.S. Office Action dated Sep. 28, 2010, which issued during prosecution of U.S. Appl. No. 12/508,367.
U.S. Office Action dated Oct. 5, 2011, which issued during prosecution of U.S. Appl. No. 13/011,775.
U.S. Office Action dated Oct. 28, 2013, which issued during prosecution of U.S. Appl. No. 13/011,775.
U.S. Office Action dated Nov. 9, 2012, which issued during prosecution of U.S. Appl. No. 13/289,172.
U.S. Office Action dated Dec. 21, 2010, which issued during prosecution of U.S. Appl. No. 11/436,906.
U.S. Office Action dated Apr. 25, 2012, which issued during prosecution of U.S. Appl. No. 13/011,775.
Ward, S. "Millipede-like lymphocyte crawling: feeling the way with filopodia" Immunity. Mar. 20, 2009; 30(3):315-317.
Weitz-Schmidt, et al. "Statins selectively inhibit leukocyte function antigen-1 by binding to a novel regulatory integrin site" Nature Med. 2001; 7(6):687-692.
Welzenbach, et al. "Small molecule inhibitors induce conformational changes in the I domain and the I-like domain of lymphocyte function-associated antigen-1" J Biological Chemistry. 2002; 277(12):10590-8.
Wermuth. "The practice of medicinal chemistry: molecular variations based on isosteric replacements" Academic Press Limited. 1996; 226-228.
Whitcup et al. "Blocking ICAM-1 (CD54) and Lfa-1 (CD11a) inhibits experimental allergic conjunctivitis" Clin Immunol. 1999; 93(2):107-13.
WO 00/72883 A3—International Search Report dated Mar. 12, 2001, which issued during prosecution of International Application No. PCT/US00/15289.
WO 01/01964 A3—International Search Report dated Apr. 9, 2001, which issued during prosecution of International Application No. PCT/US00/17223.
WO 01/49249 A3—International Search Report dated Nov. 5, 2001, which issued during prosecution of International Application No. PCT/US01/00030.
WO 1994/15587 A3—International Search Report dated Jun. 29, 1994, which issued during prosecution of International Application No. PCT/US94/00148.
WO 1997/40085 A3—International Search Report dated Dec. 8, 1997, which issued during prosecution of International Application No. PCT/IE97/00031.
WO 1998/25642 A3—International Search Report dated Jun. 10, 1998, which issued during prosecution of International Application No. PCT/US97/22881.
WO 1999/49856 A3—International Search Report dated Sep. 29, 1999, which issued during prosecution of International Application No. PCT/US99/06410.
WO 2001/12233 A3—International Search Report dated Jun. 15, 2001, which issued during prosecution of International Application No. PCT/US00/22464.
WO 2002/058672 A3—International Search Report dated Oct. 25, 2002, which issued during prosecution of International Application No. PCT/CH02/00048.
WO 2002/074247 A3—International Search Report dated Sep. 18, 2002, which issued during prosecution of International Application No. PCT/US02/08453.
WO 2002/30398 A3—International Search Report dated Aug. 13, 2002, which issued during prosecution of International Application No. PCT/GB01/04423.
WO 2002/38129 A3—International Search Report dated Aug. 12, 2002, which issued during prosecution of International Application No. PCT/GB01/04980.
WO 2003/053401 A3—International Search Report dated Jul. 24, 2003, which issued during prosecution of International Application No. PCT/US02/41031.
WO 2005/014533 A3—International Search Report dated Jan. 26, 2005, which issued during prosecution of International Application No. PCT/US2004/025463.
WO 2006/047788 A3—International Search Report dated Jul. 3, 2008, which issued during prosecution of International Application No. PCT/US05/39672.
WO 2009/139817 A3—International search report and written opinion dated Sep. 24, 2009 for PCT Application No. US2009/02391.
Zhong, et al. "Discovery and Development of Potent LFA-1/ICAM-1 Antagonist SAR 1118 as an Ophthalmic Solution for Treating Dry Eye" ACS Med. Chem. Lett. DOI: 10.1021/ml2002482. Publication Date (Web): Jan. 31, 2012.

MODULATORS OF CELLULAR ADHESION

PRIORITY

This application claims priority under 35 U.S.C. §120 as a continuation of U.S. application Ser. No. 13/223,557, filed Sep. 1, 2011, which is a continuation of U.S. application Ser. No. 13/020,992, filed Feb. 4, 2011, issued as U.S. Pat. No. 8,071,617, which is a continuation of U.S. application Ser. No. 12/537,147, filed Aug. 6, 2009, issued as U.S. Pat. No. 7,928,122, which is a continuation of U.S. application Ser. No. 11/934,049, filed Nov. 1, 2007, issued as U.S. Pat. No. 7,790,743, which is a divisional application of U.S. application Ser. No. 10/982,463, filed Nov. 5, 2004, issued as U.S. Pat. No. 7,314,938, which claims the benefit under 35 U.S.C. §119(e) of U.S. Provisional Application Ser. Nos. 60/560,517, filed Apr. 8, 2004 and 60/517,535, filed Nov. 5, 2003; the contents of each application are incorporated herein by reference in their entirety.

BACKGROUND OF THE INVENTION

Research conducted over the last decade has helped elucidate the molecular events attending cell-cell interactions in the body, especially those events involved in the movement and activation of cells in the immune system. See generally, Springer, T. *Nature,* 1990, 346, 425-434. Cell surface proteins, and especially the Cellular Adhesion Molecules ("CAMs") and "leukointegrins", including LFA-1, MAC-1 and gp150.95 (referred to as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the leukointegrins is a vital step in the normal functioning of the immune system. It is believed that immune processes such as antigen presentation, T-cell mediated cytotoxicity and leukocyte extravasation all require cellular adhesion mediated by ICAMs interacting with the leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

Clearly, because of the role that the interaction of the CAMs and the leukointegrins plays in the immune response, it would be desirable to modulate these specific interactions to achieve a desired therapeutic result (e.g., inhibition of the interaction in the event of an overactive immune response). Significantly, it has been demonstrated that the antagonism of the interaction between the CAMs and the leukointegrins can be realized by agents directed against either component. Specifically, blocking of the CAMs, such as for example ICAM-1, or the leukointegrins, such as for example LFA-1, by antibodies directed against either or both of these molecules effectively inhibits inflammatory responses. In vitro models of inflammation and immune response inhibited by antibodies to CAMs or leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today,* 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: Adhesion Molecules; Wegner, C. D., Ed.; 1994, 1-38, Cosimi, C. B.; et al., *J. ImmunoL.* 1990, 144, 4604-4612 and Kavanaugh, A.; et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet,* 1989, 2, 1058-1060 and Le Mauff, B.; et al., *Transplantation,* 1991, 52, 291-295).

As described above, the use of anti-LFA-1 or anti-ICAM-1 antibodies to antagonize this interaction has been investigated. Additionally, the use of LFA-1 or ICAM-1 peptides, fragments or peptide antagonists (see, for example, U.S. Pat. Nos. 5,149,780, 5,288,854, 5,340,800, 5,424,399, 5,470,953, Published PCT applications WO 90/03400, WO90/13316, WO90/10652, WO91/19511, WO92/03473, WO94/11400, WO95/28170, JP4193895, EP314863, EP362526, EP362531), and small molecule antagonists have been investigated. For example, several small molecules have been described in the literature which affect the interaction of CAMs and leukointegrins. A natural product isolated from the root of Trichilia rubra was found to be inhibitory in an in vitro cell binding assay (Musza, L. L.; et al., *Tetrahedron,* 1994, 50, 11369-11378). One series of molecules (Boschelli, D. H.; et al., *J. Med. Chem.* 1994, 37, 717 and Boschelli, D. H.; et al., *J. Med. Chem.* 1995, 38, 4597-4614) was found to be orally active in a reverse passive Arthus reaction, an induced model of inflammation that is characterized by neutrophil accumulation (Chang, Y. H.; et al., *Eur. J. PharmacoL.* 1992, 69, 155-164). Another series of molecules was also found to be orally active in a delayed type hypersensitivity reaction in rats (Sanfilippo, P. J.; et al., *J. Med. Chem.* 1995, 38, 1057-1059). All of these molecules appear to act nonspecifically, either by inhibiting the transcription of ICAM-1 along with other proteins or act intracellularly to inhibit the activation of the leukointegrins by an unknown mechanism, and none appear to directly antagonize the interaction of the CAMs with the leukointegrins.

Clearly, although several classes of compounds have been investigated for therapeutic use, there remains a need for the development of novel therapeutics that are capable of modulating interactions between CAMs and leukointegrins. In particular, it would be desirable to develop therapeutics capable of selectively targeting (preferably inhibiting) the interaction between LFA-1 and ICAM-1 that would be useful as a therapeutic agent for immune and/or inflammatory disorders.

SUMMARY OF THE INVENTION

As discussed above, there remains a need for the development of novel therapeutics that are capable of modulating interactions between CAMs and leukointegrins. The present invention provides novel compounds of general formula (I),

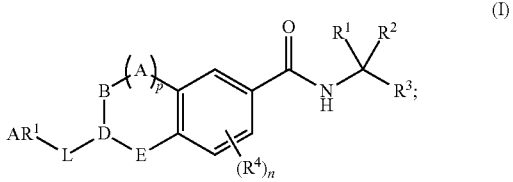

and pharmaceutical compositions thereof, as described generally and in subclasses herein, which compounds are useful as modulators of the CD11/CD18 family of cellular adhesion molecules. Thus these compounds are useful, for example, for the treatment of various LFA-1-related disorders including immune and/or inflammatory disorders.

In yet another aspect, the present invention provides methods for treating any disorder mediated through the CD11/CD18 family of cellular adhesion molecules comprising administering to a subject in need thereof a therapeutically effective amount of a compound of the invention.

DEFINITIONS

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, iso-butyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Example s of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Example s of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Example s that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least on eheteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Example s that are described herein.

The term "cycloalkyl", as used herein, refers specifically to groups having three to seven, preferably three to ten carbon atoms. Suitable cycloalkyls include, but are not limited to, cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; -OC(O)R$_x$; -OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Example s that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —IC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Example s, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Example s that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$, and R$_z$ are independently an aliphatic, alicyclic, heteroaliphatic, heterocyclic, aromatic or heteroaromatic moiety, as defined herein. Example s of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "sulfonamido", as used herein, refers to a group of the general formula —SO$_2$NR$_x$R$_y$, where R$_x$ and R$_y$ are independently hydrogen, or an aliphatic, alicyclic, heteroaliphatic, heterocyclic, aromatic, heteroaromatic or acyl moiety, as defined herein.

The term "benzamido", as used herein, refers to a group of the general formula PhNR$_x$—, where R$_x$ is hydrogen, or an aliphatic, alicyclic, heteroaliphatic, heterocyclic, aromatic, heteroaromatic or acyl moiety, as defined herein.

The term "C$_{1-6}$alkylidene", as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (T-butyldimethylsilyl ether), tribenzyl silyl ether, TBDPS (T-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. This includes, for example, or α-, β-, D-, L-amino acid residues, and compounds of the general formula

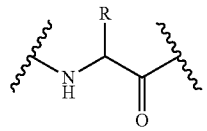

wherein the side chain R is other than the amino acid side chains occurring in nature.

More generally, the term "amino acid", as used herein, encompasses natural amino acids and unnatural amino acids.

The term "bioisosteres", as used herein, generally refers to two or more compounds or moieties that possess similar molecular shapes and/or volumes. In certain embodiments, bioisosteres have approximately the same distribution of electrons. In certain other embodiments, bioisosteres exhibit similar biological properties. In preferred embodiments, bioisosteres possess similar molecular shapes and volumes; have approximately the same distribution of electrons; and exhibit similar biological properties.

As used herein, the term "isolated", when applied to the compounds of the present invention, refers to such compounds that are (i) separated from at least some components with which they are associated in nature or when they are made and/or (ii) produced, prepared or manufactured by the hand of man.

The term, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Example s of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, lauratc, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Example s of particular esters include formates, acetates, propionates, butyrates, acrylates and ethylsuccinates.

As used herein, the term "pharmaceutically acceptable prodrugs" refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, VoL. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "LFA-1 mediated disorders", as used herein refers generally to pathological states caused by cell adherence interactions involving the LFA-1 receptor on lymphocytes. Example s of such disorders include, but are not limited to T-cell inflammatory responses such as inflammatory skin diseases including psoriasis; responses associated with inflammatory bowel disease (such as Crohn's disease and ulcerative colitis); adult respiratory distress syndrome, dermatitis, meningitis, encephalitis, uveitic, allergic conditions such as eczema and asthma and other conditions involving infiltration of T-cells and chronic inflammatory responses, skin hypersensitivity reactions (including poison ivy and poison oak), atherosclerosis, leukocyte adhesion deficiency, autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, type 1 diabetes, juvenile onset diabetes, and immune responses associated with delayed hypersensitivity mediated by cytokines and T-lymphocytes typically found in tuberculosis, sarcoidosis, polymyositis, granulomatosis, and vasculitis, pernicious anemia, diseases involving leukocyte diapedesis, CNS inflammatory disorder, multiple organ injury syndrome secondary to septicaemia or trauma, autoimmune haemolytic anemia, myethamia gravis, antigen-antibody complex mediated diseases, and all types of transplantations, including graft vs. host or host vs. graft disease.

The term "LFA-1 antagonist", as used herein, generally refers to inventive compounds, as described herein, that act as a competitive inhibitors of the CD11a and/or CD18 interaction with ICAM-1, ICAM-2 or ICAM-3.

The term "treating", as used herein generally means that the compounds of the invention can be used in humans or animals with at least a tentative diagnosis of disease. The compounds of the invention will delay or slow the progression of the disease thereby extending the individual's life span.

The term "preventing" as used herein generally means that the compounds of the present invention are useful when administered to a patient who has not been diagnosed as possibly having the disease at the time of administration, but who would normally be expected to develop the disease or be at increased risk for the disease. In certain embodiments, compounds of the invention slow the development of disease symptoms, delay the onset of disease, or prevent the individual from developing the disease at all.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION

The present invention provides compounds that modulate interactions between intracellular adhesion molecules (e.g., ICAM-1, -2 and -3) and the leukocyte integrin family of receptors. In certain embodiments, the inventive compounds are antagonists and are useful for the treatment of CD11/CD18 mediated disorders. In certain embodiments of special interest, the inventive compounds are useful for the treatment of Mac-1 and LFA-1 mediated disorders. In still other embodiments, the compounds are useful for the treatment of LFA-1 mediated disorders, for example, inflammatory disorders and autoimmune disorders to name a few.

1) General Description of Compounds of the Invention

The compounds of the invention include compounds of the general formula (I) as further defined below:

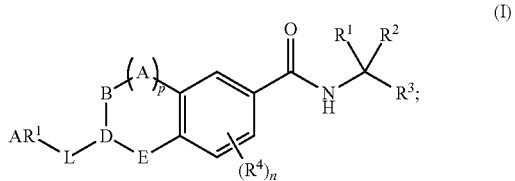

and pharmaceutically acceptable derivatives thereof;
wherein $R^1$ and $R^2$ are each independently hydrogen, an amino acid side chain, an aliphatic, alicyclic, heteroaliphatic, heterocyclic, aromatic or heteroaromatic moiety, or wherein $R^1$ and $R^2$ taken together are an alicyclic or heterocyclic moiety, or together are

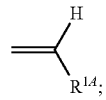

wherein $R^{14}$ is hydrogen, an aliphatic, alicyclic, heteroaliphatic, heterocyclic, aromatic or heteroaromatic moiety;

$R^3$ is —C(=O)OR$^{3A}$, —C(=O)H, —CH$_2$OR$^{3A}$, —CH$_2$O—C(=O)-alkyl, —C(=O)NH(R$^{3A}$) or —CH$_2$X$^0$; wherein each occurrence of $R^{3A}$ is independently hydrogen, a protecting group, an aliphatic, alicyclic, heteroaliphatic, heterocyclic, aromatic or heteroaromatic moiety, or $R^{3A}$, taken together with $R^1$ or $R^2$, forms a heterocyclic moiety; wherein $X^0$ is a halogen selected from F, Cl, Br or I;

$R^4$, for each occurrence, is independently hydrogen, halogen, —CN, —NO$_2$, an aliphatic, alicyclic, heteroaliphatic, heterocyclic, aromatic or heteroaromatic moiety, or is -GR$^{G1}$ wherein G is —O—, —S—, —NR$^{G2}$—, —CO—, —SO—, —SO$_2$—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heterocyclic, aromatic or heteroaromatic moiety;

n is an integer from 0-3;
AR$^1$ is an aromatic, heteroaromatic, alicyclic or heterocyclic moiety;

A, B, D and E are connected by either a single or double bond, as valency permits; wherein each occurrence of A, B, D and E is independently C=O, CR$^i$R$^{ii}$, NR$^i$, CR$^i$, N, O, S, S(=O) or SO$_2$; wherein each occurrence of $R^i$ is independently hydrogen, halogen, —CN, —NO$_2$, an aliphatic, alicyclic, heteroaliphatic, heterocyclic, aromatic or heteroaromatic moiety, or is -GR$^{G1}$ wherein G is —O—, —S—, —CO—, —SO—, —SO$_2$—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heterocyclic, aromatic or heteroaromatic moiety, or any two adjacent occurrences of $R^i$, taken together, represent an alicyclic, heterocyclic, aromatic or heteroaromatic moiety;

p is an integer from 0-4; and

L is absent or is V—W—X—Y—Z, wherein each occurrence of V, W, X, Y and Z is independently absent, C=O, NR$^{L1}$, —O—, —C(R$^{L1}$)=, =C(R$^{L1}$), —C(R$^{L1}$)(R$^{L2}$), C(=N—O—R$^{L1}$), C(=N—R$^{L1}$), —N=, S(O)$_{0-2}$; a substituted or unsubstituted C$_{1-6}$alkylidene or C$_{2-6}$alkenylidene chain wherein up to two non-adjacent methylene units are independently optionally replaced by —C(=O)—, —CO$_2$—, —C(=O)C(=O)—, —C(=O)NR$^{L3}$—, —OC(=O)—, —OC(=O)NR$^{L3}$—, —NR$^{L3}$NR$^{L4}$—, —NR$^{L3}$NR$^{L4}$C(=O)—, —NR$^{L3}$C(=O)—, —NR$^{L3}$CO$_2$—, —NR$^{L3}$C(=O)NR$^{L4}$—, —S(=O)—, —SO$_2$—, —NR$^{L3}$SO$_2$, —SO$_2$NR$^{L3}$—, —NR$^{L3}$SO$_2$NR$^{L4}$—, —O—, —S—, or —NR$^{L3}$—; wherein each occurrence of R$^{L3}$ and R$^{L4}$ is independently hydrogen, alkyl, heteroalkyl, aromatic, heteroaromatic or acyl; or an aliphatic, alicyclic, heteroaliphatic, heterocyclic, aromatic or heteroaromatic moiety; and each occurrence of R$^{L1}$ and R$^{L2}$ is independently hydrogen, hydroxyl, protected hydroxyl, amino, protected amino, thio, protected thio, halogen, cyano, isocyanate, carboxy, carboxyalkyl, formyl, formyloxy, azido, nitro, ureido, thioureido, thiocyanato, alkoxy, aryloxy, mercapto, sulfonamide, benzamido, tosyl, or an aliphatic, alicyclic, heteroaliphatic, heterocyclic, aromatic or heteroaromatic moiety, or wherein one or more occurrences of R$^{L1}$ and R$^{L2}$, taken together, or taken together with one of V, W, X, Y or Z form an alicyclic or heterocyclic moiety or form an aromatic or heteroaromatic moiety.

In another aspect, the invention provides compounds of formula (II):

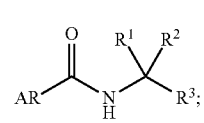

wherein AR has one of the following structures:

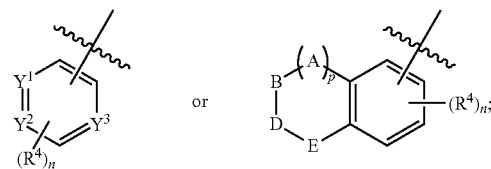

and pharmaceutically acceptable derivatives thereof;
wherein R$^1$, R$^2$, R$^3$, R$^4$, A, B, D, E, n, p are as defined generally above and in classes and subclasses herein; and
Y$^1$, Y$^2$ and Y$^3$ are each independently CR$^4$ or N;

with the proviso that, when AR has the structure:

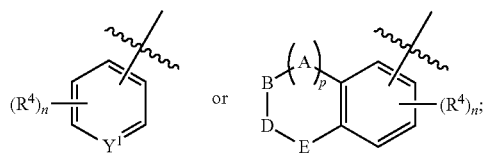

wherein $Y^1$ is CH or N and p is 0-2, then $R^4$ is not carbocycle, aryl, heteroaryl or heterocyle, and A, B, D and E do not comprise a carbocyclic, aryl, heteroaryl or heterocyclic moiety.

In certain embodiments, for compounds of formula (II), AR represents a moiety having one of the following structures:

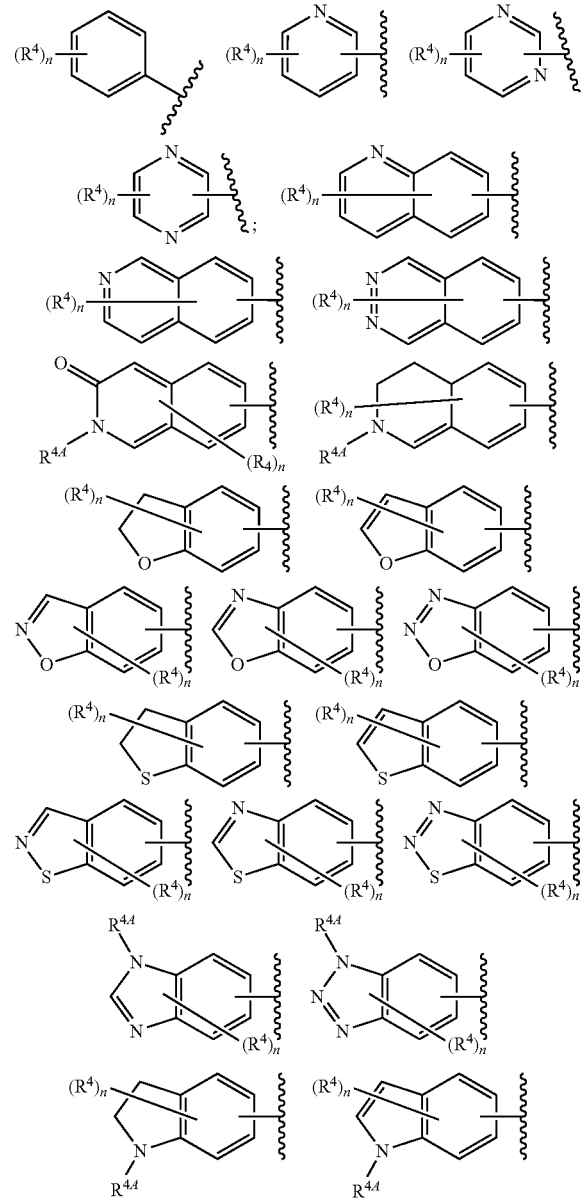

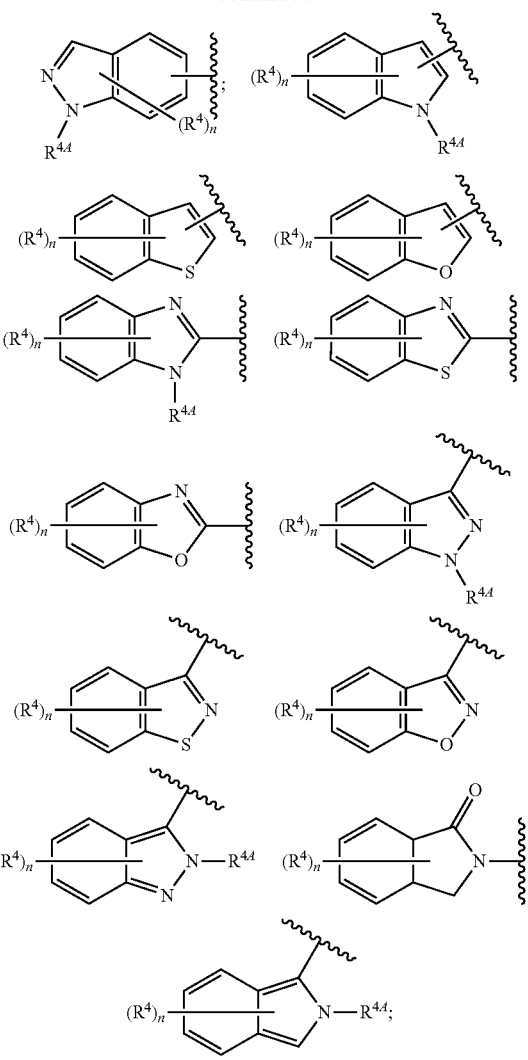

wherein each occurrence of n is an integer from 0-6; each occurrence of $R^4$ is independently hydrogen, halogen, CN, isocyanate, $NO_2$, $-P(=O)(YR^{P5})_2$, an alkyl, cycloalkyl, heteroalkyl, heterocyclic moiety, or is $-GR^{G1}$ wherein G is $-O-$, $-S-$, $-NR^{G2}-$, $-CO-$, $-SO-$, $-SO_2-$, $-C(=O)O-$, $-C(=O)NR^{G2}-$, $-OC(=O)-$, $-NR^{G2}C(=O)-$ or $-SO_2NR^{G2}-$, and $R^{G1}$ and $R^{G2}$ are independently hydrogen, an alkyl, cycloalkyl, heteroalkyl, heterocyclic moiety; each occurrence of Y is independently a bond or O; each occurrence of $R^{P5}$ is independently alkyl, heteroalkyl, aryl or heteroaryl, or when Y is O $R^{P5}$ may also be hydrogen; and each occurrence of $R^{4A}$ is independently hydrogen, an alkyl, cycloalkyl, heteroalkyl, heterocyclic moiety or a nitrogen protecting group; wherein any two adjacent occurrences of $R^4$ and $R^{4A}$, taken together, may form a cycloalkyl, heterocyclic, aryl or heteroaryl moiety. In certain exemplary embodiments, AR has the structure:

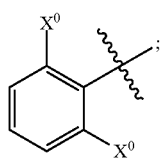

In yet other exemplary embodiments, AR has the structure:

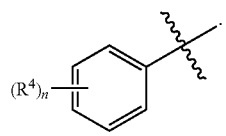

wherein each occurrence of $X_0$ is independently a halogen selected from F, Cl, Br and I. In certain embodiments, each occurrence of $X^0$ is Cl.

A number of important subclasses of each of the foregoing classes deserve separate mention; these subclasses include subclasses of the foregoing classes in which:

i) $R^1$ and $R^2$ are each independently hydrogen, an amino acid side chain, —$(CH_2)_m OH$, —$(CH_2)_m aryl$, —$(CH_2)_m heteroaryl$, wherein m is 0-6, —$CH(R^{1A})(OR^{1B})$, —$CH(R^{1A})(NHR^{1B})$, U-T-Q, or an alkyl, cycloalkyl, heteroalkyl or heterocyclic moiety optionally substituted with U-T-Q, wherein U is absent, —O—, —S(O)$_{0-2}$—, —$SO_2N(R^{1A})$, —$N(R^{1A})$—, —$N(R^{1A})C(=O)$—, —$N(R^{1A})C(=O)$—O—, —$N(R^{1A})C(=O)$—$N(R^{1B})$—, —$N(R^{1A})$—$SO_2$—, —C(=O)—, —C(=O)—O—, —O—C(=O)—, aryl, heteroaryl, alkylaryl, alkylheteroaryl, —C(=O)—$N(R^{1A})$—, —O—C(=O)—$N(R^{1A})$—, —C(=N—$R^{1E}$)—, —C(=N—$R^{1E}$)—O—, —C(=N—$R^{1E}$)—$N(R^{1A})$—, —O—C(=N—$R^{1E}$)—$N(R^{1A})$—, —$N(R^{1A})C(=N—R^{1E})$—, —$N(R^{1A})C(=N—R^{1E})$—O—, $N(R^{1A})C(=N—R^{1E})$—$N(R^{1B})$—, —$P(=O)(OR^{1A})$—O—, or —$P(=O)(R^{1A})$—O—; wherein T is absent, an alkyl, cycloalkyl, heteroalkyl, heterocyclic, aryl, heteroaryl, alkylaryl, alkylheteroaryl, heteroalkylaryl or heteroalkylheteroaryl moiety, and wherein Q is hydrogen, halogen, cyano, isocyanate, —$OR^{1B}$, —$SR^{1B}$; —$N(R^{1B})_2$, —$NHC(=O)OR^{1B}$, —$NHC(=O)N(R^{1B})_2$, —$NHC(=O)R^{1B}$, —$NHSO_2R^{1B}$, —$NHSO_2N(R^{1B})_2$, —$NHSO_2NHC(=O)OR^{1B}$, —$NCH(=O)NHSO_2R^{1B}$, —$C(=O)NHC(=O)OR^{1B}$, —$C(=O)NHC(=O)R^{1B}$, —$C(=O)NHC(=O)N(R^{1B})_2$, —$C(=O)NHSO_2R^{1B}$, —$C(=O)NHSO_2N(R^{1B})_2$, —$C(=S)N(R^{1B})_2$, —$SO_2R^{1B}$, —$SO_2$—O—$R^{1B}$, —$SO_2$—$N(R^{1B})_2$, —$SO_2$—$NHC(=O)OR^{1B}$, —$SO_2$—$NHC(=O)$—$N(R^{1B})_2$, —$SO_2$—$NHC(=O)R^{1B}$, —O—$C(=O)N(R^{1B})_2$, —O—$C(=O)R^{1B}$, —O—$C(=O)NHC(=O)R^{1B}$, —O—C(=O)NH—$SO_2R^{1B}$, —O—$SO_2R^{1B}$, or an alkyl, cycloalkyl, heteroalkyl, heterocyclic, aryl or heteroaryl moiety, or wherein $R^1$ and $R^2$ taken together are a cycloalkyl or heterocyclic moiety, or together are

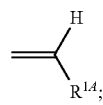

wherein each occurrence of $R^{1A}$ and $R^{1B}$ is independently hydrogen, an alkyl, cycloalkyl, heteroalkyl, heterocyclic, aryl or heteroaryl moiety, —$COR^{1C}$, or —$CONR^{1C}R^{1D}$; wherein each occurrence of $R^{1C}$ and $R^{1D}$ is independently hydrogen, hydroxyl, or an alkyl, cycloalkyl, heteroalkyl, heterocyclic, aryl or heteroaryl moiety; and $R^{1E}$ is hydrogen, an aliphatic, alicyclic, heteroaliphatic, heterocyclic, aryl, heteroaryl, alkylaryl or alkylheteroaryl moiety, —CN, —$OR^{1C}$, —$NR^{1C}R^{1D}$ or —$SO_2R^{1C}$;

ii) $R^3$ is carboxyl, protected carboxyl or a prodrug thereof, wherein $R^3$ is $C(=O)R^{3A}$, wherein $R^{3A}$ is hydroxy, alkoxy, cycloalkoxy, aralkoxy, arcycloalkoxy, aryloxy, alkylcarbonyloxyalkyloxy, alkoxycarbonyloxyalkyloxy, alkoxycarbonylalkyloxy, cycloalkylcarbonyloxyalkyloxy, cycloalkoxycarbonyloxyalkyloxy, cycloalkoxycarbonylalkyloxy, arylcarbonyloxyalkyloxy, aryloxycarbonyloxyalkyloxy, arylcarbonyloxyalkyloxy, alkoxyalkylcarbonyloxyalkyloxy, or one or the structures:

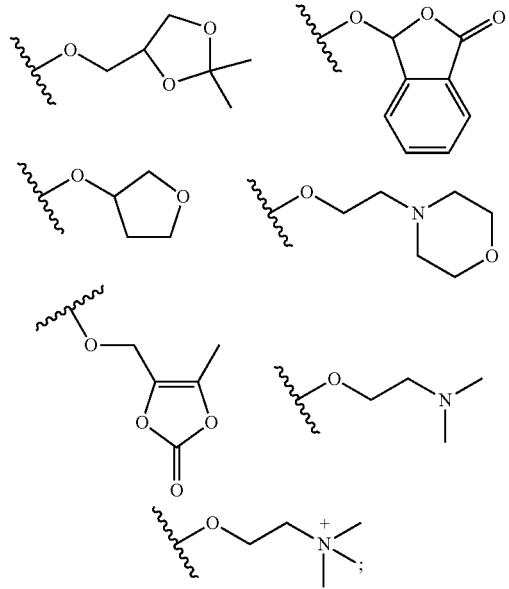

iii) $R^3$ is —$C(=O)OR^{3A}$, —C(=O)H, —$CH_2OR^{3A}$, —$CH_2O$—C(=O)-alkyl, —$C(=O)NH(R^{3A})$, or —$CH_2X^0$; wherein each occurrence of $R^{3A}$ is independently hydrogen, a protecting group, an alkyl, cycloalkyl, heteroalkyl, heterocyclic, aryl, heteroaryl, alkylaryl or alkylheteroaryl moiety, or $R^{3A}$, taken together with $R^1$ or $R^2$, forms a heterocyclic moiety; wherein $X^0$ is a halogen selected from F, Cl, Br or I;

iv) $R^3$ is —$C(=O)OR^{3A}$; wherein $R^{3A}$ is hydrogen, a protecting group, an alkyl, cycloalkyl, heteroalkyl, heterocyclic, aryl, heteroaryl, alkylaryl or alkylheteroaryl moiety, or $R^{3A}$, taken together with $R^1$ or $R^2$, forms a heterocyclic moiety;

v) $R^3$ is —$C(=O)OR^{3A}$; wherein $R^{3A}$ is $C_{1-5}$alkyl;
vi) $R^3$ is —$C(=O)OR^{3A}$; wherein $R^{3A}$ is $C_{1-3}$alkyl;
vii) $R^3$ is —$C(=O)OR^{3A}$; wherein $R^{3A}$ is ethyl;
viii) $R^3$ is —$C(=O)OR^{3A}$; wherein $R^{3A}$ is benzyl;
ix) $R^3$ is $CO_2H$;
x) $R^3$ —$C(=O)OR^{3A}$, wherein $R^{3A}$ is as defined in any one of subsets ii)-ix) above, and —$C(=O)NHC(R^1)(R^2)R^3$ is a moiety having the following structure:

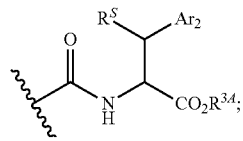

wherein $Ar_2$ is a cycloalkyl, heterocyclic, aryl or heteroaryl moiety; and $R^S$ is hydrogen, alkyl, heteroalkyl, aryl, heteroaryl, or is -$G^0R^{G1}$ wherein $G^0$ is —O—, —S— or —$NR^{G2}$—, and $R^{G1}$ and $R^{G2}$ are independently hydrogen, an aliphatic, alicyclic, heteroaliphatic, heterocyclic, aromatic or heteroaromatic moiety;

xi) Compounds of subset x) above wherein —C(=O)NHCH(CO$_2$R$^{3A}$)CH(R$^S$)Ar$_2$ has the following stereochemistry:

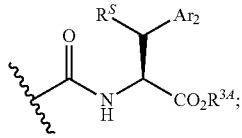

xii) R$^3$ is —C(=O)OR$^{3A}$, wherein R$^{3A}$ is as defined in any one of subsets ii)-ix) above, and —C(=O)NHC(R$^1$)(R$^2$)R$^3$ is a moiety having the following structure:

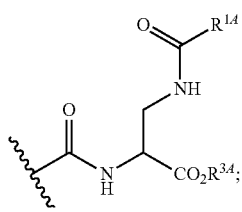

wherein R$^{1A}$ is Ar$_2$, —OR$^{1B}$, —SR$^{1B}$ or —NR$^{1B}$R$_{1C}$; or an alkyl or heteroalkyl moiety; and Ar$_1$ is a cycloalkyl, heterocyclic, aryl or heteroaryl moiety; wherein R$^{1B}$ and R$^{1C}$ are independently hydrogen, alkyl, heteroalkyl, cycloalkyl, heterocyclic, aryl, heteroaryl, or R$^{1B}$ and R$^{1C}$, taken together with the nitrogen atom to which they are attached, form a heterocylic or heteroaryl moiety;

xiii) Compounds of subset xii) above wherein —C(=O)NHCH(CO$_2$R$^{3A}$)CH$_2$NHC(=O)R$^{1A}$ has the following stereochemistry:

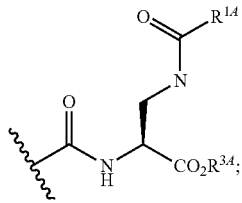

xiv) R$^3$ is —C(=O)OR$^{3A}$, wherein R$^{3A}$ is as defined in any one of subsets ii)-ix) above, and —C(=O)NHC(R$^1$)(R$^2$)R$^3$ is a moiety having the following structure:

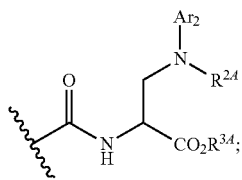

wherein Ar$_2$ is a cycloalkyl, heterocyclic, aryl or heteroaryl moiety; and R$^{2A}$ is hydrogen, C$_{1-6}$alkyl, C$_{2-6}$alkenyl, —C(=O)R$^{2B}$ or —SO$_2$R$^{2B}$, wherein R$^{2B}$ is alkyl, cycloalkyl, heteroalkyl, heterocyclyl, aryl or heteroaryl; or R$^{2A}$, taken together with a substituent on Ar$_2$, forms a substituted or unsubstituted heterocyclic or heteroaryl moiety;

xv) Compounds of subset xiv) above wherein —C(=O)NHCH(CO$_2$R$^{3A}$)CH$_2$N(R$^{2A}$)Ar$_2$ has the following stereochemistry:

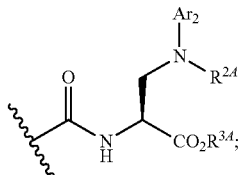

xvi) R$^3$ is —C(=O)OR$^{3A}$, wherein R$^{3A}$ is as defined in any one of subsets ii)-ix) above, and —C(=O)NHC(R$^1$)(R$^2$)R$^3$ is a moiety having the following structure:

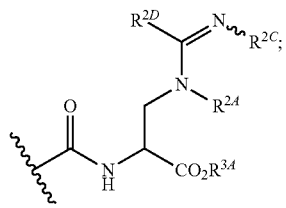

wherein R$^{2A}$ is hydrogen, C$_{1-6}$alkyl, C$_{2-6}$alkenyl, aryl, heteroaryl, —C(=O)R$^{2B}$ or —SO$_2$R$^{2B}$, wherein R$^{2B}$ is alkyl, cycloalkyl, heteroalkyl, heterocyclyl, aryl or heteroaryl; or R$^{2A}$, taken together with R$^{2C}$ or R$^{2D}$, forms a substituted or unsubstituted heterocyclic or heteroaryl moiety; R$^{2C}$ is hydrogen, CN, —C=NMe, =NO$_2$, =NC(=O)NH$_2$, =NS(O)$_2$R, =NS(O)$_2$NRR', —SO$_2$R$^{2G}$, or an aliphatic, alicyclic, heteroaliphatic, heteroalicyclic, aryl, heteroaryl, alkylaryl or alkylheteroaryl moiety; wherein R and R' are each independently hydrogen or methyl, and R$^{2G}$ is lower alkyl; and R$^{2D}$ is Ar$_2$, hydrogen, halogen, CN, NO$_2$, an aliphatic, heteroaliphatic, alkylaryl or alkylheteroaryl moiety, or is -GR$^{G1}$ wherein G is —O—, —S—, —NR$^{G2}$—, —CO—, —SO—, —SO$_2$—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heteroalicyclic, aryl, heteroaryl, alkylaryl or alkylheteroaryl moiety;

xvii) Compounds of subset xvi) above wherein —C(=O)NHCH(CO$_2$R$^{3A}$)CH$_2$N(R$^{2A}$)C(=NR$^{2C}$)R$^{2D}$ has the following stereochemistry:

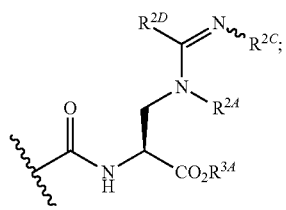

xviii) Compounds of subset xvii) above wherein —C(=O)NHCH(CO$_2$R$^{3A}$)CH$_2$N(R$^{2A}$)C(=NR$^{2C}$)R$^{2D}$ has the following structure:

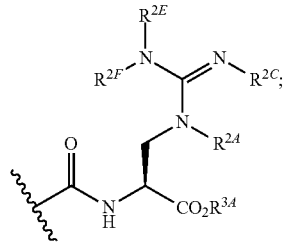

wherein R$^{2E}$ and R$^{2F}$ are each independently hydrogen, or an aliphatic, alicyclic, heteroaliphatic, heteroalicyclic, aryl, heteroaryl, alkylaryl or alkylheteroaryl moiety, or R$^{2E}$ and R$^{2F}$, taken together, form a substituted or unsubstituted heterocyclic or heteroaryl moiety;

xix) Compounds of subset xvii) above wherein —C(=O)NHCH(CO$_2$R$^{3A}$)CH$_2$N(R$^{2A}$)C(=NR$^{2C}$)$^{2D}$ has the following structure:

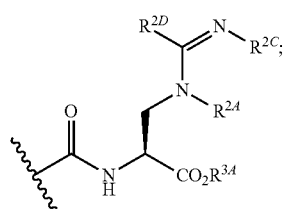

wherein R$^{2C}$ is hydrogen, CN, —C=NMe, =NO$_2$, =NC(=O)NH$_2$, =NS(O)$_2$R, or =NS(O)$_2$NRR'; wherein R and R' are each independently hydrogen or methyl;

xx) Compounds of subset xvii) above wherein —C(=O)NHCH(CO$_2$R$^{3A}$)CH$_2$N(R$^{2A}$)C(=NR$^{2C}$)R$^{2D}$ has the following structure:

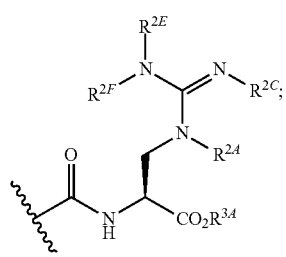

wherein R$^{2C}$ is hydrogen, CN, —C=NMe, =NO$_2$, =NC(=O)NH$_2$, =NS(O)$_2$R, or =NS(O)$_2$NRR'; wherein R and R' are each independently hydrogen or methyl;

xxi) Compounds of subset xvii) above wherein —C(=O)NHCH(CO$_2$R$^{3A}$)CH$_2$N(R$^{2A}$)C(=NR$^{2C}$)R$^{2D}$ has the following structure:

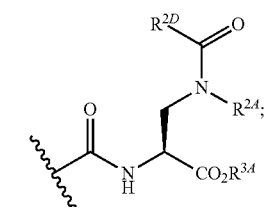

xxii) Compounds of subset xvii) above wherein —C(=O)NHCH(CO$_2$R$^{3A}$)CH$_2$N(R$^{2A}$)C(=NR$^{2C}$)R$^{2D}$ has the following structure:

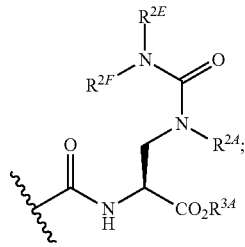

xxiii) Compounds of subsets xvii) and xviii) above wherein —C(=O)NHCH(CO$_2$R$^{3A}$)CH$_2$N(R$^{2A}$)C(=NR$^{2C}$)R$^{2D}$ has the following structure:

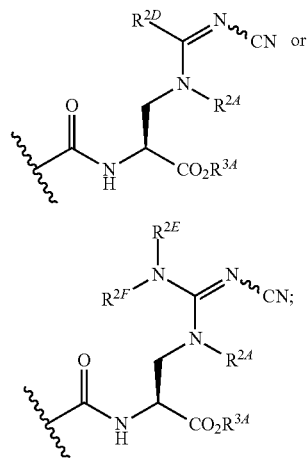

or bioisosteres thereof;

wherein R$^{2A}$, R$^{2D}$, R$^{2E}$ and R$^{2F}$ are as defined in xvi) and xviii) above;

xxiv) Compounds of subset xxiii) above wherein the bioisosteres have one of the following structures:

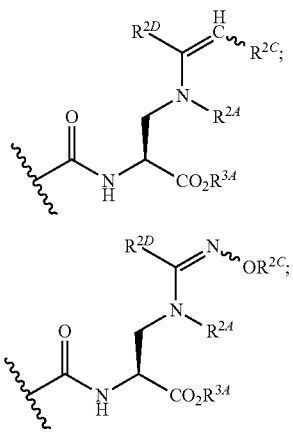

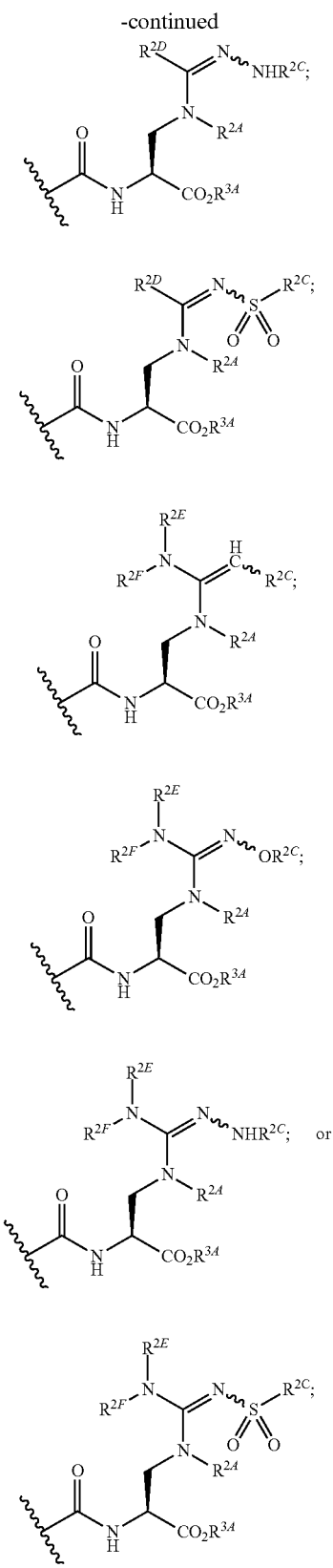

wherein $R^{2C}$ is lower alkyl;

xxv) Compounds of subset xxiii) above wherein $R^{2D}$ is, or $R^{2E}$ and $R^{2F}$ together with the nitrogen atom to which they are attached form, a moiety having one of the structures:

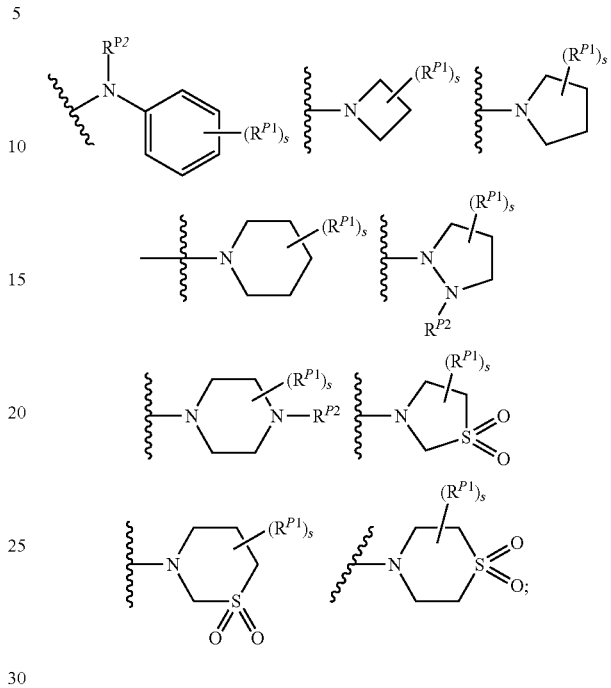

wherein s is an integer between 0 and 6; each occurrence of $R^{P1}$ is independently hydrogen, halogen, CN, isocyanate, $NO_2$, $-P(=O)(YR^{P5})_2$, an alkyl, cycloalkyl, heteroalkyl, heterocyclic, aryl, heteroaryl, alkylaryl or alkylheteroaryl moiety, or is $-GR^{G1}$ wherein G is $-O-$, $-S-$, $-NR^{G2}-$, $-CO-$, $-SO-$, $-SO_2-$, $-C(=O)O-$, $-C(=O)NR^{G2}-$, $-OC(=O)-$, $-NR^{G2}C(=O)-$ or $-SO_2NR^{G2}-$, and $R^{G1}$ and $R^{G2}$ are independently hydrogen, an alkyl, cycloalkyl, heteroalkyl, heterocyclic, aryl, heteroaryl, alkylaryl or alkylheteroaryl moiety; each occurrence of Y is independently a bond or O; each occurrence of $R^{P5}$ is independently alkyl, heteroalkyl, aryl or heteroaryl, or when Y is O $R^{P5}$ may also be hydrogen; and each occurrence of $R^{P2}$ is independently hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group; wherein any two adjacent occurrences of $R^{P1}$ and $R^{P2}$, taken together, may form a cycloalkyl, heterocyclic, aryl or heteroaryl moiety;

xxvi) Compounds of subset xxv) above wherein $R^{2D}$ is, or $R^{2E}$ and $R^{2F}$ together with the nitrogen atom to which they are attached form, a moiety having one of the structures:

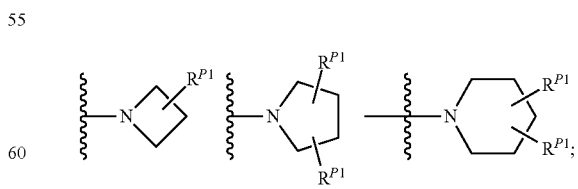

wherein each occurrence of $R^{P1}$ is independently hydrogen, halogen, methyl, $-OCH_3$, $-OH$, $-NH_2$, $-NHCH_3$ or $-N(CH_3)_2$;

xxvii) Compounds of subset xxvi) above wherein $R^{2D}$ is, or $R^{2E}$ and $R^{2F}$ together with the nitrogen atom to which they are attached form, a moiety having one of the structures:

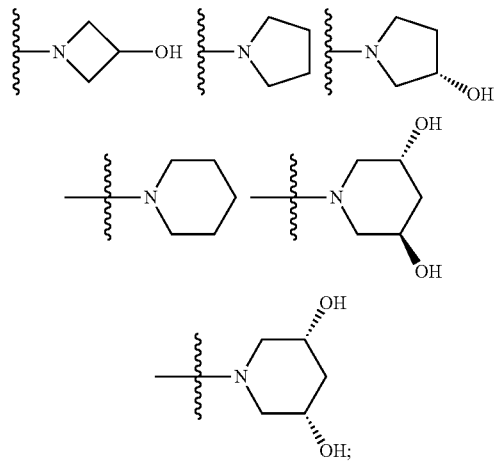

xxviii) $R^3$ is —C(=O)OR$^{3A}$, wherein $R^{3A}$ is as defined in any one of subsets ii)-ix) above, and —C(=O)NHC(R$^1$)(R$^2$) $R^3$ is a moiety having the following structure:

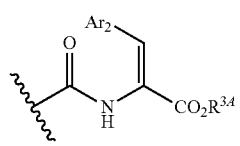

wherein Ar$_2$ is a cycloalkyl, heterocyclic, aryl or heteroaryl moiety;

xxix) Compounds of subsets x)-xii), xiv)-xv) and xxviii); and compounds of subset xvi) wherein $R^{2D}$ is Ar$_2$; wherein Ar$_2$ is one of the following structures:

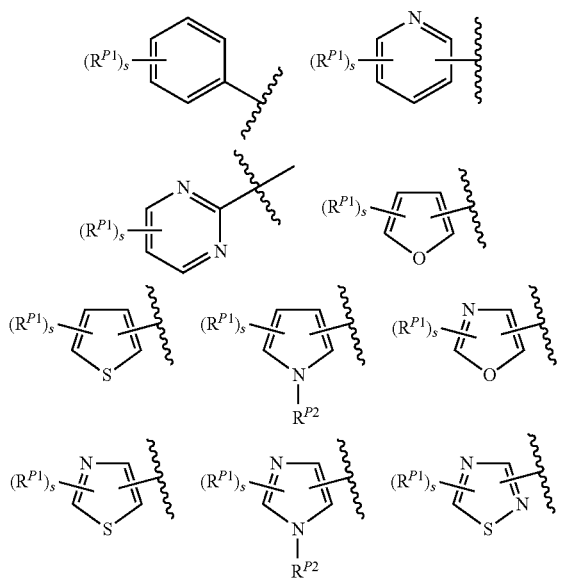
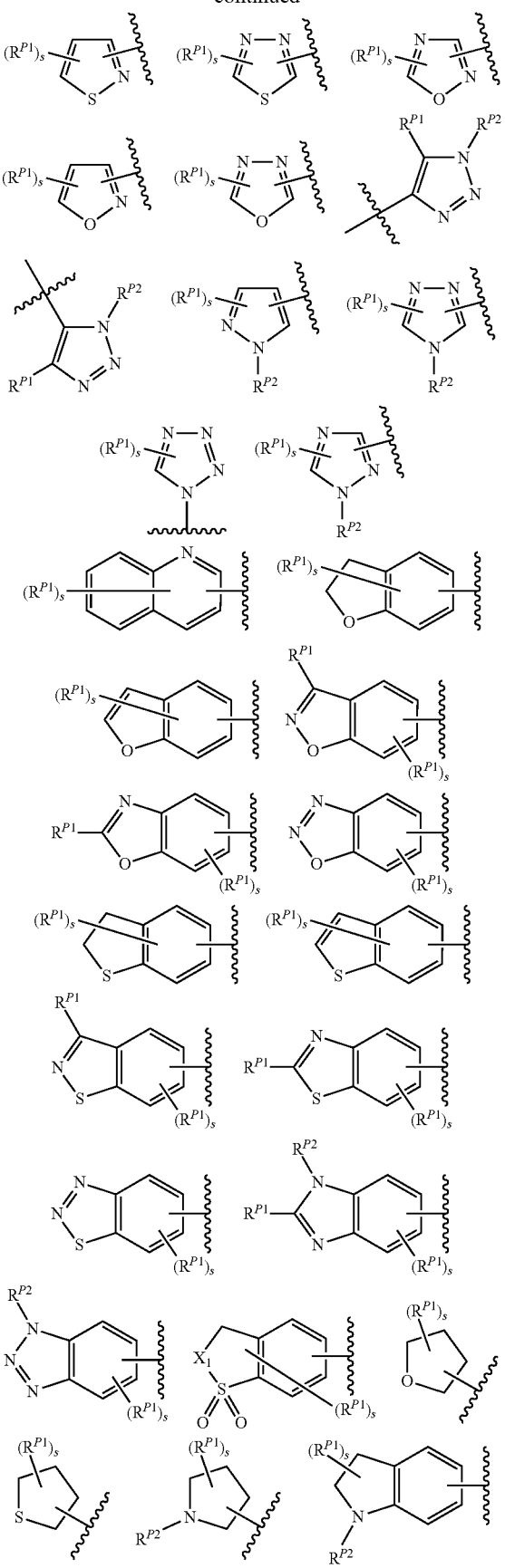

-continued

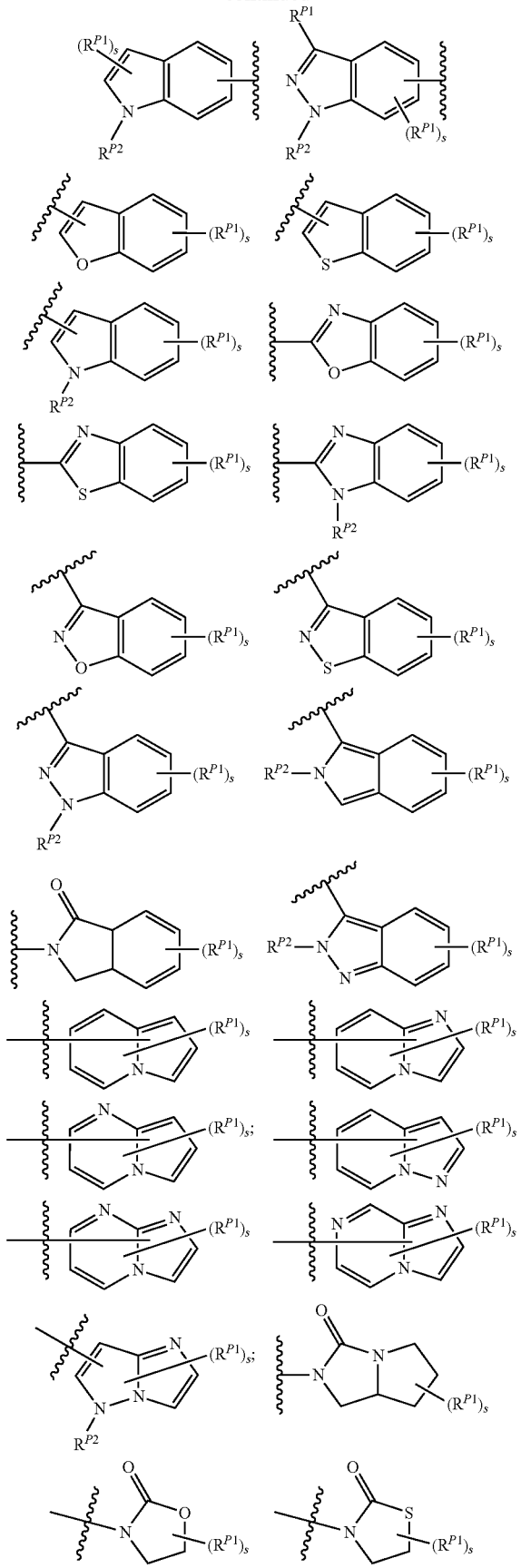
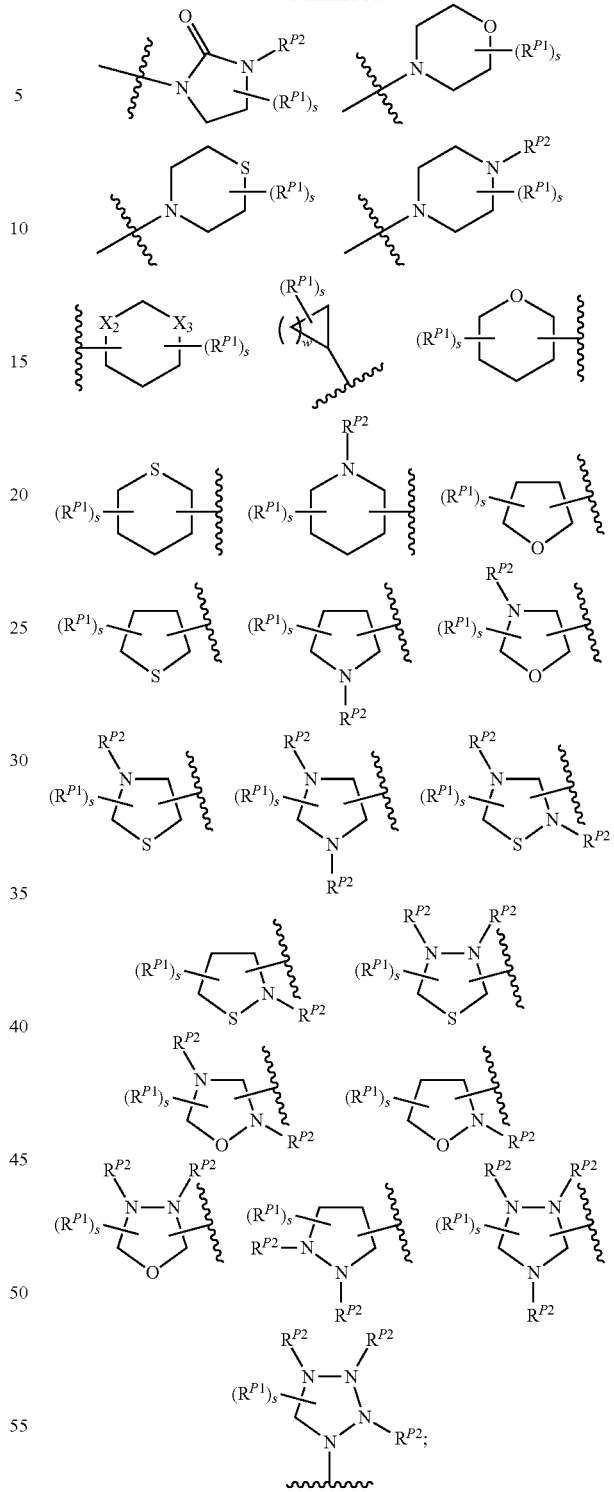

wherein each occurrence of s is an integer from 0-6; w is an integer from 1-6; $X_1$ is $CHR^{P1}$ or $NR^{P2}$; $X_2$ and $X_3$ are independently $CHR^{P1}$, $NR^{P2}$, $CHSO_2R^{P3}$ or $NSO_2R^{P3}$; each occurrence of $R^{P1}$ is independently hydrogen, halogen, CN, isocyanate, $NO_2$, $—P(=O)(YR^{P5})_2$, an aliphatic, alicyclic, heteroaliphatic, heterocyclic, aryl, heteroaryl, -(aliphatic)aryl or -(aliphatic)heteroaryl moiety, or is $-GR^{G1}$ wherein G is $—O—$, $—S—$, $—NR^{G2}—$, $—CO—$, $—SO—$, $—SO_2—$, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heterocyclic, aryl, heteroaryl, -(aliphatic)aryl or -(aliphatic)heteroaryl moiety; each occurrence of Y is independently a bond or O; each occurrence of R$^{P5}$ is independently alkyl, heteroalkyl, aryl or heteroaryl, or when Y is O R$^{P5}$ may also be hydrogen; and each occurrence of R$^{P2}$ is independently hydrogen, an aliphatic, alicyclic, heteroaliphatic, heterocyclic, awl, heteroaryl, alkylaryl, alkylheteroaryl, heteroalkylaryl, or heteroalkylheteroaryl moiety or a nitrogen protecting group; wherein any two adjacent occurrences of R$^{P1}$ and R$^{P2}$, taken together, may form a cycloalkyl, heterocyclic, aryl or heteroaryl moiety; and each occurrence of R$^{P3}$ is independently alkyl, aryl, heteroaryl or —N(R$^{P2}$)$_2$.

xxx) Compounds of subset xxix) above wherein Ar$_2$ is one of the following structures:

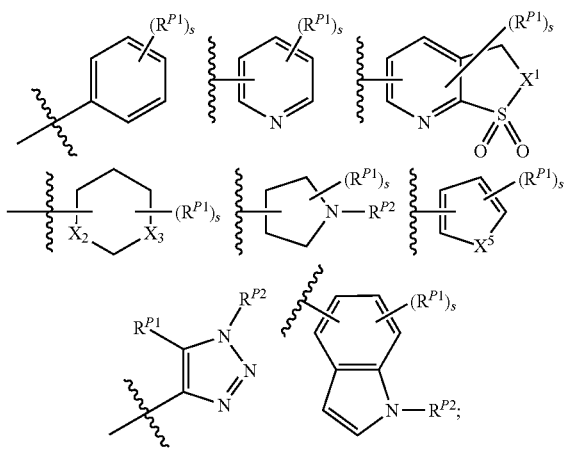

wherein s, X$^1$, X$^2$ and X$^3$ are as defined in xx) above; X$^5$ is O, S or NR$^{P2}$; each occurrence of R$^{P1}$ is independently hydrogen, halogen, CN, isocyanate, NO$_2$, —P(=O)(YR$^{P5}$)$_2$, an alkyl, cycloalkyl, heteroalkyl, heterocyclic, aryl, heteroaryl, alkylaryl or alkylheteroaryl moiety, or is -GR$^{G1}$ wherein G is —O—, —S—, —NR$^{G2}$—, —CO—, —SO—, —SO$_2$—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an alkyl, cycloalkyl, heteroalkyl, heterocyclic, aryl, heteroaryl, alkylaryl or alkylheteroaryl moiety; each occurrence of Y is independently a bond or O; each occurrence of R$^{P5}$ is independently alkyl, heteroalkyl, aryl or heteroaryl, or when Y is O R$^{P5}$ may also be hydrogen; each occurrence of R$^{P2}$ is independently hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group; wherein any two adjacent occurrences of R$^{P1}$ and R$^{P2}$, taken together, may form a cycloalkyl, heterocyclic, awl or heteroaryl moiety; and each occurrence of R$^{P3}$ is independently alkyl, aryl, heteroaryl or —N(R$^{P2}$)$_2$;

xxxi) Compounds of subset xxx) above wherein each occurrence of R$^{P1}$ is independently hydrogen, halogen, —P(=O)(YR$^{P5}$)$_2$, lower alkyl or heteroalkyl moiety, or is -GR$^{G1}$ wherein G is —O—, —S—, —NR$^{G2}$— or —SO$_2$—, and R$^{G1}$ and R$^{G2}$ are independently hydrogen, lower alkyl or aryl; each occurrence of Y is independently a bond or O; each occurrence of R$^{P5}$ is independently lower alkyl, or when Y is OR$^{P5}$ may also be hydrogen; and each occurrence of R$^{P2}$ is independently hydrogen, lower alkyl or a nitrogen protecting group; wherein any two adjacent occurrences of R$^{P1}$ and R$^{P2}$, taken together, may form a cycloalkyl, heterocyclic, awl or heteroaryl moiety;

xxxii) Compounds of subset xxx) above wherein Ar$_2$ has one of the following structures:

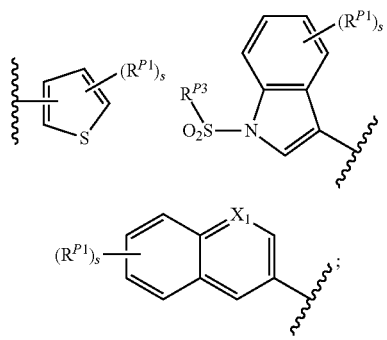

wherein X$_1$ is N or CR$^{P1}$; s is an integer from 0-6; each occurrence of R$^{P1}$ is independently hydrogen, halogen, CN, NO$_2$, an alkyl, cycloalkyl, heteroalkyl, heterocyclic, aryl, heteroaryl, alkylaryl or alkylheteroaryl moiety, or is -GR$^{G1}$ wherein G is —O—, —S—, —CO—, —SO—, —SO$_2$—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an alkyl, cycloalkyl, heteroalkyl, heterocyclic, aryl, heteroaryl, alkylaryl or alkylheteroaryl moiety; and R$^{P3}$ is independently lower alkyl or aryl;

xxxiii) Compounds of subsets xxix), xxx) and xxxii) wherein s is 0;

xxxiv) Compounds of subsets xxix), xxx) and xxxii) wherein s is 1;

xxxv) Compounds of subsets xxix), xxx) and xxxii) wherein s is 2;

xxxvi) Compounds of subsets x) and xi) above wherein Ar$_2$ is one of the following structures:

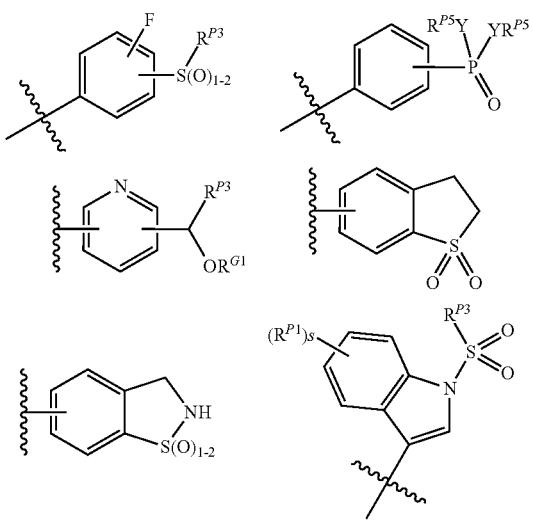

-continued

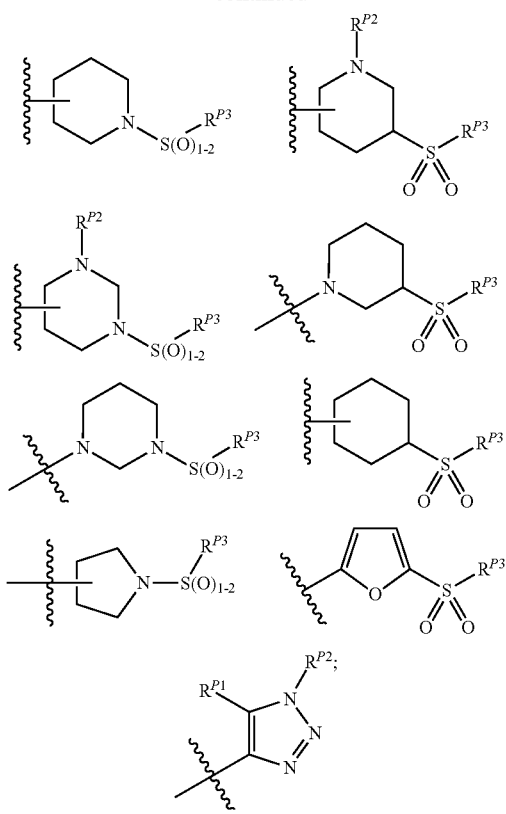

wherein s is an integer from 0-2; each occurrence of $R^{P1}$ is independently hydrogen, halogen, CN, isocyanate, $NO_2$, $-OR^{G1}$, $-SR^{G1}$, $-NR^{G1}R^{G2}$—, an alkyl, cycloalkyl, heteroalkyl, heterocyclic, aryl, heteroaryl, alkylaryl or alkylheteroaryl moiety; each occurrence of Y is independently a bond or O; each occurrence of $R^{P5}$ is independently lower alkyl, or when Y is O $R^{P5}$ may also be hydrogen; each occurrence of $R^{P2}$ is independently hydrogen, alkyl, cycloalkyl, heteroalkyl, heterocyclic, aryl, heteroaryl, alkylaryl, alkylheteroaryl, heteroalkylaryl, or heteroalkylheteroaryl moiety or a nitrogen protecting group; $R^{P3}$ is lower alkyl or $-N(R^{P2})_2$; and $R^{G1}$ and $R^{G2}$ are independently hydrogen, an alkyl, cycloalkyl, heteroalkyl, heterocyclic, aryl, heteroaryl, alkylaryl or alkylheteroaryl moiety;

xxxvii) Compounds of subsets x) and xi) above wherein $Ar_2$ is one of the following structures:

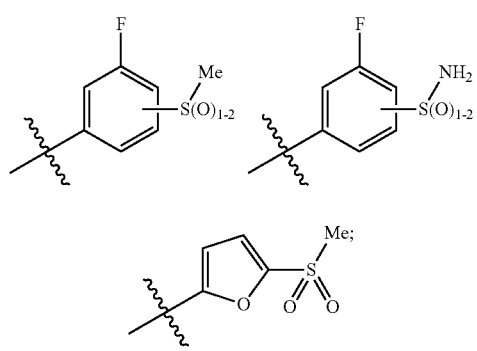

xxxviii) Compounds of subsets x) and xi) above wherein $Ar_2$ is one of the following structures:

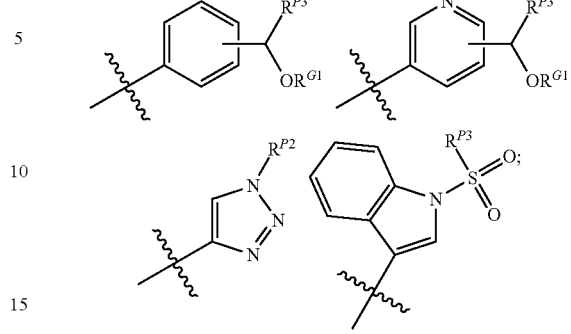

wherein $R^{P3}$ is lower alkyl; and $R^{P2}$ and $R^{G1}$ are independently hydrogen or lower alkyl;

xxxix) Compounds of subsets x) and xi) above wherein $Ar_2$ is one of the following structures:

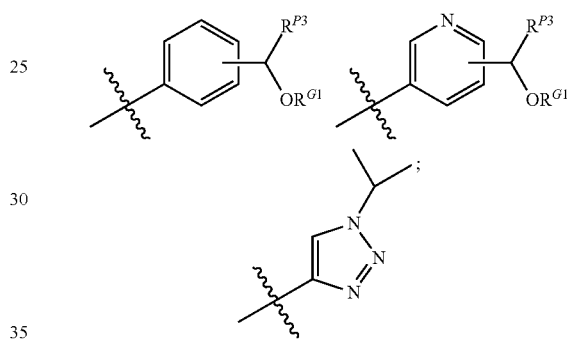

wherein $R^{P3}$ is lower alkyl and $R^{G1}$ is hydrogen or lower alkyl;

xl) Compounds of subsets x) and xi) above wherein $R^S$ is hydrogen, hydroxyl or lower alkoxy and $Ar_2$ is one of the following structures:

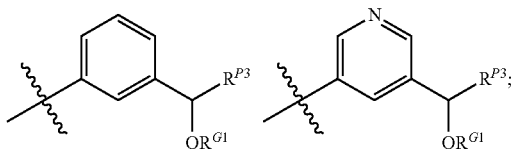

wherein $R^{P3}$ is lower alkyl; and $R^{G1}$ is hydrogen or lower alkyl;

xli) Compounds of subsets xii) and xiii) wherein $R^{1A}$ is alkyl or $-NR^{1B}R^{1C}$; wherein $R^{1B}$ and $R^{1C}$ are independently hydrogen or lower alkyl;

xlii) Compounds of subsets xii) and xiii) wherein $R^{1A}$ is $-NH_2$ or a moiety having the structure:

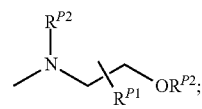

wherein $R^{P1}$ is independently hydrogen, hydroxyl, lower alkyl or lower heteroalkyl; and each occurrence of $R^{P2}$ is independently hydrogen or lower alkyl;

xliii) Compounds of subsets xii) and xiii) wherein $R^{1A}$ is —NH$_2$ or a moiety having the structure:

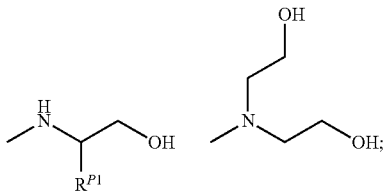

wherein $R^{P1}$ is hydrogen or lower alkyl;

xliv) Compounds of subsets xii) and xiii) wherein $R^{1A}$ is cycloalkyl, aryl, or a moiety having one of the structures:

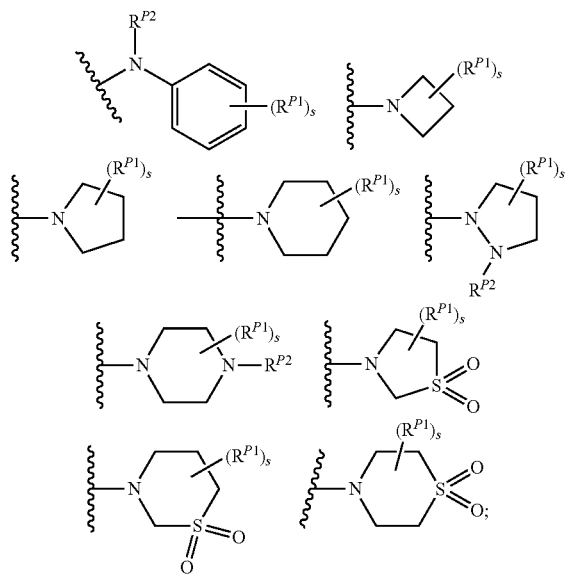

wherein s is an integer between 0 and 6; each occurrence of $R^{P1}$ is independently hydrogen, halogen, CN, isocyanate, NO$_2$, —P(=O)(YR$^5$)$_2$, an alkyl, cycloalkyl, heteroalkyl, heterocyclic, aryl, heteroaryl, alkylaryl or alkylheteroaryl moiety, or is -GR$^{G1}$ wherein G is —O—, —S—, —NR$^{G2}$—, —CO—, —SO—, —SO$_2$—, —C(=O)O—, —C(=O)NR$^{G2}$—, —OC(=O)—, —NR$^{G2}$C(=O) or —SO$_2$NR$^{G2}$—, and R$^{G1}$ and R$^{G2}$ are independently hydrogen, an alkyl, cycloalkyl, heteroalkyl, heterocyclic, aryl, heteroaryl, alkylaryl or alkylheteroaryl moiety; each occurrence of Y is independently a bond or O; each occurrence of R$^{P5}$ is independently alkyl, heteroalkyl, aryl or heteroaryl, or when Y is O R$^{P5}$ may also be hydrogen; and each occurrence of R$^{P2}$ is independently hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group; wherein any two adjacent occurrences of R$^{P1}$ and R$^{P2}$, taken together, may form a cycloalkyl, heterocyclic, aryl or heteroaryl moiety;

xlv) Compounds of subset xliv) wherein s is an integer between 0 and 2; each occurrence of R$^{P1}$ is independently lower alkyl or is -GR$^{G1}$ wherein G is —O— or —NR$^{G2}$—, and R$^{G1}$ and R$^{G2}$ are independently hydrogen, an alkyl, cycloalkyl, heteroalkyl, heterocyclic, aryl, heteroaryl, alkylaryl or alkylheteroaryl moiety; and each occurrence of R$^{P2}$ is independently hydrogen, lower alkyl, aryl or heteroaryl;

xlvi) Compounds of subsets xxi) and xxii) wherein R$^{1A}$ is a moiety having one of the structures:

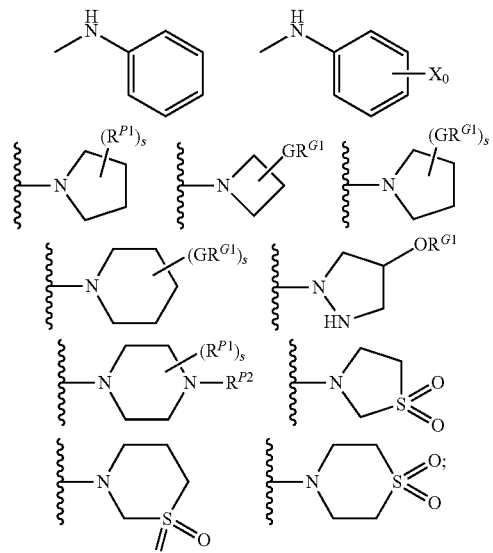

wherein s is an integer between 0 and 2; X$^0$ is halogen; each occurrence of R$^{P1}$ is independently hydrogen, hydroxyl, lower alkyl or lower heteroalkyl; G is —O— or —NR$^{G2}$—, and R$^{G1}$ and R$^{G2}$ are independently hydrogen or lower alkyl; and R$^{P2}$ is independently hydrogen or lower alkyl;

xlvii) Compounds of subset xlvi) wherein R$^{1A}$ is a moiety having one of the structures:

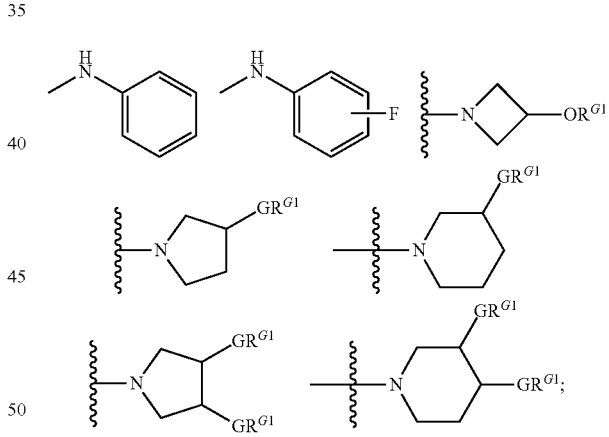

wherein G is —O— or —NR$^{G2}$—, and R$^{G1}$ and R$^{G2}$ are independently hydrogen or lower alkyl;

xlix) compounds of subsets xiv)-xv) above wherein —NH(R$^{2A}$)Ar$_2$ has one of the following structures:

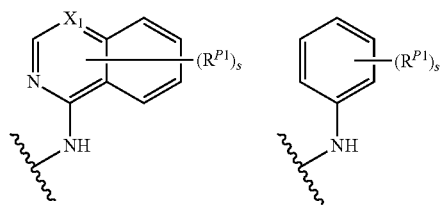

-continued

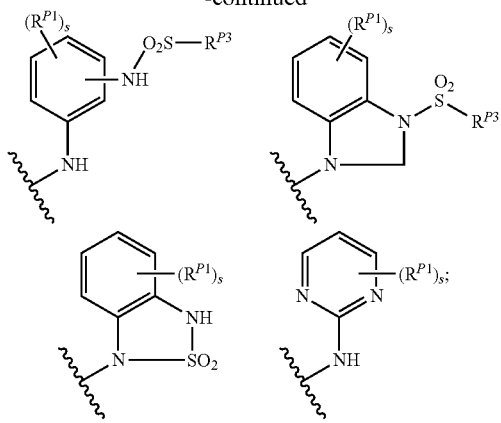

wherein $X_1$ is N or $CR^{P1}$; s is an integer from 0-5; and each occurrence of $R^{P1}$ is independently hydrogen, halogen, CN, $NO_2$, an alkyl, cycloalkyl, heteroalkyl, heterocyclic, aryl, heteroaryl, alkylaryl or alkylheteroaryl moiety, or is $-GR^{G1}$ wherein G is $-O-$, $-S-$, $-NR^{G2}-CO-$, $-SO-$, $-SO_2-$, $-C(=O)O-$, $-C(=O)NR^{G2}-$, $-OC(=O)-$, $-NR^{G2}C(=O)-$ or $-SO_2NR^{G2}-$, and $R^{G1}$ and $R^{G2}$ are independently hydrogen, an alkyl, cycloalkyl, heteroalkyl, heterocyclic, aryl, heteroaryl, alkylaryl or alkylheteroaryl moiety; and $R^{P3}$ is alkyl, heteroalkyl, aryl or heteroaryl;

l) compounds of subset xlix) above wherein s is 0;

li) compounds of subset xlix) above wherein $R^{P1}$ is hydrogen, halogen or lower alkyl;

lii) compounds of subset li) above wherein $R^{P1}$ is hydrogen, chloro or methyl;

liii) compounds of subset xlix) above wherein $R^{P3}$ is lower alkyl;

liv) compounds of subset liii) above wherein $R^{P3}$ is methyl;

lv) compounds of subset xlix) above wherein $-NH(R^{2A})$ $Ar_2$ has the following structure:

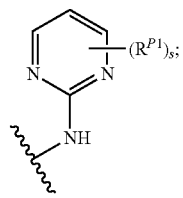

wherein $R^{P1}$ is hydrogen, halogen or lower alkyl;

lvi) compounds of subset xlix) above wherein $-NH(R^{2A})$ $Ar_2$ has the following structure:

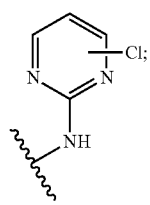

lvii) Compounds of subsets xvii) having the following structure:

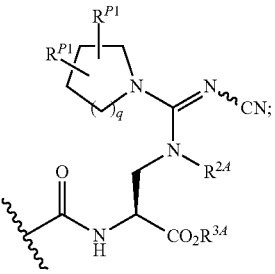

or bioisosteres thereof;
wherein each occurrence of $R^{P1}$ is independently hydrogen, halogen, methyl, $-OCH_3$, $-OH$, $-NH_2$, $-NHCH_3$ or $-N(CH_3)_2$; $R^{2A}$ is hydrogen, $C_{1-6}$alkyl, $C_{2-6}$alkenyl, aryl, heteroaryl, $-C(=O)R^{2B}$ or $-SO_2R^{2B}$, wherein $R^{2B}$ is alkyl, cycloalkyl, heteroalkyl, heterocyclyl, aryl or heteroaryl; and q is 1 or 2;

lviii) Compounds of subset lvii) above wherein the bioisosteres have one of the following structures:

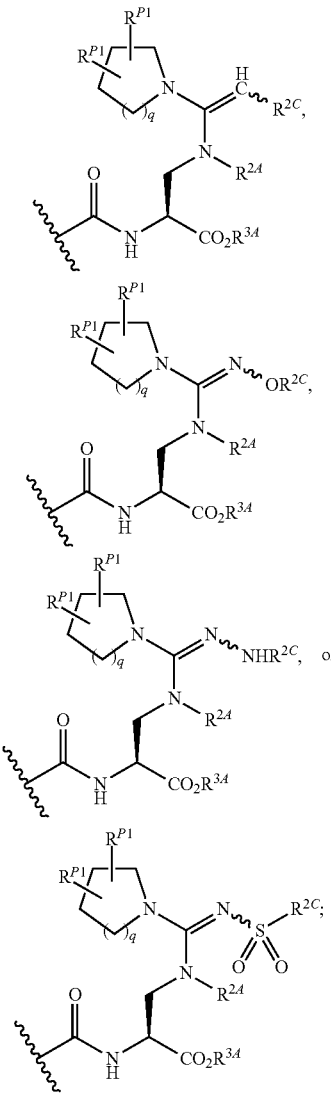

wherein q is 1 or 2; and $R^{2C}$ is lower alkyl;

lix) Compounds of subset xxviii) wherein —C(=O)NHC(=CHAr₂)CO₂R³ᴬ has one of the following structures:

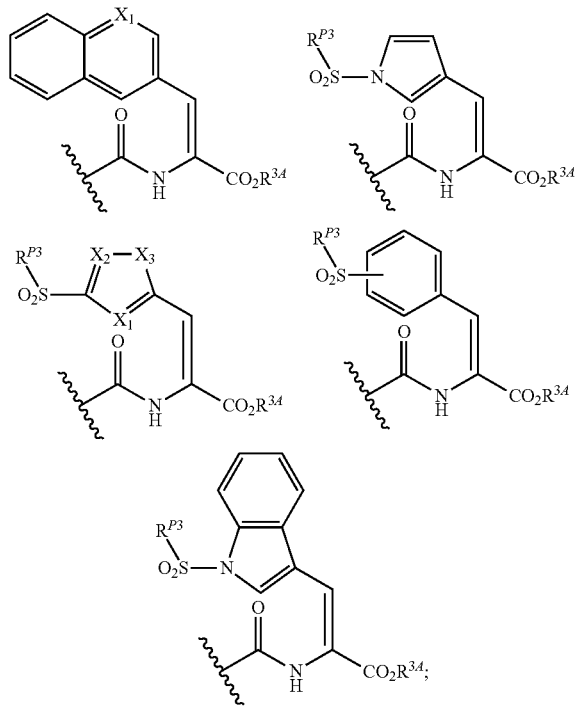

wherein R^{P3} is lower alkyl or aryl; X₁ and X₂ are independently N or CR^{P1}; X₃ is O, S or NR^{P2}; wherein R^{P1} is hydrogen, halogen, CN, NO₂, an alkyl, cycloalkyl, heteroalkyl, heterocyclic, aryl, heteroaryl, alkylaryl or alkylheteroaryl moiety, or is -GR^{G1} wherein G is O, S, NR^{G2}—, —CO—, —SO—, —SO₂—, —C(=O)O—, —C(=O)NR^{G2}—, —OC(=O)—, —NR^{G2}C(=O)— or —SO₂NR^{G2}—, and R^{G1} and R^{G2} are independently hydrogen, an alkyl, cycloalkyl, heteroalkyl, heterocyclic, aryl, heteroaryl, alkylaryl or alkylheteroaryl moiety; and R^{P2} is hydrogen, an aliphatic, alicyclic, heteroaliphatic, heterocyclic, aryl, heteroaryl, alkylaryl, alkylheteroaryl, heteroalkylaryl, or heteroalkylheteroaryl moiety;

lx) Compounds of subset xxviii) wherein —C(=O)NHC(=CHAr₂)CO₂R³ᴬ has the following structure:

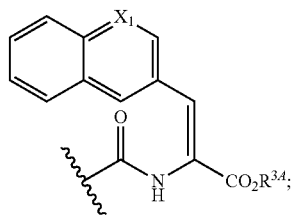

wherein X₁ is N or CH;

lxi) R³ is —C(=O)OR³ᴬ, wherein R³ᴬ is as defined in any one of subsets ii)-ix) above, and —C(=O)NHC(R¹)(R²)R³ has the structure —C(=O)NHC(=C(R^S)Ar₂)CO₂R³ᴬ wherein R³ᴬ and R^S, taken together, form a substituted or unsubstituted heterocyclic moiety;

lxii) Compounds of subset lxi) wherein —C(=O)NHC(=C(R^S)Ar₂)CO₂R³ᴬ has one of the following structures:

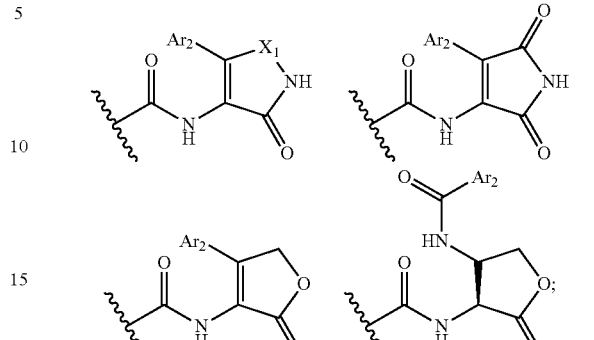

wherein Ar₂ is as defined in classes and subclasses herein; and X₁ is O, S or NH;

lxiii) Compounds of subset lxi) wherein —C(=O)NHC(=C(R^S)Ar₂)CO₂R³ᴬ has one of the following structures:

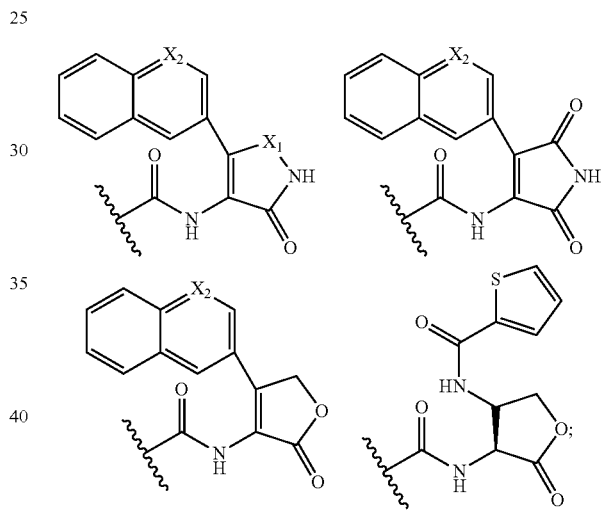

wherein X₁ is O, S or NH; and X₂ is N or CH;

lxiv) L is absent, —C(=O)—, —CH₂C(=O)NH—, —CH₂NH—C(=O)—, —O—CH₂—C(=O)—, —CH₂—CH₂—C(=O)—, —CH=CH—C(=O)NH—CH₂—, —CH(OH)—CH₂—O—, —CH(OH)—CH₂—N(CH₃)—, —CH(OH)—CH₂—CH₂—, —CH₂—CH₂—CH(OH)—, —O—CH₂—CH(OH)—, —O—CH₂—CH(OH)—CH₂—, —O—CH₂—CH₂—CH(OH)—, O—CH₂—CH₂—O—, —CH₂—CH₂—CH₂—O—, —CH₂—CH(OH)—CH₂—O, —CH₂—CH₂—O—, —CH—(CH₃)—NH—C(=O)—, —CH₂—NH—SO₂—, —NH—SO₂—CH₂—, —CH₂—SO₂—NH—, —SO₂NH—CH₂—, —C(=O)—NH—C(=O)—, —NH—C(=O)—NH—, —NH—C(=O)—NH—CH₂—, —CH₂—NH—C(=O)—NH—, —C(=O)—NH—CH₂—C(=O)—NH, —NH—C(=O)—O—, —O—C(=O)—NH—; or a substituted or unsubstituted C₁₋₆alkylidene or C₂₋₆alkenylidene chain wherein up to two non-adjacent methylene units are independently optionally replaced by —C(=O)—, —CO₂—, —C(=O)C(=O)—, —C(=O)NR^{L3}—, —OC(=O)—, —OC(=O)NR^{L3}—, —NR^{L3}NR^{L4}—, —NR^{L3}NR^{L4}C(=O)—, —NR^{L3}C(=O)—, —NR^{L3}CO₂—, —NR^{L3}C(=O)NR^{L4}—, —S(=O)—, —SO₂—, —NR^{L3}SO₂—, —SO₂NR^{L3}—, —NR^{L3}SO₂NR^{L4}—, —O—, —S—, or —NR^{L3}—; wherein each occurrence of $R^{L3}$ and $R^{L4}$ is independently hydrogen, alkyl, heteroalkyl, aryl, heteroaryl or acyl;

lxv) L is absent, —C(=O), or a substituted or unsubstituted $C_{1-6}$alkylidene or $C_{2-6}$alkenylidene chain wherein up to two non-adjacent methylene units are independently optionally replaced by —C(=O)—, —CO₂—, —C(=O)C(=O)—, —C(=O)NR^{L3}—, —OC(=O)—, —OC(=O)NR^{L3}—, —NR^{L3}NR^{L4}—, —NR^{L3}NR^{L4}C(=O)—, —NR^{L3}C(=O)—, —NR^{L3}CO₂—, —NR^{L3}C(=O)NR^{L4}—, —S(=O)—, —SO₂—, —NR^{L3}SO₂—, —SO₂NR^{L3}—, —NR^{L3}SO₂NR^{L4}—, —O—, —S—, or —NR^{L3}—; wherein each occurrence of $R^{L3}$ and $R^{L4}$ is independently hydrogen, alkyl, heteroalkyl, aryl, heteroaryl or acyl;

lxvi) L is absent;

lxvii) L is —C(=O);

lxviii) L is absent, —C(=O), —CH₂C(=O)NH—, —CH₂NH—C(=O)—, —O—CH₂—C(=O)—, —CH₂—CH₂—C(=O)—, —CH=CH—C(=O)NH—CH₂—, —CH(OH)—CH₂—O—, —CH(OH)—CH₂—N(CH₃)—, —CH(OH)—CH₂—CH₂—, —CH₂—CH₂—CH(OH)—, —O—CH₂—CH(OH)—, —O—CH₂—CH(OH)—CH₂—, —O—CH₂—CH₂—CH(OH)—, O—CH₂—CH₂—O—, —CH₂—CH₂—CH₂—O—, —CH₂—CH(OH)—CH₂—O, —CH₂—CH₂—O—, —CH—(CH₃)—NH—C(=O)—, —CH₂—NH—SO₂—, —NH—SO₂—CH₂—, —CH₂—SO₂—NH—, —SO₂NH—CH₂—, —C(=O)—NH—C(=O)—, —NH—C(=O)—NH—, —NH—C(=O)—NH—CH₂—, —CH₂—NH—C(=O)—NH—, —C(=O)—NH—CH₂—C(=O)—NH, —NH—C(=O)—O—, or —O—C(=O)—NH—;

lxix) L is —(CH₂)_q— wherein q is 1-5;

lxx) L is —CH₂—;

lxxi) L is —(CH₂)₃—;

lxxii) L is a moiety having the structure:

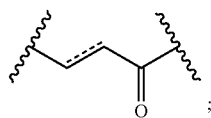

;

lxxii) AR¹ is one of the following structures:

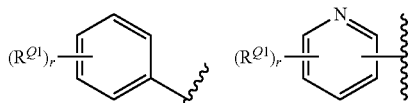

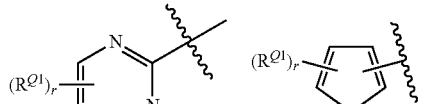

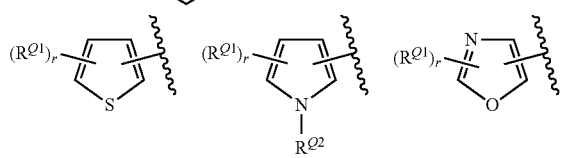

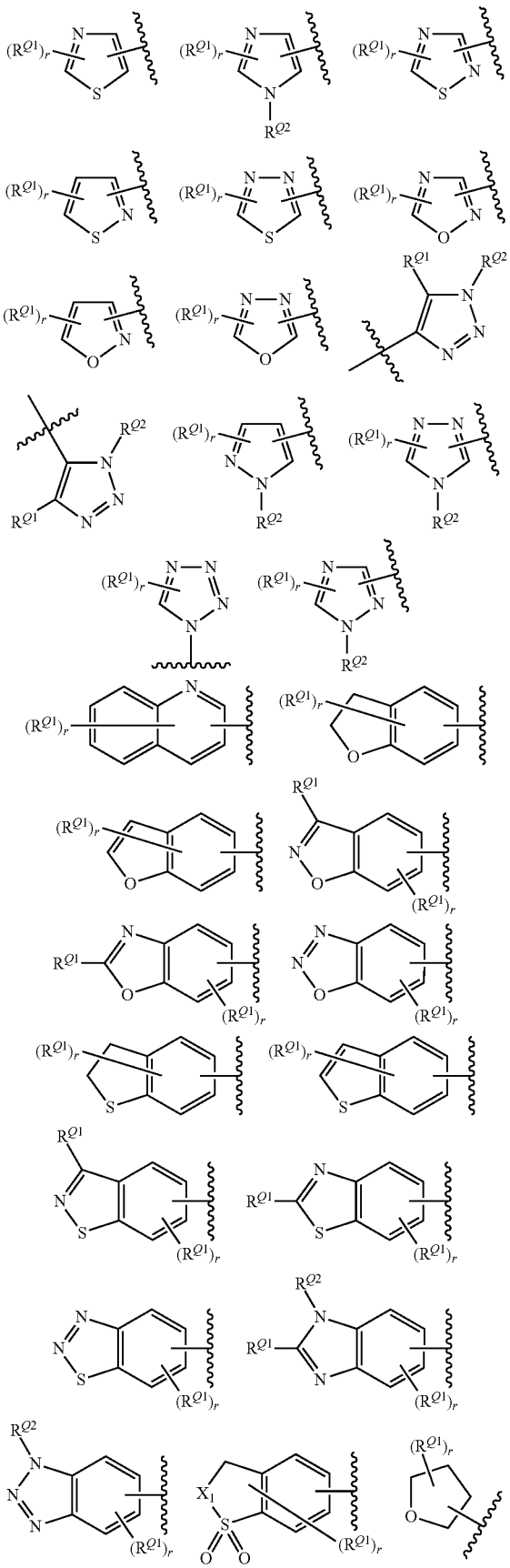

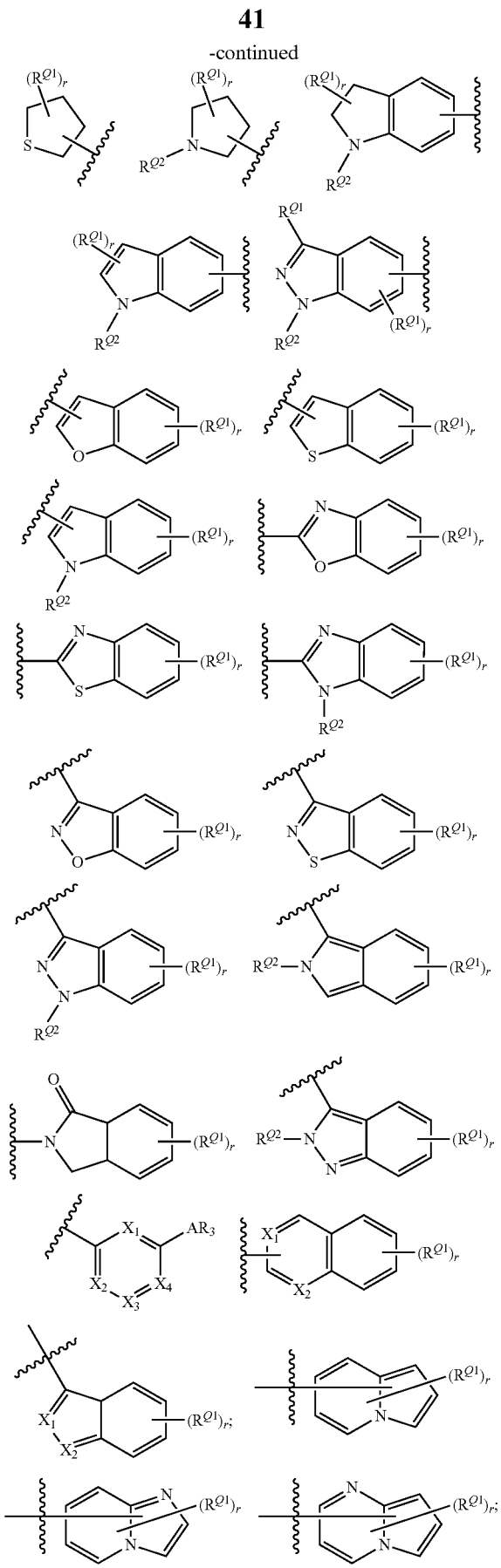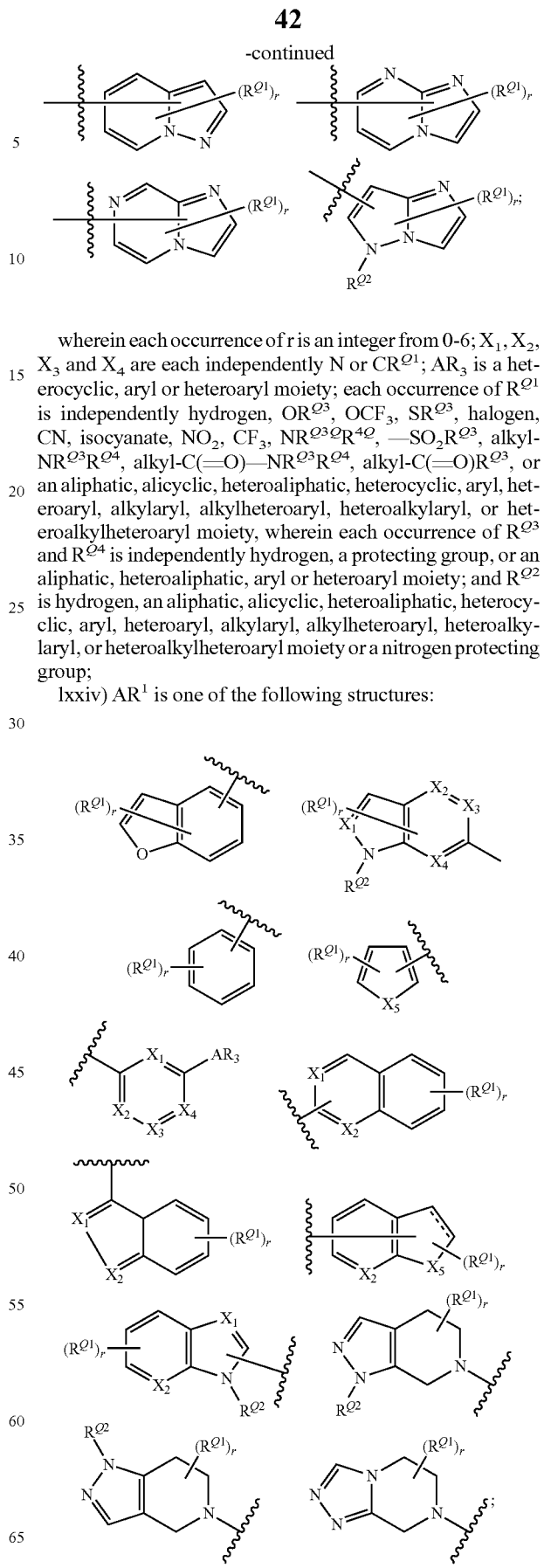

wherein each occurrence of r is an integer from 0-6; $X_1$, $X_2$, $X_3$ and $X_4$ are each independently N or $CR^{Q1}$; $AR_3$ is a heterocyclic, aryl or heteroaryl moiety; each occurrence of $R^{Q1}$ is independently hydrogen, $OR^{Q3}$, $OCF_3$, $SR^{Q3}$, halogen, CN, isocyanate, $NO_2$, $CF_3$, $NR^{Q3}R^{Q4}$, $-SO_2R^{Q3}$, alkyl-$NR^{Q3}R^{Q4}$, alkyl-C(=O)—$NR^{Q3}R^{Q4}$, alkyl-C(=O)$R^{Q3}$, or an aliphatic, alicyclic, heteroaliphatic, heterocyclic, aryl, heteroaryl, alkylaryl, alkylheteroaryl, heteroalkylaryl, or heteroalkylheteroaryl moiety, wherein each occurrence of $R^{Q3}$ and $R^{Q4}$ is independently hydrogen, a protecting group, or an aliphatic, heteroaliphatic, aryl or heteroaryl moiety; and $R^{Q2}$ is hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group;

lxxiv) $AR^1$ is one of the following structures:

-continued

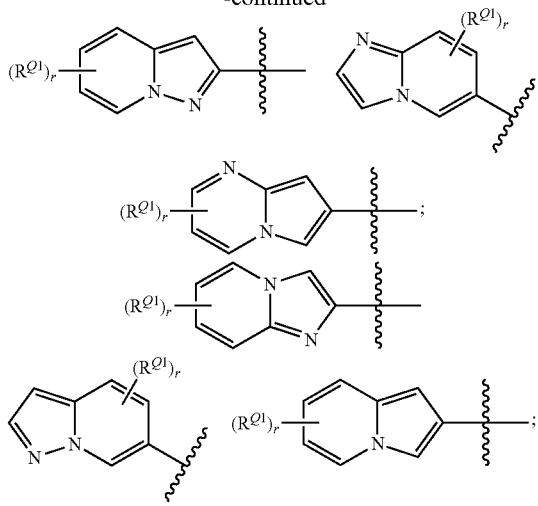

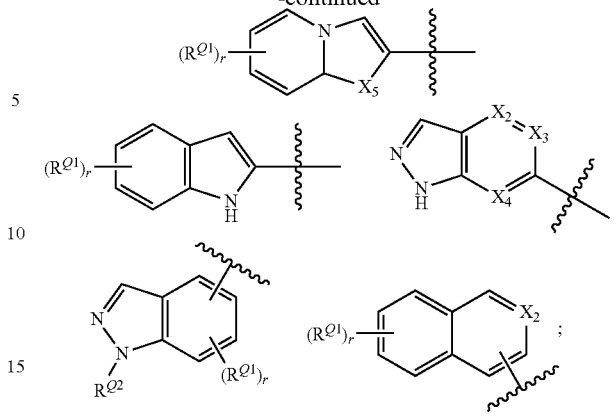

wherein each occurrence of r is an integer from 0-6; $X_1$, $X_2$, $X_3$ and $X_4$ is independently N or $CR^{Q1}$; $X_5$ is O, S or $NR^{Q2}$; $AR^3$ is a heterocyclic, aryl or heteroaryl moiety; each occurrence of $R^{Q1}$ is independently hydrogen, $OR^{Q3}$, $OCF_3$, $SR^{Q3}$, halogen, CN, isocyanate, $NO_2$, $CF_3$, $NR^{Q3}R^{Q4}$, $-SO_2R^{Q3}$, alkyl-$NR^{Q3}R^{Q4}$, alkyl-C(=O)—$NR^{Q3}R^{Q4}$, alkyl-C(=O)$R^{Q3}$, or an aliphatic, alicyclic, heteroaliphatic, heterocyclic, aryl, heteroaryl, alkylaryl, alkylheteroaryl, heteroalkylaryl, or heteroalkylheteroaryl moiety, wherein each occurrence of $R^{Q3}$ and $R^{Q4}$ is independently hydrogen, a protecting group, or an aliphatic, heteroaliphatic, aryl or heteroaryl moiety; and $R^{Q2}$ is hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group;

lxxv) $AR^1$ is one of the following structures:

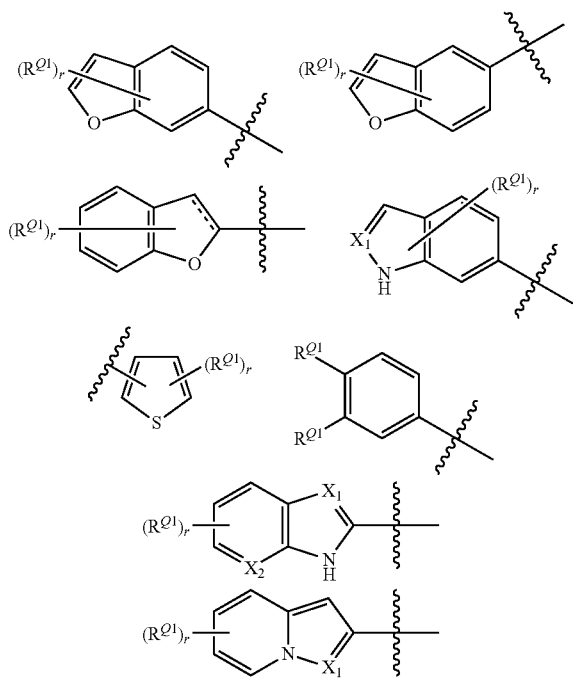

wherein r is as defined above; $X_1$, $X_2$, $X_3$ and $X_4$ is independently N or CH; $X_5$ is $CHR^{Q1}$ or NH; each occurrence of $R^{Q1}$ is independently hydrogen, $R^{Q3}$, $OCF_3$, $SR^{Q3}$, halogen, CN, isocyanate, $NO_2$, $CF_3$, $NR^{Q3}R^{Q4}$, $-SO_2R^{Q3}$, alkyl $NR^{Q3}R^{Q4}$ alkyl-C(=O)—$NR^{Q3}R^{Q4}$, alkyl-C(=O)$R^{Q3}$, or an aliphatic, alicyclic, heteroaliphatic, heterocyclic, aryl, heteroaryl, alkylaryl, alkylheteroaryl, heteroalkylaryl, or heteroalkylheteroaryl moiety, wherein each occurrence of $R^{Q3}$ and $R^{Q4}$ is independently hydrogen, a protecting group, or an aliphatic, heteroaliphatic, aryl or heteroaryl moiety; and $R^{Q2}$ is hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group;

lxxvi) $AR^1$ is one of the following structures:

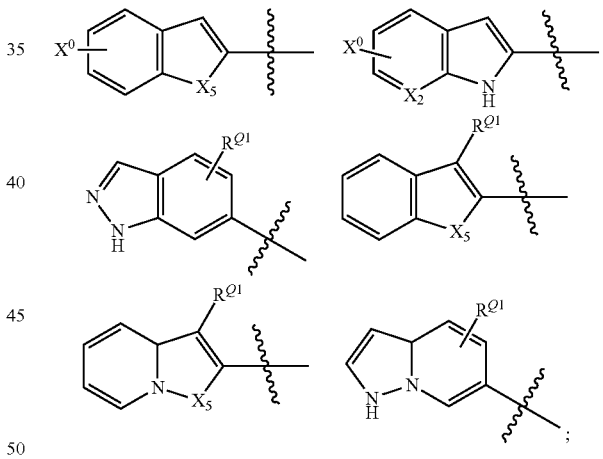

wherein $X^0$ is F or Cl; $X_2$ is N or $CR^{Q1}$; $X_5$ is CH, O, S or NH; $R^{Q1}$ is hydrogen, methyl, $-CF_3$, $-OCH_3$, $-OCF_3$ or halogen;

lxxvii) $AR^1$ is one of the following structures:

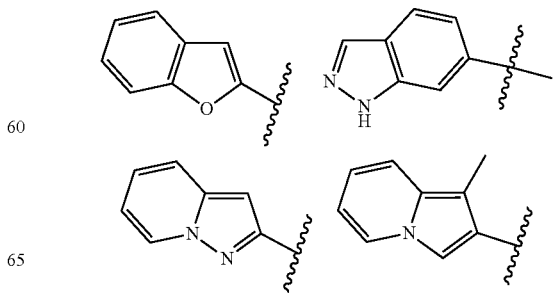

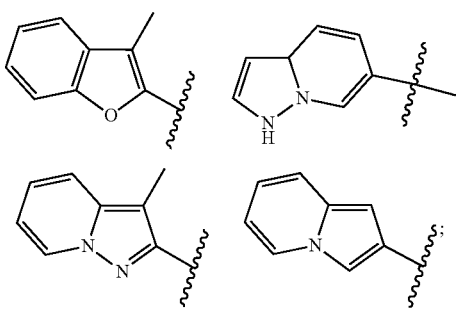

lxxviii) AR$^1$ is one of the following structures:

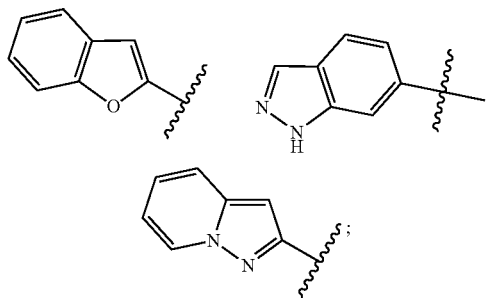

lxxix) AR$^1$-L- is one of the following structures:

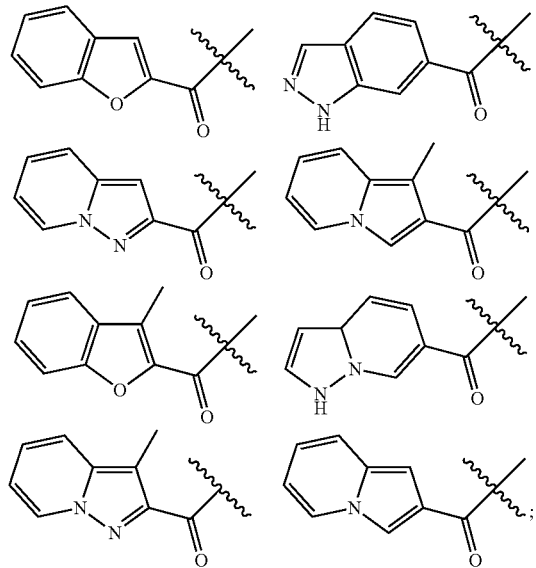

lxxx) AR$^1$-L- is one of the following structures:

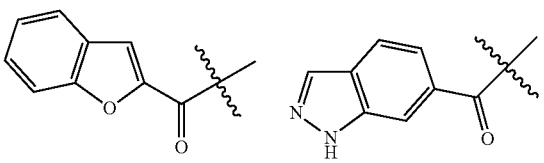

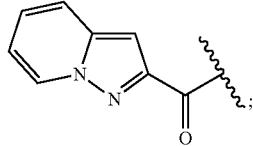

lxxxi) R$^4$, for each occurrence, is independently hydrogen, halogen, —CN, —NO$_2$, an alkyl, alkylenyl; alkynyl; cycloalkyl, heteroalkyl, heterocyclic, aryl, heteroaryl, alkylaryl or alkylheteroaryl moiety, or is -GR$^{G1}$ wherein G is —O—, —S—, —NR$^{G2}$—, —CO—, —SO—, —SO$_2$—, —C(=O)O—, —C(=O)NR$^{G2}$—, —NR$^{G2}$C(=O)— or —SO$_2$NR$^{G2}$—, and R$^{G1}$ and R$^{G2}$ are independently hydrogen, an alkyl, alkylenyl; alkynyl; cycloalkyl, heteroalkyl, heterocyclic, aryl, heteroaryl, alkylaryl or alkylheteroaryl moiety;

lxxxii) R$^4$, for each occurrence, is independently hydrogen, halogen, or lower alkyl;

lxxxiii) R$^4$, for each occurrence, is independently hydrogen or chloro;

lxxxiv) n is 0;

lxxxv) n is 2;

lxxxvi) n is 2 and each occurrence of R$^4$ is a halogen;

lxxxvii) n is 2 and each occurrence of R$^4$ is Cl;

lxxxviii) p is 1;

lxxxix) p is 2; and/or xc) Compounds of formula (II) wherein when —C(=O)NHC(R$^1$)(R$^2$)R$^3$ has the structure:

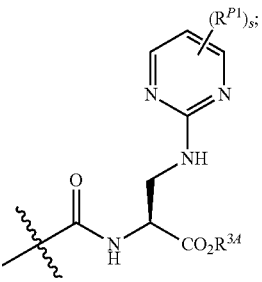

then AR$^1$ is not one of:

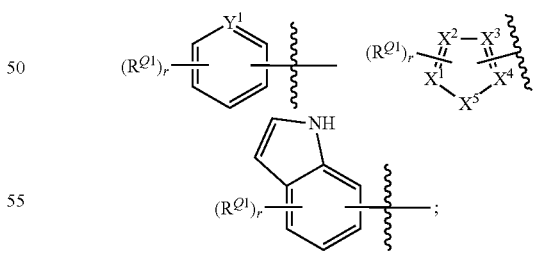

wherein Y$^1$ is N or CR$^{Q1}$; X$^1$, X$^2$, X$^3$ and X$^4$ are independently CR$^{Q1}$; X$^5$ is NR$^{Q1}$, O or S; r is 0-3; and each occurrence of R$^{Q1}$ is independently CN, NO$_2$, halogen, CF$_3$, an alkyl, cycloalkyl, heteroalkyl, heterocyclic, aryl, heteroaryl, alkylaryl or alkylheteroaryl moiety or is GR$^{G1}$ wherein G is —O—, —S—, —NR$^{G2}$—, —CO—, —SO—, —C$_{0-6}$alkylSO$_2$—, —C$_{0-6}$alkylSO$_2$NR$^{G2}$—, —C(=O)O—, —C(=O)NR$^{G2}$—, —OC(=O)— or —NR$^{G2}$C(=O)—, and R$^{G1}$ and R$^{G2}$ are independently hydrogen, an alkyl, cycloalkyl, heteroalkyl, heterocyclic, aryl, heteroaryl, alkylaryl or alkylheteroaryl moiety.

It will be appreciated that for each of the classes and subclasses described above and herein, any one or more occurrences of aliphatic or heteroaliphatic may independently be substituted or unsubstituted, cyclic or acyclic, linear or branched and any one or more occurrences of aryl, heteroaryl, cycloaliphatic, cycloheteroaliphatic may be substituted or unsubstituted.

The reader will also appreciate that all possible combinations of the variables described in i)-through xc) above (e.g., R1, $R^2$, $R^3$, $R^4$, L, and $AR^1$, among others) are considered part of the invention. Thus, the invention encompasses any and all compounds of formula I or II generated by taking any possible permutation of variables $R^1$, $R^2$, $R^3$, $R^4$, L, $AR^1$, etc. and other variables/substituents (e.g., $X^1$, $X^2$, $X^3$, $X^4$, $R^{1A}$, $R^{2A}$, $R^{2C}$, $R^{2D}$, etc.) as further defined for $R^1$, $R^2$, $R^3$, $R^4$, L, $AR^1$, etc. described in i)-through xc) above.

For example, an exemplary combination of variables described in i)-through xc) above includes those compounds of Formula I wherein:

$R^1$ and $R^2$ are each independently hydrogen, an amino acid side chain, —$(CH_2)_m$OH, —$(CH_2)_m$aryl, —$(CH_2)_m$heteroaryl, wherein m is 0-6, —CH($R^{1A}$)($OR^{1B}$), —CH($R^{1A}$)($NHR^{1B}$), U-T-Q, or an aliphatic, alicyclic, heteroaliphatic or heteroalicyclic moiety optionally substituted with U-T-Q, wherein U is absent, —O—, —S(O)$_{0-2}$—, —SO$_2$N($R^{1A}$), —N($R^{1A}$)—, —N($R^{1A}$)C(=O)—, —N($R^{1A}$)C(=O)—O—, —N($R^{1A}$)C(=O)—N($R^{1B}$)—, —N($R^{1A}$)—SO$_2$—, —C(=O)—, —C(=O)—O—, —O—C(=O)—, aryl, heteroaryl, alkylaryl, alkylheteroaryl, —C(=O)—N($R^{1A}$)—, —O—C(=O)—N($R^{1A}$)—, —C(=N—$R^{1E}$)—, —C(=N—$R^{1E}$)—O—, —C(=N—$R^{1E}$)—N($R^{1A}$)—, —O—C(=N—$R^{1E}$)—N($R^{1A}$)—, —N($R^{1A}$)C(=N—$R^{1E}$)—, —N($R^{1A}$)C(=N—$R^{1E}$)—O—, N($R^{1A}$)C(=N—$R^{1E}$)—N($R^{1B}$)—, —P(=O)($OR^{1A}$)—O—, or —P(=O)($R^{1A}$)—O—; T is absent, an aliphatic, heteroaliphatic, aryl, heteroaryl, alkylaryl or alkylheteroaryl moiety; and Q is hydrogen, halogen, cyano, isocyanate, —$OR^{1B}$, —$SR^{1B}$; —N($R^{1B}$)$_2$, —NHC(=O)$OR^{1B}$, —NHC(=O)N($R^{1B}$)$_2$, —NHC(=O)$R^{1B}$, —NHSO$_2$$R^{1B}$, —NHSO$_2$N($R^{1B}$)$_2$, —NHSO$_2$NHC(=O)$OR^{1B}$, —NHC(=O)NHSO$_2$$R^{1B}$, —C(=O)NHC(=O)$OR^{1B}$, —C(=O)NHC(=O)$R^{1B}$, —C(=O)NHC(=O)N($R^{1B}$)$_2$, —C(=O)NHSO$_2$$R^{1B}$, —C(=O)NHSO$_2$N($R^{1B}$)$_2$, —C(=S)N($R^{1B}$)$_2$, —SO$_2$$R^{1B}$, —SO$_2$—O—$R^{1B}$SO$_2$—N($R^{1B}$)$_2$, —SO$_2$—NHC(=O)$OR^{1B}$, —SO$_2$—NHC(=O)—N($R^{1B}$)$_2$, —SO$_2$—NHC(=O)$R^{1B}$, —O—C(=O)N($R^{1B}$)$_2$, —O—C(=O)$R^{1B}$, —O—C(=O)NHC(=O)$R^{1B}$, —O—C(=O)NH—SO$_2$$R^{1B}$, —O—SO$_2$$R^{1B}$, or an aliphatic heteroaliphatic, aryl or heteroaryl moiety, or wherein $R^1$ and $R^2$ taken together are an alicyclic or heterocyclic moiety, or together are

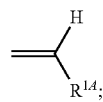

wherein each occurrence of $R^{1A}$ and $R^{1B}$ is independently hydrogen, an aliphatic, alicyclic, heteroaliphatic, heterocyclic, aryl, heteroaryl, alkylaryl or alkylheteroaryl moiety, —$COR^{1C}$, or —$CONR^{1C}R^{1D}$; wherein each occurrence of $R^{1C}$ and $R^{1D}$ is independently hydrogen, hydroxyl, or an aliphatic, heteroaliphatic, aryl, heteroaryl, alkylaryl or alkylheteroaryl moiety; and $R^{1E}$ is hydrogen, an aliphatic, alicyclic, heteroaliphatic, heterocyclic, aryl, heteroaryl, alkylaryl or alkylheteroaryl moiety, —CN, —$OR^{1C}$, —$NR^{1C}R^{1D}$ or —SO$_2$$R^{1C}$;

$R^3$ is —C(=O)$OR^{3A}$, —C(=O)H, —CH$_2$$OR^{3A}$, —CH$_2$O—C(=O)-alkyl, —C(=O)NH($R^{3A}$), —CH$_2$$X^0$; wherein each occurrence of $R^{3A}$ is independently hydrogen, a protecting group, an aliphatic, alicyclic, heteroaliphatic, heteroalicyclic, aryl, heteroaryl, alkylaryl, alkylheteroaryl, heteroalkylaryl or heteroalkylheteroaryl moiety, or $R^{3A}$, taken together with $R^1$ or $R^2$, forms a heterocyclic moiety; wherein $X^0$ is a halogen selected from F, Cl, Br or I;

$R^4$, for each occurrence, is independently hydrogen, halogen, —CN, —NO$_2$, an aliphatic, alicyclic, heteroaliphatic, heteroalicyclic, aryl, heteroaryl, alkylaryl or alkylheteroaryl moiety, or is -$GR^{G1}$ wherein G is —O—, —S—, $NR^{G2}$—, —CO—, —SO—, —SO$_2$—, —C(=O)O—, —C(=O)$NR^{G2}$—, —OC(=O)—, —$NR^{G2}$C(=O)— or —SO$_2$$NR^{G2}$—, and $R^{G1}$ and $R^{G2}$ are independently hydrogen, an aliphatic, alicyclic, heteroaliphatic, heteroalicyclic, aryl, heteroaryl, alkylaryl or alkylheteroaryl moiety;

$AR^1$ is a monocyclic or polycyclic aryl, heteroaryl, alkylaryl, alkylheteroaryl, alicyclic or heterocyclic moiety;

A, B, D and E are connected by either a single or double bond, as valency permits; wherein each occurrence of A, B, D and E is independently C=O, $CR^iR^{ii}$, $NR^i$, N, O, S, S(=O) or SO$_2$; wherein each occurrence of $R^i$ is independently hydrogen, halogen, —CN, —NO$_2$, an aliphatic, alicyclic, heteroaliphatic, heteroalicyclic, aryl, heteroaryl, alkylaryl or alkylheteroaryl moiety, or is -$GR^{G1}$ wherein G is —O—, —S—, —$NR^{G2}$—, —CO—, —SO—, —C(=O)O—, —C(=O)$NR^{G2}$—, —OC(=O)—, —$NR^{G2}$C(=O)— or —SO$_2$$NR^{G2}$—, and $R^{G1}$ and $R^{G2}$ are independently hydrogen, an aliphatic, alicyclic, heteroaliphatic, heteroalicyclic, aryl, heteroaryl, alkylaryl or alkylheteroaryl moiety, or any two adjacent occurrences of $R^i$, taken together, represent an alicyclic, heteroalicyclic, aryl, or heteroaryl moiety; and L is absent or is V—W—X—Y—Z, wherein each occurrence of V, W, X, Y and Z is independently absent, C=O, $NR^{L1}$, —O—, —C($R^{L1}$)=, =C($R^{L1}$)—, —C($R^{L1}$)($R^{L2}$), C(=N—O—$R^{L1}$), C(=N—$R^{L1}$), —N=, S(O)$_{0-2}$; a substituted or unsubstituted C$_{1-6}$alkylidene or C$_{2-6}$alkenylidene chain wherein up to two non-adjacent methylene units are independently optionally replaced by —C(=O)—, —CO$_2$—, —C(=O)C(=O)—, —C(=O)$NR^{L3}$—, —OC(=O)—, —OC(=O)$NR^{L3}$—, —$NR^{L3}$$NR^{L4}$—, —$NR^{L3}$$NR^{L4}$C(=O)—, —$NR^{L3}$C(=O)—, —$NR^{L3}$CO$_2$—, —$NR^{L3}$C(=O)$NR^{L4}$—, S(=O)—, —SO$_2$—, —$NR^{L3}$SO$_2$—, —SO$_2$$NR^{L3}$—, —$NR^{L3}$SO$_2$$NR^{L4}$—, —O—, —S—, or —$NR^{L3}$—; wherein each occurrence of $R^{L3}$ and $R^{L4}$ is independently hydrogen, alkyl, heteroalkyl, aryl, heteroaryl or acyl; or an aliphatic, alicyclic, heteroaliphatic, heteroalicyclic, aryl, heteroaryl, alkylaryl or alkylheteroaryl moiety; and each occurrence of $R^{L1}$ and $R^{L2}$ is independently hydrogen, hydroxyl, protected hydroxyl, amino, protected amino, thio, protected thio, halogen, cyano, isocyanate, carboxy, carboxyalkyl, formyl, formyloxy, azido, nitro, ureido, thioureido, thiocyanato, alkoxy, aryloxy, mercapto, sulfonamido, benzamido, tosyl, or an aliphatic, alicyclic, heteroaliphatic, heteroalicyclic, aryl, heteroaryl, alkylaryl or alkylheteroaryl moiety, or wherein one or more occurrences of $R^{L1}$ and $R^{L2}$, taken together, or taken together with one of V, W, X, Y or Z form an alicyclic or heterocyclic moiety or form an aryl or heteroaryl moiety.

Other exemplary combinations are illustrated by compounds of the following subgroups I through XIV:

I) Compounds Having the Structure (and Pharmaceutically Acceptable Derivatives Thereof):

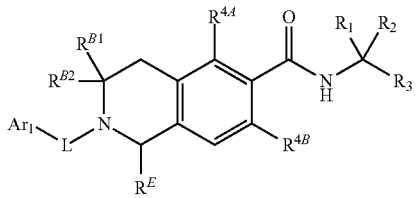

wherein $R^{4A}$ and $R^{4B}$ are independently a halogen selected from F, Cl, Br or I; and $R^{B1}$, $R^{B2}$ and $R^E$ are independently hydrogen or substituted or unsubstituted lower alkyL. In certain embodiments, $R^{4A}$ and $R^{4B}$ are each CL. In yet other embodiments, one of $R^{B1}$ and $R^{B2}$ is hydrogen, the other is substituted or unsubstituted lower alkyL. In certain exemplary embodiments, $R^{B1}$ and $R^{B2}$ are each hydrogen. In certain other exemplary embodiments, $R^{B1}$ and $R^{B2}$ are each lower alkyL. In certain exemplary embodiments, $R^{B1}$ and $R^{B2}$ are each methyL. In other embodiments, $R^E$ is hydrogen. In yet other embodiments, $R^E$ is substituted or unsubstituted lower alkyL. In yet other embodiments, $R^E$ is substituted or unsubstituted methyl, ethyl, propyl, i-propyl, n-butyl, sec-butyl, tert-butyl, n-pentyl, sec-pentyl, tert-pentyl or n-hexyL. In certain embodiments, $R^{4A}$ and $R^{4B}$ are each Cl; and $R^{B1}$ and $R^{B2}$ are each hydrogen.

II) Compounds Having the Structure (and Pharmaceutically Acceptable Derivatives Thereof):

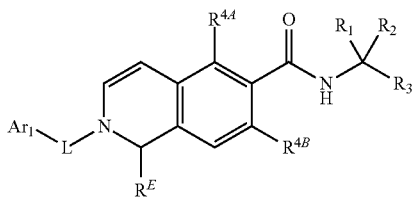

wherein $R^{4A}$ and $R^{4B}$ are independently a halogen selected from F, Cl, Br or I; and $R^E$ is hydrogen or substituted or unsubstituted lower alkyL. In certain embodiments, $R^{4A}$ and $R^{4B}$ are each CL. In other embodiments, $R^E$ is hydrogen. In yet other embodiments, $R^E$ is substituted or unsubstituted lower alkyL. In yet other embodiments, $R^E$ is substituted or unsubstituted methyl, ethyl, propyl, i-propyl, n-butyl, sec-butyl, tert-butyl, n-pentyl, sec-pentyl, tert-pentyl or n-hexyl.

III) Compounds Having the Structure (and Pharmaceutically Acceptable Derivatives Thereof):

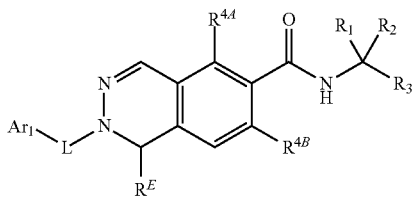

wherein $R^{4A}$ and $R^{4B}$ are independently a halogen selected from F, Cl, Br or I; and $R^E$ is hydrogen or substituted or unsubstituted lower alkyL. In certain embodiments, $R^{4A}$ and $R^{4B}$ are each CL. In other embodiments, $R^E$ is hydrogen. In yet other embodiments, $R^E$ is substituted or unsubstituted lower alkyL. In yet other embodiments, $R^E$ is substituted or unsubstituted methyl, ethyl, propyl, i-propyl, n-butyl, sec-butyl, tert-butyl, n-pentyl, sec-pentyl, tert-pentyl or n-hexyl.

IV) Compounds Having the Structure (and Pharmaceutically Acceptable Derivatives Thereof):

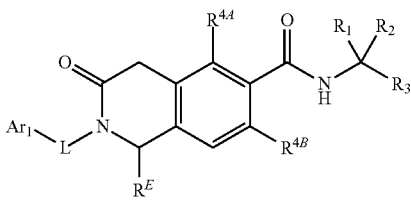

wherein $R^{4A}$ and $R^{4B}$ are independently a halogen selected from F, Cl, Br or I; and $R^E$ is hydrogen or substituted or unsubstituted lower alkyL. In certain embodiments, $R^{4A}$ and $R^{4B}$ are each CL. In other embodiments, $R^E$ is hydrogen. In yet other embodiments, $R^E$ is substituted or unsubstituted lower alkyL. In yet other embodiments, $R^E$ is substituted or unsubstituted methyl, ethyl, propyl, i-propyl, n-butyl, sec-butyl, tert-butyl, n-pentyl, sec-pentyl, tert-pentyl or n-hexyl.

V) Compounds Having the Structure (and Pharmaceutically Acceptable Derivatives Thereof):

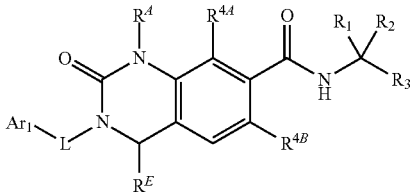

wherein $R^{4A}$ and $R^{4B}$ are independently a halogen selected from F, Cl, Br or I; $R^A$ is hydrogen, lower alkyl or acyl; and $R^E$ is hydrogen or substituted or unsubstituted lower alkyL. In certain embodiments, $R^{4A}$ and $R^{4B}$ are each CL. In other embodiments, $R^E$ is hydrogen. In yet other embodiments, $R^E$ is substituted or unsubstituted lower alkyL. In yet other embodiments, $R^E$ is substituted or unsubstituted methyl, ethyl, propyl, i-propyl, n-butyl, sec-butyl, tert-butyl, n-pentyl, sec-pentyl, tert-pentyl or n-hexyl.

VI) Compounds Having the Structure (and Pharmaceutically Acceptable Derivatives Thereof):

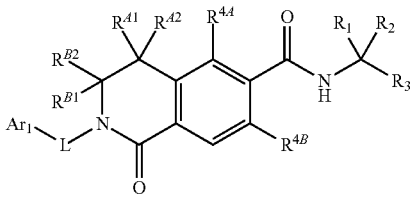

wherein $R^{4A}$ and $R^{4B}$ are independently a halogen selected from F, Cl, Br or I; $R^{A1}$, $R^{A2}$, $R^{B1}$ and $R^{B2}$ are independently hydrogen or substituted or unsubstituted lower alkyL. In certain embodiments, $R^{4A}$ and $R^{4B}$ are each CL. In certain embodiments, $R^{A1}$, $R^{A2}$, $R^{B1}$ and $R^{B2}$ are each hydrogen.

VII) Compounds Having the Structure (and Pharmaceutically Acceptable Derivatives Thereof):

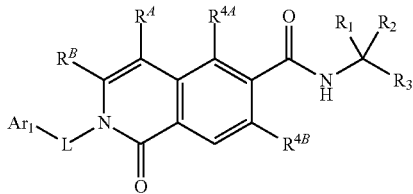

wherein $R^{4A}$ and $R^{4B}$ are independently a halogen selected from F, Cl, Br or I; and $R^A$ and $R^B$ are independently hydrogen or substituted or unsubstituted lower alkyL. In certain embodiments, $R^{4A}$ and $R^{4B}$ are each CL. In certain embodiments, $R^A$ and $R^B$ are each hydrogen.

VIII) Compounds Having the Structure (and Pharmaceutically Acceptable Derivatives Thereof):

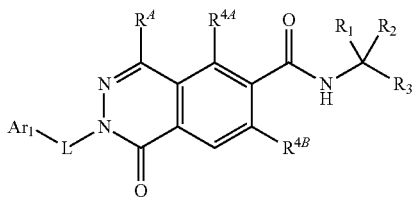

wherein $R^{4A}$ and $R^{4B}$ are independently a halogen selected from F, Cl, Br or I; and $R^A$ is hydrogen or substituted or unsubstituted lower alkyL. In certain embodiments, $R^{4A}$ and $R^{4B}$ are each CL. In certain embodiments, $R^A$ is hydrogen.

IX) Compounds Having the Structure (and Pharmaceutically Acceptable Derivatives Thereof):

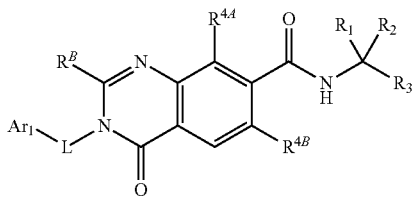

wherein $R^{4A}$ and $R^{4B}$ are independently a halogen selected from F, Cl, Br or I; and $R^B$ is hydrogen or substituted or unsubstituted lower alkyL. In certain embodiments, $R^{4A}$ and $R^{4B}$ are each CL. In certain embodiments, $R^B$ is hydrogen.

X) Compounds Having the Structure (and Pharmaceutically Acceptable Derivatives Thereof):

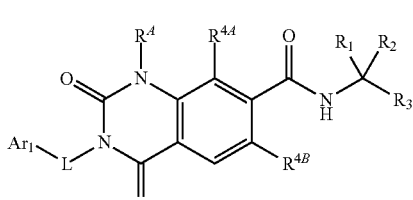

wherein $R^{4A}$ and $R^{4B}$ are independently a halogen selected from F, Cl, Br or I; and $R^A$ is hydrogen or substituted or unsubstituted lower alkyL. In certain embodiments, $R^{4A}$ and $R^{4B}$ are each CL. In certain embodiments, $R^A$ is hydrogen.

XI) Compounds Having the Structure (and Pharmaceutically Acceptable Derivatives Thereof):

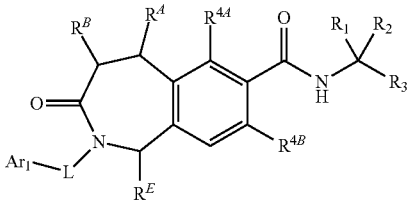

wherein $R^{4A}$ and $R^{4B}$ are independently a halogen selected from F, Cl, Br or I; $R^A$, $R^B$ and $R^E$ are independently hydrogen or substituted or unsubstituted lower alkyL. In certain embodiments, $R^{4A}$ and $R^{4B}$ are each CL. In certain embodiments, $R^A$ and $R^B$ are each hydrogen. In certain other embodiments, $R^E$ is hydrogen. In yet other embodiments, $R^A$, $R^B$ and $R^E$ are each hydrogen.

XII) Compounds Having the Structure (and Pharmaceutically Acceptable Derivatives Thereof):

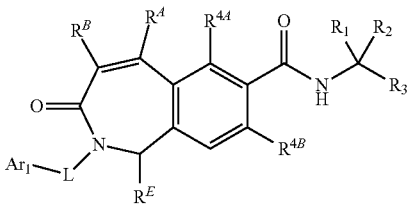

wherein $R^{4A}$ and $R^{4B}$ are independently a halogen selected from F, Cl, Br or I; $R^A$, $R^B$ and $R^E$ are independently hydrogen or substituted or unsubstituted lower alkyL. In certain embodiments, $R^{4A}$ and $R^{4B}$ are each CL. In certain embodiments, $R^A$ and $R^B$ are each hydrogen. In certain other embodiments, $R^E$ is hydrogen. In yet other embodiments, $R^A$, $R^B$ and $R^E$ are each hydrogen.

XIII) Compounds Having the Structure (and Pharmaceutically Acceptable Derivatives Thereof):

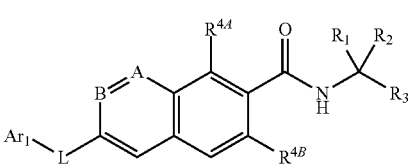

wherein $R^{4A}$ and $R^{4B}$ are independently a halogen selected from F, Cl, Br or I; and A and B are independently N or CH. In certain embodiments, $R^{4A}$ and $R^{4B}$ are each CL. In certain embodiments, A is N. In certain embodiments, A is CH. In certain embodiments, B is N. In certain embodiments, A is CH. In certain embodiments, A and B are each N. In certain embodiments, A is CH. In certain embodiments, A and B are each CH.

XIV) Compounds Having the Structure (and Pharmaceutically Acceptable Derivatives Thereof):

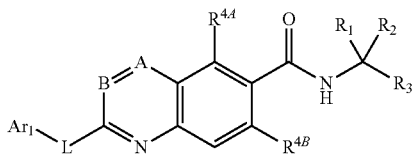

wherein $R^{4A}$ and $R^{4B}$ are independently a halogen selected from F, Cl, Br or I; and A and B are independently N or CH. In certain embodiments, $R^{4A}$ and $R^{4B}$ are each CL. In certain embodiments, A is N. In certain embodiments, A is CH. In certain embodiments, B is N. In certain embodiments, A is CH. In certain embodiments, A and B are each N. In certain embodiments, A is CH. In certain embodiments, A and B are each CH.

In certain embodiments, for compounds of classes T-XIV above, $AR^1$-L- is a moiety having one of the following structures:

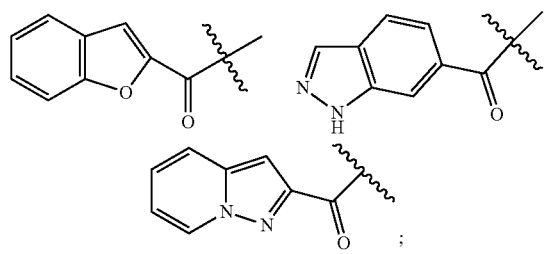

and —C(=O)NHC($R^1$)($R^2$)$R^3$ is a moiety having one of the following structures:

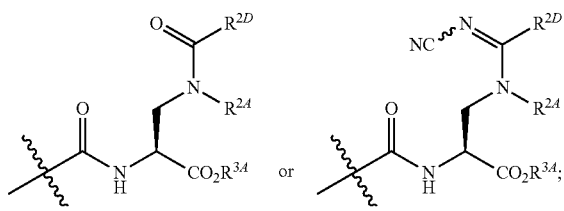

or bioisosteres thereof;

wherein $R^{2A}$ and $R^{3A}$ are as defined in classes and subclasses herein; and $R^{2D}$ is a moiety having one of the following structures:

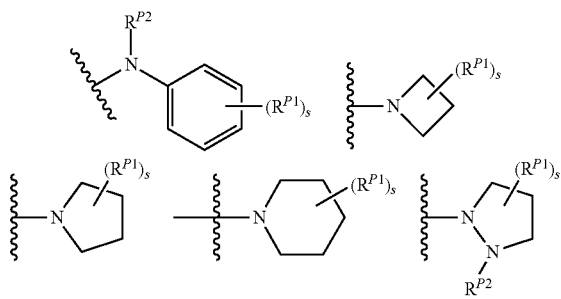

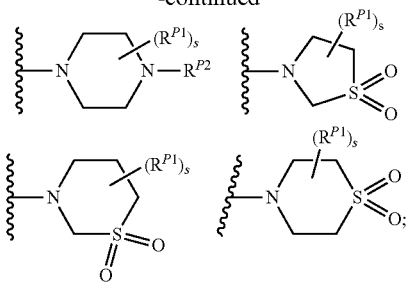

wherein s is an integer between 0 and 6; each occurrence of $R^{P1}$ is independently hydrogen, halogen, CN, isocyanate, $NO_2$, —P(=O)(Y$R^{P5}$)$_2$, an alkyl, cycloalkyl, heteroalkyl, heterocyclic, aryl, heteroaryl, alkylaryl or alkylheteroaryl moiety, or is -G$R^{G1}$ wherein G is —O—, —S—, —N$R^{G2}$—CO—, —SO—, —SO$_2$—, —C(=O)O—, —C(=O)N$R^{G2}$—, —OC(=O)—, —N$R^{G2}$C(=O)— or —SO$_2$N$R^{G2}$—, and $R^{G1}$ and $R^{G2}$ are independently hydrogen, an alkyl, cycloalkyl, heteroalkyl, heterocyclic, aryl, heteroaryl, alkylaryl or alkylheteroaryl moiety; each occurrence of Y is independently a bond or P; each occurrence of $R^{P5}$ is independently alkyl, heteroalkyl, aryl or heteroaryl, or when Y is O $R^{P5}$ may also be hydrogen; and each occurrence of $R^{P2}$ is independently hydrogen, an aliphatic, alicyclic, heteroaliphatic, heterocyclic, aryl, heteroaryl, alkylaryl, alkylheteroaryl, heteroalkylaryl, or heteroalkylheteroaryl moiety or a nitrogen protecting group; wherein any two adjacent occurrences of $R^{P1}$ and $R^{P2}$, taken together, may form a cycloalkyl, heterocyclic, aryl or heteroaryl moiety.

In certain embodiments, $R^{2A}$ and $R^{3A}$ are each hydrogen.

In certain embodiments, $R^{2D}$ is a moiety having one of the structures:

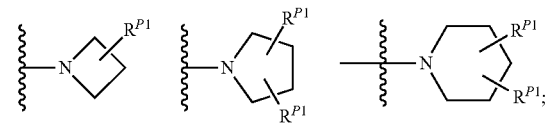

wherein each occurrence of $R^{P1}$ is independently hydrogen, halogen, methyl, —OCH$_3$, —OH, —NH$_2$, —NHCH$_3$, or —N(CH$_3$)$_2$.

In certain embodiments, $R^{2D}$ is a moiety having one of the structures:

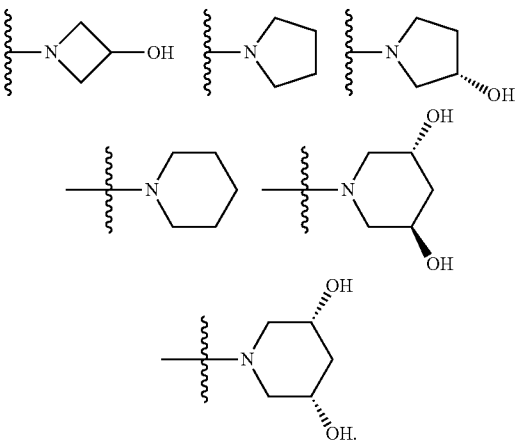

It will also be appreciated that for each of the subgroups I-XIV described above, a variety of other subclasses are of special interest, including, but not limited to those classes described above i)-xc) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) or (II) under different conditions and may exist as one or a combination of polymorphs of compound of general formula (I) or (II) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Pharmaceutical Compositions

As discussed above this invention provides novel compounds that have biological properties useful for the treatment of Mac-1 and LFA-1 mediated disorders.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder mediated by Mac-1 or LFA-1. It will also be appreciated that certain of the compounds of present invention can exist in free form for treatment, or where appropriate, as a pharmaceutically acceptable derivative thereof.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactidc-polyglycolidc. Depending upon the ratio of drug to polymer and the nature of the particular polymer employed, the rate of drug release can be controlled. Example s of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredients) only, or preferentially, in a certain part of the intestinal tract, optionally, in a delayed manner. Example s of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of arT-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Example s of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycoL. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, FlA. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, IlL. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, ear-drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

3) Research Uses, Pharmaceutical Uses and Methods of Treatment

Research Uses

According to the present invention, the inventive compounds may be assayed in any of the available assays known in the art for identifying compounds having the ability to modulate adhesion between intracellular adhesion molecules and the leukocyte integrin family of receptors; to antagonize CD11/CD18 receptors associated with leukocytes and/or to antagonize Mac-1 and/or LFA-1. For example, the assay may be cellular or non-cellular, in vivo or in vitro, high- or low-throughput format, etc.

Thus, in one aspect, compounds of this invention which are of particular interest include those which:
 modulate adhesion between intracellular adhesion molecules (e.g., ICAM-1, -2 and -3) and the leukocyte integrin family of receptors;
 exhibit the ability to antagonize CD11/CD18 receptors associated with leukocytes;
 exhibit the ability to antagonize Mac-1 and/or LFA-1; and are useful for the treatment of LFA-1 mediated disorders.

As detailed in the exemplification herein, in assays to determine the ability of compounds to modulate T-cell adhesion to 5dICAM-Ig (e.g., cell attachment assay), certain inventive compounds exhibited $IC_{50}$ values ≤50 µM. In certain other embodiments, inventive compounds exhibit $IC_{50}$ values ≤40 µM. In certain other embodiments, inventive compounds exhibit $IC_{50}$ values ≤30 µM. In certain other embodiments, inventive compounds exhibit $IC_{50}$ values ≤20 µM. In certain other embodiments, inventive compounds exhibit $IC_{50}$ values ≤10 µM. In certain other embodiments, inventive compounds exhibit $IC_{50}$ values ≤7.5 µM. In certain embodiments, inventive compounds exhibit $IC_{50}$ values ≤5 µM. In certain other embodiments, inventive compounds exhibit $IC_{50}$ values ≤2.5 µM. In certain embodiments, inventive compounds exhibit $IC_{50}$ values ≤1 µM. In certain other embodiments, inventive compounds exhibit $IC_{50}$ values ≤750 nM. In certain other embodiments, inventive compounds exhibit $IC_{50}$ values ≤500 nM. In certain other embodiments, inventive compounds exhibit $IC_{50}$ values ≤250 nM. In certain other embodiments, inventive compounds exhibit $IC_{50}$ values ≤100 nM. In other embodiments, exemplary compounds exhibited $IC_{50}$ values ≤75 nM. In other embodiments, exemplary compounds exhibited $IC_{50}$ values ≤50 nM. In other embodiments, exemplary compounds exhibited $IC_{50}$ values ≤40 nM. In other embodiments, exemplary compounds exhibited $IC_{50}$ values ≤30 nM. In other embodiments, exemplary compounds exhibited $IC_{50}$ values ≤20 nM. In other embodiments, exemplary compounds exhibited $IC_{50}$ values ≤10 nM. In other embodiments, exemplary compounds exhibited $IC_{50}$ values ≤5 nM.

Pharmaceutical Uses and Methods of Treatment

As discussed above, certain of the compounds as described herein exhibit activity generally as modulators of adhesion between intracellular adhesion molecules. More specifically, compounds of the invention demonstrate the ability to antagonize CD11/CD18 receptors associated with leukocytes and in certain embodiments exhibit the ability to antagonize LFA-1 interactions. Thus, in certain embodiments, compounds of the invention are useful for the treatment of LFA-1 mediated disorders.

Accordingly, in another aspect of the invention, methods for treating (or preventing) of LFA-1 mediated disorders are provided comprising administering a therapeutically effective amount of a compound of formula (I) or (II) as described herein, to a subject in need thereof. In certain embodiments, a method for the treatment of LFA-1 mediated disorders is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it.

As discussed above this invention provides novel compounds that have biological properties useful for the treatment of Mac-1 and/or LFA-1 mediated disorders. In certain embodiments, the inventive compounds as useful for the treatment of psoriasis, responses associated with inflammatory bowel disease (such as Crohn's disease and ulcerative colitis), dermatitis, meningitis, encephalitis, uveitis, allergic conditions such as eczema and asthma, conditions involving infiltration of T-cells and chronic inflammatory responses, skin hypersensitivity reactions (including poison ivy and poison oak), artherosclerosis, autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes and immune responses associated with delayed hypersensitivity mediated by cytokines and T-lymphocytes typically found in tuberculosis, sarcoidosis, polymyositis, granulomatosis and vasculitis, pernicious anemia, diseases involving leukocyte diapedeses, CNS inflammatory disorder, multiple organ injury syndrome secondary to septicaemia or trauma, autoimmune hemolytic anemia, myasthemia gravis, antigen-antibody complex mediated diseases, all types of transplantations, including graft versus host or host versus graft disease, HIV and rhinovirus infection, and pulmonary fibrosis to name a few.

As described in more detail herein, in general, compounds of the invention are useful as antagonists of the interaction between intracellular adhesion molecules (e.g., ICAM-1, 2 or 3) and the leukocyte integrin family of receptors. Thus, in certain embodiments, the present invention provides compounds useful for the treatment of disorders mediated by the CD11/CD18 family of cellular adhesion molecules. In certain embodiments of special interest, the present invention provides compounds useful for the treatment of disorders mediated by Mac-1 and/or LFA-1. For example, compounds of the invention are particularly useful for the treatment inflammatory disorders, organ graft rejection and autoimmune disorders, to name a few.

Thus, as described above, in another aspect of the invention, a method for the treatment of disorders mediated by the CD11/CD18 family of cellular adhesion molecules is provided comprising administering a therapeutically effective amount of a compound of formula (I) or (II) as described herein, to a subject in need thereof. In certain embodiments of special interest the inventive method is used for the treatment of disorders mediated by Mac-1 or LFA-1. It will be appreciated that the compounds and compositions, according to the method of the present invention, may be administered using any amount and any route of administration effective for the treatment of disorders mediated by the CD11/CD18 family of cellular adhesion molecules. For example, in certain exemplary embodiments, compounds of the invention are useful as antagonists of the interaction between Mac-1 or LFA-1 and intracellular adhesion molecules (e.g., ICAM-1) and thus the compounds are useful for the treatment of LFA-1 mediated disorders including, but not limited to, psoriasis, responses associated with inflammatory bowel disease (such as Crohn's disease and ulcerative colitis), dermatitis, meningitis, encephalitis, uveitis, allergic conditions such as eczema and asthma, conditions involving infiltration of T-cells and chronic inflammatory responses, skin hypersensitivity reactions (including poison ivy and poison oak), atherosclerosis, autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis, pernicious anemia, diseases involving leukocyte diapedesis, CNS inflammatory disorder, multiple organ injury syndrome secondary to septicaemia or trauma, autoimmune hemolytic anemia, myasthemia gravis, antigen-antibody complex mediated diseases, all types of transplantations, including graft versus host or host versus graft disease, HIV and rhinovirus infection, pulmonary fibrosis and the like, to name a few. Thus, the expression "effective amount" as used herein, refers to a sufficient amount of agent to antagonize the interaction between intracellular adhesion molecules (e.g., ICAM) and the leukocyte integrin family of receptors, and to exhibit a therapeutic effect. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Another aspect of the invention relates to a method for inhibiting the interaction between LFA-1 and ICAM-1 in a biological sample or a patient, which method comprises administering to the patient, or contacting said biological sample with a compound of formula I or II or a composition comprising said compound.

Another aspect of the invention relates to a method for inhibiting the CD11a and/or CD18 interaction with ICAM-1, ICAM-2 or ICAM-3 in a biological sample or a patient, which method comprises administering to the patient, or contacting said biological sample with a compound of formula I or II or a composition comprising said compound.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of macrolide chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2nd ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

1) Synthesis of Exemplary Compounds:

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein. In addition, synthetic guidance can be found in published PCT applications WO 99/49856 and WO 02/059114, the entire contents of which are hereby incorporated by reference.

EXAMPLE 1

This example describes the synthesis of

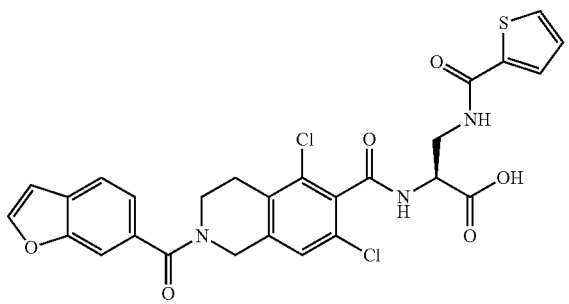 [SMILES: O=C(NC[C@H](NC(=O)c1c(Cl)cc2c(c1Cl)CCN(C(=O)c1ccc3ccoc3c1)C2)C(=O)O)c1cccs1]

which was prepared according to Scheme 1A and the procedure below.

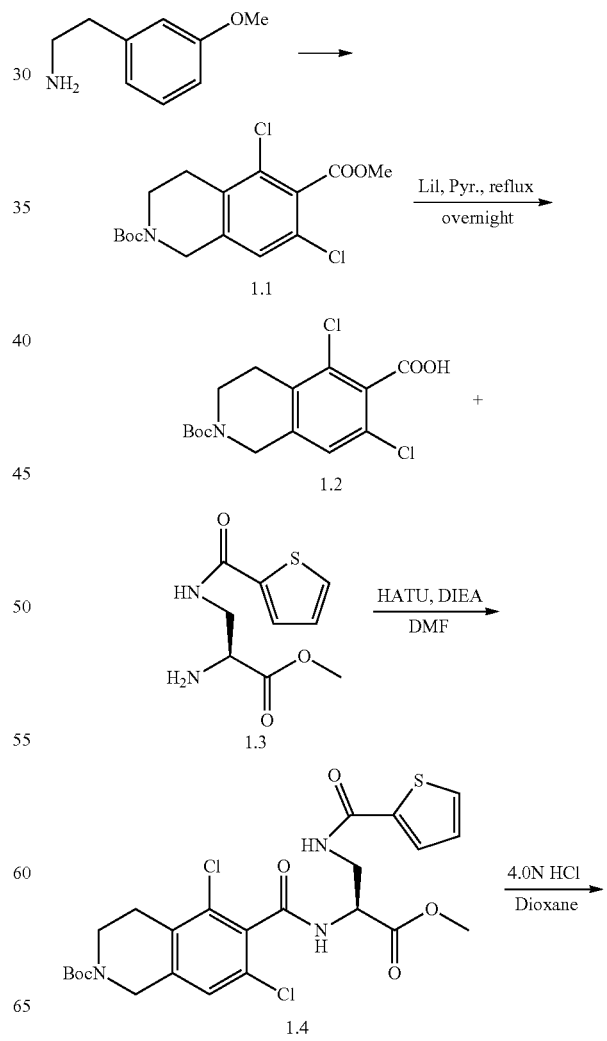

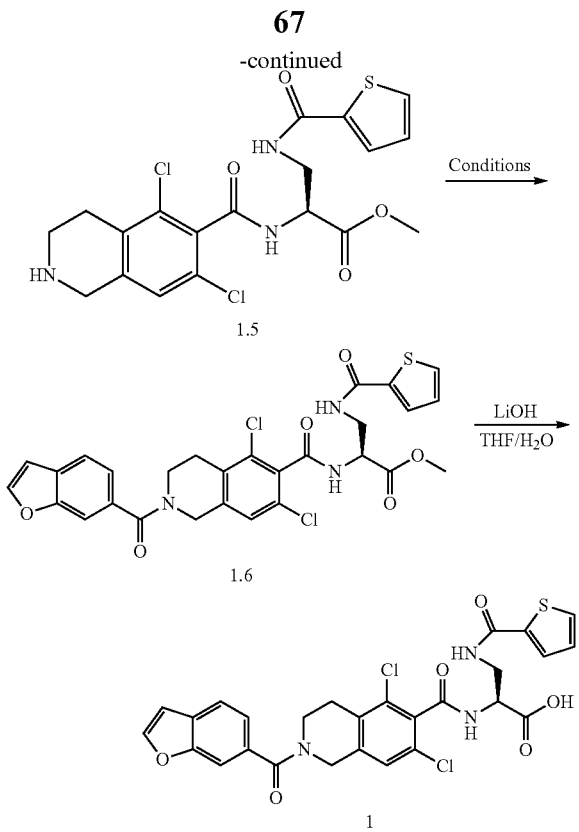

a) A solution of 3-methoxyphenylethylamine (0.2 mol) and formaldehyde (0.22 mol) in aqueous HCl (20%, 500 mL) was heated at 80° C. for 4 hours. The reaction was then concentrated to dryness, and the residue was dissolved in hydrobromic acid (40% aqueous, 500 mL), and refluxed for 24 hours. The reaction was concentrated to give a brownish solid, which was used without purification. To the residue was added water (200 mL) and tetrahydrofuran ("THF") (300 mL), and to the resulting mixture was very carefully added with sodium carbonate (solid, 0.5 mol), followed by di-tert-butyl dicarbonate (0.3 mol). After 15 hours at room temperature, the reaction was extracted with ethyl acetate (1 L), and the organic extract was washed with saturated potassium dihydrophosphate and brine, dried over anhydrous magnesium sulfate and filtered.

The residue after concentration of the filtrate was dissolved in dichloromethane ("DCM"; 100 mL), and to it was slowly added acetic acid (500 mL) and surfuryl chloride (0.6 mol). After the reaction mixture was stirred at room temperature for 24 hours, the reaction was concentrated to dryness, and further dried under high vacuum for 2 hours. The crude product was used without further purification for next step. The crude product was dissolved in water/THF (200 mL/400 mL), and to it was added carefully and slowly sodium carbonate (0.5 mol) with good stirring, followed by di-tert-butyl dicarbonate (0.3 mol). After the reaction mixture was stirred for 12 hours, the reaction was carefully neutralized with phosphoric acid (2 M) to pH about 7. The resulting mixture was extracted with ethyl acetate (500 mL×2), and the combined extracts were washed with water and brine, dried over anhydrous magnesium sulfate, filtered and concentrated. The crude solid was recrystallized from ethyl acetate and hexane (about 1:2 ratio) to yield a white solid. The mother liquid was concentrated and purified by column, eluting with 0-10% ethyl acetate in 4:1 hexane:methylene chloride. The combined yield is 14.5 g (23% from commercial 3-methoxyphenethylamine) MS (API-ES$^+$) m/z: 262, 264, 266 (M+H-tert-butyl$^+$).

The product obtained above was dissolved in DCM (100 mL) and pyridine (50 mL). The resulting solution was cooled to −40° C., and to it was added triflic anhydride (51 mmol) slowly. After the reaction mixture was gradually warmed to room temperature over 4 hours, the reaction mixture was partitioned between ethyl acetate (500 mL) and water (100 mL), and the organic layer was washed with water (100 mL, twice) and brine (50 mL), dried over anhydrous magnesium sulfate, filtered and concentrated. The residue was purified by column, eluting with 0-5% ethyl acetate in 5:1 hexane:DCM to give the corresponding triflate (9.73 g, 48% yield).

A mixture of 10 mmol of the triflate, 1.0 mmol of 1,3-diphenylphosinepropane ("dppp") and 40 mmol of diisopropylethylamine ("DIEA") in 100 mL of dry dimethylformamide ("DMF") and 50 mL of anhydrous CH3OH was flushed with CO for 15 min, and then 1.0 mmol of Pd(OAc)$_2$ was added under the atmosphere of CO. Subsequently, the resulting mixture was stirred at 70° C. overnight under an atmosphere of CO. The solvent was removed and the residue was purified by column chromatography using EtOAc/hexane=1/4 (v/v) as the eluent to give compound 1.1 with a 56% yield. ESI-MS (m/z): (M$^+$)+Na 382.1; $^1$H NMR (CD3OD, 400 MHz): δ 7.32 (s, 1H), 4.60 (s, 2H), 3.95 (s, 3H), 3.69 (m, 2H), 2.84 (m, 2H), 1.50 (s, 9H) ppm.

b) A mixture of 1.1 (5 mmol) and 30 mmol of LiI in 20 mL of pyridine was reflux overnight. The solvent was removed and the residue was dissolved in EtOAc. The resulting solution was then washed with saturated aqueous NH4Cl and dried with anhydrous Na2SO4. The solvent was removed and the residue was dried in vacuo to give a quantitative yield of compound 1.3. The crude product was carried on the next step without further purification. ESI-MS (m/z): (M-tBu+1), 290.

c) A solution of Boc-Dap-OH (10 mmol) in methanol (30 mL) was treated with trimethylsilyldiazomethane until the color remained light yellow for 10 seconds. The mixture was concentrated, and the residue was dissolved in DCM (30 mL). To the solution was added triethylamine (20 mmol) and followed by 3-thienylcarboxyl chloride (11 mmol). After 0.5 hour at room temperature, the reaction was filtered through silica gel, and concentrated. The residue was purified by column with 10-50% ethyl acetate in hexane. The product obtained this way was dissolved in DCM (10 mL) and treated with HCl (4 M in dioxane, 10 mL). After 5 hours, the reaction was concentrated to give the title compound (60-80% overall yield).

d) A mixture of 1.2 (4 mmol), 1.3 (4.4 mmol), 5.0 mmol of o-(7-azabenzotriazol-1-yl)-N,N,N',N'-tetramethyluronium fluorophosphate ("HATU") and 20 mmol of Et3N in 20 mL of DMF was stirred at room temperature overnight. The solvent was removed and the residue was purified by column chromatography using CH$_2$Cl$_2$/EtOAc=6/4 (v/v) as eluent to give compound 1.4 with a 60% yield. ESI-MS (m/z): (M+1) 556.1.

e) A solution of 2 mmol of 1.4 in 9 mL of TFA and 3 mL of CH$_2$Cl$_2$ was stirred at room temperature for 6 hours. The solvent was then removed and the residue was diluted with saturated aqueous NaHCO$_3$. The mixture was extracted with EtOAc for 3 times. The extracts were then dried with anhydrous Na$_2$SO$_4$. The solvent was removed and the residue was dried in vacuo to give compound 1.5 which was used without further purification. ESI-MS (m/z): (M+1) 456.1.

f) Intermediate compound 1.11 was prepared according to Scheme 1B and the procedure below.

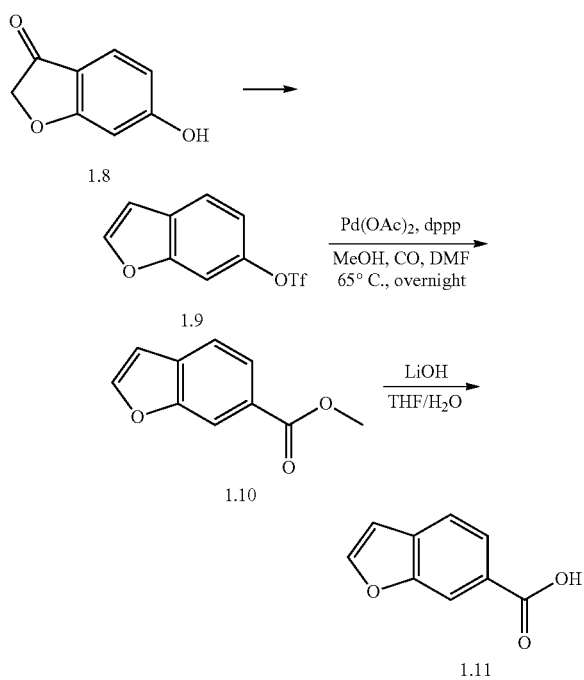

To a solution of 100 mmol of commercially available 6-hydroxy-[2H]-benzofuran-3-one (compound 1.8) and 150 mmol of imidazole in 300 mL of dry DMF was added 110 mmol of tert-butyldimethylsilylchloride ("TBDMSCl") at room temperature, the resulting mixture was stirred at room temperature overnight. The solvent was removed, and the residue was diluted with 100 mL of EtOAc, washed with saturated aqueous $NH_4Cl$, and dried with anhydrous $Na_2SO_4$. The solvent was removed, and the residue was purified to give corresponding intermediate in 70% yield. ESI-MS (m/z): $(M+H^+)$ 265.1.

The intermediate is dissolved in 100 mL of $CH_3OH$ was added 20 mmol of $NaBH_4$ at room temperature. After stirring at room temperature for 12 hours, the reaction mixture was treated with 10 mL of acetone. Subsequently, 60 mL of 4.0 N HCl were added to the mixture, and the mixture was stirred at room temperature overnight. The organic solvent was removed, and the residue was extracted with EtOAc for several times. The extract was then washed with brine and dried with anhydrous $Na_2SO_4$. The solvent was removed and the residue was dissolved in 100 mmol of $Et_3N$ and 180 mL of dry $CH_2Cl_2$ was added 66 mmol of $PhNTf_2$ at 0° C., the resulting mixture was stirred at room temperature overnight. The solvent was removed, and the residue was purified to give compound 1.9 in 90% yield. $^1H$ NMR (400 MHz, CD3Cl): δ 7.75 (d, J=1.9 Hz, 1H), 7.66 (d, J=8.5 Hz, 1H), 7.50 (s, 1H), 7.21 (d, J=8.5 Hz, 1H), 6.85 (d, J=1.9 Hz, 1H) ppm.

A mixture of 50 mmol of compound 1.9, 2.5 mmol of dppp (diphenylphosphine-1,3-propane) and 2.5 mmol of $Pd(OAc)_2$ in 100 mmol of DIEA, 125 mL of dry DMF, and 125 mL of anhydrous MeOH was stirred at 65° C. under an atmosphere of CO overnight. The solvent was removed and the residue was purified by column chromatography to give compound 1.10 in 65% yield. $^1H$ NMR (400 MHz, $CDCl_3$): δ 8.23 (s, 1H), 7.99 (d, J=8.3 Hz, 1H), 7.78 (s, 1H), 7.65 (d, J=8.3 Hz, 1H), 6.85 (s, 1H), 3.97 (s, 3H) ppm; ESI-MS (m/z): (M+1) 177.10.

A mixture of 20 mmol of compound 1.10 and 80 mmol of $LiOH \cdot H_2O$ in 60 mL of THF and 15 mL of $H_2O$ was stirred at room temperature for 1 hour, followed by adding 80 mL of 1.0N aq. HCl. The organic solvent was removed and the residue was diluted with 50 mL of brine. The mixture was then extracted with EtOAc, and the extract was dried with anyhydrous Na2SO4. The solvent was removed and the residue was dried in vacuo to give a quantitative yield of compound 1.11. $^1H$ NMR (400 MHz, $CD_3OD$): δ 8.14 (s, 1H), 7.92 (m, 2H), 7.67 (d, J=8.5 Hz, 1H), 6.92 (s, 1H) ppm; ESI-MS (m/z): $(M+H^+)$ 163.1.

g) A mixture of 0.25 mmol of compound 1.11 and 0.26 mmol of HATU in 1 mmol of DIEA and 2 mL of DMF was stirred at room temperature for 30 min, followed by adding a solution of 0.22 mmol of compound 1.5 in 1 mL of DMF. The resulting mixture was stirred 45° C. for 12 hours. The solvent was removed, and the residue was purified to give compound 1.6 in 50-65% yield. Subsequently, compound 1.6 was hydrolyzed with LiOH (1.0 M aqueous, 0.5 mL) in THF (3 mL) for 2 hours. The reaction mixture was then acidified with HCl (aqueous), extracted with ethyl acetate (50 mL), dried over anhydrous magnesium sulfate and concentrated to give compound 1 in quantitative yield. $^1H$ NMR (400 MHz, $CD_3OD$): δ 7.91 (s, 1H), 7.75 (d, J=8.0 Hz, 1H), 7.67 (s, 3H), 7.36 (d, J=8.0 HZ, 1H), 7.13 (s, 1H), 6.96 (s, 1H), 5.01 (t, J=6.8 Hz, 1H), 4.68 and 4.89 (m, 2H), 3.85 (d, J=6.8 Hz, 2H), 3.70 and 4.02 (m, 2H), 2.93 (m, 2H) ppm; ESI-MS (m/z): (M+1) 586.10.

EXAMPLE 2

This example describes the synthesis of

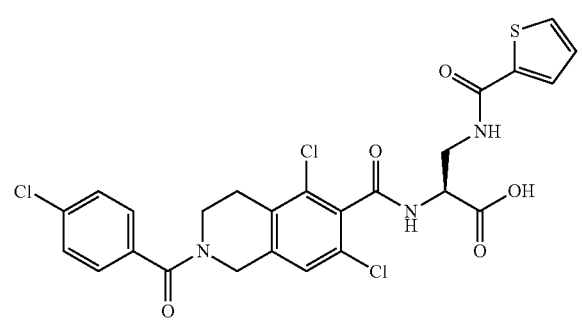 [SMILES: O=C(NC[C@H](NC(=O)c1c(Cl)cc2c(c1Cl)CCN(C(=O)c1ccc(Cl)cc1)C2)C(=O)O)c1cccs1]

which was prepared according to the procedure of Example 1g except that 4-chlorobenzoic acid was used instead of compound 1.11. $^1H$ NMR (400 MHz, CD3OD): δ 7.64 (m, 2H), 7.35-7.49 (m, 5H), 7.11 (s, 1H), 4.98 (t, J=8.0 Hz, 1H), 4.63 and 4.88 (m, 2H), 3.83 (d, J=8.0 Hz, 2H), 3.68 and 3.98 (m, 2H), 2.89 (m, 2H) ppm; ESI-MS (m/z): (M+1) 579.90.

EXAMPLE 3

This example describes the synthesis of

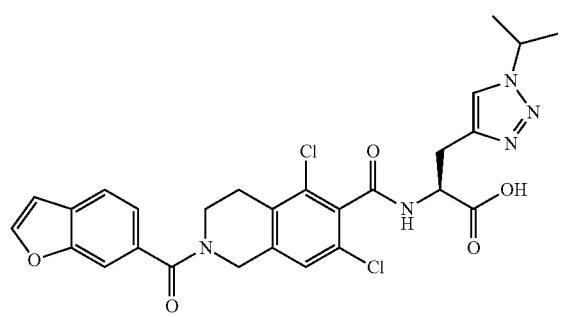 [SMILES: CC(C)n1cc(C[C@H](NC(=O)c2c(Cl)cc3c(c2Cl)CCN(C(=O)c2ccc4ccoc4c2)C3)C(=O)O)nn1]

which was prepared according to Scheme 2 and the procedure below.

SCHEME 2

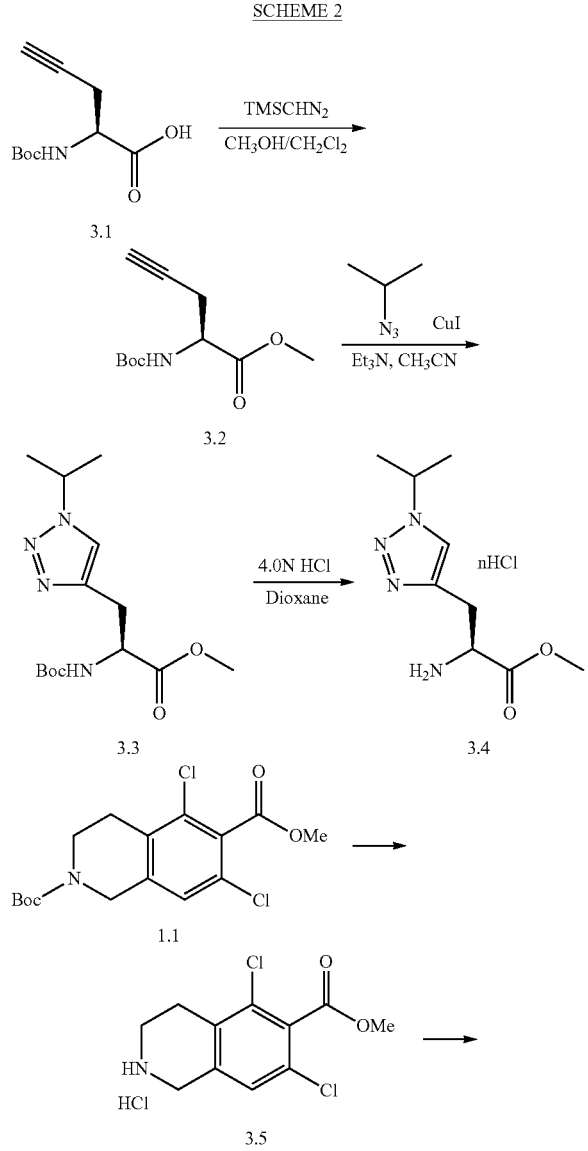

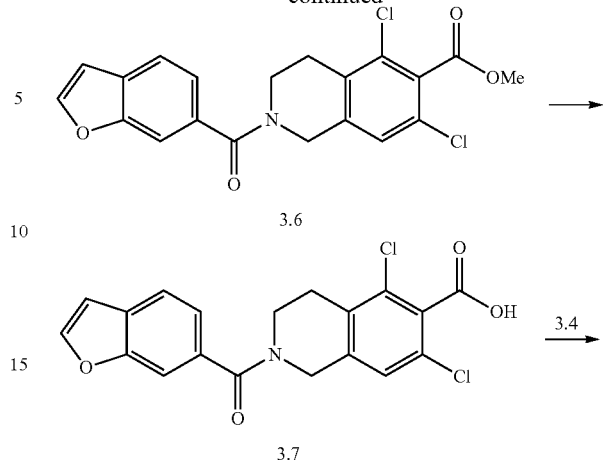

a) To a solution of 10 mmol of commercially available 3.1 in 20 mL of MeOH and 20 mL of $CH_2Cl_2$ was slowly added 20 mmol of 2.0M $TMSCHN_2$, in hexanes at 0° C., and the resulting mixture was stirred at room temperature for 30 minutes. The solvent was removed and the residue was dried in vacuo to give crude 3.2.

b) Compound 3.2 was then stirred with 15 mmol of isopropylazide in the presence of 0.2 mmol of CuI, 0.2 mmolf of $Et_3N$ in 50 mL of $CH_3CN$ at room temperature overnight. The solvent was removed and the residue was purified by column chromatography to give compound 3.3 in 55% yield. ESI-MS (m/z): (M+1) 313.20.

c) A mixture of 2 mmol of compound 3.3 in 10 mL of 4.0 N HCl in dioxane was stirred at room for 12 hours. The solvent was removed and the residue was dried in vacuo to give compound 3.4 in quantitative yield. ESI-MS (m/z): (M+1) 213.10.

d) A solution of 1.1 (3.60 g, 10 mmol) in DCM (20 mL) was treated with HCl in 1,4-dioxane (4.0 M, 10 mL) at room temperature. After 2 hours, the reaction was concentrated to give compound 3.5 in quantitative yield.

e) Example 3.5 (10 mmol) was mixed with EDC (2.11 g, 11 mmol), NA-dimethylaminopyridine ("DMAP", 0.1 g), triethylamine (2.02 g) and Example 1.11 (1.62 g, 10 mmol) in anhydrous DMF (50 mL). After 15 hours at room temperature, the reaction mixture was diluted with ethyl acetate (200 mL), washed with water (30 mL, 3 times), dried with anhydrous magnesium sulfate and filtered. The residue after concentration of the filtrate was purified by column eluting with 10-30% ethyl acetate in hexane to give the title compound (3.7 g, 92%): ESI-MS (m/z): (M+1) 213.1.

f) Compound 3.7 was made according to Example 1b except that compound 3.6 was used instead of compound 1.1.

g) A mixture of 0.25 mmol of compound 3.7 and 0.26 mmol of HATU in 1 mmol of DIEA and 2 mL of DMF was stirred at room temperature for 30 minutes, followed by adding a solution of 0.22 mmol of compound 3.4 in 1 mL, of DMF. The resulting mixture was stirred 45° C. for 4 hours. The solvent was removed, and the residue was purified to give intermediate ester, which was subsequently treated with LiOH in THF and water to give the desired compound 3 in quantitative yield. $^1$H NMR (400 MHz, CD$_3$OD) δ 7.90 (s, 2H), 7.74 (m, 1H), 7.64 (s, 1H), 7.34 (m, 1H), 6.93 (s, 1H), 5.03 (m, 1H), 4.82 (m, 1H), 4.65 and 4.88 (m, 2H), 3.72 and 3.97 (m, 2H), 3.40 (m, 1H), 3.18 (m, 1H), 2.90 (m, 2H), 1.55 (m, 6H) ppm; ESI-MS (m/z): (M+1) 570.1.

EXAMPLE 4

This example describes the synthesis of

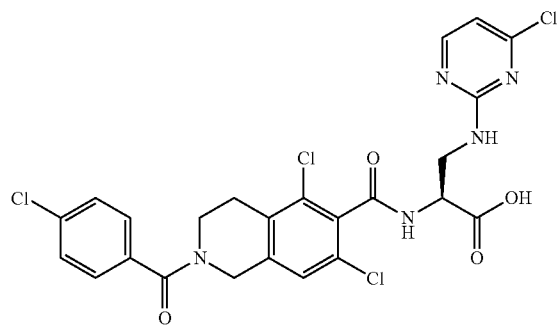 [SMILES: O=C(N[C@@H](CNc1nccc(Cl)n1)C(=O)O)c1c(Cl)cc2c(c1Cl)CCN(C(=O)c1ccc(Cl)cc1)C2]

which was prepared according to Scheme 3 and the procedure below.

SCHEME 3

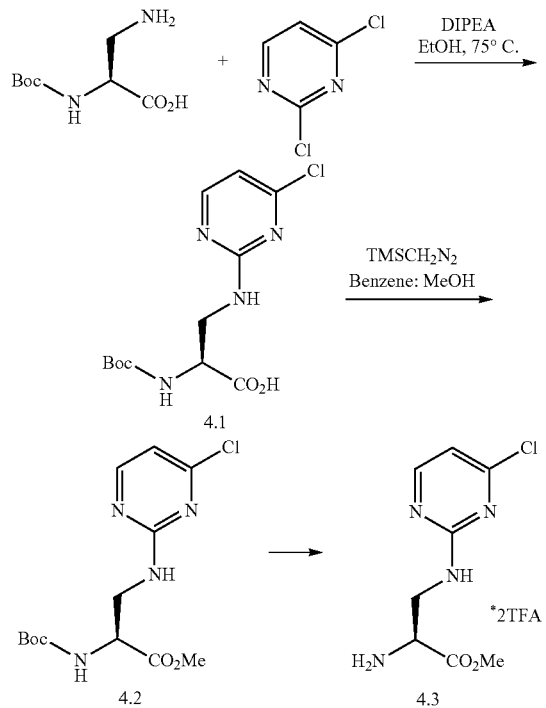

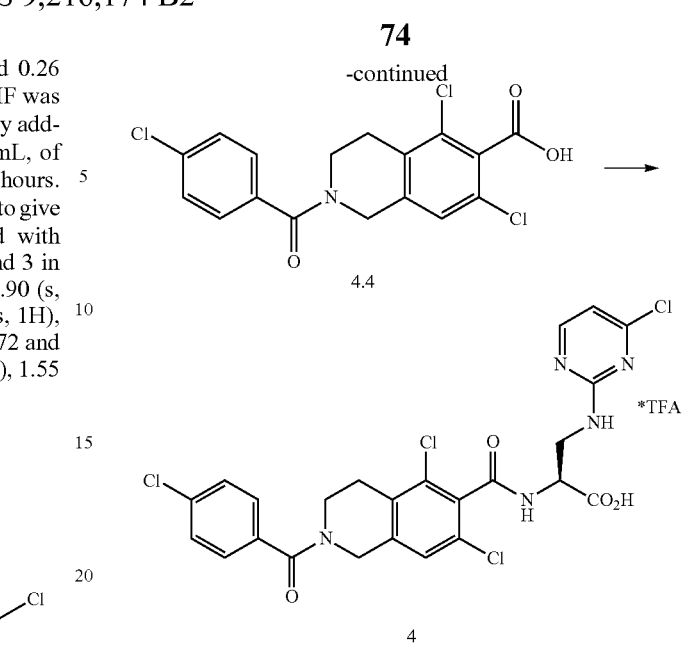

a) Boc-DAP-OH (0.2 g, 1.0 mmol), 2,4-dichloropyrimidine (0.29 g, 2.0 mmol), and diisopropylethylamine (0.51 mL, 2.9 mmol) in ethanol (5 mL) were heated to 75° C. for 14 hours. The reaction mixture was cooled to room temperature and the solvent removed under reduced pressure. The resulting crude product 4.1 was pure enough to carry forward to the next chemical transformation.

b) Crude residue 4.1 (0.31 g, 1.0 mmol) was dissolved in 9:1 benzene:methanol (5 mL). Trimethylsilyldiazomethane (1.0 mL, 2.0M in hexanes) was added slowly to the stirring reaction mixture and stirred for an additional 1 hour. The solvents were removed under reduced pressure to obtain oily crude residue. Purification by silica gel column chromatography using 50% ethyl acetate in hexanes was performed to afford pure 4.2 (0.21 g, 65%).

c) Compound 4.2 (0.21 g, 0.6 mmol) was dissolved in dichloromethane (5 mL). Trifluoroacetic acid (2.5 mL) was added and the reaction was stirred for 1 hour. The resulting reaction mixture was concentrated to remove any excess trifluoroacetic acid to afford amine 4.3 in quantitative yield.

d) Compound 4.4 was made according to Example 3d-f except that 4-chlorobenzoic acid was used instead of compound 1.11.

e) Compound 4 was made according to Example 3g except that compound 4.4 was used instead of compound 3.7 and compound 4.3 was used instead of compound 3.4.

EXAMPLE 5

This example describes the synthesis of

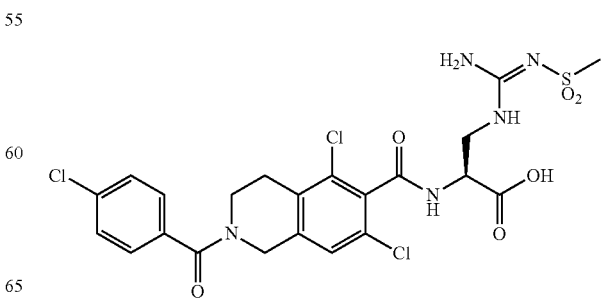

which was prepared according to Scheme 4 and the procedure below.

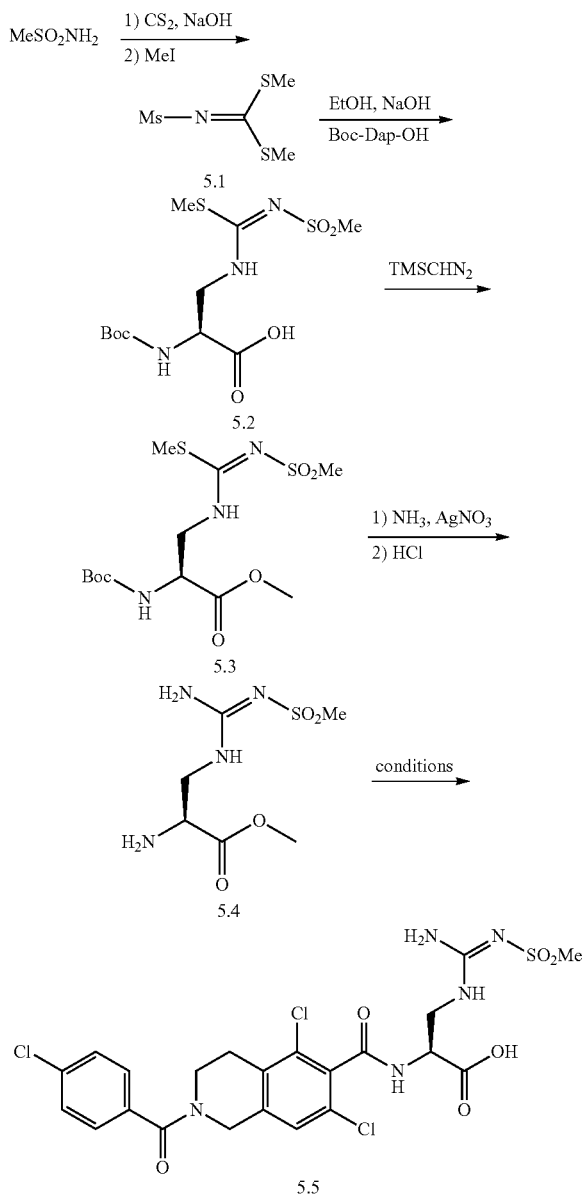

a) To a solution of methane sulfonamide (1.01 g, 10.7 mmol) in 15 mL DMF was added 20 M aqueous NaOH (0.68 mL, 13.6 mmol), resulting in a white precipitate. The solution was cooled to 0° C., carbon disulfide (0.4 mL, 6.63 mmol) slowly added, and stirred at 0° C. for 15 minutes. Additional 20M aqueous NaOH (0.32 mL, 6.4 mmol) and carbon disulfide (0.2 mL, 3.31 mmol) were added and the reaction stirred at 0° C. for 20 minutes, then raised to room temperature. At 30 minutes all precipitate had returned to solution, and the reaction mixture was cooled to 0° C. Methyl iodide (1.33 mL, 21.364 mmol) was added and the reaction stirred at 0° C. for 20 minutes and at room temperature for 1.5 hours. 20 mL water was added to the reaction and extracted five times with ethyl acetate. The combined organic extracts were dried over $MgSO_4$ and concentrated to dryness. Recrystallization from hot ethyl acetate and hexanes afforded 1.44 g compound 5.1. ESI-MS (m/z): (M+H$^+$) 200.0.

b) To a solution of Boc-Dap-OH (109 mg, 0.53 mmol) and compound 5.1 (125.7 mg, 0.632 mmol) in 5 mL ethanol was added 1.0M aqueous NaOH (0.8 mL, 0.8 mmol). The reaction was stirred until conversion was complete, and then concentrated to dryness. The residue was dissolved in water and washed three times with ether. The aqueous layer was acidified to pH 1 with 2.0M phosphoric acid, and extracted four times with ethyl acetate. The combined ethyl acetate extracts were dried over $MgSO_4$ and concentrated to dryness to afford 160.4 mg of compound 5.2. ESI-MS (m/z): (M+Na$^+$) 378.0.

c) To a solution of compound 5.2 (160.4 mg, 0.452 mmol) in 1:1 dichloromethane:methanol was added trimethylsilyl-diazomethane as a 2.0 M solution in ether (0.4 mL, 0.8 mmol). The reaction was stirred at room temperature until conversion to the methyl ester was complete, and then concentrated to dryness. The product was purified via flash chromatography to afford 146.6 mg of compound 5.3. ESI-MS (m/z): (M+Na$^+$) 270.0; $^1$H NMR (400 MHz, chloroform-d) δ 1.46 (s, 9H), 2.42 (s, 3H), 3.02 (s, 3H), 3.63 (m, 1H), 3.75 (m, 1H), 3.82 (s, 3H), 4.51 (m, 1H).

d) To a solution of compound 5.3 (146.6 mg, 0.40 mmol) in 2 mL methanol was added ammonia, 7N in methanol (0.6 mL, 4.2 mmol). This mixture was cooled to 0° C., and a solution of silver nitrate (75.5 mg, 0.444 mmol) in 0.4 mL acetonitrile was dropwise added. The reaction was stirred and allowed to reach room temperature. At three hours solvent was removed, the residue suspended in ethyl acetate, and filtered through celite. The filtrate was concentrated to dryness and redissolved in dichloromethane, to which was added HCl, 4.0 M in dioxane (0.5 mL, 2.0 mmol). This solution was stirred at room temperature for 8 hours and concentrated to dryness to afford compound 5.4 as an HCl salt. ESI-MS (m/z): (M+H$^+$) 239.

e) Compound 5 was made according to Example 3g except that compound 4.1 was used instead of 3.7 and compound 5.4 was used instead of compound 3.4. ESI-MS (m/z): (M+H$^+$) 590.0.

EXAMPLE 6

This example describes the synthesis of

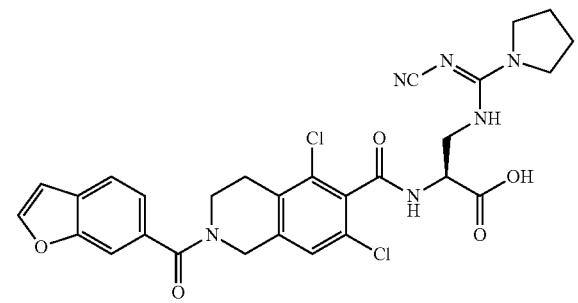 [SMILES: N#C/N=C(\NC[C@H](NC(=O)c1c(Cl)cc2c(c1Cl)CCN(C(=O)c1ccc3ccoc3c1)C2)C(=O)O)N1CCCC1]

which was prepared according to Scheme 5 and the procedure below.

SCHEME 5

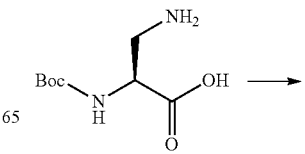

EXAMPLE 7

This example describes the synthesis of

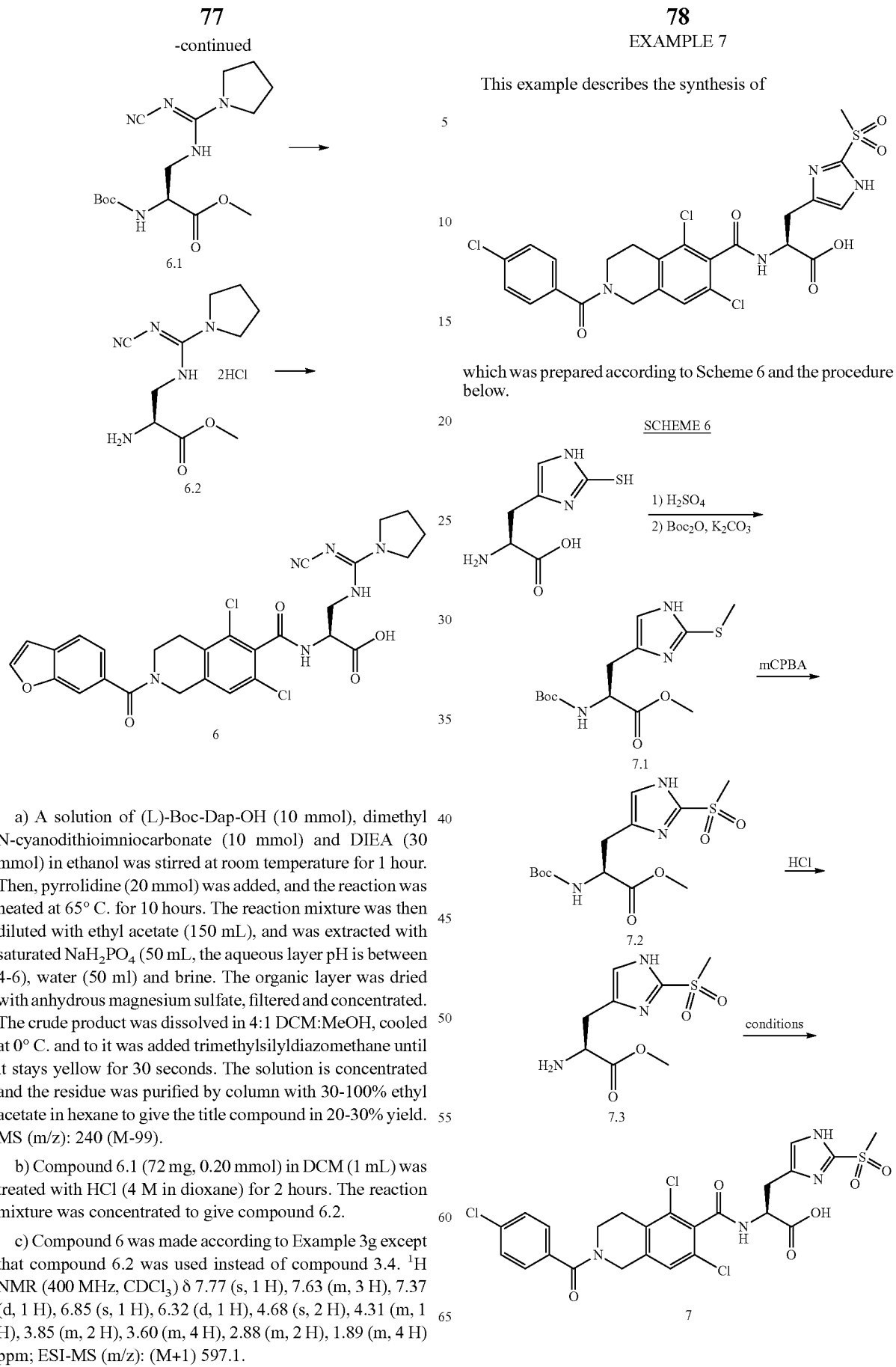

which was prepared according to Scheme 6 and the procedure below.

a) A solution of (L)-Boc-Dap-OH (10 mmol), dimethyl N-cyanodithioimniocarbonate (10 mmol) and DIEA (30 mmol) in ethanol was stirred at room temperature for 1 hour. Then, pyrrolidine (20 mmol) was added, and the reaction was heated at 65° C. for 10 hours. The reaction mixture was then diluted with ethyl acetate (150 mL), and was extracted with saturated $NaH_2PO_4$ (50 mL, the aqueous layer pH is between 4-6), water (50 ml) and brine. The organic layer was dried with anhydrous magnesium sulfate, filtered and concentrated. The crude product was dissolved in 4:1 DCM:MeOH, cooled at 0° C. and to it was added trimethylsilyldiazomethane until it stays yellow for 30 seconds. The solution is concentrated and the residue was purified by column with 30-100% ethyl acetate in hexane to give the title compound in 20-30% yield. MS (m/z): 240 (M-99).

b) Compound 6.1 (72 mg, 0.20 mmol) in DCM (1 mL) was treated with HCl (4 M in dioxane) for 2 hours. The reaction mixture was concentrated to give compound 6.2.

c) Compound 6 was made according to Example 3g except that compound 6.2 was used instead of compound 3.4. $^1$H NMR (400 MHz, $CDCl_3$) δ 7.77 (s, 1 H), 7.63 (m, 3 H), 7.37 (d, 1 H), 6.85 (s, 1 H), 6.32 (d, 1 H), 4.68 (s, 2 H), 4.31 (m, 1 H), 3.85 (m, 2 H), 3.60 (m, 4 H), 2.88 (m, 2 H), 1.89 (m, 4 H) ppm; ESI-MS (m/z): (M+1) 597.1.

a) To a solution of H-2-Mercapto-His-OH (598.8 mg, 3.2 mmol) in 5 mL methanol was added 0.26 mL sulfuric acid. This mixture was stirred at room temperature for 18 hours. Additional sulfuric acid (0.1 mL, 0.6 mmol) was added and the reaction stirred at 50° C. for 4.5 hours. Sodium carbonate (850.3 mg, 8.02 mmol) was slowly added, and the reaction concentrated via rotary evaporation to remove most of the methanol. 6 mL THF and 3 mL water were added with sodium carbonate (0.851 g, 8.03 mmol) and Boc$_2$O (696.5 mg, 3.19 mmol). The reaction was stirred at room temperature for 1 hour, diluted with ethyl acetate, and washed with water and brine. The organic layer was dried over MgSO$_4$ and concentrated to dryness. Purification via flash chromatography afforded 283.5 mg of compound 7.1. EST-MS (m/z): (M+H$^+$) 316.1.

b) Compound 7.1 (283.5 mg, 0.90 mmol) and 3-chloroperoxybenzoic acid (568.4 mg, 2.53 mmol) were dissolved in 6 mL dichloromethane and stirred at room temperature for 1.5 hours. The reaction was diluted with dichloromethane and poured into 1.0 M potassium carbonate. The aqueous layer was adjusted to neutral pH with 2.0 M phosphoric acid and extracted three times with dichloromethane. The combined organic extracts were dried over MgSO$_4$ and concentrated to dryness. Purification via flash chromatography afforded 240.8 mg of compound 7.2. ESI-MS (m/z): 370.1 (M+Na$^+$), 248.1 (M-Boc+H$^+$); $^1$H NMR (400 MHz, CDCl$_3$) δ 1.43 (s, 9H), 3.14 (m, 2H), 3.26 (s, 3H), 3.74 (s, 3H), 4.61 (m, 1H), 7.02 (s, 1H).

c) To a solution of compound 7.2 (240.8 mg, 0.6931 mmol) in dichloromethane was added HCl, 4.0 M in dioxane (1.0 mL, 4.0 mmol). The reaction was stirred at room temperature for 1.5 hours and then concentrated to dryness to afford compound 7.3 as an HCl salt. ESI-MS (m/z): (M+H$^+$) 248.

d) Compound 7 was made according to Example 3g except that compound 4.1 was used instead of compound 3.7 and compound 7.3 was used instead of compound 3.4. ESI-MS (m/z): (M+H$^+$) 599.0; $^1$H NMR (400 MHz, CDCl$_3$) δ 2.88 (s, 2H), 3.10 (m, 1H), 3.21 (s, 3H), 3.34 (m, 1H), 3.67 (1H), 3.97 (1H), 4.63 (1H), 4.85 (1H), 5.04 (dd, 1H), 7.19 (s, 1H), 7.49 (m, 5H).

EXAMPLE 8

This example describes the synthesis of

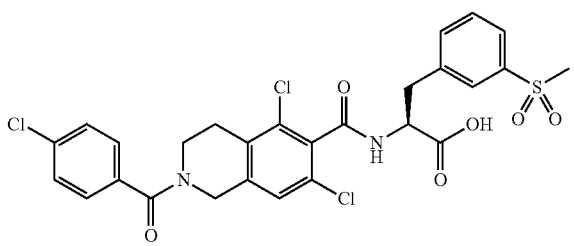 [SMILES: CS(=O)(=O)c1cccc(C[C@H](NC(=O)c2c(Cl)cc3c(c2Cl)CCN(C(=O)c2ccc(Cl)cc2)C3)C(=O)O)c1]

which was prepared in according to Scheme 7A and the procedure below.

SCHEME 7A

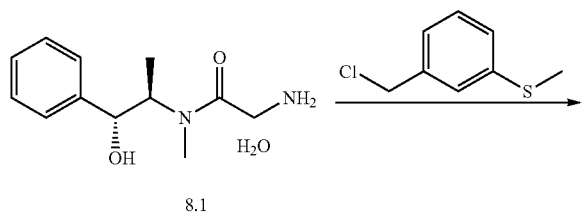

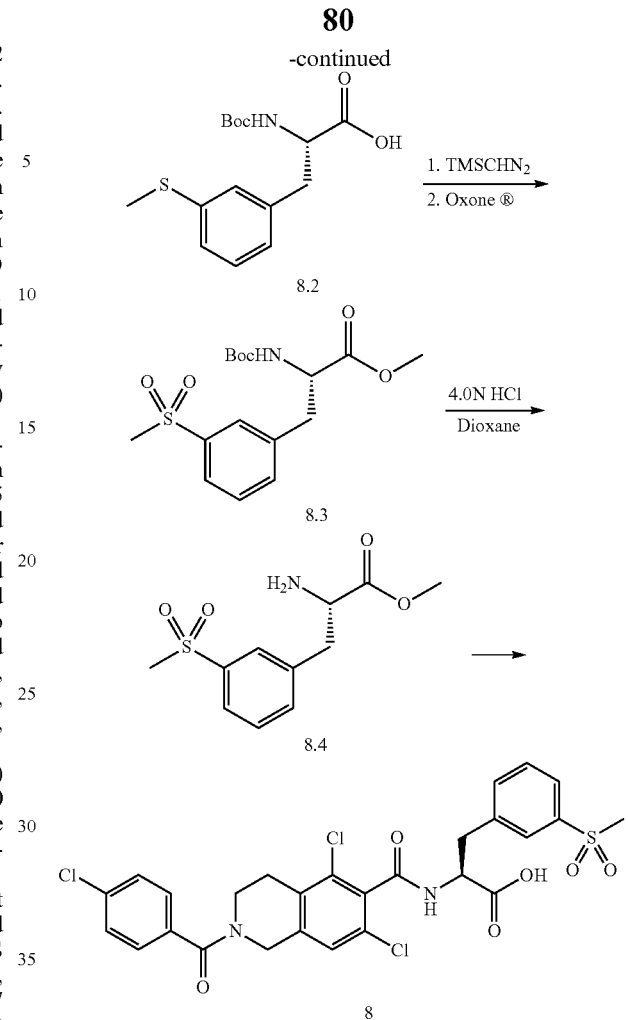

a) A three-neck flask containing 32 mmol of LiCl was flamed with a gas lamp in vacuo, followed by flushing with N$_2$. This sequence was repeated for 3 times in order to get dry LiCl. To the flask was added 10 mmol of (R,R)-(−)-pseudoephedrine glycinamide hydrate (A. G. Myers et al *J. Org. Chem.* 64: 3322-3327 (1999)) and 30 mL of dry THF at room temperature under an atmosphere of N$_2$. The suspension was then treated with 31 mmol of LiHMDS (1.0 M in THF) at 0° C. with stirring for 1 hour, followed by adding a solution of 10 mmol of 3-methylthiobenzyl chloride (S. Laufer et al *J. Med. Chem.* 45: 2733-2740 (2002)) in 5 mL of dry THF. The resulting mixture was stirred at 0° C. overnight and quenched by adding 10 mL of water. The solvent was removed, and the residue was diluted with 50 mL of water. The mixture was extracted with CH$_2$Cl$_2$ for 3 times. The organic extract was combined and dried with anhydrous Na$_2$SO$_4$. Subsequently, the solvent was removed, and the residue was purified to give the desired alkylated intermediate in 70% yield. ESI-MS (m/z): (M+H$^+$) 359.2.

A mixture of 5 mmol of the alkylated intermediate in 12 mL of 1.0 N NaOH was refluxed until the starting material was consumed. The mixture was diluted with 20 mL, of water and extracted with CH$_2$Cl$_2$ for 3 times. The aqueous phase was then stirred with 6 mmol of (Boc)$_2$O and 12 mmol of NaHCO$_3$ in 30 mL of 1,4-dioxane for 15 hours. The organic solvent was removed, and the residue was diluted with 30 mL of water and extracted with CH$_2$Cl$_2$. The aqueous phase was subsequently treated with solid citric acid to adjust the pH value to 4.0, flowed by extracting with EtOAc for 3 times. The organic extract was dried with anyhydrous Na₂SO₄. The solvent was removed, and the residue was dried in vacuo to give compound 8.2 in quantitative yield. ESI-MS (m/z): (M+H⁺) 334.10.

b) A mixture of 5 mmol of compound 8.2 in 10 mL of CH₃OH and 10 mL of CH₂Cl₂ was added 10 mmol of (trimethylsilyl)diazomethane (2.0 M in hexanes) at 0° C., the resulting mixture was stirred at room temperature for 30 minutes. The solvent was removed, and the residue was dried in vacuo to give the desired ester in quantitative yield. ESI-MS (m/z): (M+H⁺) 348.10.

To a solution of the ester in 20 mL of CH₃OH and 2 mL of water was added 12 mmol of Oxone® at room temperature, and the resulting suspension was stirred at room temperature for 15 hours. The reaction mixture was concentrated and diluted with 50 mL of EtOAc, washed with water, and dried with anhydrous Na₂SO₄. The solvent was removed and the residue was dried in vacuo to give compound 8.3 in quantitative yield. ¹H NMR (400 MHz, CD₃Cl): δ 7.82 (m, 1H), 7.69 (s, 1H), 7.50 (m, 1H), 7.43 (m, 1H), 5.03 (m, 1H), 4.62 (m, 1H), 3.74 (s, 3H), 3.26 (m, 1H), 3.09 (m, 1H), 3.03 (s, 3H), 1.39 (s, 9H) ppm; ESI-MS (m/z): (M-tBoc+H⁺) 258.1.

c) A mixture of 2 mmol of compound 8.3 in 10 mL of 4.0 N HCl in dioxane was stirred at room temperature for 15 hours. The solvent was removed, and the residue was dried in vacuo to give compound 8.4 in quantitative yield as an HCl salt. ¹H NMR (400 MHz, CD₃OD): δ 7.95 (m, 1H), 7.87 (s, 1H), 7.64 (m, 2H), 4.44 (t, J=6.85 Hz, 1H), 3.82 (s, 3H), 3.41 (m, 1H), 3.29 (m, 1H), 3.13 (s, 3H) ppm; ESI-MS (m/z): (M+H⁺) 258.10.

d) Compound 8 was made according to Example 3g except that compound 4.1 was used instead of compound 3.7 and compound 8.4 was used instead of compound 3.4. ¹HNMR (400 MHz, CD₃OD): δ 7.92 (s, 1H), 7.81 (d, J=7.92 Hz, 1H), 7.68 (d, J=7.83 Hz), 7.56 (t, J=7.83 Hz, 1H), 7.30-7.49 (m, 5H), 5.06 (m, 1H), 4.60 and 4.83 (m, 2H), 3.95 and 3.66 (m, 2H), 3.44 (d, J=13.44 Hz, 1H), 3.14 (m, 1H), 3.08 (s, 3H), 2.85 (m, 2H) ppm; ESI-MS (m/z): (M+H⁺) 609.05.

c) Compound 8.4 can also be prepared according to Scheme 7B and the procedure below.

SCHEME 7B

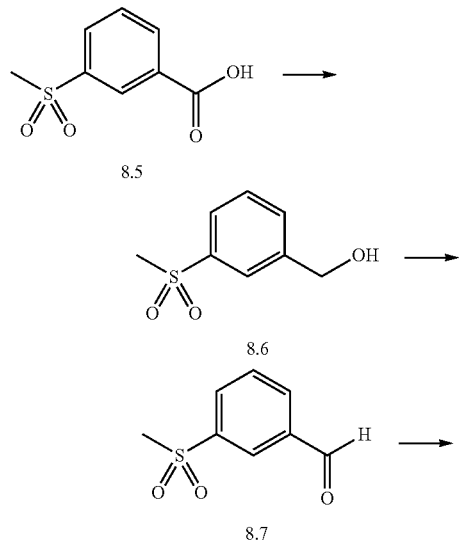

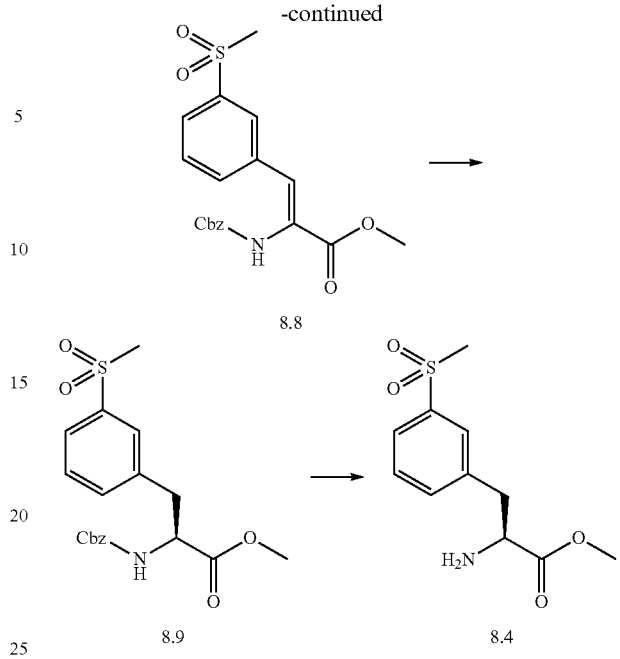

A mixture of 8.5 (1.0 mmoL), methyl iodide (1.2 mmoL) and potassium carbonate (2 mmoL) in 20 mL of acetone was heated at 50° C. for 3 hours. The solvent of the reaction mixture was removed under reduced pressure. The residue was partitioned between EtOAc and water. The aqueous solution was extracted with EtOAc, and combined organic solution was washed with brine, dried over Na₂SO₄, filtered, concentrated. The crude product as a white solid (yield 98%) was used for next step without purification.

To a solution of the compound (1 mmoL) made above in 4 mL. of THF at 0° C. was added LiAlH₄ (1.1 mmoL) slowly. The reaction mixture was allowed to warm to room temperature and stirred for 1 hour. The reaction was added consecutively with water, 15% aqueous NaOH and water with strong stirring. The filtration and evaporation of filtrate provided the crude product 8.6 (yield 92%). No purification was needed. ¹H NMR (400 MHz, CDCl₃) δ 3.05 (s, 3 H), 4.75 (s, 2 H), 7.53 (t, J=7.58 Hz, 1 H), 7.62 (d, J=7.34 Hz, 1 H), 7.81 (d, J=7.83 Hz, 1 H), 7.93 (s, 1 H).

Solid tetrapropylammonium perruthenate ("TPAP", 0.05 mmol) was added in one portion to a stirred mixture of compound 8.6 (1 mmoL), 4-methylmorpholine N-oxide ("NMO"; 1.5 mmoL) and powdered 4A molecular sieve (equal weight to that of NMO) in 5 mL of DCM at room temperature under N₂. The reaction mixture was stirred at room temperature. for 1 hour, and then filtered through a short pad of silica gel, eluting with mixture of DCM and AcOEt (1:1). The filtrate was concentrated and the residue was purified with chromatography (SiO2, AcOEt/hexane 2:1) to afford compound 8.7 (yield 72%). ¹H NMR (400 MHz, CDCl₃) δ 3.14 (s, 3 H), 7.81 (t, J=7.58 Hz, 1 H), 8.21 (t, J=9.05 Hz, 2 H), 8.46 (s, 1 H), 10.12 (s, 1 H) ppm.

The N,N,N',N',-tetramethylguanidine ("TMG"; 1.05 mmole) was added slowly to a solution of (d,1)-Cbz-α-phosphonoglycine trimethylester (1.1 mmole) in 4 ml of DCM at room temperature. After 15 minutes, the mixture was cooled to −30° C. and compound 8.7 (1 mmole) added dropwise. The mixture was kept at −30° C. for 20 minutes and slowly allowed to warm to 0° C. The solution was diluted with AcOEt and washed consecutively with 1 N NaHSO₄ and brine. The solution was dried (Na₂SO₄), and solvent evaporated to provide crude product. Purification of the crude product on chromatography (SiO2, AcOEt/hexanes/DCM 3:3:1) to give product 8.8 (yield 72%). ¹H NMR (400 MHz, CDCl₃) δ 2.97 (s, 3 H), 3.86 (s, 3 H), 5.08 (s, 2 H), 6.78 (s, 1 H), 7.34 (d, J=6.36 Hz, 5 H), 7.50 (t, J=7.83 Hz, 1 H), 7.72 (d, J=7.34 Hz, 1 H), 7.85 (d, J=7.34 Hz, 1 H), 8.04 (s, 1 H). Olefinic proton in the minor trans isomer at 7.19 ppm (s, 1 H). ESI-MS (m/z): (M+H⁺) 346.

To the solution of 8.8 (1 mmole) in MeOH (20 mL, presparged with nitrogen gas) in a glass pressure vessel was added chiral catalyst (+)-bis((2S,5S)-2,5-dimethylphospholano)benzene(cyclooctadiene)rhodium(I)tetrafluoroborate (0.01 mmole). The reactor was then pressurized with H₂ to 40 psi and shaking was continued at room temperature for 17 hours. The solvent was evaporated. The residue was dissolved in AcOEt and filtered through a plug of SiO₂ with AcOEt. The filtrate was evaporated to provide the crude product 8.9. (yield, 72%). ¹H NMR (400 MHz, CDCl₃) δ 2.98 (s, 3 H), 3.13 (dd, J=13.69, 6.36 Hz, 1 H), 3.29 (m, 1 H), 3.76 (s, 3 H), 4.69 (m, 1 H), 5.06 (m, 2 H), 5.44 (d, J=6.85 Hz, 1 H), 7.31 (m, 5 H), 7.41 (d, J=7.34 Hz, 1 H, 7.47 (t, J=7.83 Hz, 1 H), 7.72 (s, 1 H), 7.82 (d, J=7.34 Hz, 1 H). ESI-MS (m/z): (M+H⁺) 348.

The compound 8.9 was hydrogenated (Pd/C, MeOH,) with a hydrogen balloon to afford compound 8.4 (yield 98%). ESI-MS (m/z): (M+H⁺) 258.

EXAMPLE 9

This example describes the synthesis of

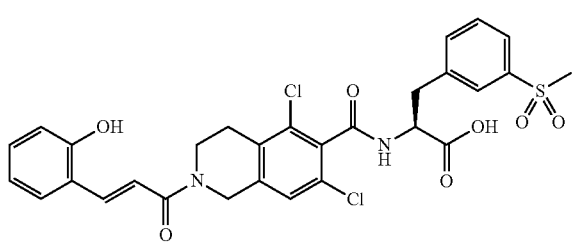 [SMILES: CS(=O)(=O)c1cccc(C[C@H](NC(=O)c2c(Cl)cc3c(c2Cl)CCN(C(=O)/C=C/c2ccccc2O)C3)C(=O)O)c1]

which was prepared in according to Scheme 8 and the procedure below.

SCHEME 8

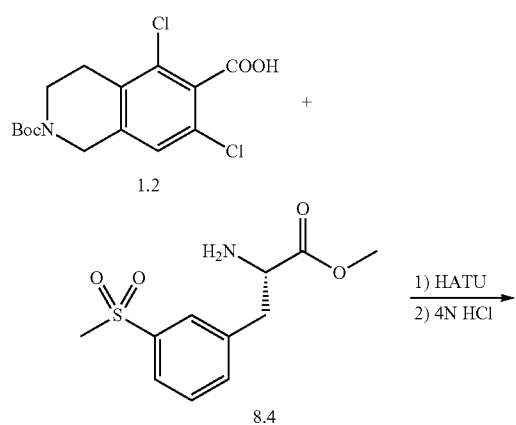

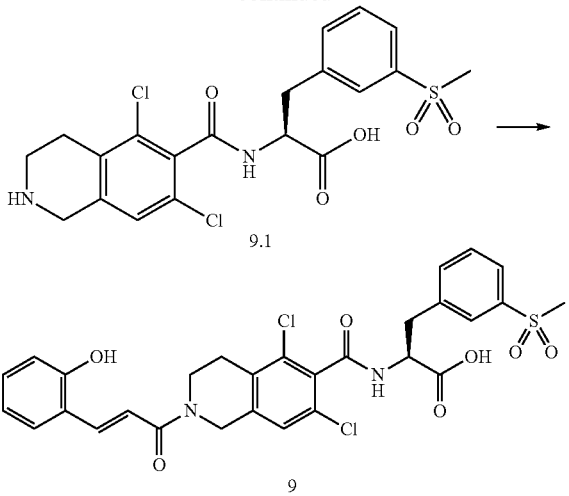

a) Compound 9.1 was made according to Example 1d-e except that compound 8.4 was used instead of compound 1.3.

b) Compound 9 was made according to Example 3g except that compound 9.1 was used instead of compound 3.7 and 2-hydroxycinnamic acid was used instead of compound 3.4. ¹H NMR (400 MHz, CD₃OD) δ 7.92 (m, 2H), 7.81 (m, 1 H), 7.68 (s, 1 H), 7.58 (m, 2 H), 7.28 (m, 2 H), 7.18 (m, 1 H), 6.84 (m, 2 H), 5.07 (m, 1 H), 4.80 and 4.88 (m, 2H), 3.96 (m, 2H), 3.42 (m, 1H), 3.15 (m, 1H), 3.08 (s, 3H), 2.71-2.91 (m, 2H) ppm; ESI-MS (m/z): (M+H⁺) 617.10.

EXAMPLE 10

This example describes the synthesis of

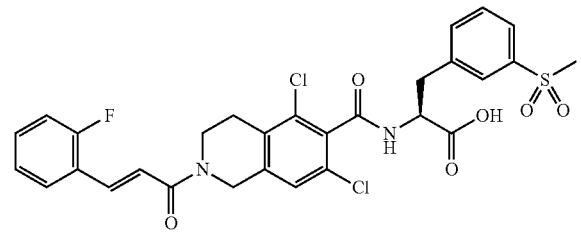 [SMILES: CS(=O)(=O)c1cccc(C[C@H](NC(=O)c2c(Cl)cc3c(c2Cl)CCN(C(=O)/C=C/c2ccccc2F)C3)C(=O)O)c1]

which was prepared according to Example 3g except that compound 9.1 was used instead of compound 3.7 and 2-fluorocinnamic acid was used instead of compound 3.4. ¹H NMR (400 MHz, CD₃OD) δ 7.92 (s, 1 H), 7.81 (m, 3H), 7.68 (m, 1H), 7.57 (m, 1H), 7.42 (m, 1H), 7.29 (m, 2H), 7.23 (m, 1H), 7.16 (m, 1H), 5.06 (m, 1H), 4.81 and 4.88 (m, 2H), 3.82 and 3.97 (m, 2H), 3.44 (m, 1 H), 3.16 (m, 1 H), 3.08 (s, 3 H), 2.86 and 2.93 (m, 2H) ppm; ESI-MS (m/z): (M+H⁺) 619.10.

EXAMPLE 11

This example describes the synthesis of

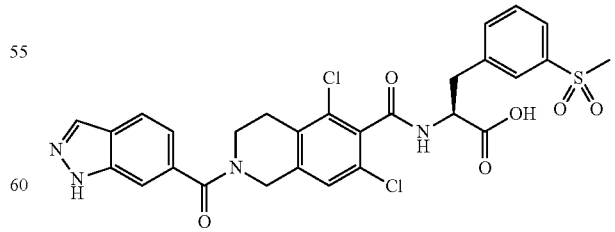

which was prepared according to Example 3g except that compound 9.1 was used instead of compound 3.7 and 6-indazolecarboxylic acid was used instead of compound 3.4. ¹H NMR (400 MHz, CD₃OD) δ 8.13 (s, 1H), 7.93 (m, 3H), 7.83 (m, 1H), 7.70 (m, 1H), 7.60 (m, 1H), 7.20 and 7.34 (m, 1H), 5.06 (m, 1H), 4.64 and 4.88 (m, 2H), 3.69 and 3.98 (m, 2H), 3.40 (m, 1H), 3.15 (m, 1H), 3.08 (s, 3H), 2.88 (m, 2H) ppm; ESI-MS (m/z): (M+H$^+$) 615.15.

EXAMPLE 12

This example describes the synthesis of

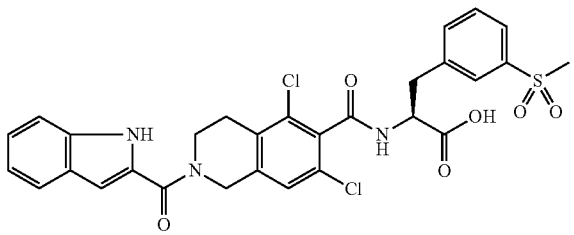 [SMILES: CS(=O)(=O)c1cccc(C[C@H](NC(=O)c2c(Cl)cc3c(c2Cl)CCN(C(=O)c2cc4ccccc4[nH]2)C3)C(=O)O)c1]

which was prepared according to Example 3g except that compound 9.1 was used instead of compound 3.7 and 2-indolecarboxylic acid was used instead of compound 3.4. $^1$H NMR (400 MHz, CD$_3$OD) δ 7.93 (s, 1H), 7.83 (m, 2H), 7.72 (m, 1H), 7.83 (m, 1H), 7.57 (m, 1H), 7.45 (m, 1H), 7.27 (s, 1H), 7.20 (m, 1H), 7.07 (m, 1H), 6.93 (s, 1H), 5.08 (m, 1H), 4.88 (m, 2H), 4.07 (m, 2H), 3.46 (m, 1H), 3.15 (m, 1H), 3.08 (s, 3H), 2.96 (m, 2H) ppm; ESI-MS (m/z): (M+H$^+$) 614.10.

EXAMPLE 13

This example describes the synthesis of

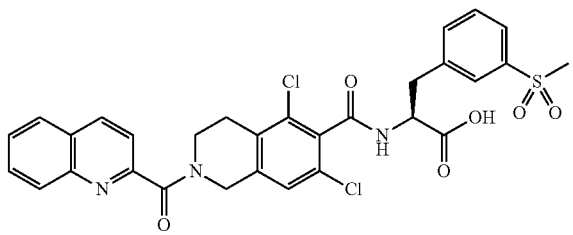 [SMILES: CS(=O)(=O)c1cccc(C[C@H](NC(=O)c2c(Cl)cc3c(c2Cl)CCN(C(=O)c2ccc4ccccc4n2)C3)C(=O)O)c1]

which was prepared according to Example 3g except that compound 9.1 was used instead of compound 3.7 and 2-quinolinecarboxylic acid was used instead of compound 3.4. $^1$H NMR (400 MHz, CD$_3$OD) δ 8.51 (m, 1H), 8.08 (m, 1H), 8.01 (m, 1H), 7.94 (m, 1H), 7.84 (m, 2H), 7.70 (m, 3H), 7.58 (m, 1H), 7.36 and 7.04 (m, 1H), 5.07 (m, 1H), 4.78 and 4.95 (m, 2H), 3.79 and 4.08 (m, 2H), 3.45 (m, 1H), 3.17 (m, 1H), 3.09 (s, 3H), 2.97 (m, 2H) ppm; ESI-MS (m/z): (M+H$^+$) 626.10.

EXAMPLE 14

This example describes the synthesis of

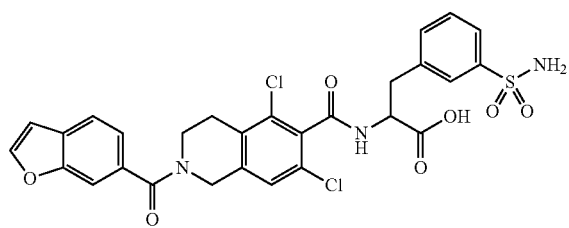 [SMILES: NS(=O)(=O)c1cccc(CC(NC(=O)c2c(Cl)cc3c(c2Cl)CCN(C(=O)c2ccc4ccoc4c2)C3)C(=O)O)c1]

which was prepared according to Scheme 9 and the procedure below.

SCHEME 9

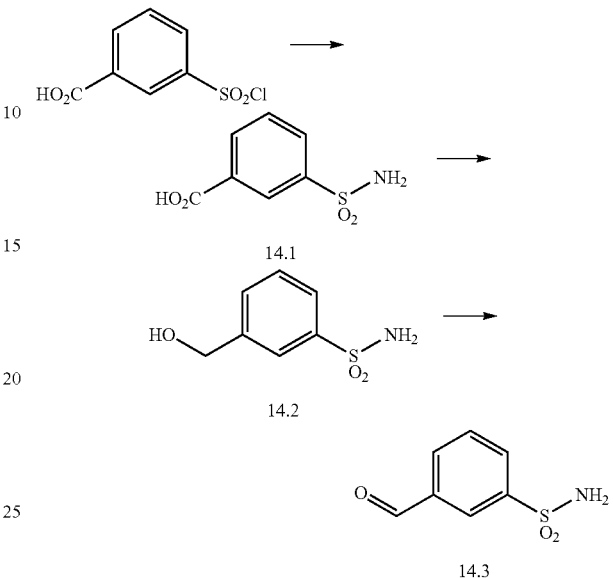

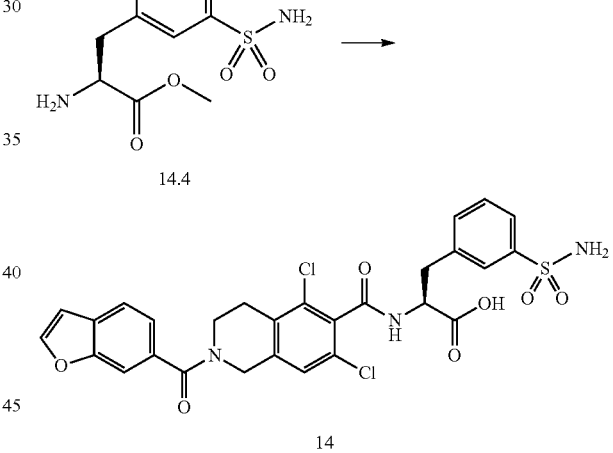

a) To a solution of 3-carboxylbenzenesulfonyl chloride (3.54 g, 16 mmol) in ethyl acetate (50 mL) at 0° C. was added concentrated ammonia (2.5 mL). The reaction was neutralized with HCl in dioance (20 mL), diluted with ethyl acetate (100 mL), dried with anhydrous sodium sulfate and filtered. Concentration of the filtrate yielded the title compound, which was used without purification.

b) Crude compound 14.1 was dissolved in THF (50 mL), to it was added borane (1.0 M in THF, 50 mL) over 20 minute period. After the reaction was stirred at room temperature for 15 hours, the reaction was diluted with brine (20 mL) and water (10 mL), extracted with ethyl acetate (100 mL). The organic extract was dried over anhydrous sodium sulfate and filtered. Concentration of the filtrate yielded the title compound, which was used without further purification.

c) To crude compound 14.2 solution in DCM (100 mL) was added activated 4A molecular sieve powder (8 g), pyridinium dichromate (7.55 g, 20 mmol). After the reaction was stirred at room temperature for 2 hours, the reaction mixture was filtered through silica gel (50 g), rinsed with ethyl acetate. The residue after concentration of the filtrate was purified by silica gel column with 30-50% ethyl acetate in hexane to give compound 14.3 (477 mg, 16%, 3 steps). ESI-MS (m/z): (M+H⁺) 186.

d) Compound 14.4 was made according to Example 8e except that compound 14.3 was used instead of compound 8.7. MS (ESI⁺) m/z: 260 (M+H¹).

e) Compound 14 was made according to Example 3g except that compound 14.4 was used instead of compound 3.4. ¹H NMR (400 MHz, CD₃OD) δ 7.89 (s, 1 H), 7.80 (s, 1 H), 7.75 (m, 2 H), 7.64 (s, 1 H), 7.57 (d, 1 H), 7.34 (d, 2 H), 6.93 9 s, 1 H), 5.00 (m, 1 H), 3.99 (m, 1 H), 3.73 (m, 1 H), 3.40 (dd, 1 H), 3.12 (dd, 1 H), 2.89 (m, 2 H) ppm; ESI-MS (m/z): 616 (M+H⁺).

EXAMPLE 15

This example describes the synthesis of

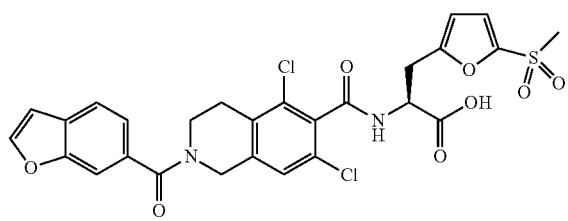 [SMILES: CS(=O)(=O)c1ccc(C[C@H](NC(=O)c2c(Cl)cc3c(c2Cl)CCN(C(=O)c2ccc4ccoc4c2)C3)C(=O)O)o1]

which was prepared according to Scheme 10 and the procedure below.

SCHEME 10

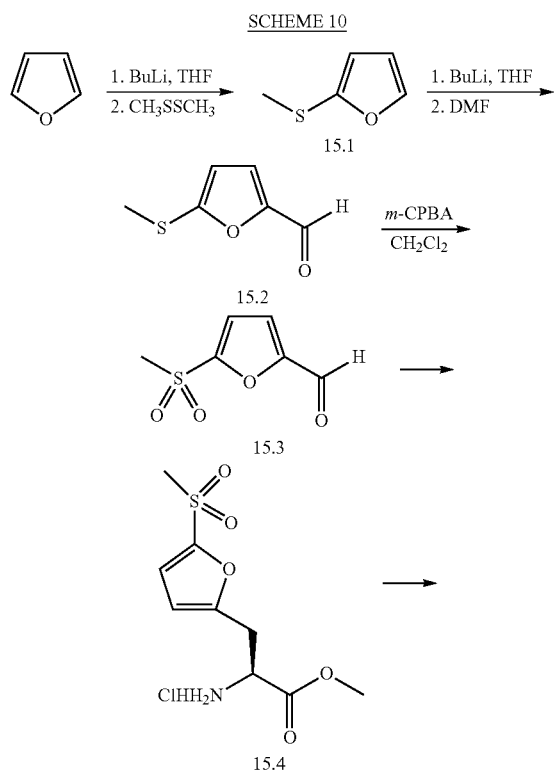

-continued

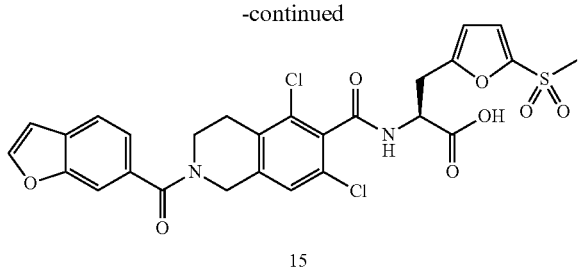

15 a) To a solution of 0.2 mol of furan in 200 mL of dry THF was added 0.2 mol of n-BuLi (1.6 M in hexanes) at −78° C., the resulting solution was stirred at room temperature for 4 hours. Subsequently, the mixture was cooled to −78° C. and treated with 0.21 mol of dimethyl disulfide, and the mixture was stirred at room temperature overnight, followed by adding 10 mL of saturated aqueous NH₄Cl. The mixture was concentrated at room temperature, and the residue was diluted with 200 mL of saturated aqueous NH₄Cl and extracted with ether. The extract was then washed with brine and dried with anhydrous Na₂SO₄. The solvent was removed, and the residue was distilled to collect the fraction at 135-140° C./760 mmHg to give compound 15.1 in 55% yield. ¹H NMR (400 MHz, CD₃Cl): δ 7.50 (s, 1H), 6.45 (m, 1H), 6.39 (s, 1H), 2.42 (s, 3H) ppm.

b) To a solution of 0.1 mol of compound 15.1 in 100 mL of dry THF was added 0.1 mol of n-BuLi (1.6 M in hexanes) at −78° C., the resulting solution was stirred at room temperature for 4 hours. Subsequently, the mixture was cooled to −78° C. and treated with 0.12 mol of dry DMF, and the mixture was stirred at room temperature overnight. The reaction was quenched by adding 10 mL of saturated aqueous NH₄Cl, and the mixture was concentrated. The residue was diluted with 100 mL of brine and extracted with EtOAC. The extract was washed with brine and dried with anhydrous Na₂SO₄. The solvent was removed and the residue was purified to give the title compound in 65% yield. ¹H NMR (400 MHz, CD₃Cl): δ 9.52 (s, 1H), 7.24 (d, J=3.4 Hz, 1H), 6.42 (d, J=3.4 Hz, 1H), 2.60 (s, 3H) ppm; ESI-MS (m/z): (M+H⁺) 143.1.

c) A mixture of 50 mmol of compound 15.2 and 120 mmol of m-CPBA in 100 mL of CH₂Cl₂ was stirred at room temperature overnight. The mixture was diluted with 150 mL of CH₂Cl₂, and the mixture was washed with saturated aqueous NaHCO₃ for several times. The solution was then dried with anhydrous Na₂SO₄ and concentrated. The residue was purified to give compound 15.3 in 70% yield. ¹H NMR (400 MHz, CD₃Cl): δ 9.83 (s, 1H), 7.33 (m, 2H), 3.27 (s, 3H) ppm; ESI-MS (m/z): (M+H⁺) 175.0.

d) Compound 15.4 was made according to Example 8e except that compound 15.3 was used instead of 8.7. ESI-MS (m/z): (M+H⁺) 248.1.

e) Compound 15 was made according to Example except that compound 15.4 was used instead of 3.4. ¹H NMR (400 MHz, CD₃OD): δ 7.92 (s, 1H), 7.76 (m, 1H), 7.67 (s, 1H), 7.34 (m, 1H), 7.13 (s, 1H), 6.69 (s, 1H), 6.49 (s, 1H), 5.11 (m, 1H), 4.73 and 4.88 (m, 2H), 3.76 and 4.02 (m, 2H), 3.46 (m, 1H), 3.30 (m, 1H), 3.17 (s, 3H), 2.94 (m, 2H) ppm; EST-MS (m/z): (M+H⁺) 605.05.

EXAMPLE 16

This example describes the synthesis of

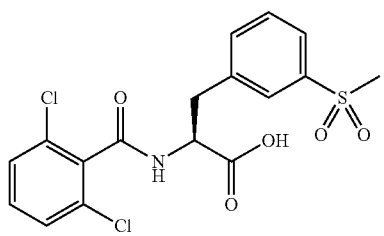 [SMILES: CS(=O)(=O)c1cccc(C[C@H](NC(=O)c2c(Cl)cccc2Cl)C(=O)O)c1]

which was prepared according to the procedure below.

To a solution of 0.2 mmol of compound 8.4 (Example 8c or 8e) in 1 mmol of Et$_3$N and 5 mL of dry CH$_2$Cl$_2$ was added 0.22 mmol of 2,6-dichlorobenzoyl chloride at 0° C., the resulting mixture was stirred at room temperature for 12 hours. The solvent was removed and the residue was dried in vacuo. Subsequently, the residue was treated with 0.8 mmol of LiOH.H$_2$O in 2 mL of THF and 0.5 mL of H$_2$O. After stirring at room temperature for 30 minutes, the reaction mixture was added 1.0 mL of 1.0N aq. HCl. The organic solvent was removed, and the residue was diluted with 10 mL of brine. The mixture was extracted with EtOAc and the extract was dried with anhydrous Na$_2$SO$_4$. The solvent was removed and the residue was dried in vacuo to give the desired compound in 65% yield. $^1$H NMR (400 MHz, CD$_3$OD) δ 7.92 (s, 1 H), 7.82 (d, J=6.85 Hz, 1 H), 7.71 (d, J=6.85 Hz, 1 H), 7.56 (t, J=7.83 Hz, 1 H), 7.34 (m, 3 H), 5.08 (dd, J=9.78, 4.89 Hz, 1 H), 3.45 (dd, J=14.67, 4.89 Hz, 1 H), 3.14 (dd, J=14.67, 9.78 Hz, 1 H), 3.08 (s, 3 H) ppm; ESI-MS (m/z): (M+H$^+$) 416.00.

EXAMPLE 17

This example describes the synthesis of

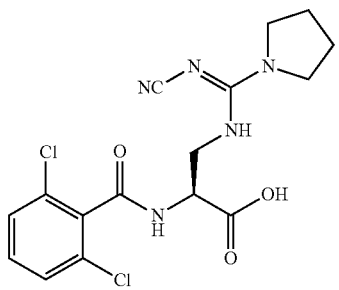 [SMILES: N#C/N=C(\NC[C@H](NC(=O)c1c(Cl)cccc1Cl)C(=O)O)N1CCCC1]

which was prepared according to the procedure basis.

Compound 6.1 (Example 6a, 0.2 mmol) in DCM (1 mL) was treated with HCl in dioxane (4.0 M, 1 mL). After 1 hour, the solvent was evaporated. The residue and 1 mmol of Et$_3$N and 5 mL of dry CH$_2$Cl$_2$ was added 0.22 mmol of 2,6-dichlorobenzoyl chloride at 0° C., the resulting mixture was stirred at room temperature for 15 hours. The solvent was removed and the residue was dried in vacuo. Subsequently, the residue was treated with 0.8 mmol of LiOH.H$_2$O in 2 mL of THF and 0.5 mL of H$_2$O. After stirring at room temperature for 30 minutes, the reaction mixture was added 1.0 mL of 1.0 N aqueous HCl. The organic solvent was removed, and the residue was diluted with 10 mL of brine. The mixture was extracted with EtOAc and the extract was dried with anhydrous Na$_2$SO$_4$. The solvent was removed and the residue was dried in vacuo to give the desired compound.

EXAMPLE 18

This example describes the synthesis of

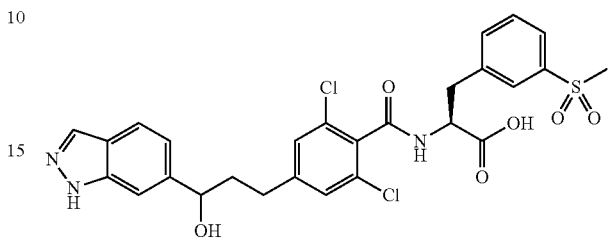

which is prepared according to Scheme 11 and the procedure below.

SCHEME 11

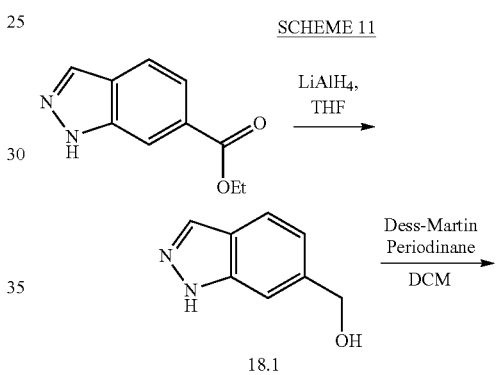

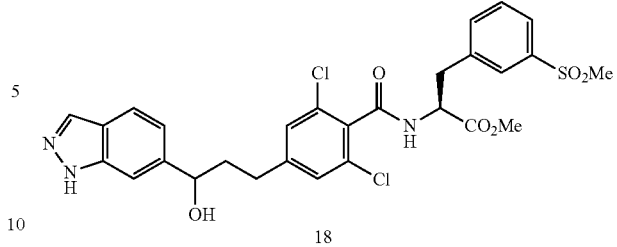
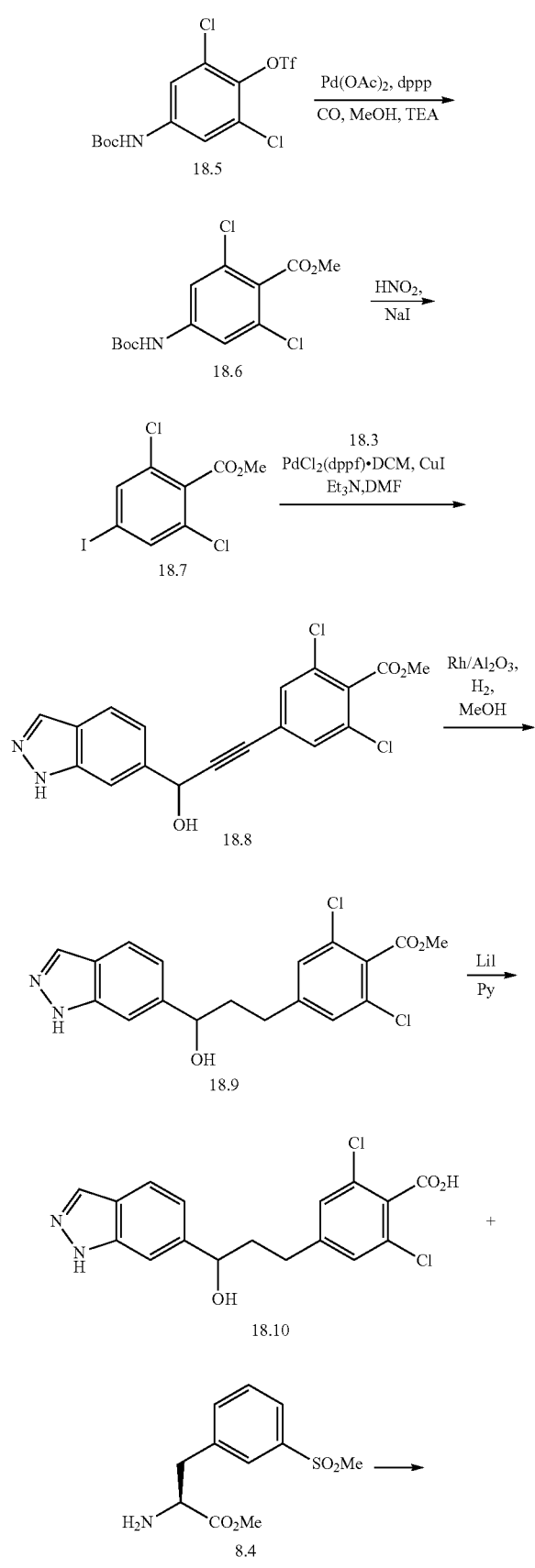

a) 1 equivalent of LiAlH$_4$ (1.0M in THF) was added to a 0° C. solution of 1 equivalent of compound ethyl 6-indazolecarboxylate (Batt, D. G., J. Med. Chem. 43: 41-58 (2000)) at −78° C. The reaction was stirred at −78° C. for another 30 minutes, and then warmed to 0° C. An aqueous solution of 1 equivalent of 1M NaOH was added slowly. The resulting slurry was filtered thru a plug of Celite and washed with a copious amount of ethyl acetate. The combined organics were dried with MgSO$_4$ and concentrated in vacuo to provide the alcohol 18.1 in high enough purity to be used without further purification.

b) 1.1 equivalent of Dess-Martin periodinane was added to 1 equivalent of 18.1 in dichloromethane. After stirring the reaction for 3 hours at room temperature, the resulting precipitate was removed by filtering thru a plug of celite. The celite plug was washed with dichloromethane. The combined organics were concentrated to provide the aldehyde 18.2 in high enough purity to be used without further purification.

c) 2.1 equivalents of ethyl magnesium bromide (0.5M in THF) were added to a pre-cooled solution containing 18.2 in THF at 0° C. After 30 minutes, the reaction was warmed to room temperature and stirred for an additional 2 hours. The resulting reaction mixture was diluted with ethyl acetate and washed with water. The organic layer was then dried with MgSO$_4$, filtered, and concentrated in vacuo. The residue was then purified on silica gel column chromatography (gradient elution using ethyl acetate and hexanes) to provide pure compound 18.3.

d) To a mixture of 4-amino-2,6-dichlorophenol (1 equivalent) in 3:2 THF/H$_2$O was added NaHCO$_3$ (1.1 equivalent) and Boc$_2$O (1.1 equivalent), after stirring overnight, the reaction was extracted with ether, and dried with MgSO$_4$, filtered, and concentrated in vacuo. The residue 18.4 was used without purification.

e) To a solution of phenol 18.4 (1 equivalent) and 2,6-lutidine (2.2 equivalent) in DCM at −78° C. was added triflic anhydride (1.2 equivalent). After the reaction mixture was gradually warmed to room temperature overnight, the reaction mixture was diluted with ether, washed with water, dried with MgSO$_4$, filtered, and concentrated in vacuo. The residue was then purified on silica gel column (gradient elution using ethyl acetate and hexanes) to provide pure compound 18.5.

f) A mixture of 10 mmol of the triflate 18.5, 1.0 mmol of dppp and 40 mmol of DIEA (in 100 mL of dry DMF and 50 mL of anhydrous CH$_3$OH was flushed with CO for 15 minutes, and then 1.0 mmol of Pd(OAc)$_2$ was added under the atmosphere of CO. Subsequently, the resulting mixture was stirred at 70° C. overnight under an atmosphere of CO. The solvent was removed and the residue was purified by column chromatography with 10-30% EtOAc in hexane to give compound 18.6.

g) 1 equivalent of Boc-aniline 18.6 was dissolved carefully in 6 M aqueous H$_2$SO$_4$, and the mixture was then cooled to 0° C. To it was added slowly with vigorous stirring sodium nitrite (1.1 equivalent in water), followed by sodium iodide (5 equivalent) in 1.5 hours. After the reaction was stirred at room temperature for overnight, the reaction was diluted with ether, washed with water, dried with MgSO$_4$, filtered, and concentrated in vacuo. The residue was then purified on silica gel column (gradient elution using ethyl acetate and hexanes) to provide pure compound 18.7.

h) 1 equivalent of iodide 18.7, 1 equivalent of alkyne 18.3, 0.05 equivalent of CuI, and 5 equivalents of triethylamine were dissolved in benzene and the solution degassed by bubbling N$_2$ thru a syringe needle and into the solution for 15 minutes. 0.05 equivalent of PdCl$_2$(dppf). DCM was added. After 4 hours, the reaction was diluted with ethyl acetate and washed with water, brine. The organic layer was then dried with MgSO$_4$, filtered, and concentrated in vacuo. The residue was then purified on silica gel column chromatography (gradient elution using ethyl acetate and hexanes) to provide pure compound 18.8.

i) 1 equivalent of 18.8 was dissolved in MeOH and 5% Rh/Al$_2$O$_3$ (20 weight %) was added. Under reduced pressure, oxygen was removed from the flask. The internal pressure was restored by the addition of hydrogen gas delivered using a hydrogen filled balloon. The reaction was stirred under an atmosphere of hydrogen gas for 14 hours. The reaction was filtered thru a pad of celite and concentrated in vacuo. The residue was then purified on silica gel column chromatography (gradient elution using ethyl acetate and hexanes) to provide pure compound 18.9.

j) 4 equivalents of LiI was added to 1 equivalent of compound 18.9 in pyridine. The reaction was refluxed for 14 hours, then allowed to cool to room temperature. The reaction was concentrated and the resulting residue was partitioned between ethyl acetate and water. The aqueous layer was extracted with ethyl acetate. The combined organic layers were dried over MgSO$_4$, filtered, and concentrated. The residue was then purified on silica gel column chromatography (gradient elution using ethyl acetate and methanol) to provide pure compound 18.10.

k) 1 equivalent of compound 18.10, 1 equivalent of compound 8.4 (Example 8c or 8e), and 3 equivalents of DIEA were dissolved in DMF. 1.1 equivalent of HATU was added. The reaction was stirred at room temperature for 14 hours. The reaction mixture was diluted with ethyl acetate and washed with water, brine. The combined organics were dried with MgSO$_4$, filtered, and concentrated. The residue was then purified on silica gel column chromatography (gradient elution using ethyl acetate and hexanes) to provide pure intermediate ester. The ester was dissolved in methanol followed by addition of 2 equivalents of 1M LiOH (aq). Upon completion, the excess solvents were removed under reduced pressure and the resulting acid was then purified by reverse phase HPLC to give pure compound 18.

EXAMPLE 19

This example describes the synthesis of

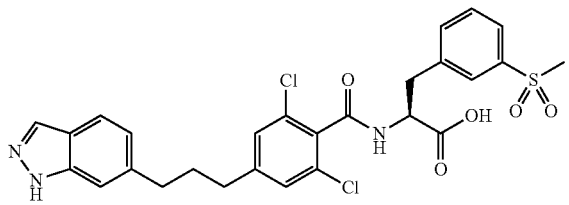 [SMILES: CS(=O)(=O)c1cccc(C[C@H](NC(=O)c2c(Cl)cc(CCCc3ccc4cn[nH]c4c3)cc2Cl)C(=O)O)c1]

which was prepared by treating a solution of compound 18 (Example 18) in DCM/TFA (1:1 ratio) with triethylsilane (10 equivalent). After LC-MS showed that the starting material was completely consumed, the reaction was concentrated, and the residue was purified by reverse phase HPLC to give the title compound.

EXAMPLE 20

This example describes the synthesis of

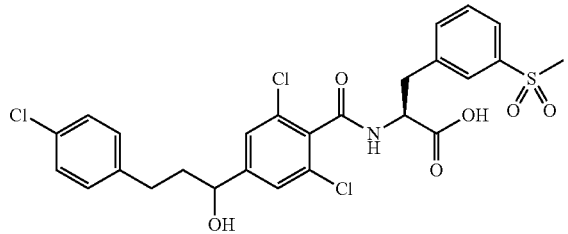 [SMILES: CS(=O)(=O)c1cccc(C[C@H](NC(=O)c2c(Cl)cc(C(O)CCc3ccc(Cl)cc3)cc2Cl)C(=O)O)c1]

which was prepared according to Scheme 12 and the procedure below.

SCHEME 12

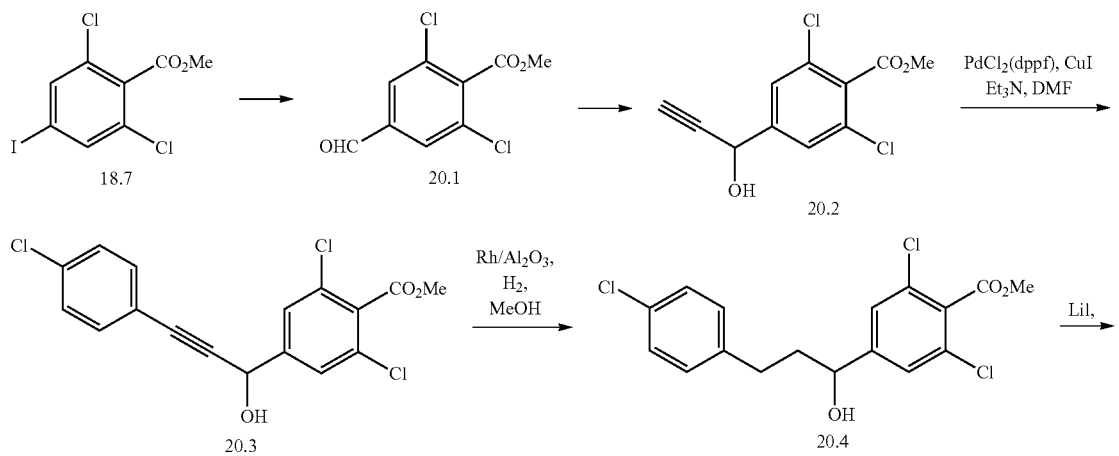

-continued

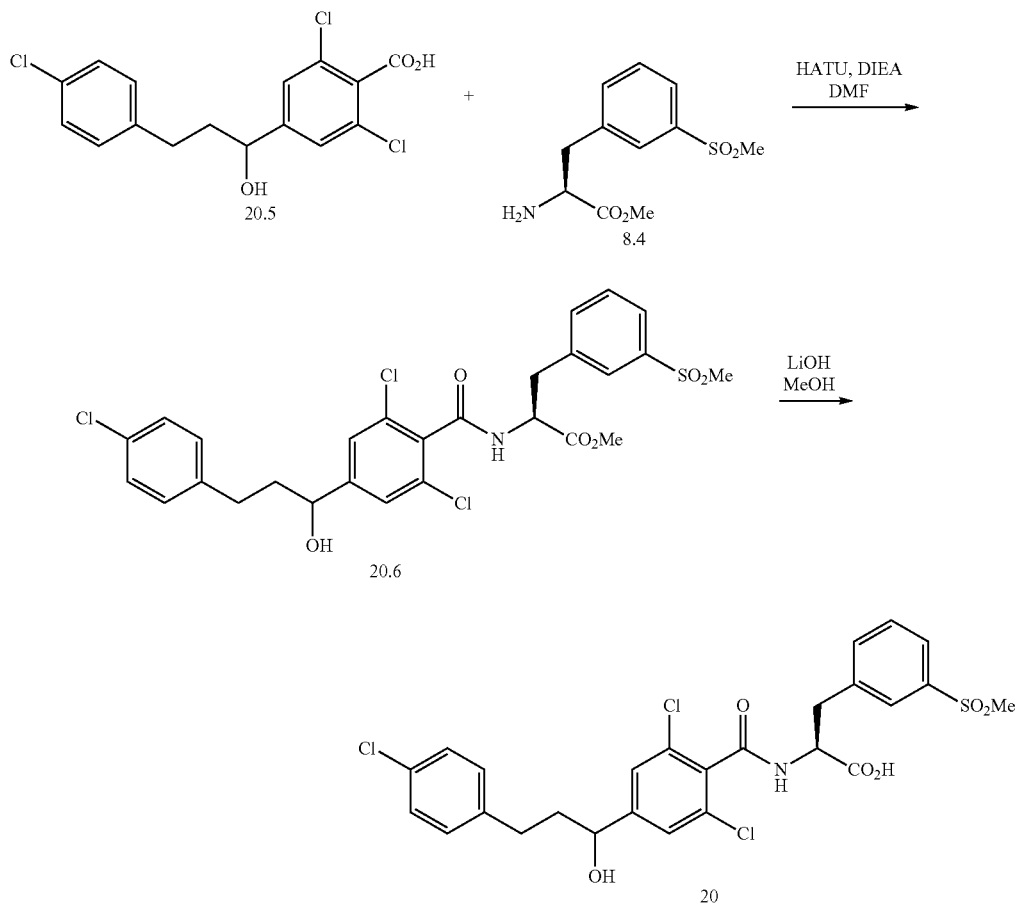

a) A solution of 1 equivalent of compound 18.7 (Example 18g) in THF at −40° C. was treated with 1.0 equivalent of isopropylmagnesium bromide. After 0.5 hour, DMF (5 equivalents) was added, and the reaction was warmed to room temperature overnight. The reaction mixture was diluted with ethyl acetate and washed with water, brine. The organic layer was then dried with $MgSO_4$, filtered, and concentrated in vacuo. The residue was then purified on silica gel column chromatography (gradient elution using ethyl acetate and hexanes) to provide pure compound 20.1.

b) To a solution of aldehyde 20.1 (1 equivalent) in THF at −78° C. was added 2.1 equivalents of ethynyl magnesium bromide (0.5 M in THF). After the reaction was warmed to room temperature and stirred for an additional 2 hours. The resulting reaction mixture was diluted with ethyl acetate and washed with water. The organic layer was then dried with $MgSO_4$, filtered, and concentrated in vacuo. The residue was then purified on silica gel column chromatography (gradient elution using ethyl acetate and hexanes) to provide pure compound 20.2.

c) 1 equivalent of compound 20.2, 1 equivalent of 1-chloro-4-iodobenzene, 0.05 equivalent of CuI, and 5 equivalents of triethylamine were dissolved in benzene and the solution degassed by bubbling $N_2$ thru a syringe needle and into the solution for 15 minutes. 0.05 equivalent of $PdCl_2$(dppf).DCM was added. After 4 hours, the reaction was diluted with ethyl acetate and washed with water, brine. The organic layer was then dried with $MgSO_4$, filtered, and concentrated in vacuo. The residue was then purified on silica gel column chromatography (gradient elution using ethyl acetate and hexanes) to provide pure compound 20.3.

d) 1 equivalent of compound 20.3 was dissolved in MeOH. 5% $Rh/Al_2O_3$ was added. Under reduced pressure, oxygen was removed from the flask. The internal pressure was restored by the addition of hydrogen gas delivered using a hydrogen filled balloon. The reaction was stirred under an atmosphere of hydrogen gas for 14 hours. The reaction was filtered thru a pad of celite and concentrated in vacuo. The residue was then purified on silica gel column chromatography (gradient elution using ethyl acetate and hexanes) to provide pure compound 20.4.

e) 4 equivalents of LiI was added to 1 equivalent of compound 20.4 in pyridine. The reaction was refluxed for 14 hours, then allowed to cool to room temperature. The reaction was concentrated and the resulting residue was partitioned between ethyl acetate and water. The aqueous layer was extracted with ethyl acetate. The combined organic layers were dried over $MgSO_4$, filtered, and concentrated. The residue was then purified on silica gel column chromatography (gradient elution using ethyl acetate and methanol) to provide pure compound 20.5.

f) 1 equivalent of compound 20.5, 1 equivalent of compound 8.4 (Example 8c or 8e), and 3 equivalents of DIEA were dissolved in DMF. 1.1 equivalent of HATU was added. The reaction was stirred at room temperature for 14 hours. The reaction mixture was diluted with ethyl acetate and washed with water, brine. The combined organics were dried with MgSO4, filtered, and concentrated. The residue was then purified on silica gel column chromatography (gradient elution using ethyl acetate and hexanes) to provide pure compound 20.6.

g) 1 equivalent of compound 20.6 was dissolved in methanol followed by 2 equivalents of 1M LiOH (aq). Upon completion, the excess solvents were removed under reduced pressure and the resulting acid was then purified by reverse phase HPLC and lyophilized to a pure powder compound 20.

EXAMPLE 21

This example describes the synthesis of

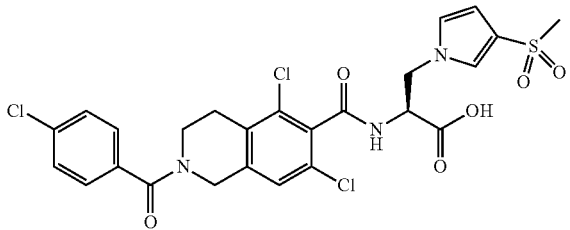 [SMILES: CS(=O)(=O)c1ccn(C[C@H](NC(=O)c2c(Cl)cc3c(c2Cl)CCN(C(=O)c2ccc(Cl)cc2)C3)C(=O)O)c1]

which was prepared according to Scheme 13 and the procedure below.

SCHEME 13

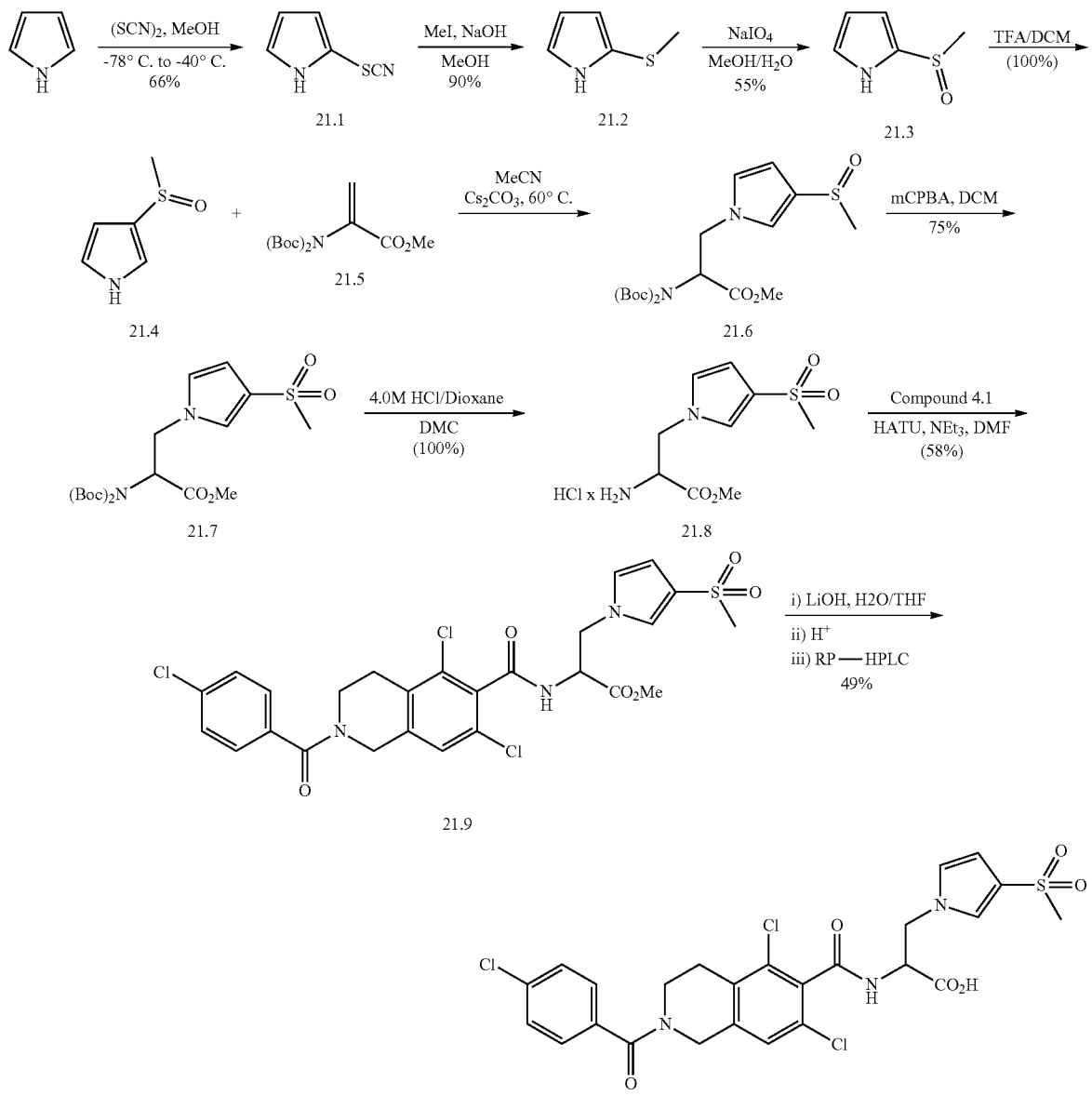

a) A solution of bromine (461 μL, 9.00 mmol) in methanol (6.0 mL) was prepared at −78° C. The cold solution was added dropwise to a mixture of KCN (1.85 g, 19.0 mmol) in methanol (6.0 mL) under nitrogen at −78° C. After 20 minutes, a solution of pyrrole (0.624 mL, 9.00 mmol) in methanol (20 mL) was added. The mixture was allowed to reach −40° C. and stirred for 0.5 hour. It was then poured into ice-water and extracted with ether (3×). The organic layers were combined and washed with saturated sodium thiosulfate and brine. The organic phase was then dried ($Na_2SO_4$) and concentrated. The crude residue was purified by flash chromatography (0-50% ethyl acetate in hexane) to yield 734 mg (66%) of compound 21.1 as a clear oil, $R_f$ 0.24 (10% ethyl acetate in hexane). $^1$H NMR ($CDCl_3$) δ 8.68 (br s, 1 H), 7.03 (s, 1 H), 6.69 (s, 1 H), 6.32 (s, 1 H). ES (+) MS m/e=125 $(M+H)^+$.

b) To a solution of 21.1 (614 mg, 4.95 mmol) and iodomethane (0.340 mL, 5.45 mmol) in methanol (40 mL) under nitrogen at −10° C. was added dropwise aqueous sodium hydroxide (9.90 mL, 1 M, 9.90 mmol). The mixture is warmed to ambient temperature and stirred for 0.5 h. Excess sodium hydroxide is then quenched by the addition of dry ice. The mixture is diluted with brine and extracted with dichloromethane (3×). The combined organic layers are dried ($Na_2SO_4$) and concentrated to yield 504 mg (90%) of compound 21.2 as a dark oil, $R_f$ 0.35 (10% ethyl acetate in hexane). $^1$H NMR ($CDCl_3$) δ 8.31 (br s, 1 H), 6.84 (s, 1 H), 6.38 (s, 1 H), 6.24 (s, 1 H), 2.36 (s, 3 H).

c) To a 0° C. solution of compound 21.2 (100 mg, 0.884 mmol) in methanol (4.0 mL) was added dropwise sodium periodate (208 mg, 0.972 mmol) in water (4.0 mL). The mixture is allowed to reach room temperature and after 15 minutes LC/MS and TLC indicated complete disappearance of compound 21.2. The mixture was then filtered, concentrated, and the residue was partitioned between ethyl acetate and water. The aqueous layer was extracted twice with ethyl acetate and the combined organic phases were washed with brine, dried ($Na_2SO_4$) and concentrated to yield 63 mg (55%) of compound 21.3 as a dark oil, $R_f$ 0.25 (ethyl acetate). $^1$H NMR ($CDCl_3$) δ 11.74 (br s, 1 H), 7.00 (s, 1 H), 6.65 (s, 1 H), 6.20 (s, 1 H), 3.03 (s, 3 H). ES (+) MS m/e=130 $(M+H)^+$.

d) To a solution of compound 21.3 (60 mg, 0.464 mmol) in dichloromethane (2.0 mL) was added trifluoroacetic acid (1.0 mL). After 15 minutes, LC/MS and TLC indicated complete consumption of compound 21.3. The solvent was removed in vacuo and the residue was dried under high vacuum to yield 60 mg (100%) of compound 21.4 as an oil, $R_f$ 0.11 (ethyl acetate). $^1$H NMR ($CDCl_3$) δ 9.16 (br s, 1 H), 7.28 (s, 1 H), 6.94 (s, 1 H), 6.66 (s, 1 H), 3.02 (s, 3 H). ES (+) MS m/e=130 $(M+H)^+$.

e) To a mixture of compound 21.4 (60 mg, 0.464 mmol) and $Cs_2CO_3$ (378 mg, 1.16 mmol) was added a solution of compound 21.5 (Ferreira et al, Tetrahedron Letters, 39: 9575 (1998); 140 mg, 0.464 mmol) in acetonitrile. The resulting mixture was stirred at 60° C. until LC/MS and TLC indicated complete consumption of the starting material (~1 hour). The mixture was cooled to room temperature, diluted with ethyl acetate and washed with water and brine. The organic layer was dried ($Na_2SO_4$) and concentrated. The crude residue was purified by flash chromatography (0-100% ethyl acetate in hexane) to yield 114 mg (57%) of compound 21.6 as a viscous oil, $R_f$ 0.31 (ethyl acetate). $^1$H NMR ($CDCl_3$) δ 7.05 (s, 1 H), 6.75 (s, 1 H), 6.50 (s, 1 H), 5.25 (m, 1 H), 4.65 (m, 1 H), 4.40 (m, 1 H), 3.79 (s, 3 H), 2.79 (s, 3 H), 1.47 (s, 18 H). ES (+) MS m/e=275 $(M-Boc-t-Bu+2H)^+$.

f) To a solution of compound 21.6 (114 mg, 0.265 mmol) in dichloromethane (1.00 mL) is added mCPBA (89.0 mg, 0.397 mmol) portionwise. After 5 minutes at room temperature, LC/MS and TLC indicated complete disappearance of compound 21.6. The mixture was filtered and concentrated. The crude residue was purified by flash chromatography (0-50% ethyl acetate in hexane) to yield 89.0 mg (75%) of compound 21.7 as a clear oil, $R_f$ 0.45 (50% ethyl acetate in hexane). $^1$H NMR ($CDCl_3$) δ 7.22 (s, 1 H), 6.69 (s, 1 H), 6.50 (s, 1 H), 5.27 (m, 1 H), 4.65 (m, 1 H), 4.45 (m, 1 H), 3.79 (s, 3 H), 305 (s, 3 H), 1.48 (s, 18 H). ES (+) MS m/e=247 $(M-2 Boc+3 H)^+$.

g) To a solution of compound 21.7 (89.0 mg, 0.0.199 mmol) in dichloromethane (0.50 mL) was added HCl (4.00 mL, 4.0 M in dioxane). The resulting mixture was stirred at ambient temperature until LC/MS indicated complete deprotection (~1 hour). The mixture was concentrated and the residue was dried under high-vacuum to yield 53 mg (100%) of compound 21.8 as white powder. ES (+) MS m/e=247 $(M+H)^+$.

h) A mixture of compound 21.8 (53.0 mg, 0.199 mmol), compound 4.1 (Example 4a, 77.0 mg, 0.199 mmol), HATU (79.0 mg, 0.209 mmol), and triethyl amine (0.111 mL, 0.796 mmol) in DMF (1.00 mL) was stirred at room temperature over night. The mixture was then diluted with ethyl acetate and washed with 1.0 M aqueous HCl, saturated $NaHCO_3$, and brine. The organic layer was dried ($Na_2SO_4$) and concentrated. The crude residue was purified by flash chromatography (0-100% ethyl acetate in hexane) to yield 70.3 mg (58%) of compound 21.9 as a white solid, $R_f$ 0.16 (75% ethyl acetate in hexane). $^1$H NMR ($CDCl_3$) δ 7.46-7.39 (m, 5 H), 7.28 (s, 1 H), 6.73 (s, 1 H), 6.69 (br s, 1 H), 6.48 (s, 1 H), 5.13 (m, 1 H), 4.83 (br s, 1 H), 4.56 (m, 1 H), 3.85 (s, 3 H), 3.70 (m, 1 H), 3.04 (s, 3 H), 2.91 (br s, 2 H), 2.81 (s, 2 H). ES (+) MS m/e=614 $(M+H)^+$.

i) To a solution of 21.9 (70.3 mg, 0.115 mmol) in THF (1.00 mL) was added LiOH (aqueous 1.0 M, 0.360 mL, 0.360 mmol). The resulting mixture was stirred at room temperature until TLC and LC/MS indicated complete hydrolysis (~0.5 hour). The reaction was then quenched by the addition of 1.0 M aqueous HCl (0.400 mL) and concentrated to dryness. The residue was taken up in dimethylsulfoxide ("DMSO"; 4.0 mL) and purified by preparative RP-HPLC. The fractions containing pure compound were consolidated and concentrated. The residue was lyophilized under high-vacuum for 48 hours to yield 33.8 mg (49%) of compound 21 as a white powder. $^1$H NMR ($CDCl_3$) δ 7.46-7.39 (m, 4 H), 7.28 (m, 2 H), 7.15 (br s, 1 H), 6.77 (s, 1 H), 6.38 (s, 1 H), 5.74 (br s, 2 H), 5.04 (m, 1 H), 4.83 (br s, 1 H), 4.53 (m, 3 H), 3.69 (m, 1 H), 3.00 (s, 3 H), 2.85 (br s, 2 H). ES (+) MS m/e=600 $(M+H)^+$.

EXAMPLE 22

This example describes the synthesis of

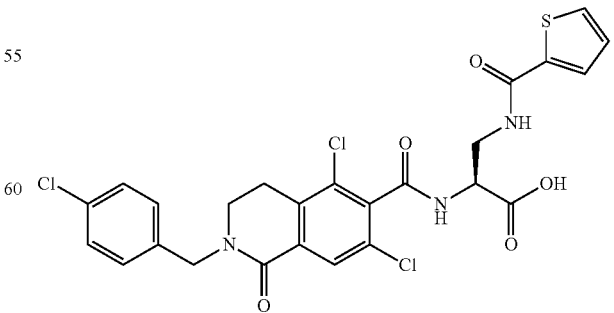

which was prepared according to Scheme 14 and the procedure below.

SCHEME 14

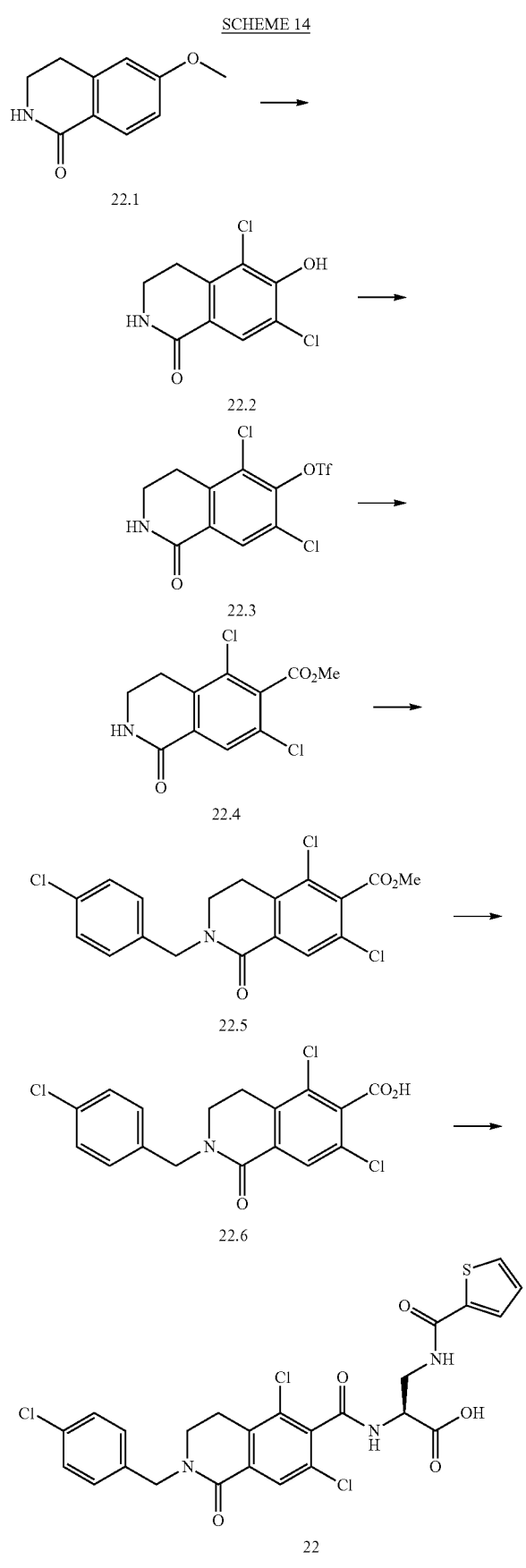

a) A solution of 5.0 g (28.2 mmol) of compound 22.1 (Plobeck et al., *J. Med. Chem.* 43:3878-3894 (2000)) and sulfuryl chloride (100 mmol each, added at the beginning of the reaction and after 15 hours) in acetic acid (50 mL) was refluxed for 36 hours. The off white solid after concentration of the reaction mixture was rinsed with ether, and to the resulting crude product was added DCM (50 mL), followed by $BBr_3$ (1.0 M in DCM, 100 mL). After 6 hours, the reaction mixture is concentrated, and water (50 mL) was carefully added. The resulting precipitate is collected by suction filtration and dried to give crude compound 22.2 in quantitative yield.

b) The crude compound 22.2 was dissolved in DCM/pyridine (50 mL/50 mL) and cooled to 0° C. To it was slowly added triflic anhydride (42.3 mmol), and the reaction was then stirred at room temperature for 6 hours. The reaction mixture was partitioned between ethyl acetate (200 mL) and water (50 mL), and the organic layer was washed with water (30 mL, twice) and brine, dried over anhydrous sodium sulfate and filtered. The residue after concentration of the filtrate was purified by silica gel column chromatography to give compound 22.3 (3.16 g, 32%). ESI-MS (m/z): (M+H$^+$) 364/366.

c) Carbon monoxide gas was bubbled through a mixture of compound 22.3 (581 mg, 1.6 mmol), BiNAP (0.2 mmol), palladium acetate (0.2 mmol), triethylamine (1 mL), anhydrous methanol (3 mL) and anhydrous DMF (3 mL) for 10 min, then the reaction was heated at 65° C. under a carbon monoxide balloon for 15 hours. The reaction mixture was partitioned between ethyl acetate (100 mL) and water (25 mL.), and the organic layer was washed with water (25 mL, twice) and brine, dried over anhydrous magnesium sulfate and filtered. The residue after concentration of the filtrate was purified by silica gel column to give compound 22.4 (213 mg, 49%). ESI-MS (m/z): (M+H$^+$) 274/276.

d) To a suspension of sodium hydride (24 mg, 1.0 mmol) in THF (2 mL) was added compound 22.4 (63 mg, 0.23 mmol), 4-chlorobenzyl chloride (55 mg, 0.34 mmol) and tetrabutylammonium iodide (10 mg). After 6 hours, the reaction was diluted with ether and filtered through silica gel, rinsed with ether. The residue after concentration of the filtrate was purified by silica gel column to give compound 22.5 (50 mg, 55%). ESI-MS (m/z): (M+H$^-$) 398/400.

e) A mixture of compound 22.5 (50 mg) and 1 mmol of LiI in 2 mL of pyridine was reflux overnight. The reaction was concentrated in vacuo and the residue was further dried by high vacuum for 2 hour. The resulting crude compound 22.6 was used without further purification. ESI-MS (m/z): (M+1), 384.

f) Compound 22 was prepared according to Example 3g except that compound 22.6 was used instead of compound 3.7 (yield: 82%). $^1$H NMR (400 MHz, dmso-d$_6$): 9.12 (d, 1 H), 8.54 (t, 1 H), 7.90 (s, 1 H), 7.77 (dd, 1H), 7.72 (dd, 1 H), 7.42 (d, 2 H), 7.35 (d, 2 H), 7.16 (dd, 1 H), 4.77 (m, 1 H), 4.70 (s, 2 H), 3.64 (m, 2 H), 3.53 (t, 2 H), 3.01 (t, 2 H) ppm. ESI-MS (m/z): (M+H$^+$) 580.

EXAMPLE 23

This example describes the synthesis of

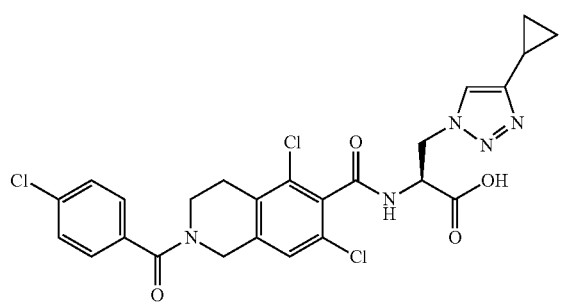 [SMILES: O=C(N[C@@H](Cn1cc(C2CC2)nn1)C(=O)O)c1c(Cl)cc2c(c1Cl)CCN(C(=O)c1ccc(Cl)cc1)C2]

which was prepared according to Scheme 15 and the procedure below.

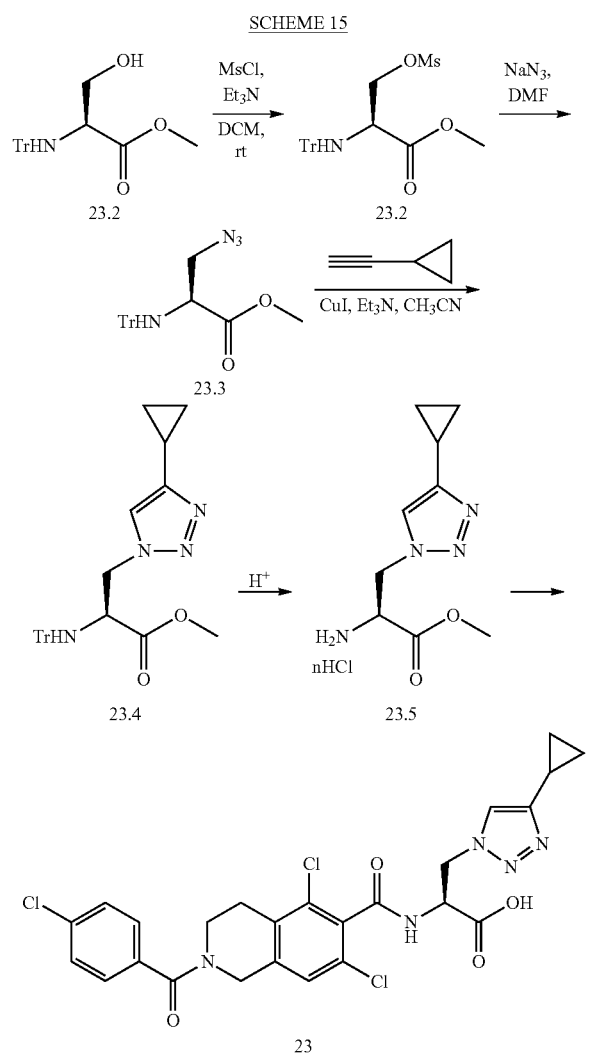

a) To a solution of Trit-Ser-Ome (compound 23.1, 10 mmol) and triethylamine in DCM (40 mL) was added slowly methanesulfhonyl chloride (11 mml), after 12 hours, the reaction was extracted with ether (100 mL), washed with water, dried over anhydrous magnesium sulfate and filtered. Concentration of the filtrate gave compound 23.2, which was used without further purification.

b) Solution of the crude compound 23.2, sodium azide (20 mmol) in DMF was stirred for 15 hours. The reaction was extracted with ether (100 mL), washed with water, dried over anhydrous magnesium sulfate and filtered. The residue after concentration of the filtrate was purified by column, eluting with 0-20% ethyl acetate in hexane to give compound 23.3.

c) A mixture of 1 mmol of compound 23.3, 1.5 mmol of cyclopropylacetylene, 0.02 mmol of CuI, and 0.02 mmol of $Et_3N$ in 6 mL of $CH_3CN$ was stirred at room temperature overnight. The solvent was removed and the residue was purified to give compound 23.4 in 65% yield. $^1$H NMR (400 MHz, $CD_3OD$): δ 7.80 (s, 1H), 7.29-7.31 (m, 6H), 7.15-7.23 (m, 9H), 4.49 (m, 2H), 3.73 (m, 1H), 3.16 (s, 3H), 1.99 (m, 1H), 0.99 (m, 2H), 0.80 (m, 2H) ppm; ESI-MS (m/z): (M+H$^+$) 453.15.

d) A mixture of 0.5 mmol of compound 23.4 in 2 mL, of 4.0 N HCl in dioxane was stirred at room temperature for 1 hours. The solvent was removed and the residue was diluted with 10 mL of water. The mixture was extracted with ether for 3 times, and the aqueous phase was dried with lyophilizer to give compound 23.5 in quantitative yield. ESI-MS (m/z): (M+H$^+$) 212.15.

e) Compound 23 was prepared according to Example 3g except that compound 4.4 was used instead of compound 3.7 and compound 23.5 was used instead of compound 3.4. $^1$H NMR (400 MHz, $CD_3OD$): δ 7.74 (s, 1H), 7.33 and 7.49 (m, 5H), 5.25 (m, 1H), 4.63-4.92 (m, 4H), 3.99 and 3.68 (m, 2H), 2.89 (m, 2H), 1.91 (m, 1H), 0.95 (m, 2H), 0.75 (m, 2H) ppm; ESI-MS (m/z): (M+H$^+$) 562.10.

EXAMPLE 24

This example describes the synthesis of

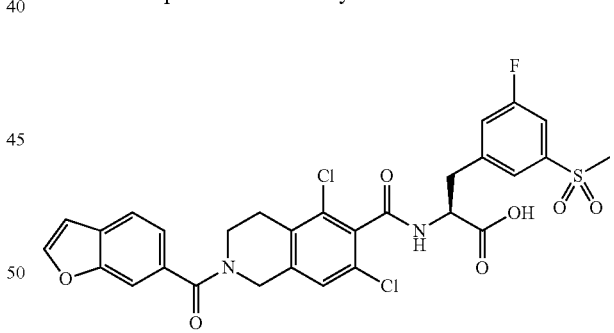

which was prepared according to Scheme 16 and the procedure below.

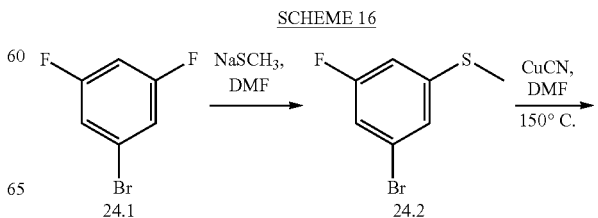

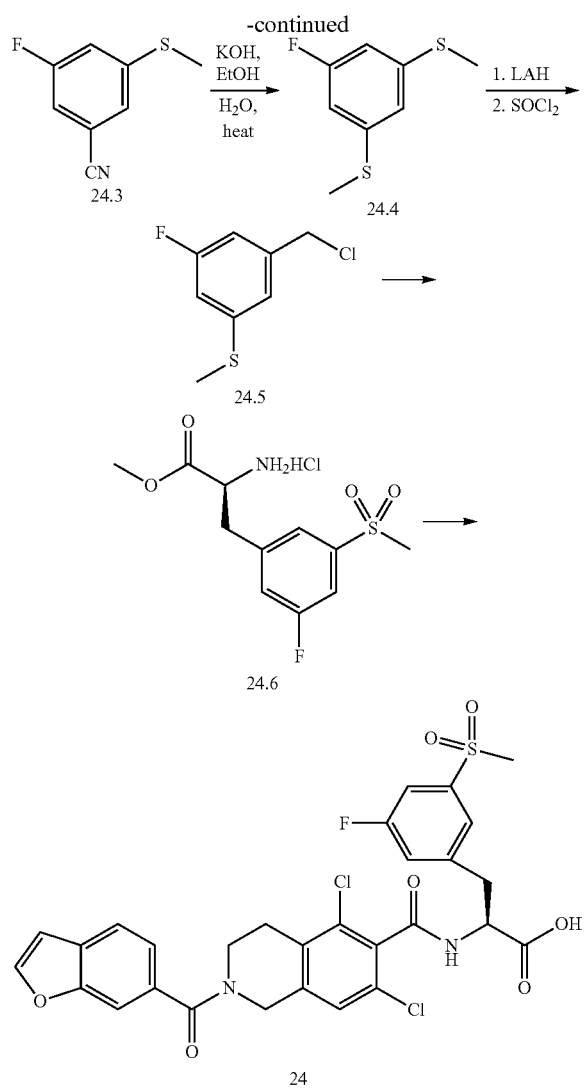

EtOAc for several time. The extract was dried with anhydrous $Na_2SO_4$. The solvent was removed and the residue was dried in vacuo to give a crude product of compound 24.4. The crude was carried on the next step without further purification. ESI-MS (m/z): (M+H$^-$) 187.0.

d) To a solution of 20 mmol of compound 24.4 in 60 mL of dry THF was added 24 mmol of LiAlH$_4$ (1.0 M in THF) at 0° C. After stirring at room temperature overnight, the reaction mixture was carefully added saturated aqueous $NH_4Cl$. The resulting suspension was then concentrated. The residue was dissolved in 200 mL of 1.0 N HCl and extracted with EtOAc for several times. The extract was dried with anhydrous $Na_2SO_4$ and concentrated. Subsequently, the residue was purified to give 5-fluoro-3-methylmercapto-1-benzeyl alcohol in 81% yield. $^1$H NMR (400 MHz, $CD_3Cl$): δ 7.03 (s, 1H), 6.86 (m, 2H), 4.69 (s, 2H), 2.51 (s, 3H) ppm; EST-MS (m/z): (M+H) 173.1.

A mixture of 15 mmol of 5-fluoro-3-methylmercapto-1-benzeyl alcohol and 20 mmol of $SOCl_2$ in 30 mL of dry $CH_2Cl_2$ was refluxed for several hours. The mixture was then diluted with 100 mL of $CH_2Cl_2$, washed with saturated aqueous $NaHCO_3$, saturated aqueous $NH_4Cl$, and brine and dried with anhydrous $Na_2SO_4$. The solvent was removed and the residue was purified to give compound 24.5 in 85% yield.

e) Compound 24.6 was prepared according to Example 3a-c except that compound 24.5 was used instead of 3-methylthiobenzyl chloride.

f) Compound 24 was prepared according to Example 3g except that compound 24.6 was used instead of compound 3.7. $^1$H NMR (400 MHz, $CD_3OD$): δ 7.92 (s, 1H), 7.80 (s, 1H), 7.75 (d, J=7.83 Hz, 1H), 7.74 (s, 1H), 7.59 (d, J=7.34 Hz, 1H), 7.49 (d, J=9.29 Hz, 1H), 7.07 and 7.35 (m, 2H), 6.96 (s, 1H), 5.10 (dd, J=9.78, 4.40 Hz, 1H), 4.72 and 4.91 (m, 2H), 3.77 and 4.00 (m, 2H), 3.50 (dd, J=14.18, 4.40 Hz, 1H), 3.20 (m, 1H), 2.91 (m, 2H) ppm; ESI-MS (m/z): (M+H$^+$) 633.10.

EXAMPLE 25

This example describes the synthesis of

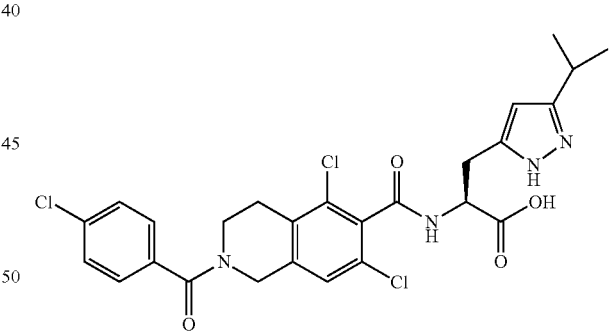

which was prepared according to Scheme 17 and the procedure below.

a) To a solution of 50 mmol of 1-bromo-3,5-difluorobenzene in 100 mL of dry DMF was added 50 mmol of NaSCH3 at 0° C., the resulting mixture was stirred at room temperature overnight and treated with 10 mL of saturated aqueous $NH_4Cl$. The mixture was diluted with 1 L of water, extracted with hexane for several times. The extract was washed with waster and dried with anhydrous $Na_2SO_4$. The solvent was removed and the residue was purified to give compound 24.2 in 90% yield. $^1$H NMR (400 MHz, $CD_3Cl$): δ 7.15 (s, 1H), 7.02 (d, J=8.3 Hz, 1H), 6.89 (d, J=9.2 Hz, 1H), 2.50 (s, 3H) ppm.

b) A mixture of 40 mmol of compound 24.2 and 42 mmol of CuCN in 100 mL of dry DMF was stirred at 150° C. overnight. The mixture was diluted with 500 mL of water, extracted with ether for several times. The mixture was then washed with diluted aqueous $NH_4OH$ and water and dried with anhydrous $Na_2SO_4$. The solvent was removed; the residue was purified to give compound 24.3 in 50% yield. $^1$H NMR (400 MHz, $CD_3Cl$): δ 7.28 (s, 1H), 7.17 (d, J=9.2 Hz, 1H), 7.11 (d, J=6.8 Hz, 1H), 2.53 (s, 3H) ppm; ESI-MS (m/z): (M+H$^+$) 168.0.

c) A mixture of 20 mmol of compound 24.3 and 22 mmol of KOH in 25 mL of EtOH and 35 mL of $H_2O$ was stirred at 60° C. for 30 minutes. The mixture was concentrated, the residue was diluted with 100 mL of water, extracted with

SCHEME 17

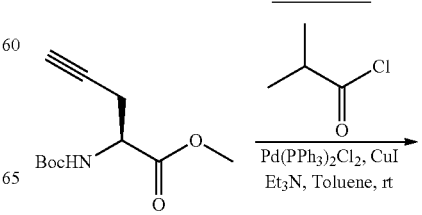

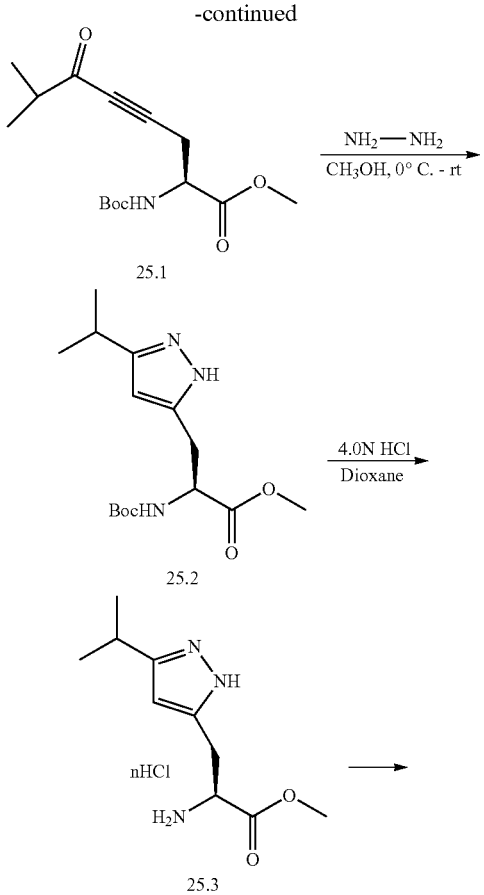

mixture was stirred at room temperature overnight and treated with 20 mL, of saturated aqueous NaHCO$_3$. The organic layer was separated and dried with anhydrous Na$_2$SO$_4$. The solvent was removed and the residue was purified by column chromatography to give compound 25.1 in 80% yield. $^1$H NMR (400 MHz, CD$_3$OD): δ 4.38 (m, 1H), 3.74 (s, 3H), 2.91 (m, 2H), 2.61 (m, 1H), 1.44 (s, 9H), 1.14 (d, J=6.85 Hz, 6H) ppm; ESI-MS (m/z): (M+H$^+$) 320.01.

b) To a solution of 1.0 mmol of compound 25.1 in 3 mL of CH$_3$OH was added 1.0 mmol of NH$_2$NH$_2$ at 0° C., the resulting mixture was stirred for another 30 minutes. The solvent was removed, and the residue was purified give compound 25.2 in 65% yield.

$^1$H NMR (400 MHz, CD$_3$OD): 6.28 and 5.95 (s, s, 1H), 4.39 and 4.19 (m, 1H), 3.72 (s, 3H), 2.91 (m, 2H), 2.70 and 2.98 (m, 1H), 1.43 and 1.45 (s, s, 9H), 1.12 and 1.27 (m, 6H) ppm; ESI-MS (m/z): (M+H$^+$) 312.20.

c) A mixture of 0.5 mmol of compound 25.2 in 4 mL of 4.0 N HCl in dioxane was stirred at room temperature for 12 hours. The solvent was removed and the residue was dried in vacuo to give compound 25.3. ESI-MS (m/z): (M+H$^+$) 212.10.

d) Compound 25 was prepared according to Example 3g except that compound 4.4 was used instead of compound 3.7 and compound 25.3 was used instead of compound 3.4.

$^1$H NMR (400 MHz, CD$_3$OD): 7.15-7.54 (m, 5H), 6.38 (s, 1H), 5.06 (dd, J=9.78, 4.89 Hz, 1H), 4.66 and 4.88 (m, 2H), 4.01 and 3.71 (m, 2H), 3.41 (dd, J=15.41, 4.65 Hz, 1H), 3.18 (dd, J=15.16, 4.65 Hz, 1H), 3.07 (m, 1H), 2.92 (m, 2H), 1.32 (d, J=7.34 Hz, 6H) ppm; ESI-MS (m/z): (M+H$^+$) 563.10.

EXAMPLE 26

This example describes the synthesis of

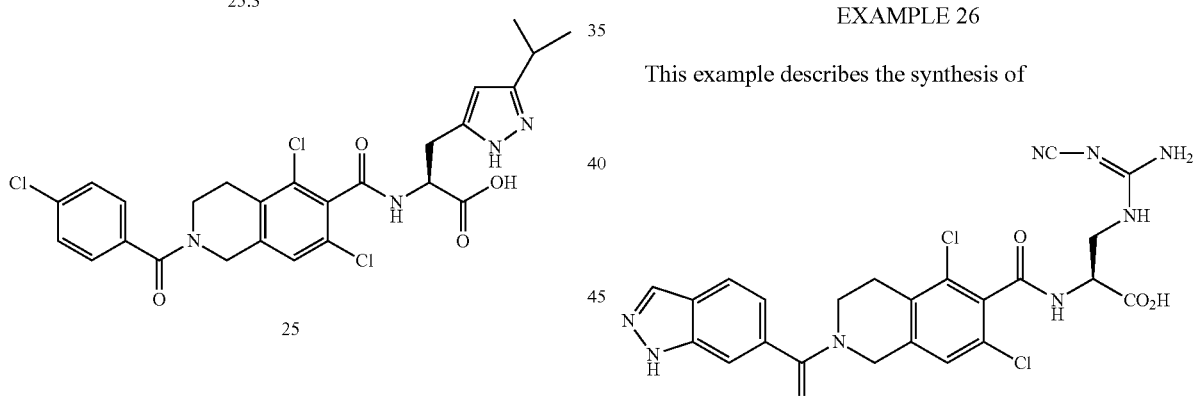

which was synthesized according Scheme 18 and the procedure below.

a) To a solution of 5.0 mmol of compound 3.2 (Example 3a), 0.25 mmol of Pd(PPh$_2$)$_2$Cl$_2$, and 0.25 mmol of CuI in 15 mmol of degassed Et$_3$N and 40 mL of degassed toluene was added 5.5 mmol of isobutyryl chloride at 0° C. The resulting

SCHEME 18

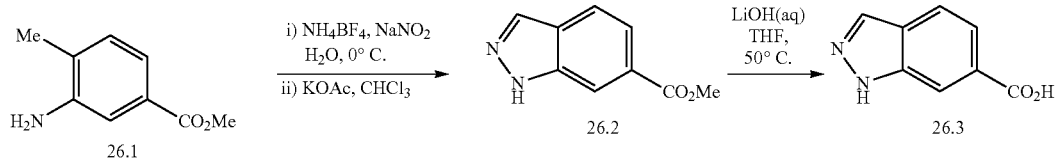

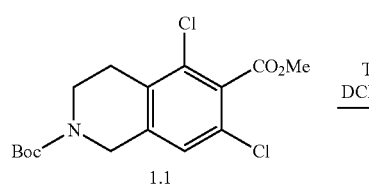
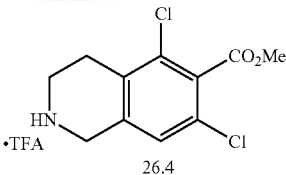
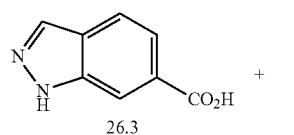
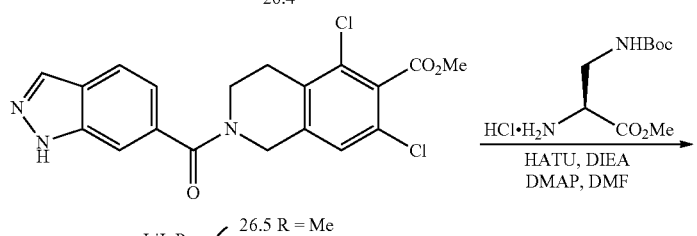
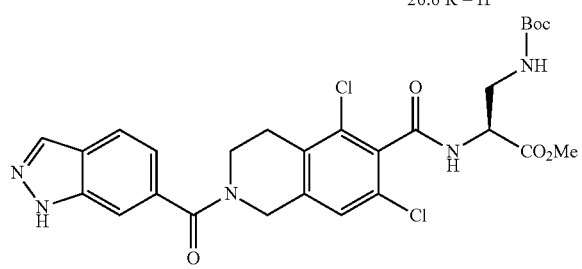
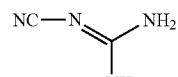
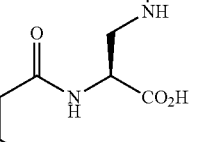

a) A solution of compound 26.1 (12.4 g, 75 mmol) and NH$_4$BF$_4$ (10.5 g, 100 mmol) in water (85 mL) was treated with concentrated HCl (15 mL), cooled to 3° C., and treated dropwise over 25 minutes with a solution of NaNO$_2$ (5.18 g, 75 mmol) in water (12 mL). The resulting thick slurry was stirred for 35 minutes, and the solid was collected by filtration, rinsed with water, methanol, and ether, and dried under N$_2$. The solid was added in one portion to a stirred mixture of KOAc (8.1 g, 82.5 mmol) and 18-crown-6 (0.5 g, 1.9 mmol) in chloroform (170 mL). After 70 minutes, water (170 mL) was added, and the layers were separated. The aqueous phase was extracted with chloroform, and the combined organic layers were rinsed with water, dried, and concentrated. The residue was triturated with hexane and the resulting solid isolated by filtration to provide 8.85 g (67% yield) of compound 26.2 as a dull yellow powder. $^1$H NMR (CDCl$_3$) δ 3.96 (s, 3H), 7.80-7.85 (m, 2H), 8.14 (s, 1H), 8.27 (s, 1H); ES (+) MS m/e=177 (M+1).

b) A solution of compound 26.2 (5.0 g, 28.4 mmol) in THF (56 mL) was treated with LiOH (21 mL of a 2M aqueous solution, 42 mmol), and the reaction mixture is stirred at 50° C. After 4 hours, the reaction mixture was cooled to room temperature and diluted with water. The basic aqueous layer was rinsed with diethyl ether, acidified to pH 3-4 by the addition of 1 M HCl, and extracted with ethyl acetate. The aqueous layer was extracted further with ethyl acetate, and the combined organic layers were rinsed with brine, dried over MgSO$_4$, and concentrated to afford 4.0 g (87% yield) of compound 26.3. $^1$H NMR (CD$_3$OD) δ 7.79-7.87 (m, 2H), 8.14 (s, 1H), 8.29 (s, 1H); ES (+) MS m/e=163 (M+1).

c) A solution of compound 1.1 (7.5 g, 20.8 mmol) in DCM (30 mL) was treated with TFA (10 mL). After 1 hour, the reaction mixture was concentrated to afford 7.8 g (100% yield) of compound 26.4. ES (+) MS m/e=261 (M+1).

d) A solution of compound 26.3 (7.8 g, 20.8 mmol), compound 26.4 (3.4 g, 20.8 mmol), 1-hydroxybenzotriazole hydrate ("HOBt", 3.5 g, 22.3 mmol), and diisopropylethylamine ("DIEA", 14 in L, 83.3 mmol) in DMF (100 mL) was treated with EDCI (4.4 g, 22.3 mmol). After 2 h, the reaction mixture was treated with 1 M HCl and extracted with ethyl acetate. The combined organic extracts were rinsed with NaHCO$_3$ (sat'd), rinsed with brine, rinsed with water, dried over MgSO$_4$, and concentrated to afford 8.4 g (99% yield) of the title compound. ES (+) MS m/e=404 (M+1).

e) A solution of compound 26.5 (8.4 g, 20.8 mmol) in pyridine (70 mL) was treated with lithium iodide (11.1 g, 83.1 mmol), and the reaction mixture was heated to 100° C. After 16 hours, the reaction mixture was cooled to room temperature and diluted with 1 M NaOH (aq). The basic aqueous layer was rinsed with diethyl ether to remove most of the pyridine. The aqueous portion was then carefully acidified with concentrated HCl to pH 3-4. The resulting slurry was filtered. The precipitate was collected and dissolved in THF, while the filtrate was extracted with ethyl acetate. The THF and ethyl acetate solutions were combined, rinsed with brine, dried over MgSO$_4$, and concentrated to afford 7.1 g (88% yield) of compound 26.6. ES (+) MS m/e=390 (M+1).

f) A solution of compound 26.6 (3.06 g, 7.83 mmol) and DIEA (4.6 mL, 25.4 mmol) in dimethylformamide ("DMF") was treated with HATU (3.06 g, 8.06 mmol), and the resulting mixture was stirred at room temperature. After 20 minutes, the reaction mixture was treated sequentially with HCl.H-DAP(Boc)-OME (2.18 g, 8.59 mmol) and N,N-dimethylaminopyridine ("DMAP", 0.568 g, 4.65 mmol). After 2.5 hours, the reaction was diluted with ethyl acetate, washed with three portions of water, washed with one portion of brine, dried over MgSO$_4$, and concentrated. Flash column chromatography afforded 3.91 g (84% yield) of compound 26.7. $^1$H NMR (400 MHz, chloroform-d) δ: 1.42 (s, 9H), 2.81 (s, 2H), 3.70 (m, 2H), 3.75 (2H), 3.81 (s, 3H), 4.82 (m, 21H), 4.99 (m, 1H), 7.21 (d, 2H), 7.59 (s, 1H), 7.81 (d, 1H), 8.10 (s, 1. MS (API-ES$^+$) m/z: 590.2 (M+H$^+$), 534.1 (M-tButyl+H$^+$), 490.1 (M-Boc+H$^-$).

g) A solution of compound 26.7 (3.91 g, 6.62 mmol) in DCM was treated with HCl (8.3 mL of a 4 M dioxane soln, 33.2 mmol), and the resulting mixture was stirred at room temperature. After 2 hours, the reaction mixture was concentrated to afford the HCl salt, which was used without further purification. The HCl salt (3.94 g, 6.99 mmol) and triethylamine ("TEA", 3.0 mL, 21.5 mmol) in methanol was treated with N-cyanoimido-S,S-dimethyl-dithiocarbonate (1.37 g, 8.43 mmol), and the reaction mixture was stirred at 50° C. After 3.5 hours, the reaction mixture was concentrated to remove most of the methanol, diluted with ethyl acetate, washed with two portions of water, washed with one portion of brine, dried over MgSO$_4$, and concentrated. Flash column chromatography afforded 3.27 g (80% yield) of compound 26.8 (MS (API-ES$^1$) m/z: 588.2 (M+H$^1$). A solution of compound 26.8 (0.10 mmol) was made in 4:1 methanol/dichloroethane ("DCE", 2.5 mL) and treated sequentially with 2 M methanolic ammonia (0.25 mmol) and silver nitrate (0.10 mmol). The reaction mixture was stirred at 50° C. until complete conversion is observed through monitoring by LCMS. The reaction mixture was then filtered through celite, and KOH (0.1 mL of a 2 M methanolic soln, 0.2 mmol) was added. The reaction mixture was stirred once again at 50° C. After 2-4 hours the reaction mixture was directly subjected to preparatory HPLC purification to afford compound 26.

EXAMPLE 27

This example describes the synthesis of

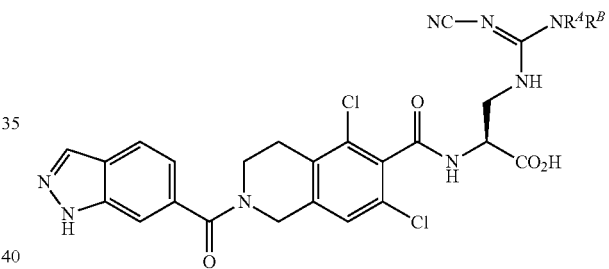

where R$^A$ and R$^B$ are each independently hydrogen, aliphatic, aromatic, heteroaromatic, or together form a cyclic moiety. These compounds are made according to the procedure of Example 26 except that a substituted amine of the formula HNR$^A$R$^B$ is used instead of ammonia in step g. Illustrative examples of substituted amines and the resulting compounds are shown in Table 1.

TABLE 1

| HNR$^A$R$^B$ | Compound |
|---|---|
| pyrrolidine (HN with 4-carbon ring) | structure with NC—N=C(NR$^A$R$^B$)NH- linked to DAP-CO$_2$H amide of dichloro-tetrahydroisoquinoline-indazole carbonyl |

TABLE 1-continued
| HNR$^A$R$^B$ | Compound |
|---|---|
| 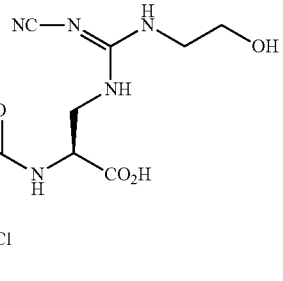 | 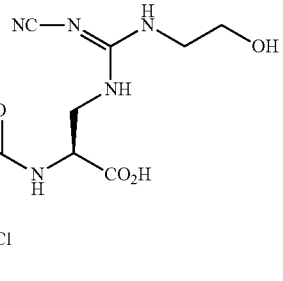 |

TABLE 1-continued
| HNR$^A$R$^B$ | Compound |
|---|---|
| 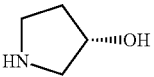 | 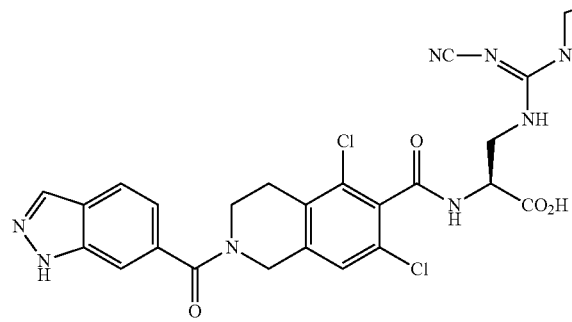 |
| 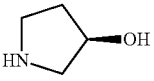 | 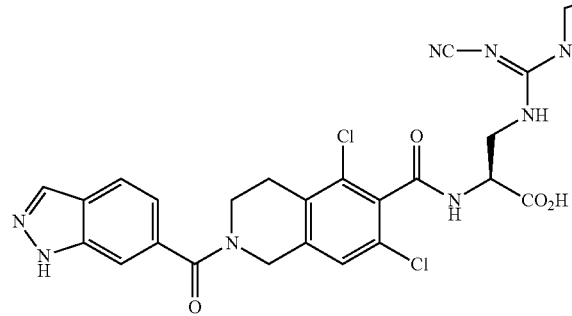 |
| 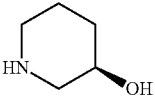 | 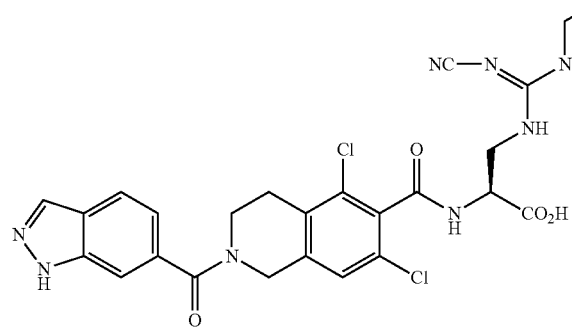 |
| 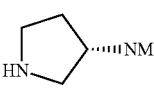 | 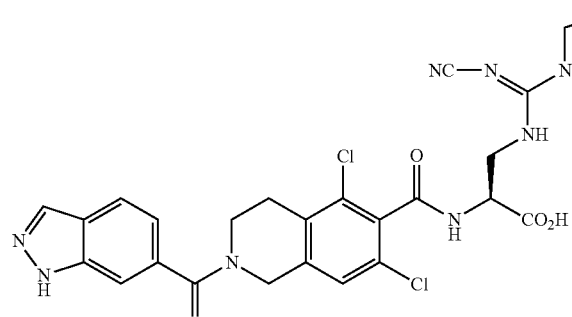 |

TABLE 1-continued

| HNR$^A$R$^B$ | Compound |
|---|---|
| 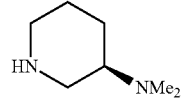 | 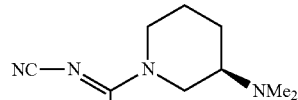 |

EXAMPLE 28

This example describes the synthesis of

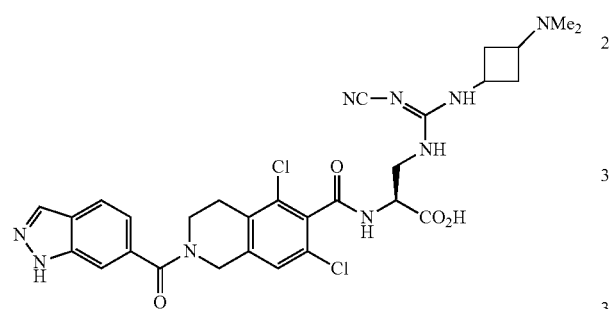

which is made according to Scheme 19 and the procedure below.

SCHEME 19

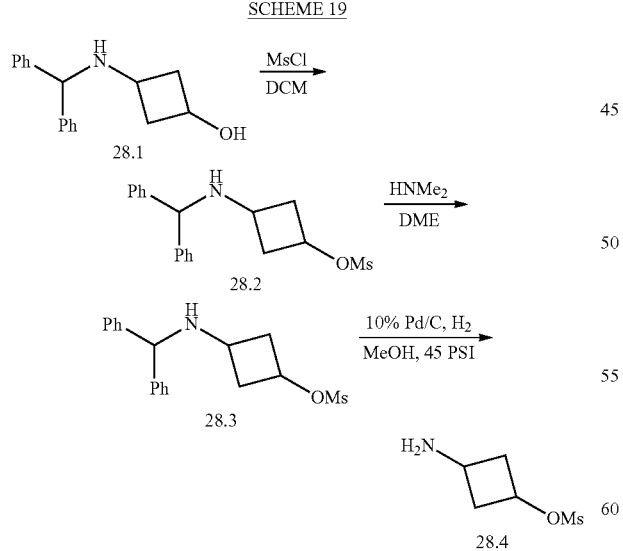

a) Compound 28.4 is prepared from 28.1 in three chemical steps, following the procedure published in Okada, T. et al *Chem. Phar. Bull.* 1993, 41(1), 126-131; Frigola, J. et al *J. Med. Chem.* 1993, 36(7), 801-810 as shown above. A solution of commercially available 28.1 in DCM is treated with trifluoromethanesulfonyl chloride in the presence of base to provide 36.2. Next, this product is dissolved in dimethoxyethane ("DME"), and the mesylate moiety is displaced by dimethylamine. Finally, Pd/C-catalyzed hydrogenolysis in MeOH at 45 PST $H_2$ (g) affords compound 28.4.

b) Compound 28 is synthesized according to the procedure of Example 26 except 3-(dimethylamino)cyclobutanol (35.1) is used instead of ammonia in step g.

EXAMPLE 29

This example describes the synthesis of

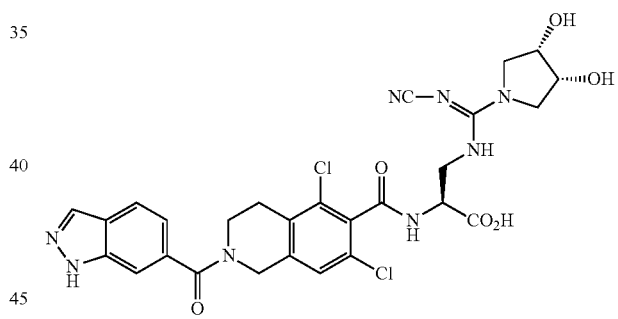

which is made according to Scheme 20 and the procedure below.

SCHEME 21

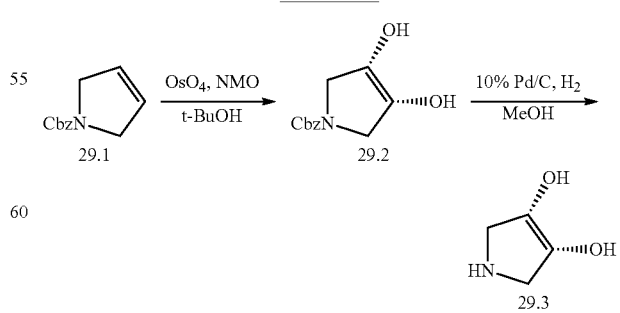

a) To a solution of benzyl-3-pyrroline-1-carboxylate (compound 29.1, 10 mmol) in THF (15 mL) was added N-methyl morphline (22 mmol) and O$_S$O$_4$ (2 mL of a 2.5 wt % in t-BuOH), and the resulting mixture was stirred at room temperature overnight. The solvent was removed; the residue was dissolved in EtOAc (100 mL), washed with dilute aq. Na$_2$SO$_3$, sat. aq. NH$_4$Cl, and brine, and dried with anhydrous Na$_2$SO$_4$. The solvent was removed and the residue was purified by column chromatography to give compound 29.2 in 55% yield. EIMS (m/z): calcd. for C$_{12}$H$_{15}$NO$_4$ (M$^-$)+Na 260.1, found 260.1; $^1$H NMR (CD$_3$OD, 400 MHz): δ 7.31-7.38 (m, 5H), 5.13 (s, 2H), 4.17 (m, 2H), 3.58 (m, 2H), 3.34 (m, 2H) ppm.

b) A mixture of compound 29.2 (1.0 mmol) and 10% Pd/C (0.1 mmol) in methanol (5 mL) is stirred at room temperature for several hours under an atmosphere of H$_2$. The reaction mixture is filtered, the filtrate is concentrated, and the residue is dried in vacuo to give compound 29.3.

c) Compound 29 is synthesized according to the procedure of Example 26 except that (3R,4S)-(dihydroxy)pyrrolidine (29.3) is used instead of ammonia in step g.

EXAMPLE 30

This example describes the synthesis of

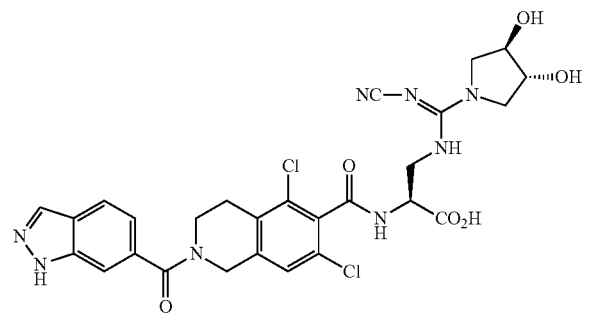 [SMILES: N#C/N=C(\NC[C@H](NC(=O)c1c(Cl)cc2c(c1Cl)CCN(C(=O)c1ccc3cn[nH]c3c1)C2)C(=O)O)N1C[C@@H](O)[C@H](O)C1]

which was prepared according to Scheme 21 and the procedure below.

SCHEME 21

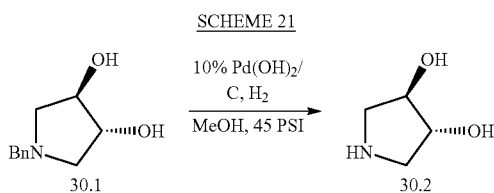 [SMILES: O[C@@H]1CN(Cc2ccccc2)C[C@H]1O ; O[C@@H]1CNC[C@H]1O]

a) A mixture of (3R,4R)-benzyl-3,4-pyrrolidindiol (compound 30.1, 1 mmol) and 20% Pd(OH)$_2$/C (0.1 mmol) in methanol (10 mL) is shaken at room temperature for several hours under 45 psi of H$_2$. (g). The reaction mixture is filtered, the filtrate is concentrated, and the residue is dried in vacuo to give compound 30.2.

b) Compound 30 is synthesized according to the procedure of Example 26 except that compound 30.2 is used instead of ammonia in step g.

EXAMPLE 31

This example describes the synthesis of

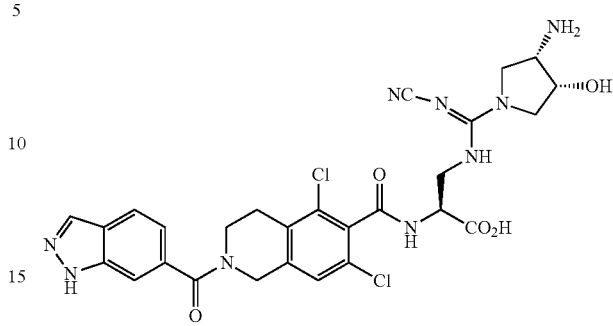

which was prepared according to Scheme 22 and the procedure below.

SCHEME 22

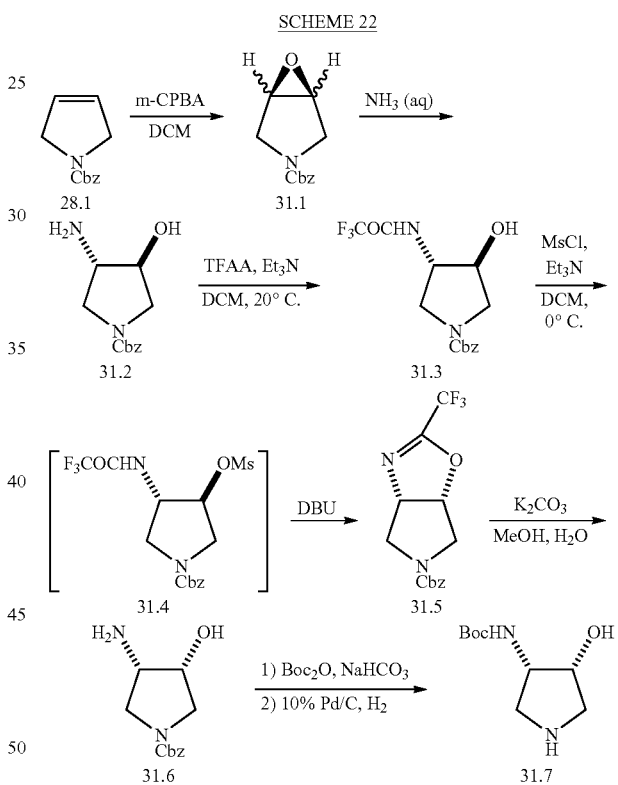

a) A mixture of commercially available benzyl 3-pyrroline-1-carboxylate (compound 28.1, 10 mmol) and m-CPBA (12 mmol) in DCM (50 mL) was stirred at room temperature overnight. The reaction mixture was diluted with DCM (100 mL) and washed sequentially with sat. aq. Na$_2$SO$_3$, and brine. The organic layer was dried with anhydrous Na$_2$SO$_4$ and then concentrated. The residue was purified by chromatography to give compound 31.1 in 80% yield. EIMS (m/z): calcd. for C$_{12}$H$_{13}$NO$_3$ (M$^+$)+Na 242.1; found 242.1; $^1$H NMR (CDCl$_3$, 400 MHz): δ 7.36-7.37 (m, 5H), 5.13 (s, 2H), 3.89 (m, 2H), 3.70 (m, 2H), 3.41 (m, 2H) ppm.

b) A mixture of compound 31.1 (5 mmol) in conc. aq. NH$_3$ (20 mL) is stirred at 65° C. overnight. The reaction mixture was concentrated and dried in vacuo to give compound 31.2. This material is used without further purification.

c) A solution of compound 31.2 (10 mmol) and Et₃N (20 mmol) in dry THF (100 mL) at −20° C. is treated dropwise with TFAA (10 mmol) over 1 hour. After 1 h, the reaction mixture is quenched with sat. aq. NH₄Cl (1 mL). The solvent is removed and the residue is dissolved in DCM (100 mL). The mixture is subsequently washed sequentially with sat. aq. NH₄Cl, sat. aq. NaHCO₃, and brine. The organic layer is dried with anhydrous Na₂SO₄, the solvent was removed, and the residue is purified by chromatography to afford compound 31.3.

d) A solution of compound 31.3 (5 mmol) and Et₃N (10 mmol) dry DCM (20 mL) at 0° C. is treated dropwise with MsCl (5.5 mmol), and the mixture is allowed to come gradually to room temperature. After 1 hour at room temperature, the reaction mixture containing in situ generated 31.4 is treated with DBU (30 mmol), and the resulting mixture is stirred at for several hours. The solvent is removed, and the residue is purified by chromatography to afford compound 31.5.

e) A mixture of compound 31.5 (3 mmol) and K₂CO₃ (6 mmol) in 2/1 (v/v) MeOH/H₂O (15 mL) is stirred at room temperature. After 24 h, the solvent is removed; the residue is treated with sat aq. NaHCO₃ (20 mL), and the mixture is extracted with DCM several times. The extract is dried with Na₂CO₃., the solvent is removed, and the residue is purified by chromatography to afford compound 31.6.

f) A mixture of compound 31.6 (2 mmol), NaHCO₂ (3 mmol), and Boc₂O (2.2 mmol) in 1:1 1,4-dioxane/water (20 mL) is stirred at room temperature for several hours. The mixture is diluted with brine (50 mL) and extracted with EtOAc several times. The combined extracts are washed with brine, dried with anhydrous Na₂SO₄, and concentrated. The residue is purified by chromatography to give the N-Boc protected intermediate. A mixture of this intermediate (1 mmol) and 10% Pd/C (0.1 mmol) in MeOH (5 mL) is stirred at room temperature for several hours under an atmosphere of H₂ (g). The reaction mixture is filtered, the filtrate is concentrated, and the residue is dried in vacuo to afford compound 31.7.

g) Compound 31 is prepared according to Example 26g except that compound 31.7 is used instead of ammonia.

EXAMPLE 32

This example describes the synthesis of

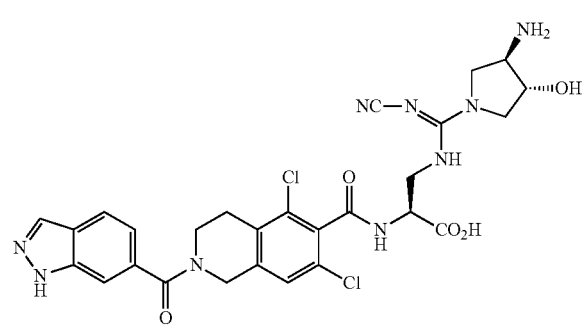 [SMILES: N#C/N=C(\NC[C@H](NC(=O)c1c(Cl)cc2c(c1Cl)CCN(C(=O)c1ccc3cn[nH]c3c1)C2)C(=O)O)N1C[C@@H](N)[C@H](O)C1]

which is prepared according to Scheme 23 and the procedure below.

SCHEME 23

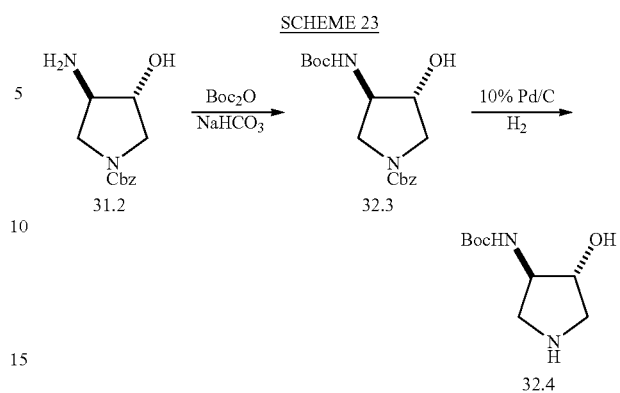

a) A mixture of compound 31.2 (2 mmol), NaHCO₃ (3 mmol), and Boc₂O (2.2 mmol) in 1:1 1,4-dioxane/water (20 mL) is stirred at room temperature for several hours. The mixture is diluted with brine (50 mL) and extracted with EtOAc several times. The combined extracts are washed with brine, dried with anhydrous Na₂SO₄, and concentrated. The residue is purified by chromatography to afford compound 32.3.

b) A mixture of compound 32.3 (1 mmol) and 10% Pd/C (0.1 mmol) in MeOH (5 mL) is stirred at room temperature for several hours under an atmosphere of H₂ (g). The reaction mixture is filtered, the filtrate is concentrated, and the residue is dried in vacuo to afford compound 32.4.

c) Compound 32 is prepared according to Example 26g except that compound 32.4 is used instead of ammonia.

EXAMPLE 33

This example describes the synthesis of

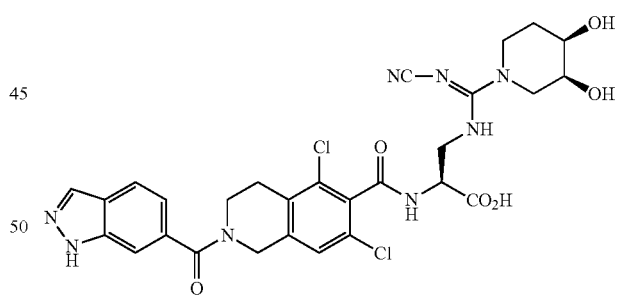

which is prepared according to Scheme 24 and the procedure below.

SCHEME 24

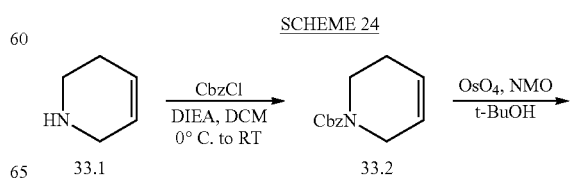

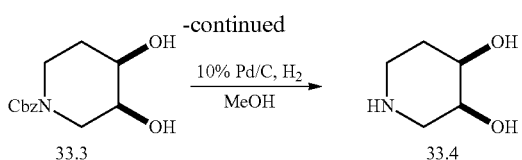

a) A solution of compound 33.1 (10 mmol) and DIEA (25 mmol) in DCM (20 mL) at 0° C. is treated dropwise with benzyl chloroformate (10 mmol), and the reaction mixture is allowed to come to room temperature. After 2 h at RT, the reaction mixture is diluted with ethyl acetate (100 mL), rinsed with 1 M HCl (50 mL), rinsed with brine, dried over MgSO$_4$, and concentrated to afford compound 33.2.

b) A solution of compound 33.2 (10 mmol) and N-methyl morpholine (22 mmol) in THF (15 mL) is treated with O$_s$O$_4$ (2 mL of a 2.5 wt % in t-BuOH), and the resulting mixture is stirred at room temperature overnight. The solvent is removed. The residue is dissolved in EtOAc (100 mL), washed with dilute aq. Na$_2$SO$_3$, sat. aq. NH$_4$Cl, and brine, and then dried over anhydrous Na$_2$SO$_4$. The solvent is removed, and the residue is purified by column chromatography to give the title compound.

c) A mixture of compound 33.3 (1.0 mmol) and 10% Pd/C (0.1 mmol) in methanol (5 mL) is stirred at room temperature for several hours under an atmosphere of H$_2$. The reaction mixture is filtered, the filtrate is concentrated, and the residue is dried in vacuo to give compound 33.4.

d) Compound 33 is prepared according to Example 26g except that compound 33.4 is used instead of ammonia.

EXAMPLE 34

This example describes the synthesis of

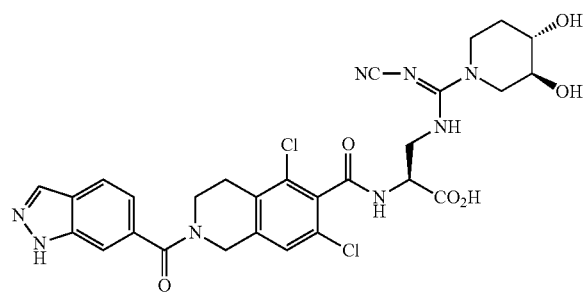 [SMILES: N#C/N=C(\NC[C@H](NC(=O)c1c(Cl)cc2c(c1Cl)CCN(C(=O)c1ccc3cn[nH]c3c1)C2)C(=O)O)N1CC[C@H](O)[C@@H](O)C1]

which is prepared according to Scheme 25 and the procedure below.

SCHEME 25

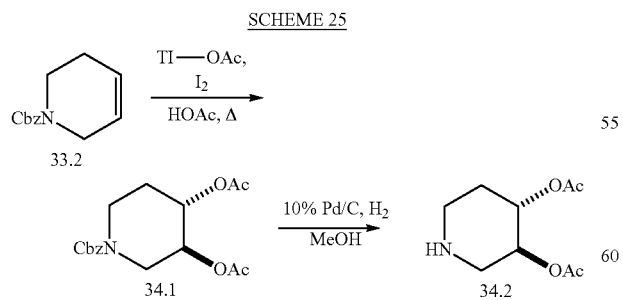

a) A mixture of Tl(OAc) (17.6 g, 54.5 mmol) in dried acetic acid (40 mL) is refluxed with stirring for 1 hour and then cooled to room temperature. Compound 32.2 (34.6 mmol) and iodine (8.46 g, 33.3 mmol) are added, and the resulting suspension is heated to reflux. After 9 hours, the reaction mixture is cooled to room temperature, and the yellow TlI precipitate is removed by filtration with ether rinses. The filtrate is concentrated, and the residue is dissolved in ethyl acetate, dried over MgSO$_4$, and reconcentrated to afford compound 34.1.

b) A mixture of 34.1 (1.0 mmol) and 10% Pd/C (0.1 mmol) in methanol (5 mL) is stirred at room temperature for several hours under an atmosphere of H$_2$. The reaction mixture is filtered, the filtrate is concentrated, and the residue is dried in vacuo to give compound 34.2.

c) Compound 34 is prepared according to Example 26g except that compound 34.2 is used instead of ammonia.

EXAMPLE 35

This example describes the synthesis of

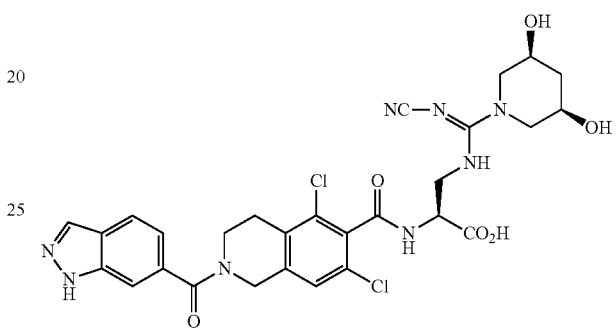

which is prepared according to Scheme 26 and the procedure below.

SCHEME 26

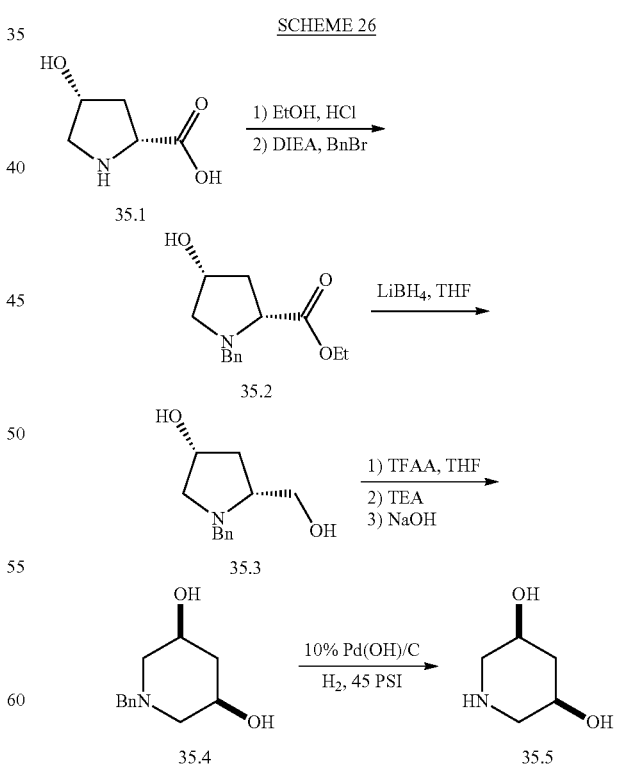

a) A mixture of compound 35.1 (10 mmol) in ethanol (20 mL) is saturated with HCl (g) and stirred at room temperature overnight. The solvent is removed, the residue is dissolved in DCM (100 mL), the resulting solution is treated sequentially with TEA (30 mmol) and BnBr (11 mmol), and the reaction mixture is heated to reflux. After 12 h, the reaction mixture is cooled to room temperature and concentrated. The residue is dissolved in EtOAc (150 mL), washed with brine, and dried over anhydrous $Na_2SO_4$. The solvent is removed and the residue is purified by chromatography to afford compound 35.2.

b) A solution of $LiBH_4$ (20 mmol) in dry THF (20 mL) at room temperature is treated in a dropwise fashion with a solution of compound 35.2 (5 mmol) in THF (5 mL). After stirring overnight, the reaction mixture is quenched by adding several drops of water. The mixture is concentrated, diluted with brine (50 mL), and extracted several times with 9/1(v/v) EtOAc/i-PrOH. The combined extracts are dried over anhydrous $Na_2SO_4$, the solvent is removed, and the residue is purified by chromatography to afford compound 35.3.

c) A solution of compound 35.3 (2 mmol) and TEA (2.2 mmol) in dry THF (10 mL) at −78° C. is treated dropwise with trifluoroacetic anhydride ("TFAA", 2.2 mmol). After several hours, the mixture is treated with TEA (6 mmol), and the reaction mixture is heated to reflux. The mixture then is concentrated, and the residue is dissolved in THF (10 mL) and treated with water (2.5 mL). This mixture is treated with NaOH (10 mmol) with vigorous stirring at room temperature for several hours. The solvent is removed, and the residue is treated with sat. aq. $NaHCO_3$ (20 mL) and extracted several times with 9/1 (v/v) EtOAc/i-PrOH. The combined extracts are dried over anhydrous $Na_2SO_4$, the solvent is removed, and the residue is purified by chromatography to afford compound 35.4.

d) A mixture of compound 35.4 (1 mmol) and 20% Pd(OH)$_2$/C (0.1 mmol) in methanol (10 mL) is shaken at room temperature for several hours under 45 psi of $H_2$. (g). The reaction mixture is filtered, the filtrate is concentrated, and the residue is dried in vacuo to give compound 35.5.

e) Compound 35 is prepared according to Example 26g except that compound 35.5 is used instead of ammonia.

EXAMPLE 36

This example describes the synthesis of

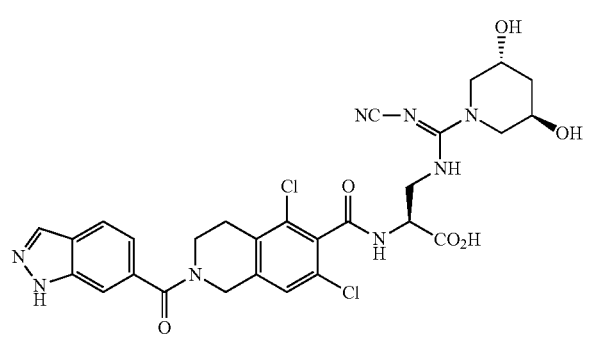 [SMILES: N#C/N=C(\NC[C@H](NC(=O)c1c(Cl)cc2c(c1Cl)CCN(C(=O)c1ccc3cn[nH]c3c1)C2)C(=O)O)N1C[C@H](O)C[C@@H](O)C1]

which was prepared according to Example 35 except that (2R,4S)-4-hydroxyproline (trans-D-Hyp-OH) was used instead of compound 35.1.

EXAMPLE 37

This example describes the synthesis of

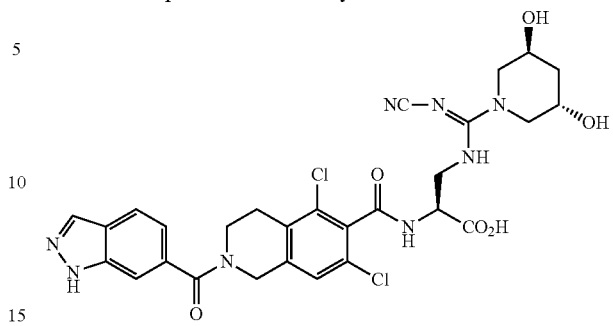

which was prepared according to Example 35 except that (2S,4R)-4-hydroxyproline (trans-L-Hyp-OH) was used instead of compound 35.1.

EXAMPLE 38

This example describes the synthesis of

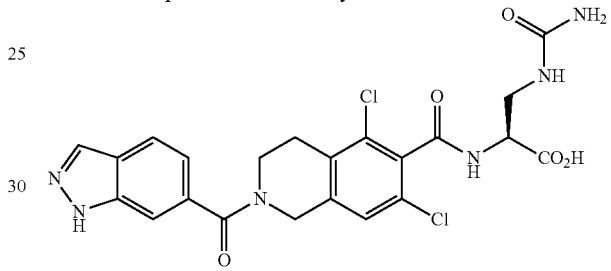

which is prepared in according to Scheme 27 and the procedure below.

SCHEME 27

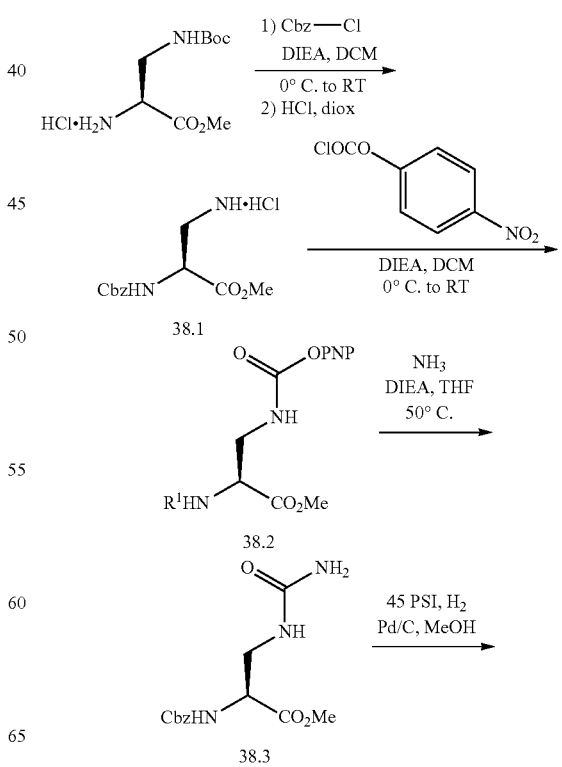

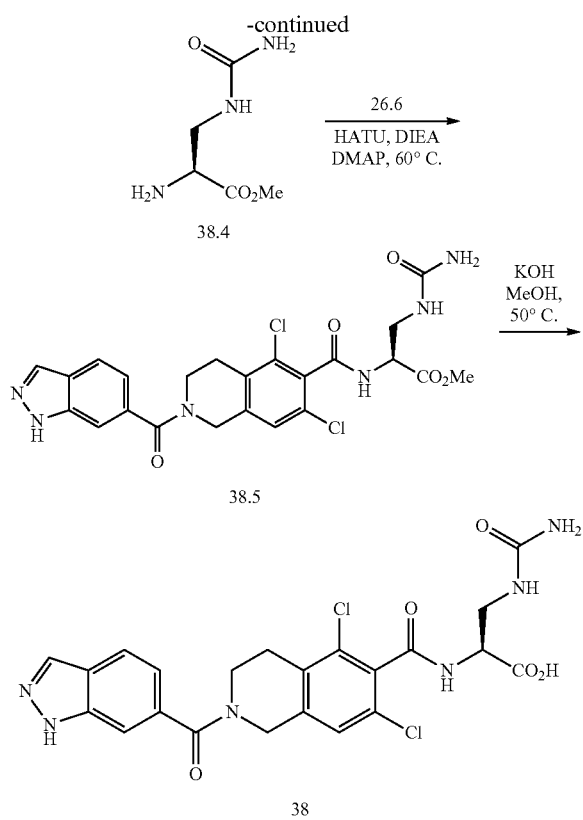

nolic ammonia (18 mmol), and the mixture is heated to 40° C. After 15 hours, the reaction mixture is concentrated, and the residue is purified by chromatography to afford compound 38.3.

d) A mixture of compound 38.3 (1.0 mmol) and 10% Pd/C (0.1 mmol) in methanol (10 mL) is shaken at room temperature for several hours under 45 psi of H$_2$. (g). The reaction mixture is filtered, the filtrate is concentrated, and the residue is dried in vacuo to give compound 38.4.

e) A solution of compound 26.6 (8.0 mmol) and DIEA (25. mmol) in DMF is treated with HATU (8.0 mmol), and the resulting mixture was stirred at room temperature. After 20 minutes, the reaction mixture is treated sequentially with compound 38.4 (8.6 mmol) and DMAP (0.5 mmol), and the mixture is then heated to 60° C. After 2.5 hours, the reaction is diluted with ethyl acetate, washed with three portions of water, washed with one portion of brine, dried over MgSO$_4$, and concentrated. Flash column chromatography affords compound 38.5.

f) A solution of compound 38.5 (0.15 mmol) in methanol (1 mL) was treated with 2 M methanolic KOH (0.45 mmol), and the reaction mixture is heated to 50° C. After 3 hours, the reaction mixture is concentrated to dryness and the residue is subjected to preparatory HPLC purification to afford compound 38.

EXAMPLE 39

This example describes the synthesis of

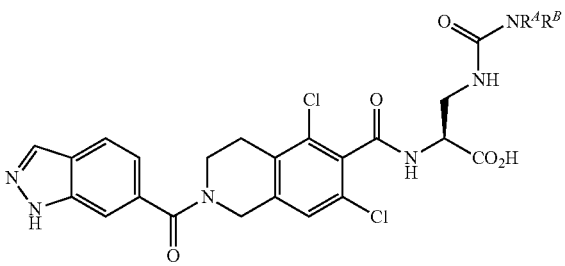

where $R^A$ and $R^B$ are each independently hydrogen, aliphatic, aromatic, heteroaromatic, or together form a cyclic moiety. These compounds are made according to the procedure in Example 38 except that a substituted amine of the formula HNR$^A$R$^B$ is used instead of ammonia in step c. Illustrative examples of substituted amines and the resulting compounds are shown in Table 2.

a) A solution of HCl.H-DAP(Boc)-OMe (10 mmol) and DIEA (11 mmol) in DCM (50 mL) at 0° C. is treated dropwise with benzoyl chloride (11 mmol). Over 3 h the reaction mixture is allowed to warm to room temperature. The reaction mixture is concentrated, and the residue is purified by chromatography. This intermediate is treated with a solution of 4 M HCl in dioxane, and the resulting mixture is stirred at room temperature. After 1 h, the solvent is removed to afford compound 38.1, which is used without further purification.

b) A solution of compound 38.1 (10 mmol) and DIEA (12 mmol) in DCM (50 mL) at 0° C. is treated dropwise with p-nitrophenyl chloroformate (11 mmol), and the reaction mixture is allowed to warm to room temperature. After 2 hours, the reaction mixture is concentrated, and the residue is purified by chromatography to afford compound 38.2.

c) A solution of compound 38.2 (10 mmol) and TEA (25 mmol) in 1:1 DCE/DMF (10 mL) is treated with 2 M metha-

TABLE 2

| HNR$^A$R$^B$ | Compound |
|---|---|

TABLE 2-continued
| HNR$^A$R$^B$ | Compound |
|---|---|
| 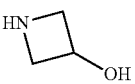 | 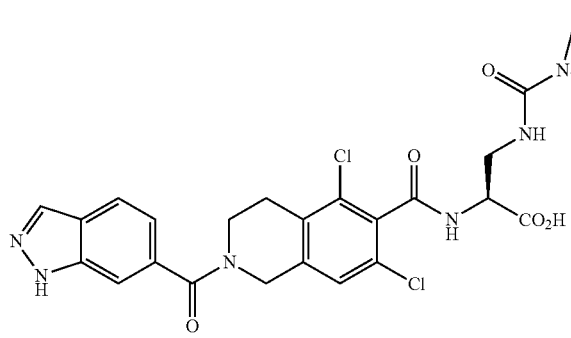 |
| 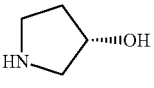 | 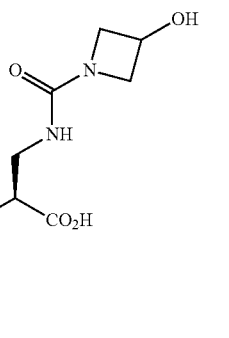 |
| 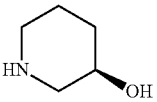 | 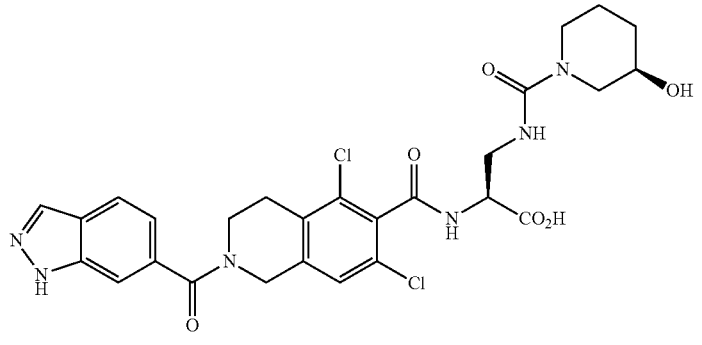 [SMILES: O=C(N[C@@H](CNC(=O)N1CCC[C@@H](O)C1)C(=O)O)c1c(Cl)cc2c(c1Cl)CCN(C(=O)c1ccc3cn[nH]c3c1)C2] |
| 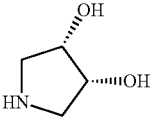 | 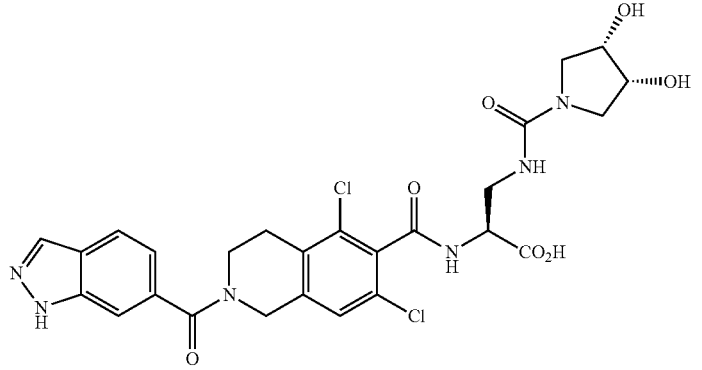 [SMILES: O=C(N[C@@H](CNC(=O)N1C[C@@H](O)[C@@H](O)C1)C(=O)O)c1c(Cl)cc2c(c1Cl)CCN(C(=O)c1ccc3cn[nH]c3c1)C2] |

TABLE 2-continued
| HNR$^A$R$^B$ | Compound |
|---|---|
| 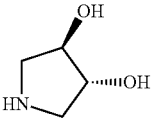 | 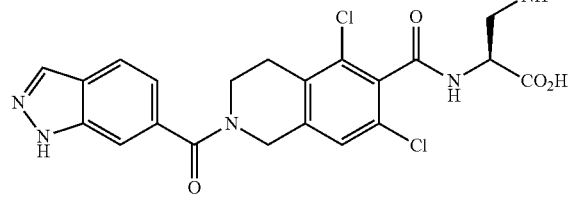 |
| 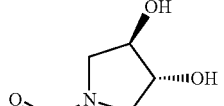 | 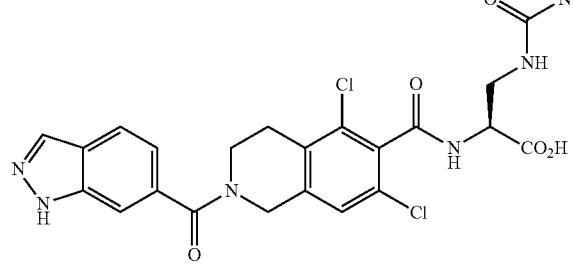 |
| 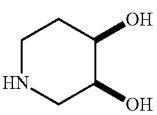 | 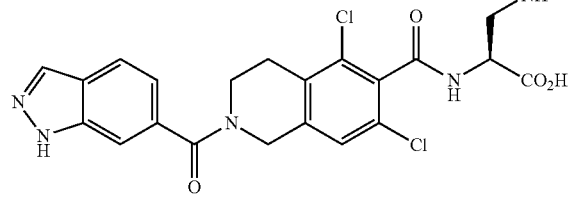 |
| 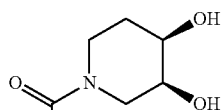 | 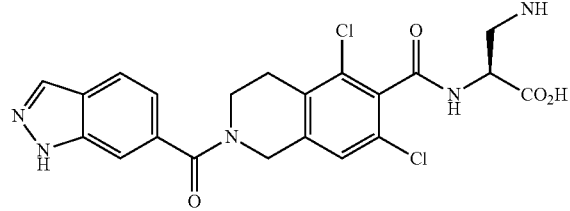 |

TABLE 2-continued
| HNR^A R^B | Compound |
|---|---|
| 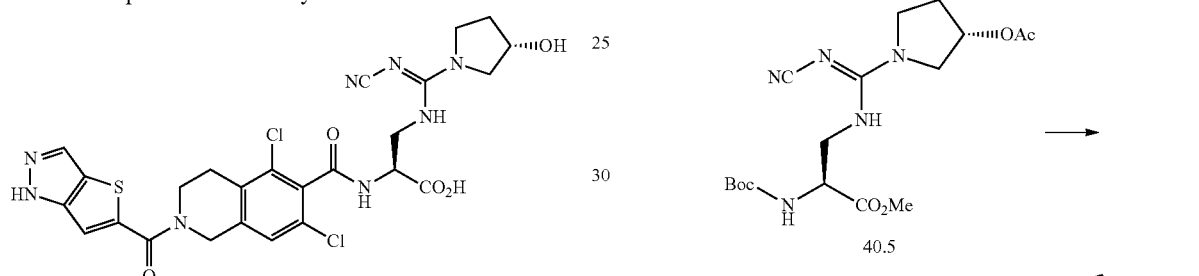 | |
EXAMPLE 40
This example describes the synthesis of
which is prepared according to Scheme 28 and the procedure below.
SCHEME 28
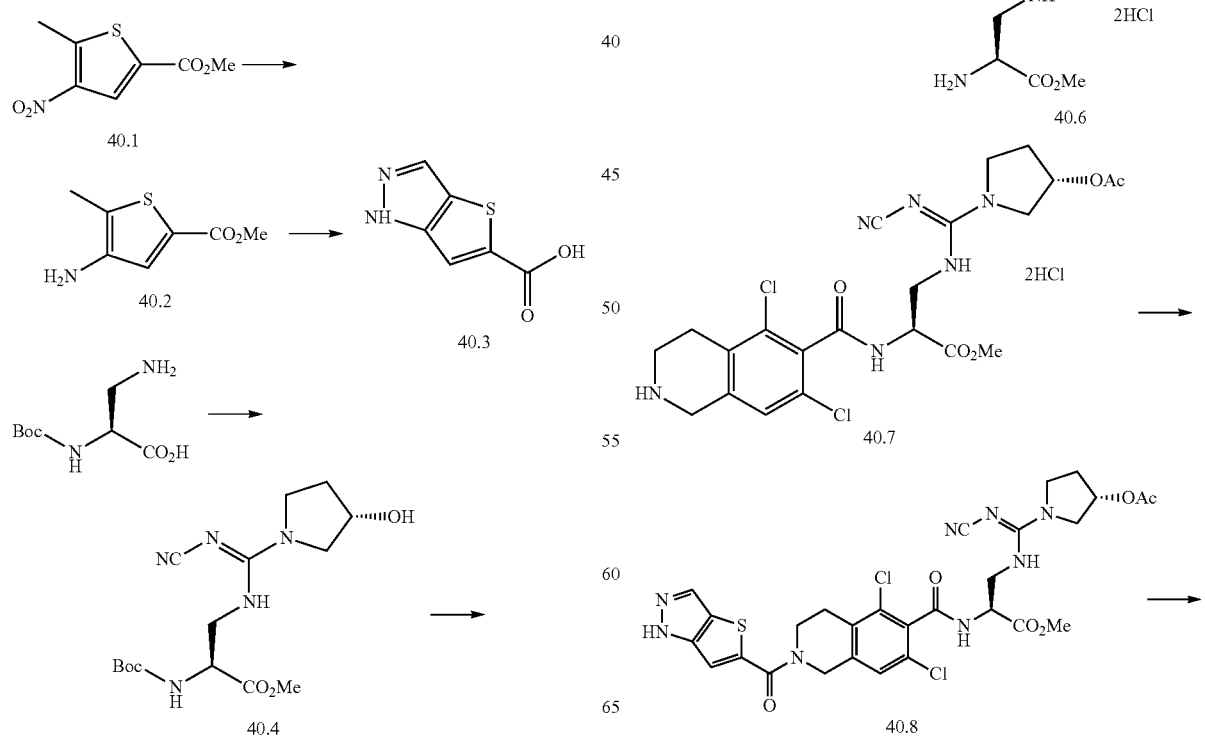

-continued

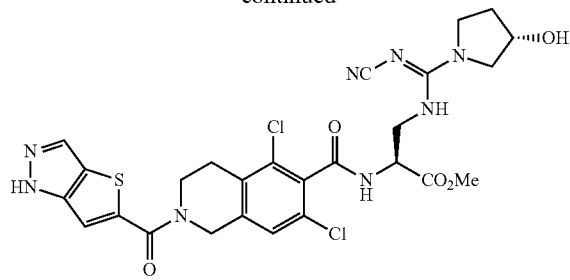

a) Commercially available compound 40.1 (10 mmol) in THF (50 mL) is treated with sodium hydrosulfite (50 mmol) in water (20 mL). After 8 hours at room temperature, the reaction is extracted with ethyl acetate (100 mL), and the organic extract is washed with water and brine, dried over anhydrous magnesium sulfate and filtered to give the crude compound 40.2.

b) To a slurry of compound 40.2 (10 mmol), ammonium tetrafluoroborate (12.5 mmol) in water (12 mL) is added concentrated HCl (2 mL). The reaction is cooled to 0° C., and to it is added sodium nitrite (10 mmol). After the reaction is stirred for 1 hour at 0° C., the solid is collected by filtration, rinsed with methol, ether and dried under vacuum. The resulting solid is added to a stirring solution of HOAc (3 mL), 18-crown-6 (0.3 mmol) in chloroform (20 mL). After 1 hour, water (10 mL) and DCM (20 mL) are added. The organic layer is separated, dried by magnesium sulfate and filtered. The residue after concentration of the filtrate is triturated with hexane to give product 40.3.

c) Compound 40.4 was made according to the procedure for the preparation of compound 6.1 except that R-3-(+)-pyrrolidinol was used instead of pyrrolidine.

d) Compound 40.4 is desolved in DCM, and is treated with triethylamine (1.5 eq) and acetic anhydride (1.2 eq). The resulting solution is filtered through silica gel, concentrated. The residue is then purified by silica gel column chromagraphy to yield compound 40.5.

e) Compound 40.5 in DCM is treated with anhydrous 4 N HCl in dioxane (2.0 eq). After starting material disappears, the reaction is concentrated to give compound 40.6.

f) Compound 40.7 is made according to the procedure for the preparation of compound 1.5 except that compound 40.6 is used instead of 1.3.

g) Compound 40.8 is made according to the procedure for the preparation of compound 1.6 except that compounds 40.7 and 40.3 are used instead of compounds 1.5 and 1.11.

h) Compound 40 is made according to the procedure for the preparation of compound I except that compound 40.8 is used instead of 1.6.

EXAMPLE 41

This example describes the synthesis of

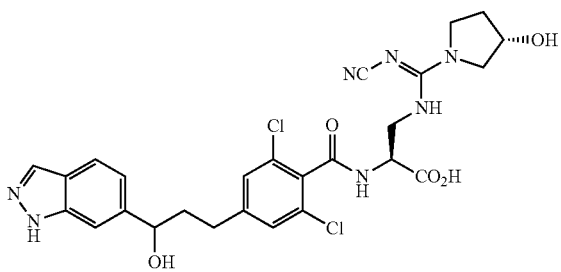 [SMILES: N#C/N=C(\NC[C@H](NC(=O)c1c(Cl)cc(CCC(O)c2ccc3cn[nH]c3c2)cc1Cl)C(=O)O)N1CC[C@H](O)C1]

which is prepared according to Scheme 29 and the procedure below.

SCHEME 29

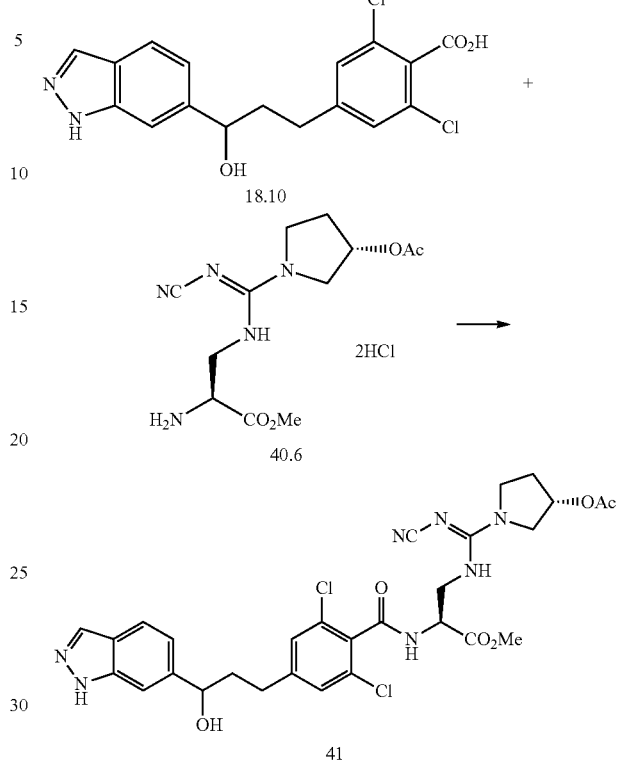

Compound 41 is made according to the procedure for the preparation of compound 3 except that compounds 18.10 and 40.6 are used instead of 3.4 and 3.7. The enantiomerically pure compounds are isolated using chiral column chromatography.

EXAMPLE 42

This example describes the synthesis of

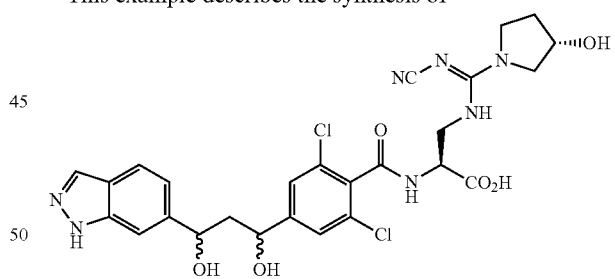

which is prepared according to Scheme 30 and the procedure below.

SCHEME 30

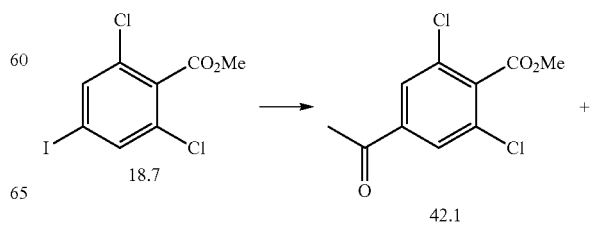

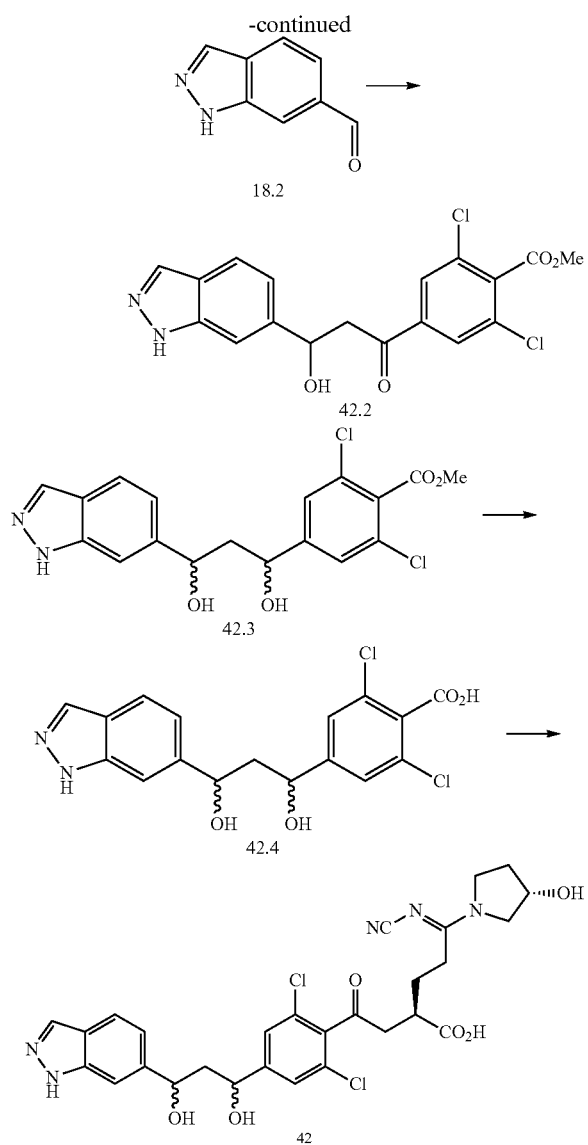

a) A solution of compound 18.7 (10 mmol), 1-ethoxy-1-ethenyltributyltin (10.5 mmol), Pd(PPh)$_4$ (0.5 mmol) in dimethoxyethane (DME, 50 mL) is heated at 80° C. until compound 18.7 disappears. The reaction is cooled to room temperature, and to it is added 4N aqueous HCl (5 mL). The reaction is stirred for 3 hours and extracted with ether (80 mL). The organic extract is washed with brine, dried with anhydrous magnesium sulfate, filtered and concentrated. The residue is purified by column chromatography to give compound 42.1.

b) A solution of compound 42.1 in THF at −78° C. is treated with LDA (2.0 eq). After 1 hour, a solution of compound 18.2 (1.0 eq) in THF is added to the dry ice cooled reaction. After another 3 hours, saturated aqueous NH$_4$Cl is added to the reaction and the mixture is allowed to warm to room temperature. The reaction mixture is partitioned between ethyl acetate and water, and the organic layer is washed with water and brine, dried with anhydrous magnesium sulfate and filtered. The residue after concentration of the filtrate is purified by silica gel column to give compound 42.2.

c) A solution of compound 42.2 in ethanol is treated with sodium borohydride (2.0 eq). After 1 hour, the reaction mixture is partitioned between ethyl acetate and water, and the organic layer is washed brine, dried with anhydrous magnesium sulfate and filtered. The residue after concentration of the filtrate is purified by silica gel column to give compound 42.3.

d) A mixture of 42.3 LiI (3 eq) in pyridine is reflux overnight. The solvent is removed and the residue is dissolved in EtOAc. The resulting solution is then washed with saturated aqueous NH$_4$Cl and dried with anhydrous Na$_2$SO$_4$. The solvent is removed and the residue is dried in vacuo to give a quantitative yield of compound 42.4. The crude product was carried on the next step without further purification.

e) Compound 42 is made according to the procedure for the preparation of compound 3 except that compounds 42.4 and 40.6 are used instead of 3.4 and 3.7. The enantiomerically pure compounds are isolated using chiral column chromatography.

EXAMPLE 43

This example describes the synthesis of

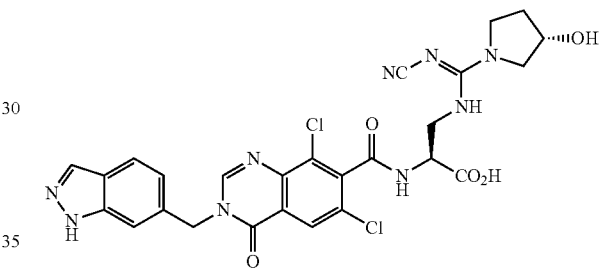

which is prepared according to Scheme 31 and the procedure below.

SCHEME 31

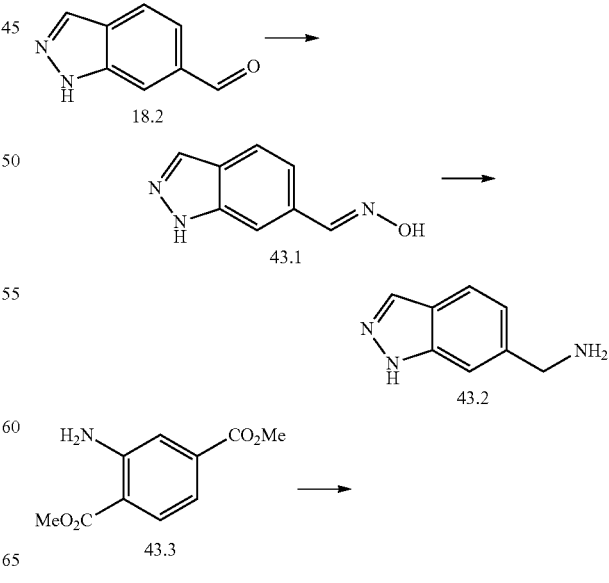

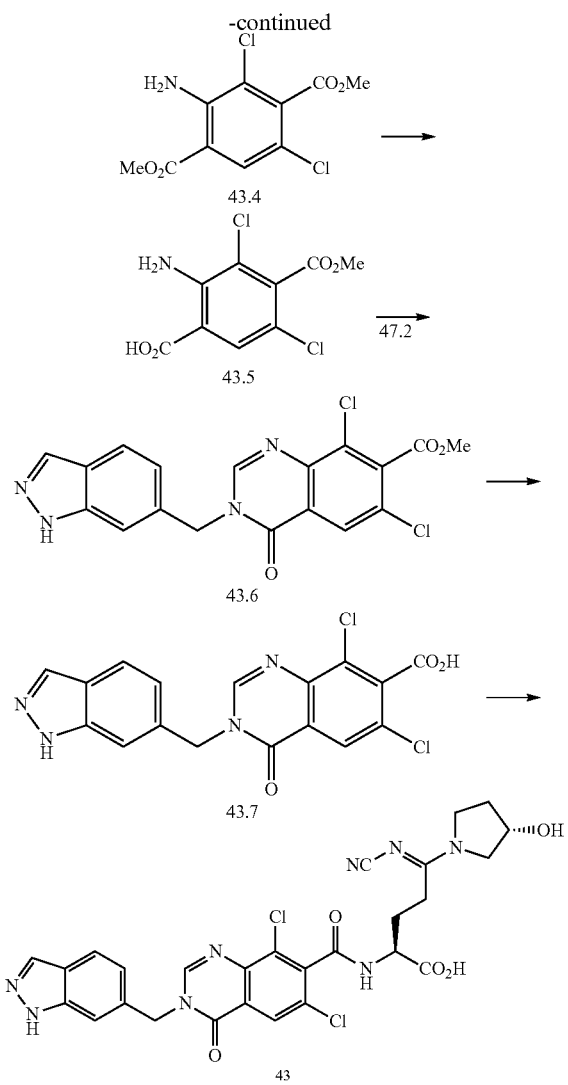

a) A solution of compound 18.2 in ethanol is treated with hydroxylamine (1.05 eq). After 10 hours, the reaction is concentrated and the residue is dried under vacuum to give compound 43.1.

b) A solution of 43.1 is hydrogenated with 20% Pd(OH)$_2$/C as a catalyst at 45 psi of hydrogen to give compound 43.2.

c) A solution of commercially available 43.3 in carbon tetrachloride is treated with N-chlorosuccinimide (NCS, 3 eq). The reaction mixture is then diluted with ethyl acetate, washed with 1N NaOH, water and brine, dried over anhydrous MgSO$_4$ and filtered. The crude product is recrystallized from hot ethanol to give compound 43.4.

d) A solution of 43.4 in THF is treated with LiOH (2 eq, 2.0 N aqueous). After most starting material is consumed, the mixture is then diluted with ethyl acetate, washed with saturated ammonium chloride, water and brine, dried over anhydrous MgSO$_4$ and filtered. The crude product is recrystallized from hot ethanol to give compound 43.5.

e) A solution of 43.5, 43.2 (1.1 eq) and EDC (1.0 eq) in DMF is stirred for 10 hours at room temperature. The mixture is then diluted with ethyl acetate, washed with saturated ammonium chloride, water and brine, dried over anhydrous MgSO$_4$ and filtered. The crude product is then refluxed with formic acid until LC-MS indicates the reaction is completed. Solvent is evaporated, and the crude product is purified by silica gel column to give compound 43.6.

f) A mixture of 43.6 LiI (3 eq) in pyridine is reflux overnight. The solvent is removed and the residue is dissolved in EtOAc. The resulting solution is then washed with saturated aqueous NH$_4$Cl and dried with anhydrous Na$_2$SO$_4$. The solvent is removed and the residue is dried in vacuo to give a quantitative yield of compound 43.7. The crude product was carried on the next step without further purification.

g) Compound 43 is made according to the procedure for the preparation of compound 3 except that compounds 43.7 and 40.6 are used instead of 3.4 and 3.7.

Diversification

It will also be appreciated that each of the components used in the synthesis of inventive compounds can be diversified either before synthesis or alternatively after the construction of the core structure of formula (I). As used herein, the term "diversifying" or "diversify" means reacting an inventive compound (I) or any of the precursor fragments (or any classes or subclasses thereof) at one or more reactive sites to modify a functional moiety or to add a functional moiety (e.g., nucleophilic addition of a substrate). Described generally herein are a variety of schemes to assist the reader in the synthesis of a variety of compounds, either by diversification of the intermediate components or by diversification of the core structures as described herein, and classes and subclasses thereof. It will be appreciated that a variety of diversification reactions can be employed to generate compounds other than those described in the Exemplification herein. As but a few examples, where a double bond is present in the compound structure, epoxidation and aziridation can be conducted to generate epoxide and aziridine derivatives of compounds described herein. For additional guidance available in the art, the practitioner is directed to "Advanced Organic Chemistry", March, J. John Wiley & Sons, 2001, 5$^{th}$ ed., the entire contents of which are hereby incorporated by reference.

2) Biological Data:

As discussed above, LFA-ICAM interactions have been directly implicated in numerous inflammatory disease states including, but not limited to graft rejection, dermatitis, psoriasis, asthma and rheumatoid arthritis. Thus, compounds capable of modulating adhesion between intracellular adhesion molecules (e.g., ICAM-1, -2 and -3) and the leukocyte integrin family of receptors would be useful in the development of novel therapeutics. Described below are certain assays used for the determination of ICAM-1:LFA Receptor binding, Human T-Cell Adhesion, and T-Cell proliferation which are described in published PCT applications WO 99/49856 and WO 02/05114, the entire contents of which are hereby incorporated by reference. WO 99/49856 also describes the preparation and purification of full-length LFA-1 from 293 cells, the preparation of a plasmid for expression of a human ICAM-1 immunoadhesion, and the generation of ICAM-1 immunoadhesion expressing 293 cell line.

ICAM-1:LFA Receptor Binding Assay (Protein/protein Assay):

Competitive inhibition of the CD11a/CD18-ICAM-1 interaction is quantitated by adding known amounts of inhibitors according to the two protein/protein assay systems described below:

Forward Format LFA-1:ICAM-1 Assay (PPFF):

Purified full length recombinant human LFA-1 protein is diluted to 2.5 µg/ml in 0.02 M Hepes, 0.15M NaCl, and 1 mM MnCl$_2$ and 96-well plates (50 µl/well) are coated overnight at 4° C. The plates are washed with wash buffer (0.05% Tween in PBS) and blocked for 1 h at room temperature with 1% BSA in 0.02M Hepes, 0.15 M NaCl, and 1 mM MnCl$_2$. Plates are washed. 50 µl/well inhibitors, appropriately diluted in assay buffer (0.5% BSA in 0.02M Hepes, 0.15M NaCl, and 1 mM MnCl$_2$), are added to a 2× final concentration and incubated for 1 h at room temperature. 50 µl/well of purified recombinant human 5 domain ICAM-Ig, diluted to 50 ng/ml in assay buffer, is added and incubated 2 h at room temperature. Plates are washed and bound ICAM-Ig is detected with Goat anti-HuIgG(Fc)-HRP for 1 h at room temperature. Plates are washed and developed with 100 µl/well TMB substrate for 10-30' at room temperature. Colorimetric development is stopped with 100 ul/well 1M $H_2PO_4$ and read at 450 nM on a platereader.

An alternative protein/protein assay system below also quantitates competitive inhibition of the CD11a/CD18-ICAM-1 interaction.

PLM2 Antibody Capture LFA-1:ICAM-1 Assay (PLM2)

A non-function blocking monoclonal antibody against human CD18, PLM-2 (as described by Hildreth, et al., Molecular Immunology, Vol. 26, No. 9, pp. 883-895, 1989), is diluted to 5 µg/ml in PBS and 96-well flat-bottomed plates are coated with 100 µl/well overnight at 4° C. The plates are blocked with 0.5% BSA in assay buffer (0.02 M Hepes, 0.15 M NaCl, and 1 mM $MnCl_2$) 1 h at room temperature. Plates are washed with 50 mM Tris pH 7.5, 0.1M NaCl, 0.05% Tween 20 and 1 mM $MnCl_2$. Purified full-length recombinant human LFA-1 protein is diluted to 2 µg/ml in assay buffer and 100 ml/well is added to plates and incubated at 1 h at 37° C. Plates are washed 3×. 50 µl/well inhibitors, appropriately diluted in assay buffer, are added to a 2× final concentration and incubated for 30' at 37° C. 50 µl/well of purified recombinant human 5 domain ICAM-Ig, diluted to 161 ng/ml (for a final concentration of 80 ng/ml) in assay buffer, is added and incubated 2 h at 37° C. Plates are washed and bound ICAM-Ig is detected with Goat anti-HuIgG(Fc)-HRP for 1 h at room temperature. Plates are washed and developed with 100 µl/well TMB substrate for 5-10' at room temperature. Colorimetric development is stopped with 100 µl/well 1M $H_3PO_4$ and read at 450 nM on a platereader.

Human T-Cell Adhesion Assay (Cell Attachment Assay)

The T-cell adhesion assay is performed using a human T-lymphoid cell line HuT 78. Goat anti-HuIgG(Fc) is diluted to 2 µg/ml in PBS and 96-well plates are coated with 50 µl/well at 37° C. for 1 h. Plates are washed with PBS and blocked for 1 h at room temperature with 1% BSA in PBS. 5 domain ICAM-Ig is diluted to 100 ng/ml in PBS and 50 µl/well was added to the plates O/N at 4° C. HuT 78 cells are centrifuged at 100 g and the cell pellet is treated with 5 mM EDTA for ~5' at 37° C. in a 5% $CO_2$ incubator. Cells are washed in 0.14 M NaCl, 0.02 M Hepes, 0.2% glucose and 0.1 mM $MnCl_2$ (assay buffer) and centrifuged. The cells are resuspended in assay buffer to $3.0\times10^6$ c/ml. Inhibitors are diluted in assay buffer to a 2× final concentration and pre-incubated with HuT78 cells for 30' at room temperature. 100 µl/well of cells and inhibitors are added to the plates and incubated at room temperature for 1 h. 100 µl/well PBS is added and the plates are sealed and centrifuged inverted at 100 g for 5'. Unattached cells are flicked out of the plate and excess PBS is blotted on a paper towel. 60 µl/well p-nitrophenyl n-acetyl-β-D-glucosaminide (0.257 g to 100 ml citrate buffer) is added to the plate and incubated for 1.5 h at 37° C. The enzyme reaction is stopped with 90 µl/well 50 mM glycine/5 mM EDTA and read on a platereader at 405 nM. HUT 78 cell adhesion to 5dICAM-Ig is measured using the p-nitrophenyl n-acetyl-β-D-glucosaminide method of Landegren, U. (1984). J. Immunol. Methods 57, 379-388.

T-Cell Proliferation Assay:

This assay is an in vitro model of lymphocyte proliferation resulting from activation, induced by engagement of the T-cell receptor and LFA-1, upon interaction with antigen presenting cells (Springer, Nature 346: 425 (1990)).

Microtiter plates (Nunc 96 well ELISA certified) are pre-coated overnight at 4° C. with 50 µl of 2 µg/ml of goat anti-human Fc(Caltag H10700) and 50 µl of 0.07 µg/ml monoclonal antibody to CD3 (Immunotech 0178) in sterile PBS. The next day coat solutions are aspirated. Plates are then washed twice with PBS and 100 µl of 17 ng/ml 5d-ICAM-1-IgG is added for 4 hours at 37° C. Plates are washed twice with PBS prior to addition of CD4+ T cells. Lymphocytes from peripheral blood are separated from heparinized whole blood drawn from healthy donors. An alternative method is to obtain whole blood from healthy donors through leukophoresis. Blood is diluted 1:1 with saline, layered and centrifuged at 2500×g for 30 minutes on LSM (6.2 g Ficoll and 9.4 g sodium diztrizoate per 100 ml) (Organon Technica, NJ). Monocytes are depleted using a myeloid cell depletion reagent method (Myeloclear, Cedarlane Labs, Hornby, Ontario, Canada). PBLs are resuspended in 90% heat-inactivated Fetal Bovine scrum and 10% DMSO, aliquoted, and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Purification of CD4+ T cells are obtained by negative selection method (Human CD4 Cell Recovery Column Kit # CL110-5 Accurate). 100,000 purified CD4+ T cells (90% purity) per microtiter plate well are cultured for 72 hours at 37° C. in 5% $CO_2$ in 100 ml of culture medium (RPMI 1640 (Gibco) supplemented with 10% heat inactivated FBS (Intergen), 0.1 mM non-essential amino acids, 1 nM Sodium Pyruvate, 100 units/ml Penicillin, 100 µg/ml Streptomycin, 50 µg/ml Gentamicin, 10 mM Hepes and 2 mM Glutamine). Inhibitors are added to the plate at the initiation of culture. Proliferative responses in these cultures are measured by addition of 1 µCi/well titrated thymidine during the last 6 hours before harvesting of cells. Incorporation of radioactive label is measured by liquid scintillation counting (Packard 96 well harvester and counter). Results are expressed in counts per minute (cpm).

In Vitro Mixed Lymphocyte Culture Model:

The mixed lymphocyte culture model, which is an in vitro model of transplantation (A. J. Cunningham, "Understanding Immunology, Transplantation Immunology" pages 157-159 (1978) examines the effects of various LFA-1 antagonists in both the proliferative and effector arms of the human mixed lymphocyte response.

Isolation of Cells: Mononuclear cells from peripheral blood (PBMC) are separated from heparanized whole blood drawn from healthy donors. Blood is diluted 1:1 with saline, layered, and centrifuged at 2500×g for 30 minutes on LSM (6.2 g Ficoll and 9.4 g sodium diztrizoate per 100 ml) (Organon Technica, NJ). An alternative method is to obtain whole blood from healthy donors through leukophoresis. PBMCs are separated as above, resuspended in 90% heat inactivated Fetal Bovine serum and 10% DMSO, aliquoted and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Mixed Lymphocyte Response (MLR): One way human mixed lymphocyte cultures are established are in 96-well flat-bottomed microtiter plates. $1.5\times10^5$ responder PBMCs are co-cultured with an equal number of allogeneic irradiated (3000 rads for 3 minutes, 52 seconds stimulator PBMSc in 200 µl of complete medium. LFA-1 antagonists are added at the initiation of cultures. Cultures are incubated at 37° C. in 5% $CO_2$ for 6 days, then pulsed with 1 µCi/well of 3H-thymidine (6.7 Ci/mmol, NEN, Boston, Mass.) for 6 hours. Cultures are harvested on a Packard cell harvester (Packard, Canberra, Canada). [³H] TdR incorporation is measured by liquid scintillation counting. Results are expressed as counts per minute (cpm).

The invention claimed is:

1. A pharmaceutical formulation comprising an LFA-1 antagonist and an excipient, wherein the formulation is for topical administration and wherein the LFA-1 antagonist comprises a compound of Formula I or its pharmaceutically acceptable salt or ester, wherein

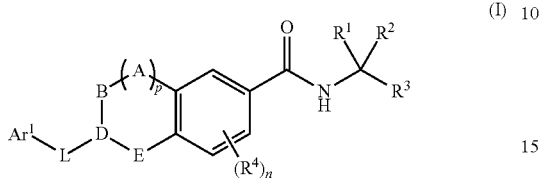

(I)

wherein R¹ and R² are each independently hydrogen, —(CH₂)ₘOH, —(CH₂)ₘaryl, —(CH₂)ₘheteroaryl, wherein m is 0-6, —CH(R¹ᴬ)(OR¹ᴮ), —CH(R¹ᴬ)(NHR¹ᴮ), U-T-Q, or an aliphatic, alicyclic, heteroaliphatic or heteroalicyclic moiety optionally substituted with U-T-Q, wherein U is absent, —O—, —S(O)₀₋₂—, —SO₂N(R¹ᴬ), —N(R¹ᴬ)—, —N(R¹ᴬ)C(=O)—, —N(R¹ᴬ)C(=O)—O—, —N(R¹ᴬ)C(=O)—N(R¹ᴮ)—, —N(R¹ᴬ)—SO₂—, —C(=O)—, —C(=O)—O—, —O—C(=O)—, aryl, heteroaryl, alkylaryl, alkylheteroaryl, —C(=O)—N(R¹ᴬ)—, —O—C(=O)—N(R¹ᴬ)—, —C(=N—R¹ᴱ)—, —C(=N—R¹ᴱ)—O—, —C(=N—R¹ᴱ)—N(R¹ᴬ)—, —O—C(=N—R¹ᴱ)—N(R¹ᴬ)—, —N(R¹ᴬ)C(=N—R¹ᴱ)—, —N(R¹ᴬ)C(=N—R¹ᴱ)—O—, N(R¹ᴬ)C(=N—R¹ᴱ)—N(R¹ᴮ)—, —P(=O)(OR¹ᴬ)—O—, or —P(=O)(R¹ᴬ)—O—; T is absent, an aliphatic, heteroaliphatic, aryl, heteroaryl, alkylaryl or alkylheteroaryl moiety; and Q is hydrogen, halogen, cyano, isocyanate, —OR¹ᴮ, —SR¹ᴮ; —N(R¹ᴮ)₂, —NHC(=O)OR¹ᴮ, —NHC(=O)N(R¹ᴮ)₂, —NHC(=O)R¹ᴮ, —NHSO₂R¹ᴮ, —NHSO₂N(R¹ᴮ)₂, —NHSO₂NHC(=O)OR¹ᴮ, —NHC(=O)NHSO₂R¹ᴮ, —C(=O)NHC(=O)OR¹ᴮ, —C(=O)NHC(=O)R¹ᴮ, —C(=O)NHC(=O)N(R¹ᴮ)₂, —C(=O)NHSO₂R¹ᴮ, —C(=O)NHSO₂N(R¹ᴮ)₂, —C(=S)N(R¹ᴮ)₂, —SO₂R¹ᴮ, —SO₂—O—R¹ᴮ, —SO₂—N(R¹ᴮ)₂, —SO₂—NHC(=O)OR¹ᴮ, —SO₂—NHC(=O)—N(R¹ᴮ)₂, —SO₂—NHC(=O)R¹ᴮ, —O—C(=O)N(R¹ᴮ)₂, —O—C(=O)R¹ᴮ, —O—C(=O)NHC(=O)R¹ᴮ, —O—C(=O)NH—SO₂R¹ᴮ, —O—SO₂R¹ᴮ, or an aliphatic heteroaliphatic, aryl or heteroaryl moiety, or wherein R¹ and R² taken together are an alicyclic or heterocyclic moiety; wherein each occurrence of R¹ᴬ and R¹ᴮ is independently hydrogen, an aliphatic, alicyclic, heteroaliphatic, heterocyclic, aryl, heteroaryl, alkylaryl or alkylheteroaryl moiety, —COR¹ᶜ, or —CONR¹ᶜR¹ᴰ; wherein each occurrence of R¹ᶜ and R¹ᴰ is independently hydrogen, hydroxyl, or an aliphatic, heteroaliphatic, aryl, heteroaryl, alkylaryl or alkylheteroaryl moiety; and R¹ᴱ is hydrogen, an aliphatic, alicyclic, heteroaliphatic, heterocyclic, aryl, heteroaryl, alkylaryl or alkylheteroaryl moiety, —CN, —OR¹ᶜ, —NR¹ᶜR¹ᴰor —SO₂R¹ᶜ;

R³ is —C(=O)OR³ᴬ, —C(=O)H, —CH₂OR³ᴬ, —CH₂O—C(=O)-alkyl, —C(=O)NH(R³ᴬ), —CH₂X⁰; wherein each occurrence of R³ᴬ is independently hydrogen, a protecting group, an aliphatic, alicyclic, heteroaliphatic, heteroalicyclic, aryl, heteroaryl, alkylaryl, alkylheteroaryl, heteroalkylaryl or heteroalkylheteroaryl moiety, or R³ᴬ, taken together with R¹ or R², forms a heterocyclic moiety; wherein X⁰ is a halogen selected from F, Cl, Br or I;

R⁴, for each occurrence, is independently hydrogen, halogen, —CN, —NO₂, an aliphatic, alicyclic, heteroaliphatic, heteroalicyclic, aryl, heteroaryl, alkylaryl or alkylheteroaryl moiety, or is —GRᴳ¹ wherein G is —O—, —S—, —NRᴳ²—, —CO—, —SO—, —SO₂—, —C(=O)O—, —C(=O)NRᴳ²—, —OC(=O)—, —NRᴳ²C(=O)— or —SO₂NRᴳ²—, and Rᴳ¹ and Rᴳ² are independently hydrogen, an aliphatic, alicyclic, heteroaliphatic, heteroalicyclic, aryl, heteroaryl, alkylaryl or alkylheteroaryl moiety;

n is an integer from 0-4;

AR¹ is a monocyclic or polycyclic aryl, heteroaryl, alkylaryl, alkylheteroaryl, alicyclic or heterocyclic moiety;

A, B, D and E are connected by single bonds; wherein D is N and each occurrence of A, B, and E is independently CHRⁱ; wherein each occurrence of Rⁱ is independently hydrogen, halogen, —CN, —NO₂, an aliphatic, alicyclic, heteroaliphatic, heteroalicyclic, aryl, heteroaryl, alkylaryl or alkylheteroaryl moiety, or is —GRᴳ¹ wherein G is —O—, —S—, —NRᴳ²—, —CO—, —SO—, —SO₂—, —C(=O)O—, —C(=O)NRᴳ²—, —OC(=O)—, —NRᴳ²C(=O)— or —SO₂NRᴳ²—, and Rᴳ¹ and Rᴳ² are independently hydrogen, an aliphatic, alicyclic, heteroaliphatic, heteroalicyclic, aryl, heteroaryl, alkylaryl or alkylheteroaryl moiety, or any two adjacent occurrences of Rⁱ, taken together, represent an alicyclic, heteroalicyclic, aryl, or heteroaryl moiety;

p is an integer from 0-4; and

L is C=O or a substituted or unsubstituted C₁₋₆alkylidene or C₂₋₆alkenylidene chain wherein up to two non-adjacent methylene units are independently optionally replaced by —C(=O)—.

2. The formulation of claim 1, wherein the LFA-1 antagonist comprises a compound of Formula I' or its pharmaceutically acceptable salt or ester, having the following structure:

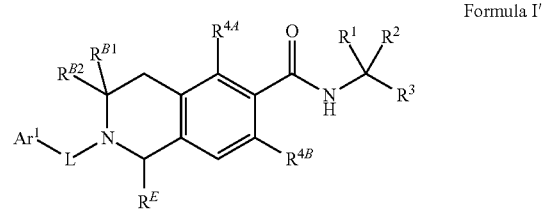

Formula I' wherein R⁴ᴬ and R⁴ᴮ are independently a halogen selected from F, Cl, Br or I; and Rᴮ¹, Rᴮ² and Rᴱ are independently hydrogen or substituted or unsubstituted lower alkyl.

3. The formulation of claim 2, wherein the LFA-1 antagonist has one of the following formulae:

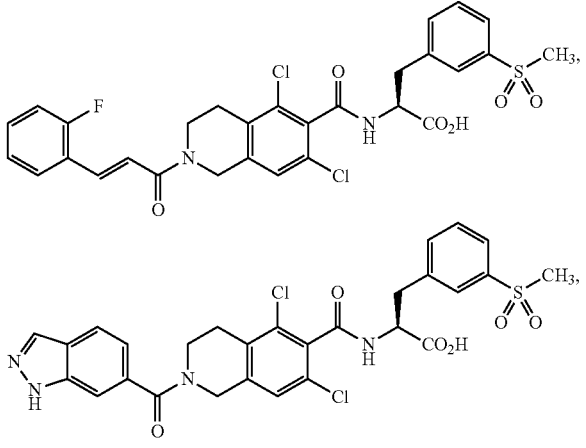

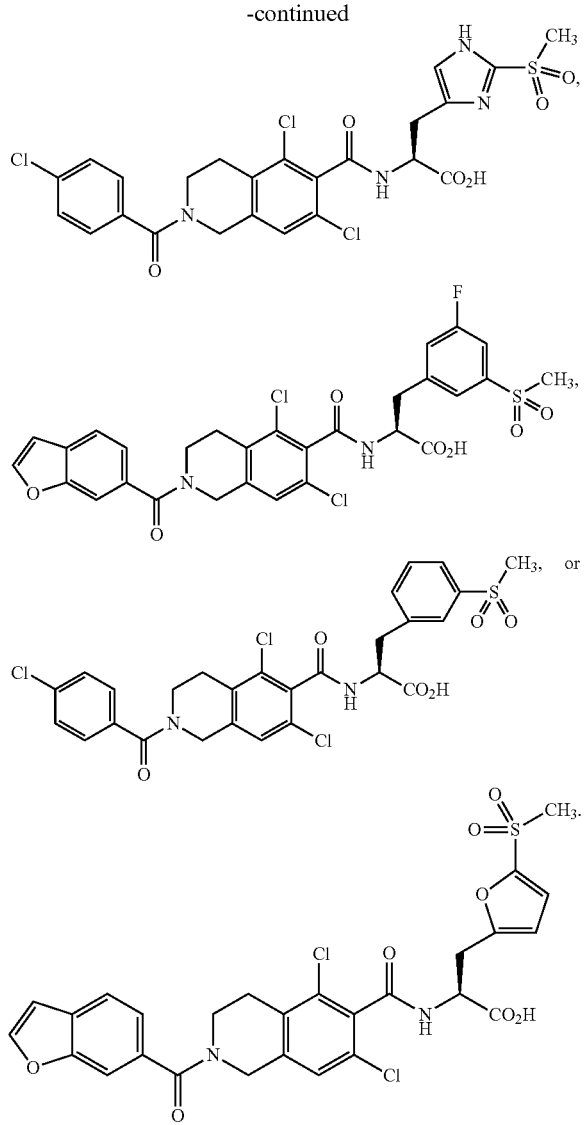

4. The formulation of claim 1, wherein the compound is present in an amount effective to modulate adhesion between intracellular adhesion molecules and the leukocyte integrin family of receptors.

5. The formulation of claim 1, wherein the compound is present in an amount effective to antagonize CD11/CD18 receptors associated with leukocytes.

6. The formulation of claim 1, wherein the LFA-1 antagonist is a sodium, potassium, lithium, magnesium, or calcium salt.

7. The formulation of claim 1, wherein the formulation is in the form of an ointment, paste, cream, lotion, gel, powder, solution, spray, inhalant, patch, suspension, emulsion, crystalline form, oil, plaster, liposome, microemulsion, or buffered solution.

8. The formulation of claim 1, wherein the excipient is selected from the group consisting of alcohols, quaternary amines, organic acids, parabens, phenols, ascorbic acid, ascorbic acid esters, sodium bisulfite, butylated hydroxytoluene, butylated hydroxyanisole, tocopherols, chelating agents, glycerine, sorbitol, polyethylene glycols, urea, propylene glycol, citric buffer, hydrochloric buffer, lactic acid buffer, quaternary ammonium chlorides, cyclodextrins, benzyl benzoate, lecithin, polysorbates, vitamin E oil, allatoin, dimethicone, glycerin, petrolatum, zinc oxide, and combinations thereof.

9. The formulation of claim 1, further comprising a topical penetration enhancer.

10. The formulation of claim 9, wherein the penetration enhancer is triglycerides, aloe compositions, ethyl alcohol, isopropyl alcohol, octolyphenylpolyethylene glycol, oleic acid, polyethylene glycol 400, propylene glycol, N-decylmethylsulfoxide, fatty acid esters, N-methylpyrrolidone, or combinations thereof.

11. The formulation of claim 1, further comprising at least one additional therapeutic agent, wherein the additional therapeutic agent is selected from the group consisting of an anti-inflammatory agent, painkillers, antinausea medications, anti-sickness drugs, a MAC-1 modulator, and an LFA-1 modulator.

12. The formulation of claim 4, wherein said intracellular adhesion molecules are selected from ICAM-1, -2 and -3.

* * * * *